(12) United States Patent
Giovannini et al.

(10) Patent No.: US 8,623,901 B2
(45) Date of Patent: Jan. 7, 2014

(54) COMPOUNDS FOR THE TREATMENT OF CNS DISORDERS

(75) Inventors: Riccardo Giovannini, Verona (IT); Cornelia Dorner-Ciossek, Warthausen (DE); Christian Eickmeier, Mittelbiberach (DE); Dennis Fiegen, Biberach (DE); Thomas Fox, Biberach (DE); Klaus Fuchs, Mittelbiberach (DE); Niklas Heine, Biberach (DE); Holger Rosenbrock, Mittelbiberach (DE); Gerhard Schaenzle, Biberach (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 345 days.

(21) Appl. No.: 12/749,904

(22) Filed: Mar. 30, 2010

(65) Prior Publication Data
US 2011/0082137 A1 Apr. 7, 2011

(30) Foreign Application Priority Data

Mar. 31, 2009 (VE) .............................. 2009-000574
Apr. 1, 2009 (WO) ................. PCT/EP2009/053907
Sep. 30, 2009 (EP) ..................................... 09171906

(51) Int. Cl.
*A61K 31/519* (2006.01)
*C07D 487/04* (2006.01)

(52) U.S. Cl.
USPC ........... 514/403; 514/359; 514/405; 514/406; 514/248; 514/261.1; 514/453; 544/238; 544/233; 544/262

(58) Field of Classification Search
USPC .............. 514/234.2, 252.02, 238, 262.1, 262, 514/118, 359, 403, 405, 406, 248, 261.1, 514/453; 544/238, 233, 262
See application file for complete search history.

(56) References Cited

U.S. PATENT DOCUMENTS

| | | |
|---|---|---|
| 3,165,520 A | 1/1965 | Schmidt et al. |
| 3,169,965 A | 2/1965 | Schmidt et al. |
| 3,211,731 A | 10/1965 | Schmidt et al. |
| 3,244,328 A | 4/1966 | Brown |
| 3,732,225 A | 5/1973 | Breuer et al. |
| 3,847,908 A | 11/1974 | Breuer et al. |
| 3,884,906 A | 5/1975 | Van Der Meer et al. |
| 4,602,023 A | 7/1986 | Kiely et al. |
| 5,002,949 A | 3/1991 | Peseckis et al. |
| 5,041,449 A | 8/1991 | Belleau et al. |
| 5,047,407 A | 9/1991 | Belleau et al. |
| 5,053,499 A | 10/1991 | Kojima et al. |
| 5,113,855 A | 5/1992 | Newhouse |
| 5,201,308 A | 4/1993 | Newhouse |
| 5,239,992 A | 8/1993 | Bougamont et al. |
| 5,256,668 A | 10/1993 | Hsu et al. |
| 5,270,315 A | 12/1993 | Belleau et al. |
| 5,294,612 A | 3/1994 | Bacon et al. |
| 5,341,801 A | 8/1994 | Zechner |
| 5,466,806 A | 11/1995 | Belleau et al. |
| 5,503,144 A | 4/1996 | Bacon |
| 5,541,187 A | 7/1996 | Bacon et al. |
| 5,563,049 A | 10/1996 | Kojima et al. |
| 5,568,884 A | 10/1996 | Bruna |
| 5,634,900 A | 6/1997 | Makino et al. |
| 5,656,629 A | 8/1997 | Bacon et al. |
| 5,684,164 A | 11/1997 | Belleau et al. |
| 5,750,673 A | 5/1998 | Martin |
| 5,948,812 A | 9/1999 | Kraft |
| 5,969,116 A | 10/1999 | Martin |

(Continued)

FOREIGN PATENT DOCUMENTS

CA 2090227 A1 3/1992
CA 1311201 C 12/1992

(Continued)

OTHER PUBLICATIONS

Rentero, Carles, et al; Identification and Distribution of Different mRNA Variants Produced by Differential Splicing in the Human Phosphodiesterase 9A Gene; Biochemical and Biophysical Research Communications (2003) vol. 301 pp. 686-692. Accessed on Dec. 18, 2008: wikipedia: "Amnesia", http://www.mentalhealth.org.uk/information/mental-health-a-z/dementia/, last accessed on Dec. 18, 2008.

(Continued)

*Primary Examiner* — Renee Claytor
*Assistant Examiner* — Sahar Javanmard
(74) *Attorney, Agent, or Firm* — Michael P. Morris; Edward S. Lazer

(57) ABSTRACT

The invention relates to novel 1,6-disubstituted pyrazolopyrimidinones of formula (I),

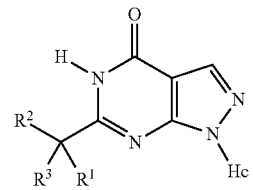

(I)

in which Hc is a tetrahydropyranyl-group and $R^1$ is the group V—W—*, whereby V and W independently of each other may be an aryl group or an heteroaryl group, which independently of each other may optionally be substituted.
According to one aspect of the invention the new compounds are for use as medicaments or for the manufacture of medicaments, in particular medicaments for the treatment of conditions concerning deficits in perception, concentration, learning or memory. The new compounds are also for the manufacture of medicaments and/or for use in the treatment of e.g. Alzheimer's disease, in particular for cognitive impairment associated with Alzheimer's disease.

22 Claims, No Drawings

(56) References Cited

U.S. PATENT DOCUMENTS

| | | |
|---|---|---|
| 5,969,499 A | 10/1999 | Shaffer |
| 5,977,118 A | 11/1999 | Bacon et al. |
| 5,977,332 A | 11/1999 | Martin |
| 6,100,037 A | 8/2000 | Phillips et al. |
| 6,174,884 B1 | 1/2001 | Haning et al. |
| 6,175,008 B1 | 1/2001 | Belleau et al. |
| 6,211,158 B1 | 4/2001 | Seela et al. |
| 6,225,315 B1 | 5/2001 | Ellis |
| 6,350,753 B1 | 2/2002 | Belleau et al. |
| 6,458,796 B1 | 10/2002 | Haning et al. |
| 6,479,463 B1 | 11/2002 | Wang et al. |
| 6,831,174 B2 | 12/2004 | Belleau et al. |
| 6,903,224 B2 | 6/2005 | Belleau et al. |
| 7,022,709 B2 | 4/2006 | Boss et al. |
| 7,067,507 B2 | 6/2006 | Pulley et al. |
| 7,122,693 B2 | 10/2006 | Belleau et al. |
| 7,375,213 B2 | 5/2008 | Deshpande et al. |
| 7,488,733 B2 | 2/2009 | Hendrix et al. |
| 7,488,766 B2 | 2/2009 | Peters et al. |
| 7,541,341 B2 | 6/2009 | Fushimi et al. |
| 7,579,449 B2 | 8/2009 | Eckhardt et al. |
| 7,615,558 B2 | 11/2009 | Hendrix et al. |
| 7,662,790 B2 | 2/2010 | Himmelsbach et al. |
| 7,683,160 B2 | 3/2010 | Eckhardt et al. |
| 7,687,469 B2 | 3/2010 | Eckhardt et al. |
| 7,708,011 B2 | 5/2010 | Hochrainer et al. |
| 7,713,938 B2 | 5/2010 | Himmelsbach et al. |
| 7,723,309 B2 | 5/2010 | Himmelsbach et al. |
| 7,737,156 B2 | 6/2010 | Bo β et al. |
| 7,745,414 B2 | 6/2010 | Eckhardt et al. |
| 7,772,191 B2 | 8/2010 | Eckhardt et al. |
| 7,772,378 B2 | 8/2010 | Himmelsbach et al. |
| 7,776,830 B2 | 8/2010 | Eckhardt et al. |
| 7,847,074 B2 | 12/2010 | Eckhardt et al. |
| 7,851,602 B2 | 12/2010 | Himmelsbach et al. |
| 7,858,587 B2 | 12/2010 | Eckhardt et al. |
| 7,870,856 B2 | 1/2011 | Boeck |
| 7,879,806 B2 | 2/2011 | Himmelsbach et al. |
| 7,879,807 B2 | 2/2011 | Himmelsbach et al. |
| 7,984,713 B2 | 7/2011 | Hochrainer et al. |
| 8,039,441 B2 | 10/2011 | Himmelsbach et al. |
| 8,039,477 B2 | 10/2011 | Hendrix et al. |
| 8,044,060 B2 | 10/2011 | Hendrix et al. |
| 8,088,769 B2 | 1/2012 | Hendrix et al. |
| 2001/0041797 A1 | 11/2001 | Belleau et al. |
| 2001/0044441 A1 | 11/2001 | Campbell et al. |
| 2002/0016348 A1 | 2/2002 | Simitchieva et al. |
| 2002/0074774 A1 | 6/2002 | Hsu et al. |
| 2002/0086160 A1 | 7/2002 | Qiu et al. |
| 2002/0100222 A1 | 8/2002 | Koenig et al. |
| 2002/0132754 A1 | 9/2002 | Boss et al. |
| 2002/0137903 A1 | 9/2002 | Ellsworth et al. |
| 2003/0064935 A1 | 4/2003 | Gougoutas |
| 2003/0087918 A1 | 5/2003 | Belleau et al. |
| 2003/0114390 A1 | 6/2003 | Washburn et al. |
| 2003/0195205 A1 | 10/2003 | DeNinno et al. |
| 2004/0185459 A1 | 9/2004 | Otsuka et al. |
| 2004/0187868 A1 | 9/2004 | Hochrainer et al. |
| 2004/0220186 A1 | 11/2004 | Bell et al. |
| 2004/0254201 A1 | 12/2004 | Belleau et al. |
| 2004/0266736 A1 | 12/2004 | Wunder et al. |
| 2005/0187168 A1 | 8/2005 | Eickelmann et al. |
| 2005/0209251 A1 | 9/2005 | Linker et al. |
| 2005/0233982 A1 | 10/2005 | Himmelsbach et al. |
| 2005/0263151 A1 | 12/2005 | Hochrainer et al. |
| 2006/0009400 A1 | 1/2006 | Eckhardt et al. |
| 2006/0025349 A1 | 2/2006 | Eckhardt et al. |
| 2006/0074031 A1 | 4/2006 | Eckhardt et al. |
| 2006/0100222 A1 | 5/2006 | Boss et al. |
| 2006/0106035 A1 | 5/2006 | Hendrix et al. |
| 2006/0111372 A1 | 5/2006 | Hendrix et al. |
| 2007/0037977 A1 | 2/2007 | Belleau et al. |
| 2007/0105876 A1 | 5/2007 | Hendrix et al. |
| 2007/0105881 A1 | 5/2007 | Hendrix et al. |
| 2007/0161662 A1 | 7/2007 | Hendrix et al. |
| 2007/0240713 A1 | 10/2007 | Boeck |
| 2007/0281940 A1 | 12/2007 | Dugi et al. |
| 2008/0255118 A1 | 10/2008 | Hendrix et al. |
| 2009/0023913 A1 | 1/2009 | Eckhardt et al. |
| 2009/0111838 A1 | 4/2009 | Hendrix et al. |
| 2009/0121919 A1 | 5/2009 | Kihara |
| 2009/0194105 A1 | 8/2009 | Besseler et al. |
| 2009/0235929 A1 | 9/2009 | Egen et al. |
| 2009/0318547 A1 | 12/2009 | Eckhardt et al. |
| 2009/0326215 A1 | 12/2009 | Eckhardt et al. |
| 2010/0024815 A1 | 2/2010 | Kladders |
| 2010/0035900 A1 | 2/2010 | Hendrix et al. |
| 2010/0069310 A1 | 3/2010 | Himmelsbach et al. |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0210839 A1 | 8/2010 | Boss et al. |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0015193 A1 | 1/2011 | Eickmeier et al. |
| 2011/0046076 A1 | 2/2011 | Eickelmann et al. |
| 2011/0046087 A1 | 2/2011 | Eickelmann et al. |
| 2011/0065730 A1 | 3/2011 | Hendrix et al. |
| 2011/0065731 A1 | 3/2011 | Dugi et al. |
| 2011/0082137 A1 | 4/2011 | Giovannini et al. |
| 2011/0098240 A1 | 4/2011 | Dugi et al. |
| 2011/0178033 A1 | 7/2011 | Eckhardt et al. |
| 2011/0184000 A1 | 7/2011 | Giovannini et al. |
| 2011/0203586 A1 | 8/2011 | Egen et al. |
| 2011/0207735 A1 | 8/2011 | Hendrix et al. |
| 2011/0212960 A1 | 9/2011 | Heine et al. |
| 2011/0236477 A1 | 9/2011 | Schneider et al. |
| 2011/0237526 A1 | 9/2011 | Weber et al. |
| 2011/0237789 A1 | 9/2011 | Weber et al. |
| 2011/0294834 A1 | 12/2011 | Hendrix et al. |
| 2012/0010224 A1 | 1/2012 | Hendrix et al. |
| 2012/0115863 A1 | 5/2012 | Fuchs et al. |
| 2012/0165349 A1 | 6/2012 | Hendrix et al. |
| 2012/0202829 A1 | 8/2012 | Heine et al. |
| 2013/0040971 A1 | 2/2013 | Heine et al. |

FOREIGN PATENT DOCUMENTS

| | | |
|---|---|---|
| CA | 2283211 A1 | 9/1998 |
| CA | 2238211 A1 | 12/1998 |
| CA | 2357146 A1 | 7/2000 |
| CA | 2437240 A1 | 8/2002 |
| CA | 2438890 A1 | 9/2002 |
| CA | 2417631 A1 | 1/2003 |
| CA | 2466824 A1 | 5/2003 |
| CA | 2484997 A1 | 11/2003 |
| CA | 2496194 A1 | 3/2004 |
| CA | 2496292 A1 | 4/2004 |
| CA | 2496306 A1 | 4/2004 |
| CA | 2496308 A1 | 4/2004 |
| CA | 2524900 A1 | 11/2004 |
| CA | 2539032 A1 | 3/2005 |
| CH | 396923 A | 8/1965 |
| CH | 396924 A | 8/1965 |
| CH | 396925 A | 8/1965 |
| CH | 396926 A | 8/1965 |
| CH | 396927 A | 8/1965 |
| CH | 398626 A | 3/1966 |
| DE | 1147234 B | 4/1963 |
| DE | 1149013 B | 5/1963 |
| DE | 1153023 B | 8/1963 |
| DE | 1156415 B | 10/1963 |
| DE | 2408906 A1 | 9/1974 |
| DE | 4004558 A1 | 9/1990 |
| DE | 4027391 A1 | 3/1992 |
| DE | 10156249 A1 | 5/2003 |
| DE | 10238722 A1 | 3/2004 |
| EP | 0130735 A1 | 1/1985 |
| EP | 0286028 A2 | 10/1988 |

(56) References Cited

FOREIGN PATENT DOCUMENTS

| | | |
|---|---|---|
| EP | 0496617 A1 | 7/1992 |
| EP | 0516510 A1 | 12/1992 |
| EP | 0546996 A2 | 6/1993 |
| EP | 0626387 A1 | 11/1994 |
| EP | 0679657 A2 | 11/1995 |
| EP | 0995751 A2 | 4/2000 |
| EP | 1460077 A1 | 9/2004 |
| GB | 937723 A | 9/1963 |
| GB | 937724 A | 9/1963 |
| GB | 937726 A | 9/1963 |
| GB | 973361 A | 10/1964 |
| JP | 2001513638 A | 9/2001 |
| JP | 2001514638 A | 9/2001 |
| JP | 2002523507 A | 7/2002 |
| JP | 2004536933 A | 12/2004 |
| JP | 2005531549 A | 10/2005 |
| JP | 2006501272 A | 1/2006 |
| JP | 2006503051 A | 1/2006 |
| WO | 9414802 A1 | 7/1994 |
| WO | 9417803 A1 | 8/1994 |
| WO | 9510506 A1 | 4/1995 |
| WO | 9628429 A1 | 9/1996 |
| WO | 9716456 A1 | 5/1997 |
| WO | 9746569 A2 | 12/1997 |
| WO | 9800434 A1 | 1/1998 |
| WO | WO 98/40384 * | 2/1998 |
| WO | 9810765 A1 | 3/1998 |
| WO | 9816184 A2 | 4/1998 |
| WO | 9840384 A1 | 9/1998 |
| WO | 9941253 A1 | 8/1999 |
| WO | 0018758 A1 | 4/2000 |
| WO | 0043394 A1 | 7/2000 |
| WO | 0160315 A2 | 8/2001 |
| WO | 0177075 A2 | 10/2001 |
| WO | 0206288 A1 | 1/2002 |
| WO | 0209713 A2 | 2/2002 |
| WO | 0216348 A1 | 2/2002 |
| WO | 02055082 A1 | 7/2002 |
| WO | 02057425 A2 | 7/2002 |
| WO | 02068423 A1 | 9/2002 |
| WO | 02074774 A1 | 9/2002 |
| WO | 02086160 A1 | 10/2002 |
| WO | 02098864 A1 | 12/2002 |
| WO | 03011923 A1 | 2/2003 |
| WO | 03011925 A1 | 2/2003 |
| WO | 03022859 A2 | 3/2003 |
| WO | 03031458 A1 | 4/2003 |
| WO | 03037432 A1 | 5/2003 |
| WO | 03037899 A1 | 5/2003 |
| WO | 03041725 A2 | 5/2003 |
| WO | 03072757 A2 | 9/2003 |
| WO | 03093269 A2 | 11/2003 |
| WO | 03099840 A1 | 12/2003 |
| WO | 2004002999 A2 | 1/2004 |
| WO | 2004018474 A1 | 3/2004 |
| WO | 2004026286 A2 | 4/2004 |
| WO | 2004026876 A1 | 4/2004 |
| WO | 2004046331 A2 | 6/2004 |
| WO | 2004096811 A1 | 11/2004 |
| WO | 2004099210 A1 | 11/2004 |
| WO | 2004099211 A1 | 11/2004 |
| WO | 2004108139 A2 | 12/2004 |
| WO | 2004113306 A1 | 12/2004 |
| WO | 2005021566 A2 | 3/2005 |
| WO | 2005051944 A1 | 6/2005 |
| WO | 2005068436 A1 | 7/2005 |
| WO | 2006076455 A2 | 7/2006 |
| WO | 2006084211 A1 | 8/2006 |
| WO | 2006091905 A1 | 8/2006 |
| WO | 2006125548 A1 | 11/2006 |
| WO | 2007025043 A2 | 3/2007 |
| WO | 2007046747 A1 | 4/2007 |
| WO | 2008005542 A2 | 1/2008 |
| WO | 2008049923 A1 | 5/2008 |
| WO | 2008055959 A1 | 5/2008 |
| WO | 2008100447 A2 | 8/2008 |
| WO | 2008104077 A1 | 9/2008 |
| WO | 2008139293 A1 | 11/2008 |
| WO | 2009064802 A2 | 5/2009 |
| WO | 2009068617 A1 | 6/2009 |
| WO | 2009121919 A1 | 10/2009 |
| WO | 2010026214 A1 | 3/2010 |
| WO | 2010092123 A1 | 8/2010 |
| WO | 2010092125 A1 | 8/2010 |
| WO | 2010112437 A1 | 10/2010 |
| WO | 2011018495 A1 | 2/2011 |
| WO | 20120064973 A2 | 5/2012 |

OTHER PUBLICATIONS

Accessed on Jun. 30, 2008, Intelihealth: "Alzheimer's Disease," http://www.intelihealth.com/IH/ihtIH/WSIHW/8303/9117/195703.html?d=dmtHelathAZ.

Accessed on Sep. 22, 2009: Intelihealth: "Dementia," http://www.intelihealth.com/IH/ihtIH/WSIHW000/244798/00084.html.

Accessed on Sep. 22, 2009: Intelihealth: "Parkinson's Disease", http://www.intelihealth.com/IH/ihtIH?d=dmtHealthAZ &c=201957.

Andreeva, Svetlana G, et al; "Expression of cGMP-Specific Phosphodiesterase 9A . . . ", J. of Neuroscience, 2001, Vo. 21, No. 22, pp. 9068-9076.

Bagli, Jehan et al; Chemistry and Positive Inotropic Effect of Pelrinone and related Derivates. A Novel Class of 2-Methylpyrimidones as Inotropic Agents; Journal of Medicinal Chemistry (1988) vol. 31 pp. 814-823.

Barger, Steven, W; Role of Cyclic GMP in the Regulation of Neuronal Calcium and Survival by Secreted Forms of Beta-Amyloid Precursor; Journal of Neurochemistry (1995) vol. 64, No. 5, pp. 2087-2096.

Bernabeu, R., et al; Hippocampal cGMP and cAMP are Differentially Involved in Memory Processing of Inhibitors Avoidance Learning; Neuroreport (1996) vol. 7, No. 2 pp. 585-588.

Byrn, Stephen, R; Solid State Chemistry of Drugs (1999) vol. 2, No. 10, pp. 232-247.

Caligiuri, Maureen, et al; A ProTeome-Wide CDK/CRK-Specific Kinase inhibitor Promotes Tumor Cell Death in the Absence of Cell Cycle Progression; Chemistry & Biology (2005) vol. 12 pp. 1103-1115.

Chem Abstracts Service, Database Accession No. ALB-H01677136, Database Chemcats, 2007, XP002556399.

Cheng, C. C. et al; Potential Purine Antagonists VII. Synthesis of 6-Alkylpyrazolo-[3,4-d]pyrimidinesn Potential Purine Antagonist VII; Gazz. Chim. Ital., (1958) vol. 23, pp. 191-200.

Ciba Geigy AG, "Nucleosides and oligonucleotides and 2'-ether groups," Data Supplied from the espacenet database, Publication Date: Nov. 30, 1994; English Abstract of EPO 626 387.

DeNinno et al. "The discovery of potent, selective, and orally bioavailable PDE9 . . . ", Bioorganic & Medicinal Chemistry Letters, 2009, vol. 19, pp. 2537-2541.

Doerwald et al., "Side reactions in organic synthesis," A Guide to Successful Synthesis Design, 2005, 4 pages.

Ebert et al., "Scopolamine model of demential: electroencephalogram findings and cognitive performance," Europ J of Clinical Investigation, 1998, vol. 28, No. 11, pp. 944-949.

Farlow, Martin, R; Pharmacokinetic Profiles of Currect Therapies for Alzheimer's Disease: Implications for Switching to Galantamine; Clinical Therapeutics (2001) vol. 23, Suppl. A, pp. A13-A-24.

Fawcett, Lindsay et al; "Molecular Cloning and Characterization of a Distinct Human . . . ", Proc. Natl. Acad. Science, 2000, vol. 97, No. 7, pp. 3702-3707.

Fischer, Douglas A., et al; "Isolation and Characterization of PDE9A, A Novel . . . ", J. of Biological Chemistry, 1998, vol. 273, No. 25, pp. 15559-15564.

Fisher, Douglas A, et al; "Isolation and Characterization of PDE8A, A Novel . . . ", Biochemical and Biophysical Research Communications, 1998, vol. 246, pp. 570-577.

Francis et al; Cortical Pyramidal Neurone Loss May Cause Glutamatergic Hypoativity and Cognitive Impairment in

(56) References Cited

OTHER PUBLICATIONS

Alzheimer's Disease: investigative and Therapeutic Perspectives; Journal of Neurochemistry (1993) vol. 60, No. 5, pp. 1589-1604.

Francis, Paul T; "Glutamatergic Systems in Alzheimer's Disease" International Journal of Geriatic Psychiatry (2003) vol. 18, pp. S15-S21.

Francis, Sharron H., et al; "Characterization of a Novel cGMP Binding Protein form Rat Lung . . . ", J. of Biological Chemistry, vol. 255, No. 2, pp. 620-626.

Fujhishige et al; Cloning and Characterization of a Novel Human Phosphodiesterase That Hydrolyzes Both cAMP and cGMP (PDE10A); Journal of Bilogical Chemistry (1999) vol. 274, No. 26, pp. 18438-18445.

Gielen, Hieke et al; A Novel Approach to Amidines from Esters; Tetrahedron Letters (2002) vol. 43 pp. 419-421.

Gillespie et al; Characterization of a Bovine Cone Photoreceptor Phosphodiesterase Purified by Cyclic Cyclic GMP-Sepharose Chromatography; J. of Biological Chemistry (1988) vol. 263, No. 17, pp. 8133-8141.

Gompper, Rudolf et al; Substituted Dithiocarboxylic Acids and Ketene Thioacetals; Institute for Organic Chemistry Technology (1962) vol. 95, pp. 2861-2870. German & English Translation.

Guipponi, Michel et al; Identification and Characterization of a Novel Cyclic Nucleotide Phosphodiesterase Gene (PDE9A) that Maps to 21q22.3: Alternative Splicing of mRNA Transcripts, Genomic Structure and Sequence; Hum Genet (1998) vol. 103, pp. 386-392.

Harb, A.-F. A., et al; Pyrazoles as Building Blocks in Heterocyclic Synthesis: Synthesis of Some Ne Substituted 1-Triazinylpyrazolo[3,4-d]pyrimidine and 1-Triazinylpyrazolo[3,4-b]pyridine Derivates; Chemical Papers (2005) vol. 59, No. 3, pp. 187-195.

Hendrix et al; "6-cyclymethyl-and 6-alkylmethyl-Substituted Pyrazolopyrimidines," Publication Date: Nov. 18, 2004, Data Supplied from the espacenet database Worlwide; English Abstract of WO 2004099211.

Hendrix et al; "Use of Pyrazolopyrimidine Against Cardiovascular Disease," Publication Date: Nov. 30, 2006, Data Supplied from the espacenet database Worldwide; English Abstract or WO 20060125548.

Hetman, J. M., et al; Cloning and Characterization of PDE7B, a cAMP-Specific Phosphodiesterase; Proc, Natl. Acad. Science (2000) vol. 97, No. 1, pp. 472-476.

http://www.nlm.nih.gov/medlineplus/ency/article/000746.htm, last accessed Jul. 15, 2010.

Huettner et al; Primary Culture of Identified Neurons from the Visual Cortex of Postnatal Rats; Journal of Neuroscience (1986) vol. 6, No. 10, pp. 3044-3060.

Hung et al., "A high-yielding synthesis of monalkylhydrazines," Journal of Organic Chemistry, 1981, vol. 46, pp. 5413-5414.

International Search Report for PCT/EP2008/066350 dated Feb. 23, 2009.

International Search Report for PCT/EP2009/053907 dated May 26, 2009.

International Search Report for PCT/EP2009/061455 dated Mar. 17, 2011.

International Search Report for PCT/EP2010/054050 dated May 27, 2010.

International Search Report for PCT/EP2010/061735 dated Sep. 24, 2010.

International Search Report for PCT/EP2004/006477 dated Oct. 27, 2004.

International Search Report for PCT/EP2004/014872 dated May 19, 2005.

International Search Report of PCT/EP2003/08880 dated Apr. 16, 2004.

International Search Report of PCT/EP2003/08923 dated Dec. 15, 2003.

International Search Report of PCT/EP2003/08979 dated Nov. 25, 2003.

International Search Report of PCT/EP2004/004412 dated Jul. 14, 2004.

International Search Report of PCT/EP2004/004455 dated Sep. 17, 2004.

Loughney, Kate, et al; Isolation and Characterization of cDNAs Corresponding to Two human Calcium, Calmodulin-regulated, 3',5'-Cyclic Nucleotide Phosphodiesterases; The Journal of Biological Chemistry (1996) vol. 271, No. 2, pp. 796-806.

Loughney, Kate, et al; Isolation and Characterization of cDNAs Encoding PDE5A, a Human cGMP-Bing, cGMP-Specific 3',5'-cyclic Nucleotide Phosphodiesterase; Gene (1998) vol. 216, pp. 139-147.

Lugnier, Claire; Cyclic Nucleotide Phosphodiesterase (PDE) Superfamily: A New Target for the Development of Specific Therapeutic Agents; Pharmacology & Therapeutics; (2006) vol. 109, pp. 366-398.

Markwalder, J. A. et al; Synthesis and Biological Evaluation of 1-Aryl-4,5-dihydro-1H-pyrazolo[3,4-d]pyrimidin-4-one Inhibitors of Cyclin-Dependent Kinases; J. of Med Chemistry (2004) vol. 47, pp. 5894-5911.

Martins, Timothy, J., et al; Purification and Characterization of a Cyclic GMP-stimulated Cyclic Nucleotide Phosphodiesterase from Bovine Tissues; The Journal of Biological Chemistry (1982) vol. 257, No. 4, pp. 1973-1979.

Merriam-Webster's Collegiate Dictionary, published 1998 by Merriam-Webster Inc. p. 924.

Miki, Takashi, et al; Characterization of the cDNA and Gene Encoding Human PDE3B, the cGIP1 Isoform of the Human Cyclic GMP-Inhibited Cyclic Nucleotide Phosphodiesterase Family; Genomics (1996) vol. 36, pp. 476-485.

Miyashita, A., et al; Studies on Pyrazolo[3,4-d]pyrimidine Derivatives XVIII Facile Preparation of 1H-Pyrazolo[3,4-d] Pyrimidin-4(5H)-Ones; Heterocycles (1990) vol. 31, No. 7, pp. 1309-1314.

Murashima, Seiko., et al; Characterization of Particulate Cyclic Nucleotide Phosphodiesterases from Bovine Brain: Purification of a Distinct cGMP-Stimulated Isoenzyme; Biochemistry (1990) vol. 29, No. 22, pp. 5285-5292.

Obernolte, Rena, et al; The cDNA of a Human Lymphocyte Cyclic AMP Phosphodiesterase (PDE IV) Reveals a Multigene Family; Gene (1993) vol. 129, pp. 239-247.

Podraza, Kenneth F.; Reductive Cyclization of Ketoesters Utilizing Sodium Cyanoborohydride: Synthesis of ?- and ?-Lactones; J. Heterocyclic Chem (1987) vol. 24. pp. 293.

Prickaerts et al; Possible Role of Nitric Oxide-Cyclic GMP Pathway in Object Recognition Memory: Effects of 7 Nitroindazole and Zaprinast; Europ J of Pharmacology (1997) vol. 337, No. 2-3, pp. 125-136.

Prickaerts, J. et al; Effects of Two Selective Phosphodiesterase Type 5 Inhibitors, Sildenafil and Vardenafil, on Object Recognition Memory and Hippocampal Cyclic GMP Levels in the Rat, Neuroscience (2002) vol. 113, No. 2, pp. 351-361.

Puzzo, Daniela, et al; Amyloid-b Peptide Inhibits Activation of the Nitric Oxide/cGMP/cAMP-Responsive Element-Binding Protein Pathway During Hippocampal Synaptic Plasticity; The Journal of Neuroscience (2005) vol. 25, No. 29, pp. 6887-6897.

Reddy, K. Hemender et al; Versatile Synthesis of 6-Alkyl/Aryl-1H-Pyrazolo[3,4-d]Pyrimidine-4[5H]-Ones; Indian Journal of Chemistry (1992) vol. 31B, pp. 163-166.

Reid I. A.; Role of Phosphodiesterase Isozymes in the Control of Renin Secretion: Effects of Selective Enzyme Inhibitors; Current Pharmaceutical Design (1999) vol. 5, No. 9, pp. 725-735.

Related U.S. Appl. No. 12/855,129, filed Aug. 12, 2010.

Related U.S. Appl. No. 12/935,686, filed Sep. 30, 2010.

Related U.S. Appl. No. 13/062,625, filed Mar. 7, 2011.

Related U.S. Appl. No. 13/099,064, filed May 2, 2011.

Reymann, Klaus, et al; The Late Maintenance of Hippocampal LTP: Requirements, Phases, 'Synaptic Tagging', 'Late-Associativity' and Implications; Neuropharmacology (2007) vol. 52, pp. 24-40.

Roenn, Magnus et al; Palladium (II)-Catalyzed Cyclization Using Molecular Oxygen as Reoxidant; Tetrahedron Letters (1995) vol. 36, No. 42, pp. 7749-7752.

(56) References Cited

OTHER PUBLICATIONS

Rosman, Guy, J., et al; Isolation and Characterization of Human cDNSs Encoding a cGMP-Stimulated 3',5'-Cyclic Nucleotide Phosphodiesterase; Gene (1997) vol. 191, pp. 89-95.

Schmidt, Richard, R. et al; Pyrazolo[3, 4-d]Pyrimidin-Nucleoside; Chemische Berichte (1977) vol. 110, pp. 2445-2455.

Schmidt, von P., et al; Heilmittelchemische Studien in der Heterocyclischen Reihe; Helvetica Chimica Acta (1962) vol. 62, No. 189, pp. 1620-1627.

Schousboe, Arne et al; Role of Ca++ and Other Second Messengers in Excitatory Amino Acid Receptor Mediated Neuogeneration: Clinical Perspective; Clinical Neuroscience (1997) vol. 4, pp. 194-198.

Skipper, Howard, E., et al; Structure-Activity Relationships Observed on Screening a Series of Pyrazolopyrimidines Against Experimental Neoplasms; Cancer Research (1957) vol. 17, pp. 579-596.

Soderling, Scott, H. et al; Identification and Characterization of a Novel Family of Cyclic Nucleotide Phosphodiesterases; The Journal of Biological Chemistry (1998) vol. 273, No. 25, pp. 15553-15558.

Soderling, Scott, H. et al; Regulation of cAMP and cGMP signalling: New Phosphodiesterases and New Functions; Current Opinion in Cell Biology (2000) vol. 12, pp. 174-179.

Thomson Innovation Record View, Publication Date: Apr. 18, 1963; English Abstract of DE 1147234B.

Thomson Innovation Record View, Publication Date: Aug. 15, 1965; English Abstract of CH 396 923.

Thomson Innovation Record View, Publication Date: May 22, 1963; English Abstract of DE 1149013B.

Timberlake, J.W. et al; Preparative Procedures: Chemistry of Hydrazo-, Azo-, and Azoxy Groups; Patai (1975) Chapter 4, pp. 69-107.

U.S. Appl. No. 12/545,175, filed Aug. 21, 2009, Inventor: Matthias Eckhardt.

U.S. Appl. No. 12/892,310, filed Sept 28, 2010. Inventor: Dirk Weber.
U.S. Appl. No. 12/892,326, filed Sept 28, 2010. Inventor: Dirk Weber.
U.S. Appl. No. 12/894,385, filed Sept 30, 2010. Inventor: Peter Schneider.

U.S. Appl. No. 13/079,424, filed Apr. 4, 2011. Inventor: Matthias Eckhardt.

U.S. Appl. No. 13/369,596, filed Feb. 9, 2012. Inventor: Niklas Heine.

U.S. Appl. No. 13/369,623, filed Feb. 9, 2012. Inventor: Niklas Heine.

Ugarkar, Bheemarao, et al; Synthesis and antiviral/Antitumor Activities of Certain Pyrazolo[3,4-d]pyrimidine-4 (5H)-selone Nucleosides and Related compounds; Journal of Medicinal Chemistry (1984) vol. 27, No. 8, pp. 1026-1030.

Ulrich, Joachim; Crystallization; Kirk-Othmer Encyclopedia of Chem Techn (2002) 7 pages.

Van Der Staay, F. Josef., et al; The Novel Selective PDE9 Inhibitor Bay 73/6691 Improves Learning and Memory in Rodents; Neuropharmacology (2008) vol. 55, pp. 908-916.

Van Staveren, W. C. G., et al; Cloning and localization of the cGMP-specific Phosphodiesterase Type 9 in the Rat Brain; Journal of Neurocytology (2002) vol. 31, pp. 729-741.

Vippagunta, Sudha, R., et al; Crystalline Solids; Advanced Drug Delivery Reviews (2001) vol. 48, pp. 3-26.

Wang, Huanchen, et al; Insight Into Binding of Phosphodiesterase-9-A Selective Inhibitors by Crystal Structures and Mutagenesis; Journal of Medicinal Chemistry (2009) pp. 1-6.

Wang, Peng., et al; Identification and Characterization of a New Human Type 9 cGMP-specific Phosphodiesterase-Splice Variant (PDE9A5) Different Tissue Distribution and Subcellular Localization of PDE9A Variants; Gene (2003) vol. 314, pp. 15-27.

Weeber, Edwin, et al; Molecular Genetics of Human Cognition; Molecular Interventions (2002) vol. 2, No. 6, pp. 376-391.

Wei, Ji-Ye, et al; Molecular and Pharmacological Analysis of Cyclic Nucleotide-Gated Channel Function in the Central Nervous System; Progress in Neurobiology (1998) vol. 56, pp. 37-64.

West, Anthony, R; Solid Solutions; Department of Chemistry, Univesity of Aberdeen (1988) vol. 10 3 pages.

Wunder, Frank et al; Characterization of the First Potent and Selective PDE9 Inhibitor Using a cGMP Reporter Cell Line; Molecular Pharmacology (2005) vol. 68, No. 6 pp. 1775-1781.

U.S. Appl. No. 13/886,850, filed May 3, 2013. Inventor: Frank-Gerhard Boss.

\* cited by examiner

COMPOUNDS FOR THE TREATMENT OF CNS DISORDERS

This application claims the benefit of Venezuelan Application 2009-000574 filed Mar. 31, 2009, of International Application PCT/EP2009/053907 filed Apr. 1, 2009, and of European Application EP 09 171 906.2 filed Sep. 30, 2009, the contents of which are incorporated herein by reference in their entireties.

The invention relates to novel 1,6-disubstituted pyrazolopyrimidinones of formula (I),

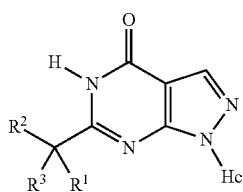

in which Hc is a tetrahydropyranyl-group and $R^1$ is the group V—W—*, whereby V and W independently of each other may be an aryl group or an heteroaryl group, which independently of each other may optionally be substituted.

According to one aspect of the invention the new compounds are for use as medicaments or for the manufacture of medicaments, in particular medicaments for the treatment of conditions concerning deficits in perception, concentration, learning or memory. Such conditions may for example be associated with Alzheimer's disease. The new compounds are also for example for the manufacture of medicaments and/or for use in the treatment of e.g. Alzheimer's disease, in particular for cognitive impairment associated with Alzheimer's disease. The compounds of the invention are PDE 9 inhibitors.

BACKGROUND OF THE INVENTION

The inhibition of phosphodiesterase 9A (PDE9A) is one of the currents concepts to find new access paths to the treatment of cognitive impairments due to CNS disorders like Alzheimer's Disease or due to any other neurodegenerative process of the brain. With the present invention, new compounds that follow this concept are presented.

Phosphodiesterase 9A is one member of the wide family of phosphodiesterases. These enzymes modulate the levels of the cyclic nucleotides 5'-3' cyclic adenosine monophosphate (cAMP) and 5'-3' cyclic guanosine monophosphate (cGMP). These cyclic nucleotides (cAMP and cGMP) are important second messengers and therefore play a central role in cellular signal transduction cascades. Each of them reactivates inter alia, but not exclusively, protein kinases. The protein kinase activated by cAMP is called protein kinase A (PKA), and the protein kinase activated by cGMP is called protein kinase G (PKG). Activated PKA and PKG are able in turn to phosphorylate a number of cellular effector proteins (e.g. ion channels, G-protein-coupled receptors, structural proteins, transcription factors). It is possible in this way for the second messengers cAMP and cGMP to control a wide variety of physiological processes in a wide variety of organs. However, the cyclic nucleotides are also able to act directly on effector molecules. Thus, it is known, for example, that cGMP is able to act directly on ion channels and thus is able to influence the cellular ion concentration (review in: Wei et al., *Prog. Neurobiol.*, 1998, 56, 37-64). The phosphodiesterases (PDE) are a control mechanism for the activity of cAMP and cGMP and thus in turn for the corresponding physiological processes. PDEs hydrolyse the cyclic monophosphates to the inactive monophosphates AMP and GMP. Currently, 11 PDE families have been defined on the basis of the sequence homology of the corresponding genes. Individual PDE genes within a family are differentiated by letters (e.g. PDE1A and PDE1B). If different splice variants within a gene also occur, this is then indicated by an additional numbering after the letters (e.g. PDE1A1).

Human PDE9A was cloned and sequenced in 1998. The amino acid identity with other PDEs does not exceed 34% (PDE8A) and is never less than 28% (PDE5A). With a Michaelis-Menten constant (Km) of 170 nanomolar (nM), PDE9A has high affinity for cGMP. In addition, PDE9A is selective for cGMP (Km for cAMP=230 micromolar (μM). PDE9A has no cGMP binding domain, suggesting that the enzyme activity is not regulated by cGMP. It was shown in a Western blot analysis that PDE9A is expressed in humans inter alia in testes, brain, small intestine, skeletal muscle, heart, lung, thymus and spleen. The highest expression was found in the brain, small intestine, kidney, prostate, colon, and spleen (Fisher et al., *J. Biol. Chem.*, 1998, 273 (25), 15559-15564; Wang et al., *Gene*, 2003, 314, 15-27). The gene for human PDE9A is located on chromosome 21q22.3 and comprises 21 exons. 4 alternative splice variants of PDE9A have been identified (Guipponi et al., *Hum. Genet.*, 1998, 103, 386-392). Classical PDE inhibitors do not inhibit human PDE9A. Thus, IBMX, dipyridamole, SKF94120, rolipram and vinpocetine show no inhibition on the isolated enzyme in concentrations of up to 100 micromolar (μM). An IC50 of 35 micromolar (μM) has been demonstrated for zaprinast (Fisher et al., *J. Biol. Chem.*, 1998, 273 (25), 15559-15564).

Murine PDE9A was cloned and sequenced in 1998 by Soderling et al. (*J. Biol. Chem.*, 1998, 273 (19), 15553-15558). This has, like the human form, high affinity for cGMP with a Km of 70 nanomolar (nM). Particularly high expression was found in the mouse kidney, brain, lung and liver. Murine PDE9A is not inhibited by IBMX in concentrations below 200 micromolar either; the IC50 for zaprinast is 29 micromolar (Soderling et al., *J. Biol. Chem.*, 1998, 273 (19), 15553-15558). It has been found that PDE9A is strongly expressed in some regions of the rat brain. These include olfactory bulb, hippocampus, cortex, basal ganglia and basal forebrain (Andreeva et al., *J. Neurosci.*, 2001, 21 (22), 9068-9076). The hippocampus, cortex and basal forebrain in particular play an important role in learning and memory processes. As already mentioned above, PDE9A is distinguished by having particularly high affinity for cGMP. PDE9A is therefore active even at low physiological concentrations, in contrast to PDE2A (Km=10 micromolar (μM); Martins et al., *J. Biol. Chem.*, 1982, 257, 1973-1979), PDE5A (Km=4 micromolar (μM); Francis et al., *J. Biol. Chem.*, 1980, 255, 620-626), PDE6A (Km=17 micromolar; Gillespie and Beavo, *J. Biol. Chem.*, 1988, 263 (17), 8133-8141) and PDE11A (Km=0.52 micromolar; Fawcett et al., *Proc. Nat. Acad. Sci.*, 2000, 97 (7), 3702-3707). In contrast to PDE2A (Murashima et al., *Biochemistry*, 1990, 29, 5285-5292), the catalytic activity of PDE9A is not increased by cGMP because it has no GAF domain (cGMP-binding domain via which the PDE activity is allosterically increased) (Beavo et al., *Current Opinion in Cell Biology*, 2000, 12, 174-179). PDE9A inhibitors may therefore lead to an increase in the baseline cGMP concentration.

This outline will make it evident that PDE9A engages into specific physiological processes in a characteristic and unique manner, which distinguish the role of PDE9A characteristically from any of the other PDE family members.

WO04099210 discloses 6-arylmethyl-substituted pyrazolopyrimidinones which are PDE9 inhibitors. The compounds do not have a non-aromatic heterocyclic moiety in the 1 position of the pyrazolopyrimidine.

WO04096811 discloses heterocyclic bicycles as PDE9 inhibitors for the treatment of diabetes, including type 1 and type 2 diabetes, hyperglycemia, dyslipidemia, impaired glucose tolerance, metabolic syndrome, and/or cardiovascular disease.

Other prior art is directed to chemically similar nucleoside derivatives. As examples it is referred to WO02057425, which discloses nucleosides derivatives, which are inhibitors of RNA-dependent RNA viral polymerase, or WO01060315, which discloses nucleoside derivatives for the treatment of hepatitis C infection or EP679657, which discloses compounds that serve as ribonucleoside analogues or US2002058635, which discloses purine L-nucleoside compounds, in which both the purine rings and the sugar are either modified, functionalized, or both. So the sugar for example must show at least one esterified OH group.

WO06084281 discloses inhibitors of the E1 activation enzyme that have a sulfonamide moiety.

WO05051944 discloses oxetane-containing nucleosides, for the treatment of nucleoside analogue related disorders such as disorders involving cellular proliferation and infection.

WO9840384 discloses pyrazolopyrimidinones which are PDE1, 2 and 5 inhibitors and can be employed for the treatment of cardiovascular and cerebrovascular disorders and disorders of the urogenital system.

CH396 924, CH396 925, CH396 926, CH396 927, DE1147234, DE1149013, describe pyrazolopyrimidines which have a coronary-dilating effect and which can be employed for the treatment of disturbances of myocardial blood flow.

U.S. Pat. No. 3,732,225 describes pyrazolopyrimidines which have an anti-inflammatory and blood glucose-lowering effect.

DE2408906 describes styrylpyrazolopyrimidinones which can be employed as antimicrobial and anti-inflammatory agents for the treatment of, for example, oedema.

OBJECTIVE OF THE INVENTION

Changes in the substitution pattern of pyrazolopyrimidinones result in interesting changes concerning biological activity, respectively changes in the affinity towards different target enzymes.

Therefore it is an objective of the present invention to provide compounds as herein described, in particular in the claims, that effectively modulate PDE9A for the purpose of the development of a medicament, in particular in view of diseases or conditions, the treatment of which is accessible via PDE9A modulation.

It is another objective of the present invention to provide compounds that are useful for the manufacture of a medicament for the treatment of CNS disorders.

Yet another objective of the present invention is to provide compounds which show a favourable safety profile.

Another objective of the present invention is to provide compounds that have a favourable selectivity profile in favour for PDE9A inhibition over other PDE family members and other pharmacological targets and by this may provide therapeutic advantage.

Yet another objective is to provide such a medicament that may not only serve for treatment but also for prevention or modification of the corresponding disease or condition.

The present invention further provides a pharmaceutical composition comprising a compound as herein described, in particular in the claims, and a pharmaceutically acceptable carrier.

The present invention further provides a method of the treatment of any of the conditions as described herein in a mammal in need of such treatment, preferably a human, comprising administering to the mammal a therapeutically effective amount of a compound as herein described, in particular in the claims.

The present invention further provides a compound as herein described, in particular in the claims, for use in a method of treatment of the human or animal body by therapy.

DETAILED DESCRIPTION OF THE PRESENT INVENTION

The compounds of the present invention are characterised by general formula (I):

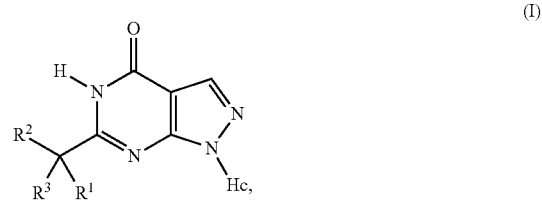

with the following definitions (substituents may be printed in bold for better reading):

Substituent Hc is defined by the following definitions $Hc^i$, whereby the index i describes the order of preference, ascending from $Hc^1$ to more preferably (i.e. $Hc^2$), and so on:

$Hc^1$:

Hc is tetrahydropyranyl-, whereby one or more carbon ring atom(s) thereof optionally may be substituted by one or—where appropriate—by one or two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo.

$Hc^2$:

Hc is 4-tetrahydropyranyl-, whereby one or more carbon ring atom(s) thereof optionally may be substituted by one or—where appropriate—by one or two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo.

$Hc^3$:

Hc is unsubstituted 4-tetrahydropyranyl.

It will be evident that whenever Hc is tetrahydropyranyl—unsubstituted or not, it will be bound to the scaffold (factually to the nitrogen No. 1, see definition "scaffold" (=N1)) by one of the ring carbon atoms of said tetrahydropyranyl.

Substituent $R^1$ is defined by the following definitions $R^{1,j}$, respectively $R^{1,j}$, whereby the index j describes the order of preference, ascending from $R^{1.1}$ to more preferred definitions like $R^{1.2}$, and so on:

$R^{1.1}$:
$R^1$ being the group

V—W—* wherein
W is phenyl or heteroaryl;
V is phenyl or heteroaryl;
V preferably is attached at the 2 position of W, whereby the 1 position of W is the attachment point of W to the $CR^2R^3$ group in formula (I);
—* is the binding point by which W is attached to the $CR^2R^3$ group in formula (I);
wherein W and V independently of each other optionally may be substituted by one or more substituents selected from the group of fluorine, chlorine, bromine, $C_{1-6}$-alkyl-, $F_3C$—, $HF_2C$—, $FH_2C$—, $F_3C$—$CH_2$—, $F_3C$—O—, $HF_2C$—O—, $C_{3-7}$-heterocycloalkyl- (thereof preferably $C_{3-5}$-heterocycloalkyl-), H—O—$C_{1-6}$-alkyl-, $C_{1-6}$-alkyl-O—$C_{1-6}$-alkyl-, $C_{3-7}$-cycloalkyl-O—$C_{1-6}$-alkyl-, $C_{3-7}$-cycloalkyl-$C_{1-3}$-alkyl-O—$C_{1-6}$-alkyl-, phenyl-O—$C_{1-6}$-alkyl-, benzyl-O—$C_{1-6}$-alkyl-, H—O—, $C_{1-6}$-alkyl-O—, $C_{3-7}$-cycloalkyl-O—, $C_{3-7}$-cycloalkyl-$C_{1-3}$-alkyl-O—, phenyl-O—, benzyl-O—, N-morpholinyl, and NC—, preferably by a substituent selected from the group of fluorine, chlorine, bromine, $C_{1-6}$-alkyl-, $F_3C$—, $F_3C$—$CH_2$—, $F_3C$—O—, $HF_2C$—O—, $C_{3-7}$-heterocycloalkyl- (thereof preferably $C_{3-5}$-heterocycloalkyl-), $C_{1-6}$-alkyl-O—, $C_{3-6}$-cycloalkyl-O—, $C_{3-6}$-cycloalkyl-$CH_2$—O—, aryl-$CH_2$—O— and NC—.

$R^{1.2}$:
$R^1$ being the group

V—W—* wherein
W is phenyl or a heteroaryl, the heteroaryl being selected from the group of oxadiazolyl, triazolyl, pyrazolyl, furanyl, pyridyl, pyrimidyl and pyridazinyl,
V is phenyl or heteroaryl, the heteroaryl being selected from the group of oxadiazolyl, triazolyl, pyrazolyl, pyrrolyl, furanyl, pyridyl, pyrimidyl and pyridazinyl,
V preferably is attached at the 2 position of W, whereby the 1 position of W is the attachment point of W to the $CR^2R^3$ group in formula (I);
—* is the binding point by which W is attached to the $CR^2R^3$ group in formula (I)
wherein W and V independently of each other optionally may be substituted by one or more substituents selected from the group of fluorine, chlorine, bromine, $C_{1-6}$-alkyl-, $F_3C$—, $HF_2C$—, $FH_2C$—, $F_3C$—$CH_2$—, $F_3C$—O—, $HF_2C$—O—, $C_{3-7}$-heterocycloalkyl- (thereof preferably $C_{3-5}$-heterocycloalkyl-), H—O—$C_{1-6}$-alkyl-, $C_{1-6}$-alkyl-O—$C_{1-6}$-alkyl-, $C_{3-7}$-cycloalkyl-O—$C_{1-6}$-alkyl-, $C_{3-7}$-cycloalkyl-$C_{1-3}$-alkyl-O—$C_{1-6}$-alkyl-, phenyl-O—$C_{1-6}$-alkyl-, benzyl-O—$C_{1-6}$-alkyl-, H—O—, $C_{1-6}$-alkyl-O—, $C_{3-7}$-cycloalkyl-O—, $C_{3-7}$-cycloalkyl-$C_{1-3}$-alkyl-O—, phenyl-O—, benzyl-O—, N-morpholinyl, and NC—, preferably by a substituent selected from the group of fluorine, chlorine, bromine, $C_{1-6}$-alkyl-, $F_3C$—, $F_3C$—$CH_2$—, $F_3C$—O—, $HF_2C$—O—, $C_{3-7}$-heterocycloalkyl- (thereof preferably $C_{3-5}$-heterocycloalkyl-), $C_{1-6}$-alkyl-O—, $C_{3-6}$-cycloalkyl-O—, $C_{3-6}$-cycloalkyl-$CH_2$—O—, aryl-$CH_2$—O— and NC—.

$R^{1.3}$:
$R^1$ being the group

V—W—* wherein
W is phenyl or a heteroaryl, the heteroaryl being selected from the group of pyridyl, pyrimidyl and pyridazinyl,
V is phenyl or heteroaryl, the heteroaryl being selected from the group of oxadiazolyl, triazolyl, pyrazolyl, pyrrolyl, furanyl, pyridyl, pyrimidyl and pyridazinyl,
V preferably is attached at the 2 position of W, whereby the 1 position of W is the attachment point of W to the $CR^2R^3$ group in formula (I);
—* is the binding point by which W is attached to the $CR^2R^3$ group in formula (I)
wherein W and V independently of each other optionally may be substituted by one or more substituents selected from the group of fluorine, chlorine, bromine, $C_{1-6}$-alkyl-, $F_3C$—, $HF_2C$—, $FH_2C$—, $F_3C$—$CH_2$—, $F_3C$—O—, $HF_2C$—O—, $C_{3-7}$-heterocycloalkyl- (thereof preferably $C_{3-5}$-heterocycloalkyl-), H—O—$C_{1-6}$-alkyl-, $C_{1-6}$-alkyl-O—$C_{1-6}$-alkyl-, $C_{3-7}$-cycloalkyl-O—$C_{1-6}$-alkyl-, $C_{3-7}$-cycloalkyl-$C_{1-3}$-alkyl-O—$C_{1-6}$-alkyl-, phenyl-O—$C_{1-6}$-alkyl-, benzyl-O—$C_{1-6}$-alkyl-, H—O—, $C_{1-6}$-alkyl-O—, $C_{3-7}$-cycloalkyl-O—, $C_{3-7}$-cycloalkyl-$C_{1-3}$-alkyl-O—, phenyl-O—, benzyl-O—, N-morpholinyl, and NC—, preferably by a substituent selected from the group of fluorine, chlorine, bromine, $C_{1-6}$-alkyl-, $F_3C$—, $F_3C$—$CH_2$—, $F_3C$—O—, $HF_2C$—O—, $C_{3-7}$-heterocycloalkyl- (thereof preferably $C_{3-5}$-heterocycloalkyl-), $C_{1-6}$-alkyl-O—, $C_{3-6}$-cycloalkyl-O—, $C_{3-6}$-cycloalkyl-$CH_2$—O—, aryl-$CH_2$—O— and NC—.

$R^{1.4}$:
$R^1$ being the group

V—W—* wherein
W is phenyl or pyridinyl,
V is phenyl or heteroaryl, the heteroaryl being selected from the group of oxadiazolyl, triazolyl, pyrazolyl, furanyl, pyridyl, pyrimidyl and pyridazinyl,
V preferably is attached at the 2 position of W, whereby the 1 position of W is the attachment point of W to the $CR^2R^3$ group in formula (I);
—* is the binding point by which W is attached to the $CR^2R^3$ group in formula (I)
wherein W and V independently of each other optionally may be substituted by one or more substituents selected from the group of fluorine, chlorine, bromine, $C_{1-6}$-alkyl-, $F_3C$—, $HF_2C$—, $FH_2C$—, $F_3C$—$CH_2$—, $F_3C$—O—, $HF_2C$—O—, $C_{3-7}$-heterocycloalkyl- (thereof preferably $C_{3-5}$-heterocycloalkyl-), H—O—$C_{1-6}$-alkyl-, $C_{1-6}$-alkyl-O—$C_{1-6}$-alkyl-, $C_{3-7}$-cycloalkyl-O—$C_{1-6}$-alkyl-, $C_{3-7}$-cycloalkyl-$C_{1-3}$-alkyl-O—$C_{1-6}$-alkyl-, phenyl-O—$C_{1-6}$-alkyl-, benzyl-O—$C_{1-6}$-alkyl-, H—O—, $C_{1-6}$-alkyl-O—, $C_{3-7}$-cycloalkyl-O—, $C_{3-7}$-cycloalkyl-$C_{1-3}$-alkyl-O—, phenyl-O—, benzyl-O—, N-morpholinyl, and NC—, preferably by a substituent selected from the group of fluorine, chlorine, bromine, $C_{1-6}$-alkyl-, $F_3C$—, $F_3C$—$CH_2$—, $F_3C$—O—, $HF_2C$—O—, $C_{3-7}$-heterocycloalkyl- (thereof preferably $C_{3-5}$-heterocycloalkyl-), $C_{1-6}$-alkyl-O—, $C_{3-6}$-cycloalkyl-O—, $C_{3-6}$-cycloalkyl-$CH_2$—O—, aryl-$CH_2$—O— and NC—,
wherein more preferably W and V independently of each other optionally may be substituted by one or more substituents selected from the group of fluorine, chlorine, $H_3C$—, $F_3C$—, $CH_3O$—, N-morpholinyl, and NC—, more preferably selected from the group of fluorine, $H_3C$—, $F_3C$—, $CH_3O$— and NC—;

$R^{1.5}$:
$R^1$ being the group

V—W—* wherein
W is phenyl or pyridyl,
V is phenyl or heteroaryl, the heteroaryl being selected from the group of oxadiazolyl, triazolyl, pyrazolyl, pyrrolyl, furanyl, pyridyl, pyrimidyl and pyridazinyl, V preferably is attached at the 2 position of W, whereby the 1 position of W is the attachment point of W to the $CR^2R^3$ group in formula (I);
—* is the binding point by which W is attached to the $CR^2R^3$ group in formula (I);
wherein W optionally may be substituted by one or more substituents selected from the group of fluorine, chlorine, bromine, $H_3C$—, $F_3C$—, $CH_3O$— and NC—, preferably selected from the group of fluorine, chlorine and $F_3C$—;
and wherein V optionally may be substituted by one or more substituents selected from the group of fluorine, chlorine, $H_3C$—, tert-butyl-, $F_3C$—, $CH_3O$—, cyclobutyloxy-, N-morpholinyl, benzyl-O— and NC—.

$R^{1.6}$:
$R^1$ being the group

V–W–* wherein
W is phenyl whereby W optionally is substituted by a fluorine, chlorine or $F_3C$—;
V is heteroaryl being selected from the group of oxadiazolyl, triazolyl, pyrazolyl, pyrrolyl, furanyl, pyridyl, pyrimidyl and pyridazinyl, whereby
V optionally is substituted by 1 to 4, preferably 1 or 2, more preferably 1 substituent independently of each other selected from the group of fluorine, chlorine, $H_3C$—, tert-butyl-, $F_3C$—, $CH_3O$—, cyclobutyloxy-, N-morpholinyl, benzyl-O— and NC—,
V is attached at the 2 position of W, whereby the 1 position of W is the attachment point of W to the $CR^2R^3$ group in formula (I);
—* is the binding point by which W is attached to the $CR^2R^3$ group in formula (I)

For each definition of $R^1$ (i.e. $R^{1.1}$, $R^{1.2}$, $R^{1.3}$, $R^{1.4}$, $R^{1.5}$, $R^{1.6}$):
whenever V may be oxadiazolyl, the preferred isomer is 1,2,4-oxadiazol-3-yl;
whenever V may be triazolyl, the preferred isomer is 1,2,4-trizaol-1-yl;
whenever V may be pyrazolyl, it is preferably pyrazol-1-yl or pyrazol-4-yl;
whenever V may be furanyl, it is preferably furan-2-yl;
whenever V may be pyridyl, preferably it may be 2-, 3- or 4-pyridyl, more preferably pyridin-2-yl;
whenever V may be pyrimidinyl, preferably it may be 5-pyrimidinyl;
whenever V may be pyridazinyl, preferably it may be 3- or 4-pyridazinyl.

$R^2$:
$R^2$ being selected from the group of H—, fluorine, $F_3C$—, $HF_2C$—, $FH_2C$—, and $C_{1-3}$-alkyl-, preferably $R^2$ being H.

$R^3$:
$R^3$ being selected from the group of H—, fluorine, $F_3C$—, $HF_2C$—, $FH_2C$—, and $C_{1-3}$-alkyl-, preferably $R^3$ being H.

Potential isoforms, tautomers, stereoisomers, solvates, hydrates, and/or the addition salts of any compound according to the invention, particularly the physiologically acceptable salts thereof with inorganic or organic acids or bases, or the combinations thereof are subject of the present invention as well.

Individual generic (genius) embodiments of compounds according to formula (I) are defined by the group of $Hc^i$, $R^{1.j}$ and $R^2$ and $R^3$ as described above. So given the above definitions, preferred individual compound embodiments of the invention are fully characterised by the term ($Hc^i$, $R^{1.j}$) if $R^2$ and $R^3$ are as defined above and if for each letter i and j an individual figure is given. Indices vary independently from each other.

The following matrix table (Table 1) shows, exemplary and in the order of increasing preference from the first line to the last line, such embodiments E-1 to E-24 of the invention that are considered preferred. This means that embodiment E-24, represented by the entries in the last row of table 1 is the most preferred embodiment:

TABLE 1

Preferred generic (genius) embodiments E-1 to E-24 of the invention:
Compounds of the present invention are characterised by general formula (I):

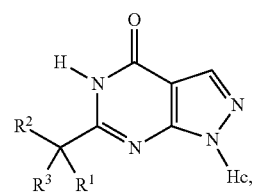

(I)

| | Hc | $R^1$ | with $R^2$ | $R^3$ |
|---|---|---|---|---|
| E-1 | $Hc^1$ | $R^{1.1}$ | defined by footnote[1] | defined by footnote[2] |
| E-2 | $Hc^1$ | $R^{1.2}$ | defined by footnote[1] | defined by footnote[2] |
| E-3 | $Hc^1$ | $R^{1.3}$ | defined by footnote[1] | defined by footnote[2] |
| E-4 | $Hc^1$ | $R^{1.4}$ | defined by footnote[1] | defined by footnote[2] |
| E-5 | $Hc^1$ | $R^{1.5}$ | defined by footnote[1] | defined by footnote[2] |
| E-6 | $Hc^1$ | $R^{1.6}$ | defined by footnote[1] | defined by footnote[2] |
| E-7 | $Hc^1$ | $R^{1.5}$ | being H | being H |
| E-8 | $Hc^1$ | $R^{1.6}$ | being H | being H |
| E-9 | $Hc^2$ | $R^{1.1}$ | defined by footnote[1] | defined by footnote[2] |
| E-10 | $Hc^2$ | $R^{1.2}$ | defined by footnote[1] | defined by footnote[2] |
| E-11 | $Hc^2$ | $R^{1.3}$ | defined by footnote[1] | defined by footnote[2] |
| E-12 | $Hc^2$ | $R^{1.4}$ | defined by footnote[1] | defined by footnote[2] |
| E-13 | $Hc^2$ | $R^{1.5}$ | defined by footnote[1] | defined by footnote[2] |
| E-14 | $Hc^2$ | $R^{1.6}$ | defined by footnote[1] | defined by footnote[2] |

TABLE 1-continued

Preferred generic (genius) embodiments E-1 to E-24 of the invention:
Compounds of the present invention are characterised by general formula (I):

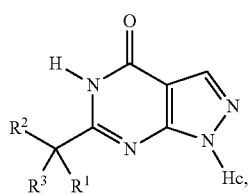

(I)

| Hc | R$^1$ | with R$^2$ | R$^3$ |
|---|---|---|---|
| E-15 | Hc$^2$ | R$^{1.5}$ | being H | being H |
| E-16 | Hc$^2$ | R$^{1.6}$ | being H | being H |
| E-17 | Hc$^3$ | R$^{1.1}$ | defined by footnote[1] | defined by footnote[2] |
| E-18 | Hc$^3$ | R$^{1.2}$ | defined by footnote[1] | defined by footnote[2] |
| E-19 | Hc$^3$ | R$^{1.3}$ | defined by footnote[1] | defined by footnote[2] |
| E-20 | Hc$^3$ | R$^{1.4}$ | defined by footnote[1] | defined by footnote[2] |
| E-21 | Hc$^3$ | R$^{1.5}$ | defined by footnote[1] | defined by footnote[2] |
| E-22 | Hc$^3$ | R$^{1.6}$ | defined by footnote[1] | defined by footnote[2] |
| E-23 | Hc$^3$ | R$^{1.5}$ | being H | being H |
| E-24 | Hc$^3$ | R$^{1.6}$ | being H | being H |

Footnotes:
[1] the definition refers to: R$^2$ being selected from the group of H—, fluorine, F$_3$C—, HF$_2$C—, FH$_2$C—, and C$_{1-3}$-alkyl-, preferably R$^2$ being H.
[2] the definition refers to: R$^3$ being selected from the group of H—, fluorine, F$_3$C—, HF$_2$C—, FH$_2$C—, and C$_{1-3}$-alkyl-, preferably R$^3$ being H.

In all these embodiments of table 1 it is preferred that each of R$^2$ and R$^3$ is H.

Where appropriate, the subject matter of the invention also refers to the isoforms, tautomers, stereoisomers, solvates, hydrates, and the salts of any compound, particularly the physiologically acceptable salts thereof with suited inorganic or organic acids or bases, or the combinations thereof.

One such embodiment according to the invention concerns a compound according to general formula (I)

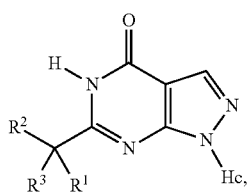

(I)

with
Hc being tetrahydropyranyl-, preferably 4-tetrahydropyranyl,
whereby one or more carbon ring atom(s) thereof optionally may be substituted by one or—where appropriate—by two substituents independently selected from the group of fluorine, NC—, F$_3$C—, HF$_2$C—, FH$_2$C—, F$_3$C—CH$_2$—, C$_{1-6}$-alkyl-, C$_{1-6}$-alkyl-O— and up to one carbon ring atom may be substituted with oxo;
R$^1$ being the group

V—W—*, wherein
W is selected from the group of phenyl or heteroaryl;
V is selected from the group of phenyl or heteroaryl;
V preferably is attached at the 2 position of W, whereby the 1 position of W is the attachment point of W to the CR$^2$R$^3$ group in formula (I);
—* is the binding point by which W is attached to the CR$^2$R$^3$ group in formula (I);
wherein W and V independently of each other optionally may be substituted by one or more substituents selected from the group of fluorine, chlorine, bromine, C$_{1-6}$-alkyl-, F$_3$O—, HF$_2$C—, FH$_2$C—, F$_3$C—CH$_2$—, F$_3$C—O—, HF$_2$C—O—, C$_{3-7}$-heterocycloalkyl- (thereof preferably C$_{3-5}$-heterocycloalkyl), H—O—C$_{1-6}$-alkyl-, C$_{1-6}$-alkyl-O—C$_{1-6}$-alkyl-, C$_{3-7}$-cycloalkyl-O—C$_{1-6}$-alkyl-, C$_{3-7}$-cycloalkyl-C$_{1-3}$-alkyl-O—C$_{1-6}$-alkyl-, phenyl-O—C$_{1-6}$-alkyl-, benzyl-O—C$_{1-6}$-alkyl-, H—O—, C$_{1-6}$-alkyl-O—, C$_{3-7}$-cycloalkyl-O—, C$_{3-7}$-cycloalkyl-C$_{1-3}$-alkyl-O—, phenyl-O—, benzyl-O—, N-morpholinyl, and NC—, preferably by a substituent selected from the group of fluorine, chlorine, bromine, C$_{1-6}$-alkyl-, F$_3$C—, F$_3$C—CH$_2$—, F$_3$C—O—, HF$_2$C—O—, C$_{3-7}$-heterocycloalkyl- (thereof preferably C$_{3-5}$-heterocycloalkyl-), C$_{1-6}$-alkyl-O—, C$_{3-6}$-cycloalkyl-O—, C$_{3-6}$-cycloalkyl-CH$_2$—O—, aryl-CH$_2$—O— and NC—;
R$^2$ being selected from the group of H—, fluorine, F$_3$C—, HF$_2$C—, FH$_2$C—, and C$_{1-3}$-alkyl-, preferably R$^2$ being H;
R$^3$ being selected from the group of H—, fluorine, F$_3$C—, HF$_2$C—, FH$_2$C—, and C$_{1-3}$-alkyl-, preferably R$^3$ being H;
and the salts thereof, preferably pharmaceutically acceptable salts thereof.

In another embodiment the compounds of the invention are compounds according to general formula (I), with
Hc being tetrahydropyranyl-, preferably 4-tetrahydropyranyl,
whereby one or more carbon ring atom(s) thereof optionally may be substituted by one or—where appropriate—by one or two substituents independently selected from the group of fluorine, NC—, F$_3$C—, HF$_2$C—, FH$_2$C—, F$_3$C—CH$_2$—, C$_{1-6}$-alkyl-, C$_{1-6}$-alkyl-O— and up to one carbon ring atom may be substituted with oxo;
R$^1$ being the group

V—W—*, wherein

W is selected from the group of phenyl or a heteroaryl, the heteroaryl being selected from the group of oxadiazolyl, triazolyl, pyrazolyl, furanyl, pyridyl, pyrimidyl and pyridazinyl, V is selected from the group of phenyl or heteroaryl, the heteroaryl being selected from the group of oxadiazolyl, triazolyl, pyrazolyl, pyrrolyl, furanyl, pyridyl, pyrimidyl and pyridazinyl, V preferably is attached at the 2 position of W, whereby the 1 position of W is the attachment point of W to the $CR^2R^3$ group in formula (I);

wherein W and V independently of each other optionally may be substituted by one or more substituents selected from the group of fluorine, chlorine, bromine, $C_{1-6}$-alkyl-, $F_3C$—, $HF_2C$—, $FH_2C$—, $F_3C$—$CH_2$—, $F_3C$—O—, $HF_2C$—O—, $C_{3-7}$-heterocycloalkyl- (thereof preferably $C_{3-5}$-heterocycloalkyl-), H—O—$C_{1-6}$-alkyl-, $C_{1-6}$-alkyl-O—$C_{1-6}$-alkyl-, $C_{3-7}$-cycloalkyl-O—$C_{1-6}$-alkyl-, $C_{3-7}$-cycloalkyl-$C_{1-3}$-alkyl-O—$C_{1-6}$-alkyl-, phenyl-O—$C_{1-6}$-alkyl-, benzyl-O—$C_{1-6}$-alkyl-, H—O—, $C_{1-6}$-alkyl-O—, $C_{3-7}$-cycloalkyl-O—, $C_{3-7}$-cycloalkyl-$C_{1-3}$-alkyl-O—, phenyl-O—, benzyl-O—, N-morpholinyl, and NC—, preferably by a substituent selected from the group of fluorine, chlorine, bromine, $C_{1-6}$-alkyl-, $F_3C$—, $F_3C$—$CH_2$—, $F_3C$—O—, $HF_2C$—O—, $C_{3-7}$-heterocycloalkyl- (thereof preferably $C_{3-5}$-heterocycloalkyl-), $C_{1-6}$-alkyl-O—, $C_{3-6}$-cycloalkyl-O—, $C_{3-6}$-cycloalkyl-$CH_2$—O—, aryl-$CH_2$—O— and NC—;

$R^2$ being selected from the group of H—, fluorine, $F_3C$—, $HF_2C$—, $FH_2C$—, and $C_{1-3}$-alkyl-, preferably $R^2$ being H;

$R^3$ being selected from the group of H—, fluorine, $F_3C$—, $HF_2C$—, $FH_2C$—, and $C_{1-3}$-alkyl-, preferably $R^3$ being H;

and the salts thereof, preferably pharmaceutically acceptable salts thereof.

In another embodiment the compounds of the invention are compounds according to general formula (I), with Hc being tetrahydropyranyl-, whereby one or more carbon ring atom(s) thereof optionally may be substituted by one or—where appropriate—by one or two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo;

$R^1$ being the group

V–W–*, wherein

W is selected from the group of phenyl or a heteroaryl, the heteroaryl being selected from the group of pyridyl, pyrimidyl and pyridazinyl, V is selected from the group of phenyl or heteroaryl, the heteroaryl being selected from the group of oxadiazolyl, triazolyl, pyrazolyl, pyrrolyl, furanyl, pyridyl, pyrimidyl and pyridazinyl, V preferably is attached at the 2 position of W, whereby the 1 position of W is the attachment point of W to the $CR^2R^3$ group in formula (I);

wherein W and V independently of each other optionally may be substituted by one or more substituents selected from the group of fluorine, chlorine, bromine, $C_{1-6}$-alkyl-, $F_3C$—, $HF_2C$—, $FH_2C$—, $F_3C$—$CH_2$—, $F_3C$—O—, $HF_2C$—O—, $C_{3-7}$-heterocycloalkyl- (thereof preferably $C_{3-5}$-heterocycloalkyl-), H—O—$C_{1-6}$-alkyl-, $C_{1-6}$-alkyl-O—$C_{1-6}$-alkyl-, $C_{3-7}$-cycloalkyl-O—$C_{1-6}$-alkyl-, $C_{3-7}$-cycloalkyl-$C_{1-3}$-alkyl-O—$C_{1-6}$-alkyl-, phenyl-O—$C_{1-6}$-alkyl-, benzyl-O—$C_{1-6}$-alkyl-, H—O—, $C_{1-6}$-alkyl-O—, $C_{3-7}$-cycloalkyl-O—, $C_{3-7}$-cycloalkyl-$C_{1-3}$-alkyl-O—, phenyl-O—, benzyl-O—, N-morpholinyl, and NC—, preferably by a substituent selected from the group of fluorine, chlorine, bromine, $C_{1-6}$-alkyl-, $F_3C$—, $F_3C$—$CH_2$—, $F_3C$—O—, $HF_2C$—O—, $C_{3-7}$-heterocycloalkyl- (thereof preferably $C_{3-5}$-heterocycloalkyl-), $C_{1-6}$-alkyl-O—, $C_{3-6}$-cycloalkyl-O—, $C_{3-6}$-cycloalkyl-$CH_2$—O—, aryl-$CH_2$—O— and NC—;

$R^2$ being selected from the group of H—, fluorine, $F_3C$—, $HF_2C$—, $FH_2C$—, and $C_{1-3}$-alkyl-, preferably $R^2$ being H;

$R^3$ being selected from the group of H—, fluorine, $F_3C$—, $HF_2C$—, $FH_2C$—, and $C_{1-3}$-alkyl-, preferably $R^3$ being H;

and the salts thereof, preferably pharmaceutically acceptable salts thereof.

In another embodiment the compounds of the invention are compounds according to general formula (I), with Hc being tetrahydropyranyl-, whereby one or more carbon ring atom(s) thereof optionally may be substituted by one or—where appropriate—by one or two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo;

$R^1$ being the group

V–W–*, wherein

W is selected from the group of phenyl or pyridinyl,

V is selected from the group of phenyl or heteroaryl, the heteroaryl being selected from the group of oxadiazolyl, triazolyl, pyrazolyl, furanyl, pyridyl, pyrimidyl and pyridazinyl, V preferably is attached at the 2 position of W, whereby the 1 position of W is the attachment point of W to the $CR^2R^3$ group in formula (I);

wherein W and V independently of each other optionally may be substituted by one or more substituents selected from the group of fluorine, chlorine, bromine, $C_{1-6}$-alkyl-, $F_3C$—, $HF_2C$—, $FH_2C$—, $F_3C$—$CH_2$—, $F_3C$—O—, $HF_2C$—O—, $C_{3-7}$-heterocycloalkyl- (thereof preferably $C_{3-5}$-heterocycloalkyl-), H—O—$C_{1-6}$-alkyl-, $C_{1-6}$-alkyl-O—$C_{1-6}$-alkyl-, $C_{3-7}$-cycloalkyl-O—$C_{1-6}$-alkyl-, $C_{3-7}$-cycloalkyl-$C_{1-3}$-alkyl-O—$C_{1-6}$-alkyl-, phenyl-O—$C_{1-6}$-alkyl-, benzyl-O—$C_{1-6}$-alkyl-, H—O—, $C_{1-6}$-alkyl-O—, $C_{3-7}$-cycloalkyl-O—, $C_{3-7}$-cycloalkyl-$C_{1-3}$-alkyl-O—, phenyl-O—, benzyl-O—, N-morpholinyl, and NC—, preferably by a substituent selected from the group of fluorine, chlorine, bromine, $C_{1-6}$-alkyl-, $F_3C$—, $F_3C$—$CH_2$—, $F_3C$—O—, $HF_2C$—O—, $C_{3-7}$-heterocycloalkyl- (thereof preferably $C_{3-5}$-heterocycloalkyl-), $C_{1-6}$-alkyl-O—, $C_{3-6}$-cycloalkyl-O—, $C_{3-6}$-cycloalkyl-$CH_2$—O—, aryl-$CH_2$—O— and NC—;

wherein preferably W and V independently of each other optionally may be substituted by one or more substituents selected from the group of fluorine, chlorine, $H_3C$—, $F_3C$—, $CH_3O$—, N-morpholinyl, and NC—, preferably selected from the group of fluorine, $H_3C$—, $F_3C$—, $CH_3O$— and NC—;

$R^2$ being selected from the group of H—, fluorine, $F_3C$—, $HF_2C$—, $FH_2C$—, and $C_{1-3}$-alkyl-, preferably $R^2$ being H;

$R^3$ being selected from the group of H—, fluorine, $F_3C$—, $HF_2C$—, $FH_2C$—, and $C_{1-3}$-alkyl-, preferably $R^3$ being H;

and the salts thereof, preferably pharmaceutically acceptable salts thereof.

In another embodiment the compounds of the invention are compounds according to general formula (I), with Hc being tetrahydropyranyl-, whereby one or more carbon ring atom(s) thereof optionally may be substituted by one or—where appropriate—by one or two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo;

$R^1$ being the group

V—W—*, wherein

W is selected from the group of phenyl or pyridyl,
V is selected from the group of phenyl or heteroaryl, the heteroaryl being selected from the group of oxadiazolyl, triazolyl, pyrazolyl, pyrrolyl, furanyl, pyridyl, pyrimidyl and pyridazinyl,
V preferably is attached at the 2 position of W, whereby the 1 position of W is the attachment point of W to the $CR^2R^3$ group in formula (I);
wherein W optionally may be substituted by one or more substituents selected from the group of fluorine, chlorine, bromine, $H_3C$—, $F_3C$—, $CH_3O$— and NC—, preferably selected from the group of fluorine, chlorine and $F_3C$—;
and wherein V optionally may be substituted by one or more substituents selected from the group of fluorine, chlorine, $H_3C$—, tert-butyl-, $F_3C$—, $CH_3O$—, cyclobutyloxy-, N-morpholinyl, benzyl-O— and NC—;
$R^2$ being selected from the group of H—, fluorine, $F_3C$—, $HF_2C$—, $FH_2C$—, and $C_{1-3}$-alkyl-, preferably $R^2$ being H;
$R^3$ being selected from the group of H—, fluorine, $F_3C$—, $HF_2C$—, $FH_2C$—, and $C_{1-3}$-alkyl-, preferably $R^3$ being H;
and the salts thereof, preferably pharmaceutically acceptable salts thereof.

In another embodiment the compounds of the invention are compounds according to general formula (I), with
Hc being tetrahydropyranyl-,
whereby one or more carbon ring atom(s) thereof optionally may be substituted by one or—where appropriate—by one or two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo;
$R^1$ being the group

V—W—*, wherein
W is phenyl whereby W optionally is substituted by a fluorine, chlorine or $F_3C$—;
V is heteroaryl being selected from the group of oxadiazolyl, triazolyl, pyrazolyl, pyrrolyl, furanyl, pyridyl, pyrimidyl and pyridazinyl, whereby
V optionally is substituted by 1 to 4, preferably 1 or 2, more preferably 1 substituent independently of each other selected from the group of fluorine, chlorine, $H_3C$—, tert-butyl-, $F_3C$—, $CH_3O$—, cyclobutyloxy-, N-morpholinyl, benzyl-O— and NC—,
V is attached at the 2 position of W, whereby the 1 position of W is the attachment point of W to the $CR^2R^3$ group in formula (I);
$R^2$ being selected from the group of H—, fluorine, $F_3C$—, $HF_2C$—, $FH_2C$—, and $C_{1-3}$-alkyl-, preferably $R^2$ being H;
$R^3$ being selected from the group of H—, fluorine, $F_3C$—, $HF_2C$—, $FH_2C$—, and $C_{1-3}$-alkyl-, preferably $R^3$ being H;
and the salts thereof, preferably pharmaceutically acceptable salts thereof.

In another embodiment the compounds of the invention are compounds according to general formula (I), with
Hc being 4-tetrahydropyranyl-,
whereby each carbon ring atom thereof optionally may be substituted by one or—where appropriate—by one or two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo,
preferably Hc being unsubstituted 4-tetrahydropyranyl-;
$R^1$ being the group

V—W—*, wherein
W is selected from the group of phenyl or pyridinyl,
V is selected from the group of phenyl or heteroaryl, the heteroaryl being selected from the group of oxadiazolyl, triazolyl, pyrazolyl, furanyl, pyridyl, pyrimidyl and pyridazinyl,
V preferably is attached at the 2 position of W, whereby the 1 position of W is the attachment point of W to the $CR^2R^3$ group in formula (I);
wherein W and V independently of each other optionally may be substituted by one or more substituents selected from the group of fluorine, chlorine, bromine, $C_{1-6}$-alkyl-, $F_3C$—, $HF_2C$—, $FH_2C$—, $F_3C$—$CH_2$—, $F_3C$—O—, $HF_2C$—O—, $C_{3-7}$-heterocycloalkyl- (thereof preferably $C_{3-5}$-heterocycloalkyl-), H—O—$C_{1-6}$-alkyl-, $C_{1-6}$-alkyl-O—$C_{1-6}$-alkyl-, $C_{3-7}$-cycloalkyl-O—$C_{1-6}$-alkyl-, $C_{3-7}$-cycloalkyl-$C_{1-3}$-alkyl-O—$C_{1-6}$-alkyl-, phenyl-O—$C_{1-6}$-alkyl-, benzyl-O—$C_{1-6}$-alkyl-, H—O—, $C_{1-6}$-alkyl-O—, $C_{3-7}$-cycloalkyl-O—, $C_{3-7}$-cycloalkyl-$C_{1-3}$-alkyl-O—, phenyl-O—, benzyl-O—, N-morpholinyl, and NC—, preferably by a substituent selected from the group of fluorine, chlorine, bromine, $C_{1-6}$-alkyl-, $F_3C$—, $F_3C$—$CH_2$—, $F_3C$—O—, $HF_2C$—O—, $C_{3-7}$-heterocycloalkyl- (thereof preferably $C_{3-5}$-heterocycloalkyl-), $C_{1-6}$-alkyl-O—, $C_{3-6}$-cycloalkyl-O—, $C_{3-6}$-cycloalkyl-$CH_2$—O—, aryl-$CH_2$—O— and NC—,
wherein more preferably W and V independently of each other optionally may be substituted by one or more substituents selected from the group of fluorine, chlorine, $H_3C$—, $F_3C$—, $CH_3O$—, N-morpholinyl, and NC—, more preferably selected from the group of fluorine, $H_3C$—, $F_3C$—, $CH_3O$— and NC—;
$R^2$ being selected from the group of H—, fluorine, $F_3C$—, $HF_2C$—, $FH_2C$—, and $C_{1-3}$-alkyl-, preferably $R^2$ being H;
$R^3$ being selected from the group of H—, fluorine, $F_3C$—, $HF_2C$—, $FH_2C$—, and $C_{1-3}$-alkyl-, preferably $R^3$ being H;
and the salts thereof, preferably pharmaceutically acceptable salts thereof.

In another embodiment the compounds of the invention are compounds according to general formula (I), with
Hc being 4-tetrahydropyranyl-,
whereby each carbon ring atom thereof optionally may be substituted by one or—where appropriate—by one or two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo,
preferably Hc being unsubstituted 4-tetrahydropyranyl-;
$R^1$ being the group

V—W—*,

W is selected from the group of phenyl or pyridyl,
V is selected from the group of phenyl or heteroaryl, the heteroaryl being selected from the group of oxadiazolyl, triazolyl, pyrazolyl, pyrrolyl, furanyl, pyridyl, pyrimidyl and pyridazinyl,
V preferably is attached at the 2 position of W, whereby the 1 position of W is the attachment point of W to the $CR^2R^3$ group in formula (I);
wherein W optionally may be substituted by one or more substituents selected from the group of fluorine, chlorine, bromine, $H_3C$—, $F_3C$—, $CH_3O$— and NC—, preferably selected from the group of fluorine, chlorine and $F_3C$—;
and wherein V optionally may be substituted by one or more substituents selected from the group of fluorine, chlorine, $H_3C$—, tert-butyl-, $F_3C$—, $CH_3O$—, cyclobutyloxy-, N-morpholinyl, benzyl-O— and NC—;

R² being selected from the group of H—, fluorine, F₃C—, HF₂C—, FH₂C—, and C₁₋₃-alkyl-, preferably R² being H;
R³ being selected from the group of H—, fluorine, F₃C—, HF₂C—, FH₂C—, and C₁₋₃-alkyl-, preferably R³ being H;
and the salts thereof, preferably pharmaceutically acceptable salts thereof.

In another embodiment the compounds of the invention are compounds according to general formula (I), with
Hc being 4-tetrahydropyranyl-,
whereby each carbon ring atom thereof optionally may be substituted by one or—where appropriate—by one or two substituents independently selected from the group of fluorine, NC—, F₃C—, HF₂C—, FH₂C—, F₃C—CH₂—, C₁₋₆-alkyl-, C₁₋₆-alkyl-O— and up to one carbon ring atom may be substituted with oxo,
preferably Hc being unsubstituted 4-tetrahydropyranyl-;
R¹ being the group

V-W-*, wherein
W is phenyl whereby W optionally is substituted by a fluorine, chlorine or F₃C—;
V is heteroaryl being selected from the group of oxadiazolyl, triazolyl, pyrazolyl, pyrrolyl, furanyl, pyridyl, pyrimidyl and pyridazinyl, whereby
V optionally is substituted by 1 to 4, preferably 1 or 2, more preferably 1 substituent independently of each other selected from the group of fluorine, chlorine, H₃C—, tert-butyl-, F₃C—, CH₃O—, cyclobutyloxy-, N-morpholinyl, benzyl-O— and NC—,
V is attached at the 2 position of W, whereby the 1 position of W is the attachment point of W to the CR²R³ group in formula (I);
R² being selected from the group of H—, fluorine, F₃C—, HF₂C—, FH₂C—, and C₁₋₃-alkyl-, preferably R² being H;
R³ being selected from the group of H—, fluorine, F₃C—, HF₂C—, FH₂C—, and C₁₋₃-alkyl-, preferably R³ being H;
and the salts thereof, preferably pharmaceutically acceptable salts thereof.

Specifically Preferred Compounds

Each of the compounds presented in the following table (Table 2) is specifically and individually preferred according to the invention. The listed compounds are described in detail in the section "Exemplary embodiments". The following list presents the specific compounds of the invention as "neutral" compounds, i.e. not in form of salts and the like. The example numbers correspond with the numbering according to the section "Exemplary embodiments". More specific information can be found in the section "Exemplary embodiments".

TABLE 2 preferred specific embodiments. The reference numbers correspond with the ones used in the experimental part. The first column refers to the example number/reference number respectively, the second column to the structure.

219

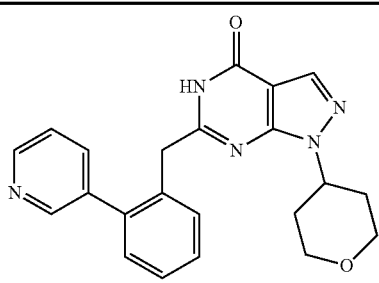

TABLE 2-continued preferred specific embodiments. The reference numbers correspond with the ones used in the experimental part. The first column refers to the example number/reference number respectively, the second column to the structure.

220

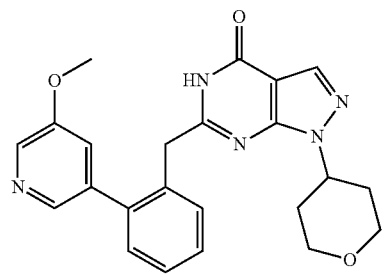 [SMILES: COc1cncc(-c2ccccc2Cc2nc3c(cnn3C3CCOCC3)c(=O)[nH]2)c1]

221

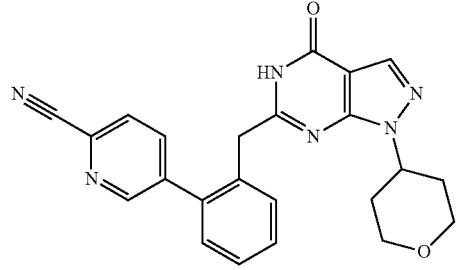 [SMILES: N#Cc1ccc(-c2ccccc2Cc2nc3c(cnn3C3CCOCC3)c(=O)[nH]2)cn1]

222

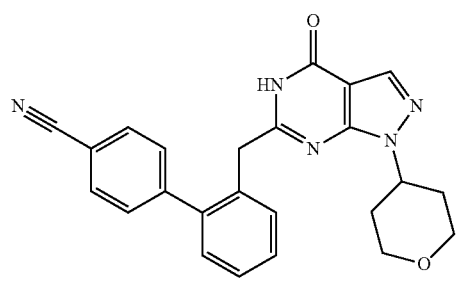 [SMILES: N#Cc1ccc(-c2ccccc2Cc2nc3c(cnn3C3CCOCC3)c(=O)[nH]2)cc1]

223

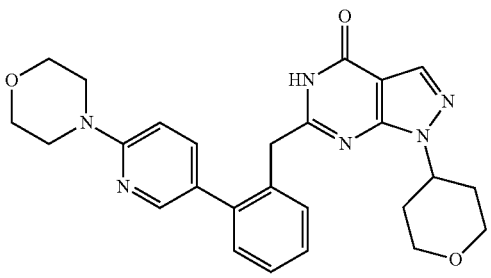 [SMILES: O=c1[nH]c(Cc2ccccc2-c2ccc(N3CCOCC3)nc2)nc2c1cnn2C1CCOCC1]

224

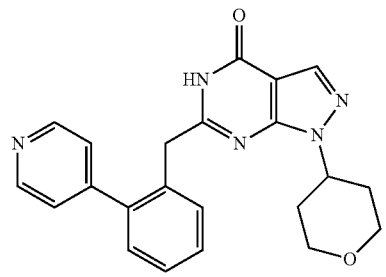 [SMILES: O=c1[nH]c(Cc2ccccc2-c2ccncc2)nc2c1cnn2C1CCOCC1]

TABLE 2-continued preferred specific embodiments. The reference numbers correspond with the ones used in the experimental part. The first column refers to the example number/reference number respectively, the second column to the structure.

225

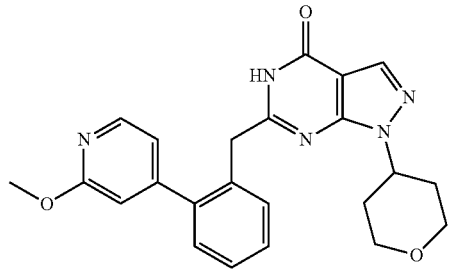 [SMILES: COc1cc(-c2ccccc2Cc2nc3c(cnn3C3CCOCC3)c(=O)[nH]2)ccn1]

226

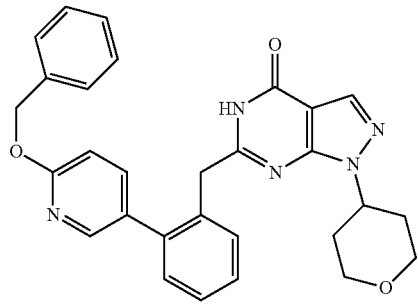 [SMILES: O=c1[nH]c(Cc2ccccc2-c2ccc(OCc3ccccc3)nc2)nc2c1cnn2C1CCOCC1]

227

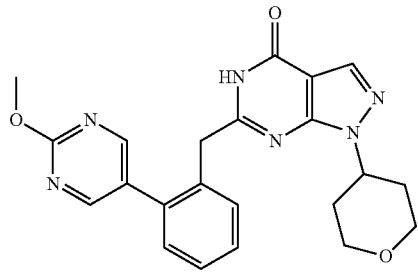 [SMILES: COc1ncc(-c2ccccc2Cc2nc3c(cnn3C3CCOCC3)c(=O)[nH]2)cn1]

228

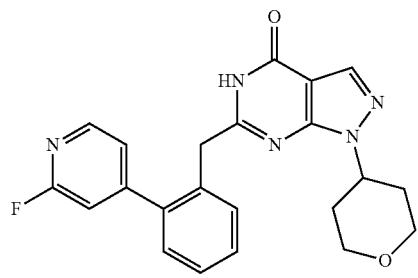 [SMILES: O=c1[nH]c(Cc2ccccc2-c2ccnc(F)c2)nc2c1cnn2C1CCOCC1]

229

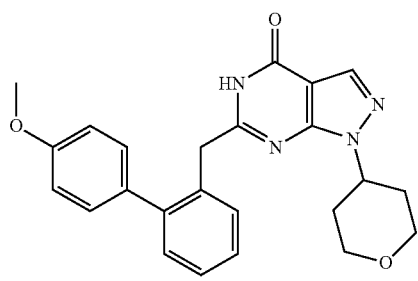 [SMILES: COc1ccc(-c2ccccc2Cc2nc3c(cnn3C3CCOCC3)c(=O)[nH]2)cc1]

TABLE 2-continued preferred specific embodiments. The reference numbers correspond with the ones used in the experimental part. The first column refers to the example number/reference number respectively, the second column to the structure.

230

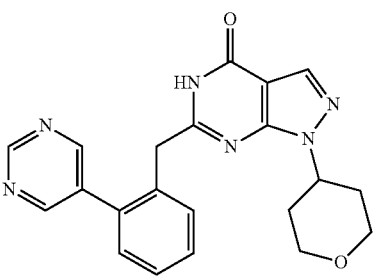 [SMILES: O=c1[nH]c(Cc2ccccc2-c2cncnc2)nc2c1cnn2C1CCOCC1]

230-1

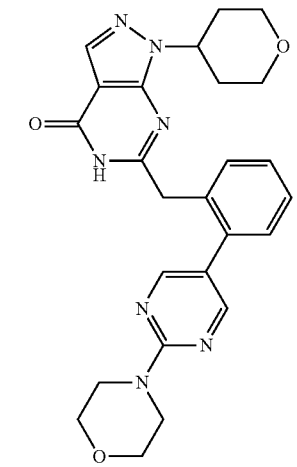 [SMILES: O=c1[nH]c(Cc2ccccc2-c2cnc(N3CCOCC3)nc2)nc2c1cnn2C1CCOCC1]

230-2

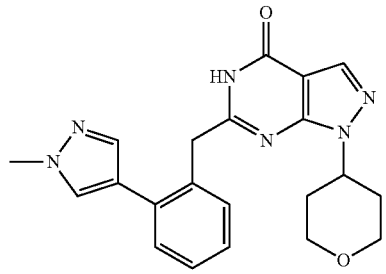 [SMILES: Cn1cc(-c2ccccc2Cc2nc3c(cnn3C3CCOCC3)c(=O)[nH]2)cn1]

230-3

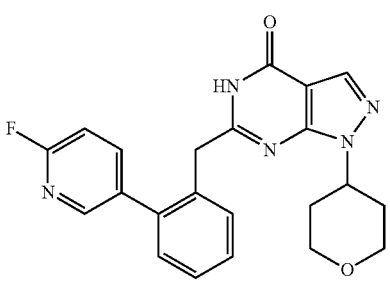 [SMILES: O=c1[nH]c(Cc2ccccc2-c2ccc(F)nc2)nc2c1cnn2C1CCOCC1]

TABLE 2-continued
preferred specific embodiments. The reference numbers correspond with the ones used in the experimental part. The first column refers to the example number/reference number respectively, the second column to the structure.
230-5 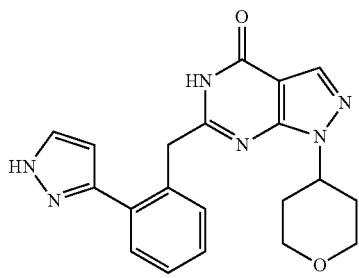 [SMILES: O=c1[nH]c(Cc2ccccc2-c2cc[nH]n2)nc2c1cnn2C1CCOCC1]
231 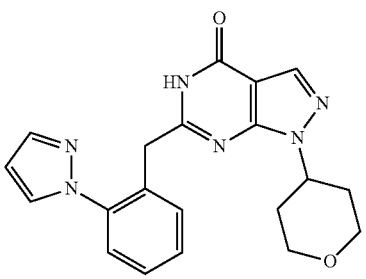 [SMILES: O=c1[nH]c(Cc2ccccc2-n2cccn2)nc2c1cnn2C1CCOCC1]
232 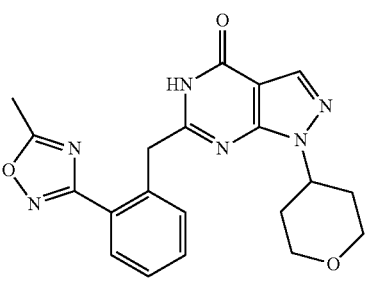 [SMILES: Cc1nc(-c2ccccc2Cc2nc3c(cnn3C3CCOCC3)c(=O)[nH]2)no1]
234 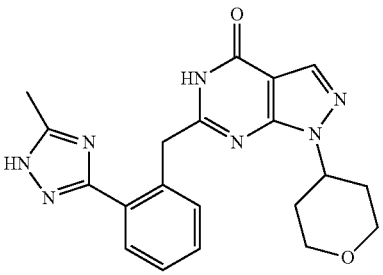 [SMILES: Cc1nc(-c2ccccc2Cc2nc3c(cnn3C3CCOCC3)c(=O)[nH]2)n[nH]1]
239 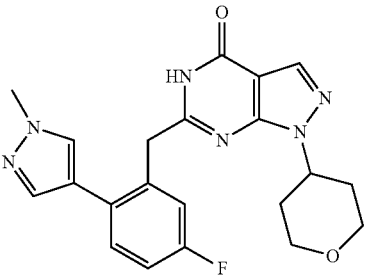 [SMILES: Cn1cc(-c2ccc(F)cc2Cc2nc3c(cnn3C3CCOCC3)c(=O)[nH]2)cn1]
240 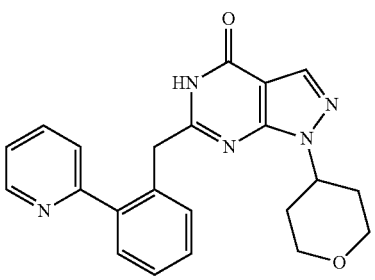 [SMILES: O=c1[nH]c(Cc2ccccc2-c2ccccn2)nc2c1cnn2C1CCOCC1]
241 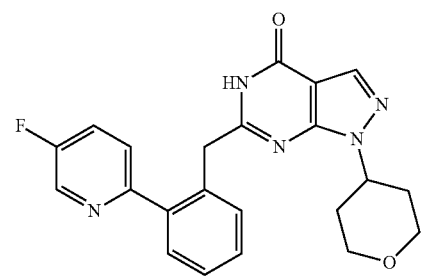 [SMILES: O=c1[nH]c(Cc2ccccc2-c2ccc(F)cn2)nc2c1cnn2C1CCOCC1]
242 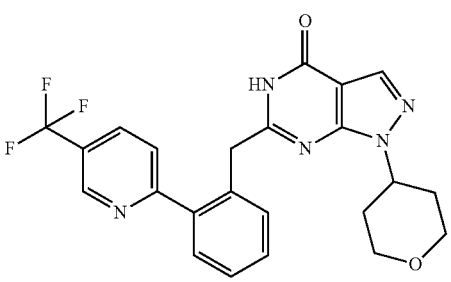 [SMILES: O=c1[nH]c(Cc2ccccc2-c2ccc(C(F)(F)F)cn2)nc2c1cnn2C1CCOCC1]
243 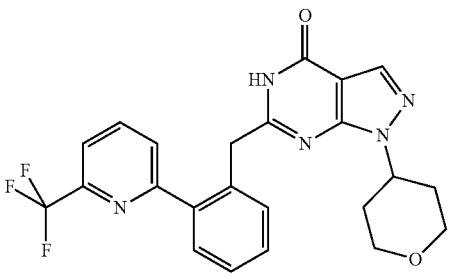 [SMILES: O=c1[nH]c(Cc2ccccc2-c2cccc(C(F)(F)F)n2)nc2c1cnn2C1CCOCC1]
244 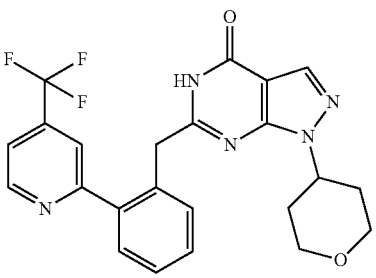 [SMILES: O=c1[nH]c(Cc2ccccc2-c2cc(C(F)(F)F)ccn2)nc2c1cnn2C1CCOCC1]

TABLE 2-continued preferred specific embodiments. The reference numbers correspond with the ones used in the experimental part. The first column refers to the example number/reference number respectively, the second column to the structure.

245
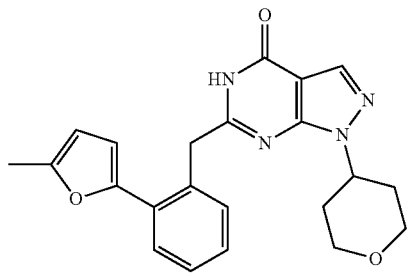 [SMILES: Cc1ccc(-c2ccccc2Cc2nc3c(cnn3C3CCOCC3)c(=O)[nH]2)o1]

246
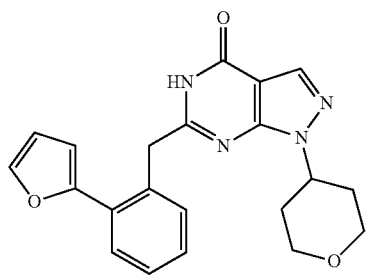 [SMILES: O=c1[nH]c(Cc2ccccc2-c2ccco2)nc2c1cnn2C1CCOCC1]

247
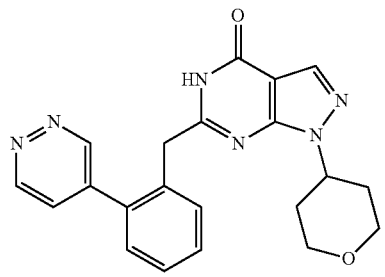

248
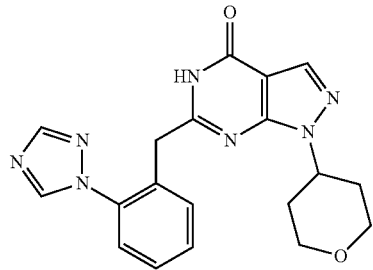 [SMILES: O=c1[nH]c(Cc2ccccc2-n2cncn2)nc2c1cnn2C1CCOCC1]

249
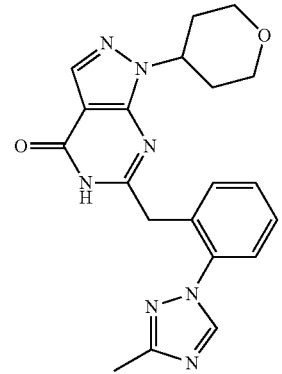 [SMILES: Cc1ncn(-c2ccccc2Cc2nc3c(cnn3C3CCOCC3)c(=O)[nH]2)n1]

TABLE 2-continued preferred specific embodiments. The reference numbers correspond with the ones used in the experimental part. The first column refers to the example number/reference number respectively, the second column to the structure.

250
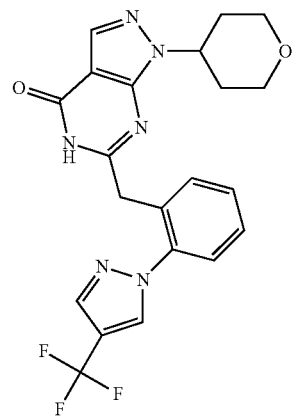 [SMILES: O=c1[nH]c(Cc2ccccc2-n2cc(C(F)(F)F)cn2)nc2c1cnn2C1CCOCC1]

251
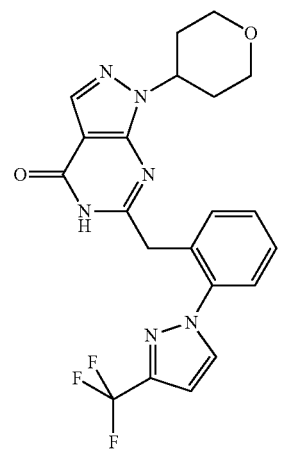 [SMILES: O=c1[nH]c(Cc2ccccc2-n2ccc(C(F)(F)F)n2)nc2c1cnn2C1CCOCC1]

252
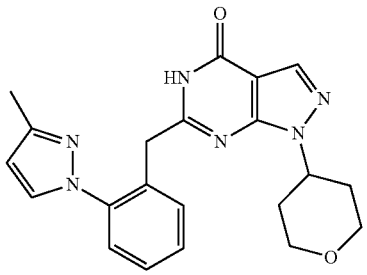 [SMILES: Cc1ccn(-c2ccccc2Cc2nc3c(cnn3C3CCOCC3)c(=O)[nH]2)n1]

253
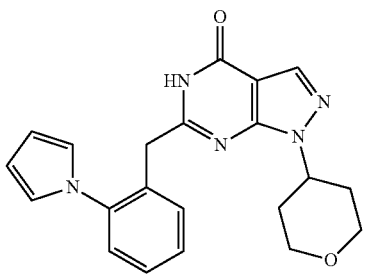 [SMILES: O=c1[nH]c(Cc2ccccc2-n2cccc2)nc2c1cnn2C1CCOCC1]

TABLE 2-continued preferred specific embodiments. The reference numbers correspond with the ones used in the experimental part. The first column refers to the example number/reference number respectively, the second column to the structure.

254
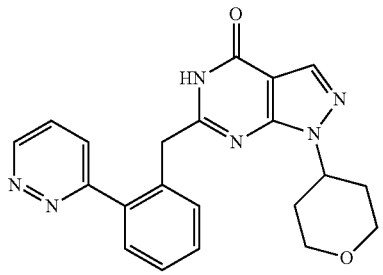 [SMILES: O=c1[nH]c(Cc2ccccc2-c2cccnn2)nc2c1cnn2C1CCOCC1]

255
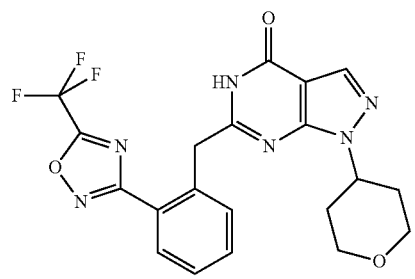 [SMILES: O=c1[nH]c(Cc2ccccc2-c2noc(C(F)(F)F)n2)nc2c1cnn2C1CCOCC1]

256
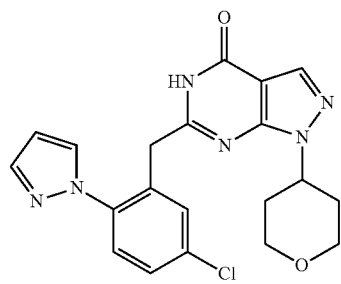 [SMILES: O=c1[nH]c(Cc2cc(Cl)ccc2-n2cccn2)nc2c1cnn2C1CCOCC1]

257
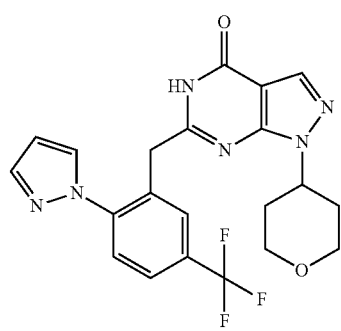 [SMILES: O=c1[nH]c(Cc2cc(C(F)(F)F)ccc2-n2cccn2)nc2c1cnn2C1CCOCC1]

258
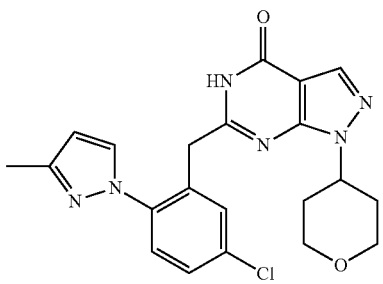 [SMILES: Cc1ccn(-c2ccc(Cl)cc2Cc2nc3c(cnn3C3CCOCC3)c(=O)[nH]2)n1]

TABLE 2-continued preferred specific embodiments. The reference numbers correspond with the ones used in the experimental part. The first column refers to the example number/reference number respectively, the second column to the structure.

259
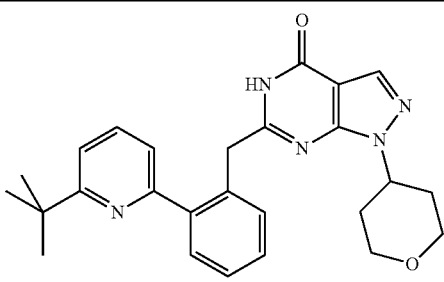

260
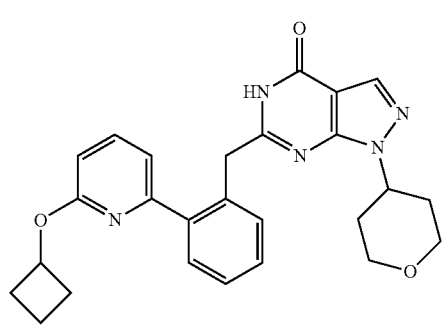 [SMILES: O=c1[nH]c(Cc2ccccc2-c2cccc(OC3CCC3)n2)nc2c1cnn2C1CCOCC1]

261
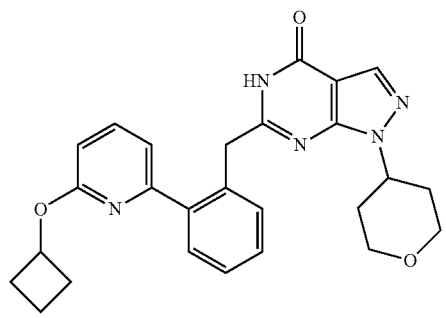

262
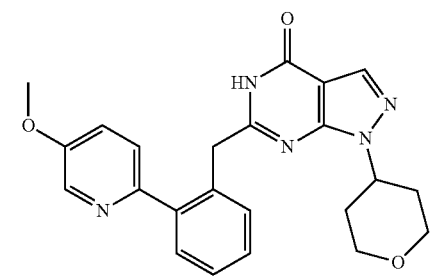 [SMILES: COc1ccc(-c2ccccc2Cc2nc3c(cnn3C3CCOCC3)c(=O)[nH]2)nc1]

263
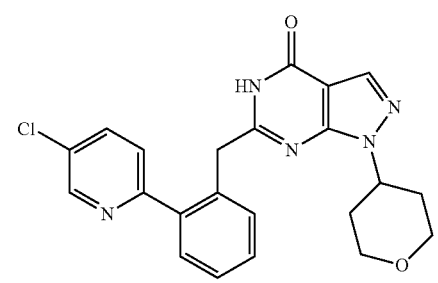 [SMILES: O=c1[nH]c(Cc2ccccc2-c2ccc(Cl)cn2)nc2c1cnn2C1CCOCC1]

The invention also concerns the compounds of table 2, in form of the isoforms, tautomers, solvates, hydrates, or the salts of any of the listed compounds, particularly the physiologically acceptable salts thereof with inorganic or organic acids or bases, or the combinations thereof.

The above table (Table 2) also further illustrates general formula (I) and how to read the generic (genius) embodiments E-1 to E-24 of Table 1 and E-25 to E-48 of Table 3: for example compound 261, 6-[2-(5-Methoxy-pyridin-2-yl)-benzyl]-1-(tetrahydro-pyran-4-yl)-1,5-dihydro-pyrazolo[3,4-d]pyrimidin-4-one, corresponds with general formula (I) in that Hc is tetrahydropyran-4-yl, V and W, which build $R^1$ (i.e. V–W–*), are defined as: W=phenyl, whereby said phenyl is attached via its 1 position to the $CR^2R^3$ group of formula (I); V=5-Methoxy-pyridin-2-yl, whereby V is attached at the 2 position of W (i.e. W has a 1, 2 substitution pattern/ortho substitution); and $R^2$ and $R^3$ being H.

FURTHER EMBODIMENTS OF THE INVENTION

Another embodiment of the invention concerns compounds according to general formula (I), whereby the compounds are selected from the group of compounds of Table 2 with the example reference numbers: 219; 220; 221; 222; 223; 224; 225; 226; 227; 228; 229; 230; 230-1; 230-2; 230-3; 231; 232; 234; and where appropriate an isoform, tautomer, stereoisomer, solvate, hydrate, or a salts of any of these compounds, in particular a physiologically acceptable salts thereof with inorganic or organic acids or bases, or the combinations thereof.

Another embodiment according to the invention concerns compounds according to general formula (I), whereby the compounds are selected from the group of compounds of Table 2 with the example reference numbers: 230-5; 239; 240; 241; 242; 243; 244; 245; 246; 247; 248; 249; 250; 251; 252; 253; 254; 255; 256; 257; 258; 259; 260; 261; 262; 263; and where appropriate an isoform, tautomer, stereoisomer, solvate, hydrate, or a salts of any of these compounds, in particular a physiologically acceptable salts thereof with inorganic or organic acids or bases, or the combinations thereof.

Another set of embodiment of the invention is defined by Table 3.

TABLE 3 a compound characterised by the general formula (I):

(I)

| | Hc | $R^1$ | with $R^2$ | $R^3$ |
|---|---|---|---|---|
| E-25 | $Hc^1$ | $R^{1.1}$ | defined by footnote[3] | defined by footnote[4] |
| E-26 | $Hc^1$ | $R^{1.2}$ | defined by footnote[3] | defined by footnote[4] |
| E-27 | $Hc^1$ | $R^{1.3}$ | defined by footnote[3] | defined by footnote[4] |
| E-28 | $Hc^1$ | $R^{1.4}$ | defined by footnote[3] | defined by footnote[4] |
| E-29 | $Hc^1$ | $R^{1.5}$ | defined by footnote[3] | defined by footnote[4] |
| E-30 | $Hc^1$ | $R^{1.6}$ | defined by footnote[3] | defined by footnote[4] |
| E-31 | $Hc^1$ | $R^{1.5}$ | being H | being H |
| E-32 | $Hc^1$ | $R^{1.6}$ | being H | being H |
| E-33 | $Hc^2$ | $R^{1.1}$ | defined by footnote[3] | defined by footnote[4] |
| E-34 | $Hc^2$ | $R^{1.2}$ | defined by footnote[3] | defined by footnote[4] |
| E-35 | $Hc^2$ | $R^{1.3}$ | defined by footnote[3] | defined by footnote[4] |
| E-36 | $Hc^2$ | $R^{1.4}$ | defined by footnote[3] | defined by footnote[4] |
| E-37 | $Hc^2$ | $R^{1.5}$ | defined by footnote[3] | defined by footnote[4] |
| E-38 | $Hc^2$ | $R^{1.6}$ | defined by footnote[3] | defined by footnote[4] |

TABLE 3-continued a compound characterised by the general formula (I):

(I)

| | Hc | $R^1$ | with $R^2$ | $R^3$ |
|---|---|---|---|---|
| E-39 | $Hc^2$ | $R^{1.5}$ | being H | being H |
| E-40 | $Hc^2$ | $R^{1.6}$ | being H | being H |
| E-41 | $Hc^3$ | $R^{1.1}$ | defined by footnote[3] | defined by footnote[4] |
| E-42 | $Hc^3$ | $R^{1.2}$ | defined by footnote[3] | defined by footnote[4] |
| E-43 | $Hc^3$ | $R^{1.3}$ | defined by footnote[3] | defined by footnote[4] |
| E-44 | $Hc^3$ | $R^{1.4}$ | defined by footnote[3] | defined by footnote[4] |
| E-45 | $Hc^3$ | $R^{1.5}$ | defined by footnote[3] | defined by footnote[4] |
| E-46 | $Hc^3$ | $R^{1.6}$ | defined by footnote[3] | defined by footnote[4] |
| E-47 | $Hc^3$ | $R^{1.5}$ | being H | being H |
| E-48 | $Hc^3$ | $R^{1.6}$ | being H | being H |

Footnotes:
[3] the definition refers to: $R^2$ being selected from the group of H—, fluorine, $F_3C$—, $HF_2C$—, $FH_2C$—, and $C_{1-3}$-alkyl-, preferably $R^2$ being H.
[4] the definition refers to: $R^3$ being selected from the group of H—, fluorine, $F_3C$—, $HF_2C$—, $FH_2C$—, and $C_{1-3}$-alkyl-, preferably $R^3$ being H.

provided that the compound is not a compound selected from the group of compounds of Table 2 with the example reference numbers: 219; 220; 221; 222; 223; 224; 225; 226; 227; 228; 229; 230; 230-1; 230-2; 230-3; 231; 232; 234 or where appropriate an isoform, tautomer, stereoisomer, solvate, hydrate, or a salts of any of these compounds, in particular not a physiologically acceptable salts thereof with inorganic or organic acids or bases, or the combinations thereof.

In all these embodiments of table 3 it is preferred that each of $R^2$ and $R^3$ is H.

Where appropriate, the subject matter of the invention also refers to the isoform, tautomer, stereoisomer, solvate, hydrate, or a salts of any of these compounds, in particular a physiologically acceptable salts thereof with inorganic or organic acids or bases, or the combinations thereof;

In another one embodiment of the invention it may be preferred that if Hc in any of the above described embodiments may be a group defined by the following formula D1

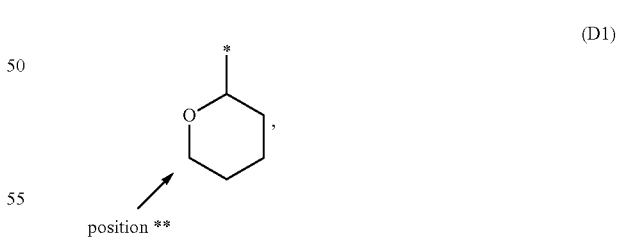

(D1)

whereby the * is the attachment point to the pyrazolo-group in general formula (I), then at the position  there is no substituent that has an integral —$CH_2$— group by which it is bound or even more preferably, at this position  there is no substituent at all.

In another embodiment of the invention it may be preferred in any of the aforementioned embodiments that for Hc being tetrahydropyranyl, then there is no $CH_3$-group that is bound at the alpha position to the ring oxygen atom.

In another embodiment of the invention it also may be preferred in any of the aforementioned embodiments that for Hc being tetrahydropyranyl, then there is no $C_{1-6}$-alkyl-group that is bound at the alpha position to the ring oxygen atom.

USED TERMS AND DEFINITIONS

Terms not specifically defined herein should be given the meanings that would be given to them by a person skilled in the art in light of the disclosure and the context. Examples include that specific substituents or atoms are presented with their 1 or 2 letter code, like H for hydrogen, N for nitrogen, C for carbon, O for oxygen, S for sulphur and the like. Optionally but not mandatory the letter is followed by a hyphen to indicate a bond. As used in the specification, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or alkyl radical having 1 to 6 carbon atoms. In general, for groups that are composed of two or more subgroups, the last named group is the radical attachment point, for example, "alkyl-O—" means a monovalent radical of the formula alkyl-O—, which is attached via the oxygen atom thereof (i.e. alkoxy). If the term of a substituent starts or ends with a minus sign or hyphen, i.e.—this sign emphasises the attachment point like in the aforementioned example alkyl-O—, where the "O" is linked to the group of which the alkyl-O— is a substituent. Unless otherwise specified below, conventional definitions of terms control and conventional stable atom valences are presumed and achieved in all formulas and groups.

In general, if terms are specifically defined with a given context, such specific definitions shall prevail the more general definitions as outlined in this paragraph.

In general, all "tautomeric forms and isomeric forms and mixtures", whether individual geometric isomers or optical isomers or racemic or non-racemic mixtures of isomers, of a chemical structure or compound are intended, unless the specific stereochemistry or isomeric form is specifically indicated in the compound name or structure. Specific definitions prevail.

The term "substituted" as used herein explicitly or implicitly, means that any one or more hydrogen(s) on the designated atom is replaced with a member of the indicated group of substituents, provided that the designated atom's normal valence is not exceeded. In case a substituent is bound via a double bond, e.g. an oxo substituent, such substituent replaces two hydrogen atoms on the designated atom. The substitution shall result in a stable compound. "Stable" in this context preferably means a compound that from a pharmaceutical point of view is chemically and physically sufficiently stable in order to be used as an active pharmaceutical ingredient of a pharmaceutical composition.

If a substituent is not defined, it shall be hydrogen.

By the term "optionally substituted" is meant that either the corresponding group is substituted or it is not.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salt(s)" refer to derivatives of the disclosed compounds wherein the parent compound is modified by making acid or base salts thereof preferably addition salts. Examples of pharmaceutically acceptable salts of a compound according to the invention that has a basic function (e.g. an amino group) include, but are not limited to, mineral or organic acid salts; and the like. Compounds with acidic properties may form salts with alkali or organic bases. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric acid, hydrobromic acid, sulfuric acid, sulfamic acid, phosphoric acid, nitric acid, and the like; and the salts prepared from organic acids such as acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid, and the like.

The pharmaceutically acceptable salts of the present invention can be synthesized from the parent compound with basic or acidic properties by conventional chemical methods. Generally, such salts can be prepared by reacting a compound of the present invention that has basic properties with a stoichiometric amount of the appropriate acid (respectively, compounds with acidic properties with a stoichiometric amount of the appropriate base) in water or in an organic solvent, or in a mixture of the two; generally, non-aqueous media like ether, ethyl acetate, ethanol, isopropanol, or acetonitrile are preferred.

"Prodrugs" are considered compounds that release an active parent drug of the present invention in vivo when such prodrug is administered to a mammalian subject. Prodrugs according to the present invention are prepared by modifying functional groups present in the compound of the invention in such a way that these modifications are retransformed to the original functional groups under physiological conditions. Prodrugs include compounds of the present invention wherein a hydroxy, amino, or sulfhydryl group is bound to any group that, when the prodrug of the present invention is administered to a mammalian subject, is retransformed to free said hydroxyl, amino, or sulfhydryl group. Examples of prodrugs include, but are not limited to, acetate, formate and benzoate derivatives of alcohol and amine functional groups in the compounds of the present invention.

"Metabolites" are considered as derivatives of the compounds according to the present invention that are formed in vivo. Active metabolites are such metabolites that cause a pharmacological effect. It will be appreciated that metabolites of the compounds according to the present inventions are subject to the present invention as well, in particular active metabolites.

Some of the compounds may form "solvates". For the purposes of the invention the term "solvates" refers to those forms of the compounds which form, in the solid or liquid state, a complex by coordination with solvent molecules. Hydrates are a specific form of solvates in which the coordination takes place with water. According to the present invention, the term preferably is used for solid solvates, such as amorphous or more preferably crystalline solvates.

"Scaffold": The scaffold of the compounds according to the present invention is represented by the following core structure. The numeration of the positions of the ring member atoms is indicated in bold:

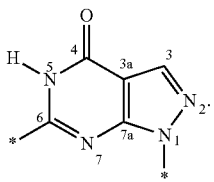

It will be evident for the skilled person in the art, that this scaffold can be described by its tautomeric "enol" form

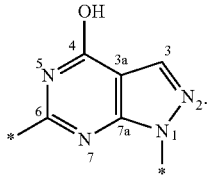

In the context of the present invention both structural representations of the scaffold shall be considered the subject of the present invention, even if only one of the two representatives is presented. Without meant to be limiting or being bound, it is believed that for the majority of compounds under ambient conditions and therewith under conditions which are the relevant conditions for a pharmaceutical composition comprising said compounds, the equilibrium of the tautomeric forms lies on the side of the pyrazolopyrimdin-4-one representation. Therefore, all embodiments are presented as pyrazolopyrimdin-4-one-derivatives or more precisely as pyrazolo[3,4-d]pyrimidin-4-one derivatives.

"Bonds": If within a chemical formula of a ring system or a defined group a substituent is directly linked to an atom or a group like "RyR" in below formula this shall mean that the substituent is only attached to the corresponding atom. If however from a substituent like "RxR" a bond is not specifically linked to an atom of the ring system but drawn towards the centre of the ring or group this means that this substituent "RxR" may be linked to any meaningful atom of the ring system/group unless stated otherwise.

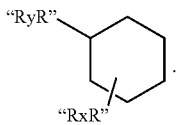

The bond symbol "–" (=minus sign) or the symbol "–*" (=minus sign followed by an asterisk sign) stands for the bond through which a substituent is bound to the corresponding remaining part of the molecule/scaffold. In cases in that the minus sign does not seem to be sufficiently clear, there may be added an asterisk to the bond symbol "–" in order to determine the point of attachment of said bond with the corresponding main part of the molecule/scaffold.

In general, the bond to one of the herein defined heterocycloalkyl or heteroaryl groups may be effected via a carbon ring atom or optionally via a nitrogen ring atom of such heterocycloalkyl or heteroaryl group.

The term "aryl" used in this application denotes a phenyl, biphenyl, indanyl, 1,2,3,4-tetrahydronaphthyl or naphthyl group, preferably it denotes a phenyl or naphtyl group, more preferably a phenyl group. This definition applies for the use of "aryl" in any context within the present description in the absence of a further definition.

The term "$C_{1-n}$-alkyl" denotes a saturated, branched or unbranched hydrocarbon group with 1 to n C atoms, wherein n is a figure selected from the group of 2, 3, 4, 5 or 6. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl etc.

This definition applies for the use of "alkyl" in any reasonable context within the present description in the absence of a further definition.

In cases in which the term "$C_{1-n}$-alkyl" is used in the middle of two other groups/substituents, like for example in "$C_{1-n}$-cycloalkyl-$C_{1-n}$-alkyl-O—", this means that the "$C_{1-n}$-alkyl"-moiety bridges said two other groups. In the present example it bridges the $C_{1-n}$-cycloalkyl with the oxygen like in "cyclopropyl-methyl-oxy-". It will be evident, that in such cases "$C_{1-n}$-alkyl" has the meaning of a "$C_{1-n}$-alkylene" spacer like methylene (—$CH_2$—), ethylene (e.g. —$CH_2$—$CH_2$—), etc. The groups that are bridged by "$C_{1-n}$-alkyl" may be bound to "$C_{1-n}$-alkyl" at any position thereof. Preferably the right hand group is located at the distal right hand end of the alkyl group and left hand group at the distal left hand side of the alkyl group (e.g. for HO—$C_3$-alkyl-: 3-hydroxy-propan-1-yl). The same applies for other substituents.

The term "$C_{3-n}$-cycloalkyl" denotes a saturated monocyclic group with 3 to n C ring atoms. n preferably has a value of 4 to 7 (=4, 5, 6 or 7). There are no ring atoms other than carbon atoms. Examples of such groups include cyclopropyl, cyclobutyl, cyclopentyl, cyclohexyl, cycloheptyl etc. This definition applies for "cycloalkyl" in any reasonable context within the present description in the absence of a further definition.

The term "heteroaryl" used in this application denotes a heterocyclic, mono- or bicyclic aromatic ring system which includes within the ring system itself in addition to at least one C atom one or more heteroatom(s) independently selected from N, O, and/or S. A monocyclic ring system preferably consists of 5 to 6 ring members, a bicyclic ring system preferably consists of 8 to 10 ring members. Preferred are heteroaryls with up to 3 heteroatoms, more preferred up to 2 heteroatoms, more preferred with 1 heteroatom. Preferred heteroatom is N. Examples of such moieties are benzimidazolyl, benzisoxazolyl, benzo[1,4]-oxazinyl, benzoxazol-2-onyl, benzofuranyl, benzoisothiazolyl, 1,3-benzodioxolyl, benzothiadiazolyl, benzothiazolyl, benzothienyl, benzoxadiazolyl, benzoxazolyl, chromanyl, chromenyl, chromonyl, cinnolinyl, 2,3-dihydrobenzo[1,4]dioxinyl, 2,3-dihydrobenzofuranyl, 3,4-dihydrobenzo[1,4]oxazinyl, 2,3-dihydroindolyl, 1,3-dihydroisobenzofuranyl, 2,3-dihydroisoindolyl, 6,7-dihydropyrrolizinyl, dihydroquinolin-2-onyl, dihydroquinolin-4-onyl, furanyl, imidazo[1,2-a]pyrazinyl, imidazo[1,2-a]pyridyl, imidazolyl, imidazopyridyl, imidazo[4,5-d]thiazolyl, indazolyl, indolizinyl, indolyl, isobenzofuranyl, isobenzothienyl, isochromanyl, isochromenyl, isoindoyl, isoquinolin-2-onyl, isoquinolinyl, isothiazolyl, isoxazolyl, naphthyridinyl, 1,2,4-oxadiazoyl, 1,3,4-oxadiazoyl, 1,2,5-oxadiazoyl, oxazolopyridyl, oxazolyl, 2-oxo-2,3-dihydrobenzimidazolyl, 2-oxo-2,3-dihydroindolyl, 1-oxoindanyl, phthalazinyl, pteridinyl, purinyl, pyrazinyl, pyrazolo[1,5-a]pyridyl, pyrazolo[1,5-a]pyrimidinyl, pyrazolyl, pyridazinyl, pyridopyrimidinyl, pyridyl (pyridinyl), pyridyl-N-oxide, pyrimidinyl, pyrimidopyrimidinyl, pyrrolopyridyl, pyrrolopyrimidinyl, pyrrolyl, quinazolinyl, quinolin-4-onyl, quinolinyl, quinoxalinyl, 1,2,3,4-tetrahydroquinolinyl, 1,2,3,4-tetrahydroisoquinolinyl, tetrazolyl, 1,2,4-thiadiazolyl, 1,3, 4-thiadiazolyl, 1,2,5-thiadiazolyl, thiazolyl, thieno[2,3-c] imidazolyl, thieno[3,2-b]pyrrolyl, thieno[3,2-b]thiophenyl, thienyl, triazinyl, or triazolyl.

Preferred heteroaryl groups are defined in the corresponding context.

The definition pyrazole includes the isomers 1H-, 3H- and 4H-pyrazole. Preferably pyrazolyl denotes 1H-pyrazolyl.

The definition imidazole includes the isomers 1H-, 2H- and 4H-imidazole. A preferred definition of imidazolyl is 1H-imidazolyl.

The definition triazole includes the isomers 1H-, 3H- and 4H-[1,2,4]-triazole as well as 1H-, 2H- and 4H-[1,2,3]-triazole. The definition triazolyl therefore includes 1H-[1,2,4]-triazol-1-, -3- and -5-yl, 3H[1,2,4]-triazol-3- and -5-yl, 4H[1,2,4]-triazol-3-, -4- and -5-yl, 1H-[1,2,3]-triazol-1-, -4- and -5-yl, 2H[1,2,3]-triazol-2-, -4- and -5-yl as well as 4H[1,2,3]-triazol-4- and -5-yl.

The term tetrazole includes the isomers 1H-, 2H- and 5H-tetrazole. The definition tetrazolyl therefore includes 1H-tetrazol-1- and -5-yl, 2H-tetrazol-2- and -5-yl and 5H-tetrazol-5-yl.

The definition indole includes the isomers 1H- and 3H-indole. The term indolyl preferably denotes 1H-indol-1-yl.

The term isoindole includes the isomers 1H- and 2H-isoindole.

This definition applies for "heteroaryl" in any reasonable context within the present description in the absence of a further definition.

The term "heterocycloalkyl" within the context of the present invention denotes a saturated 3 to 8 membered, preferably 5-, 6- or 7-membered ring system or a 5-12 membered bicyclic ring system, the ring atoms of which are carbon atoms and 1, 2, 3 or 4 heteroatoms, selected from N, O, and/or S, the S optionally in form of SO or $SO_2$. Preferred are 1, 2, or 3, more preferred 1 heteroatoms.

The preferred number of carbon ring atoms is 3 to 7 beside said 1, 2, 3 or 4 heteroatoms selected from N, O, and/or S. Such heterocycloalkyl groups are addressed as $C_{3-7}$-heterocycloalkyl.

Preferred are saturated heterocycloalkyl rings with 5, 6, or 7 ring atoms, of which 1 or 2 are heteroatoms and the remaining are C-atoms.

Preferred example for heterocycloalkyl include morpholinyl, piperidinyl, piperazinyl, thiomorpholinyl, oxathianyl, dithianyl, dioxanyl, pyrrolidinyl, tetrahydrofuranyl, dioxolanyl, oxathiolanyl, imidazolidinyl, tetrahydropyranyl, pyrrolinyl, tetrahydrothienyl, oxazolidinyl, homopiperazinyl, homopiperidinyl, homomorpholinyl, homothiomorpholinyl, azetidinyl, 1,3-diazacyclohexanyl or pyrazolidinyl group.

This definition applies for "heterocycloalkyl" in any reasonable context within the present description in the absence of a further specific definition.

The term "oxo" denotes an oxygen atom as substituent that is bonded by a double bond, preferably it is bonded to a C-atom. In case oxo is used as a substituent, the oxo replaces two hydrogen atoms of the corresponding atom of the unsubstituted compound.

The terms "pyridyl" and "pyridinyl" are used equally (in parallel) to define a pyridine-substituent.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" preferably means therapeutic treatment of (e.g. human) patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition, disorder or a symptom thereof. Treatment includes the administration of the active compounds to eliminate or control the disease, condition or disorder as well as to alleviate the symptoms or complications associated with the disease, condition or disorder.

The following schemes shall illustrate generally ways to manufacture the compounds of the present invention by way of example. The abbreviated substituents may be as defined for the embodiments of formula (I) if not defined otherwise within the context for the schemes:

Scheme 1

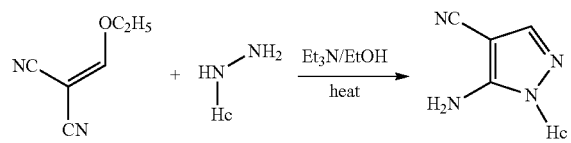

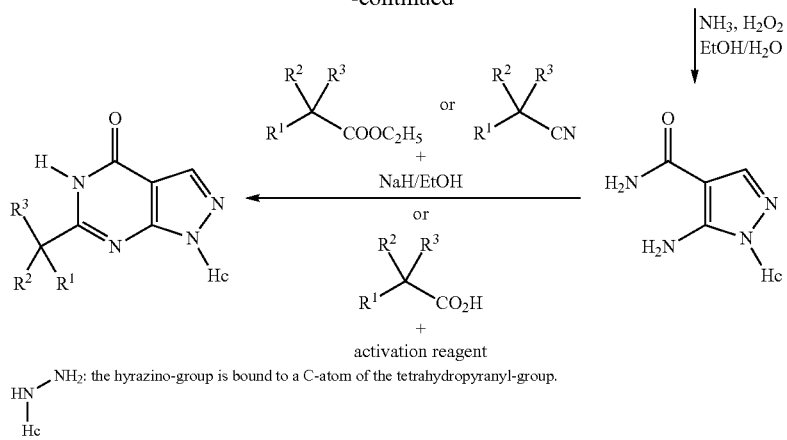

NH₂: the hyrazino-group is bound to a C-atom of the tetrahydropyranyl-group.

Scheme 1: In a first step 2-ethoxymethylene-malononitrile is condensed with mono-substituted hydrazines by heating in an appropriate solvent like ethanol in the presence of a base (e.g. triethylamine) to form the corresponding 5-amino-1H-pyrazole-4-carbonitriles. These compounds are converted in a second step to the corresponding amides, e.g. by treatment of an ethanolic solution with ammonia (25% in water) and hydrogen peroxide (35% in water). In a third step, heating with carboxylic esters under basic conditions (e.g. sodium hydride in ethanol) or carboxylic acids with an activation reagent (e.g. polyphosphoric acid) leads to pyrazolo[3,4-d]pyrimidin-4-ones as final products [cf., for example, A. Miyashita et al., *Heterocycles* 1990, 31, 1309ff].

Schemes 2 and 3 illustrate alternative methods to prepare the final compounds: in these exemplified manufacturing methods 5-amino-1H-pyrazole-4-carboxylic acid amides are condensed in a first step with an appropriate ester derivative followed in a second step by alkylation with suitable electrophiles.

Scheme 3

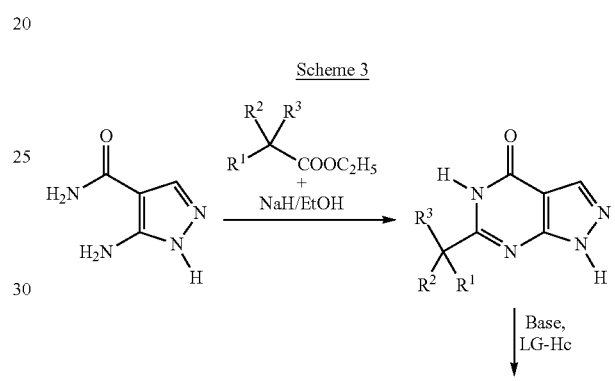

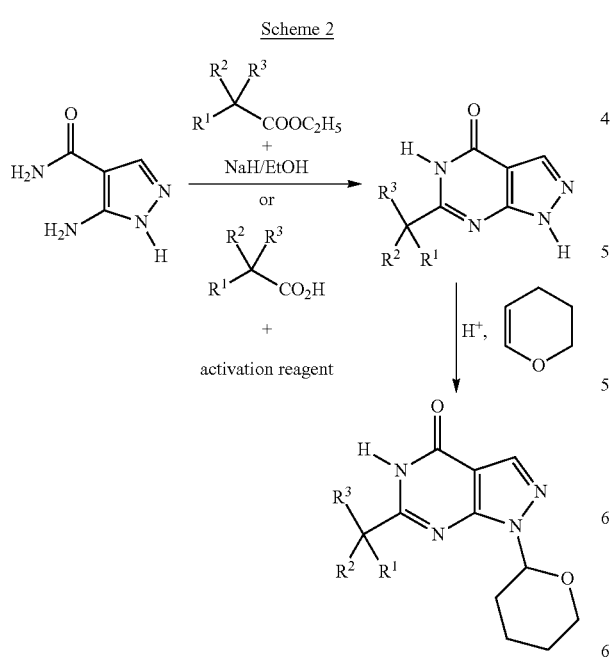

LG = Br—, Cl—, I—, CH₃—SO₂—O—, p-toluenesulphonyl-, which is bound to Hc by one of the ring carbon atoms of the tetrahydropyranoyl group.
Base = N(C₂H₅)₃, KOtBu, NaH Schemes 4 and 5 illustrate alternative methods to prepare the final compounds: in the exemplified manufacturing methods 5-amino-1H-pyrazole-4-carboxylic acid amides are condensed in a first step with (2-bromo-phenyl)-acetic acid ester derivatives followed in a second step by substitution of the bromine atom by an aromatic or heteroaromatic residue e.g. using Suzuki or Ullmann type reaction conditions. Alternatively, as depicted in scheme 5, the aromatic or heteroaromatic residue is first inserted into a phenyl-acetonitrile residue and condensed with 5-amino-1H-pyrazole-4-carboxylic acid amides in a second step.

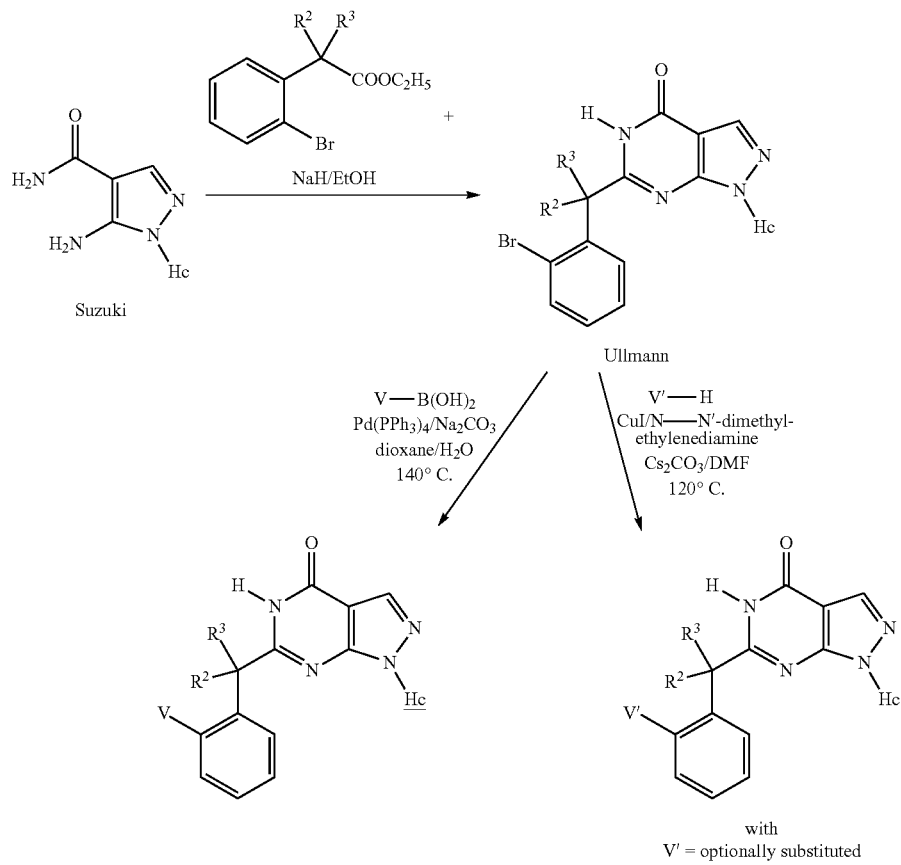
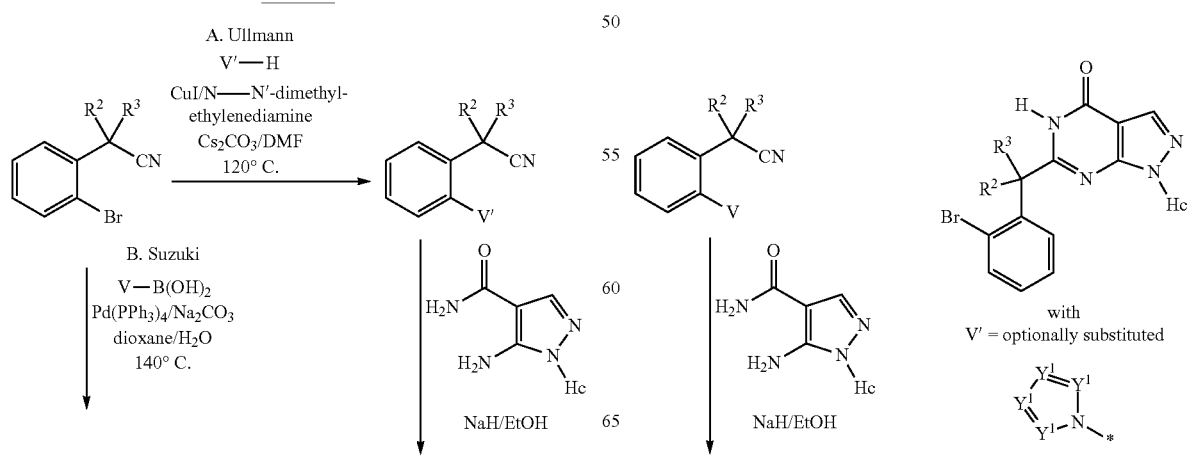

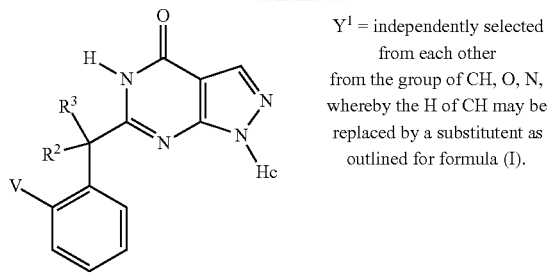

Y¹ = independently selected from each other from the group of CH, O, N, whereby the H of CH may be replaced by a substitutent as outlined for formula (I).

Furthermore, the synthesis of final compounds can also be accomplished through the preparation of a boronic acid derivative, followed by a Suzuki type cross coupling in a second step (Scheme 6).

Scheme 7 illustrates an alternative method to prepare the final compounds: in the exemplified manufacturing method 5-amino-1H-pyrazole-4-carboxylic acid amides are condensed in a first step with (2-cyano-phenyl)-acetic acid ester derivatives followed in a second step by transformation of the nitrile group into a 5-membered heteroaromatic group.

Scheme 6

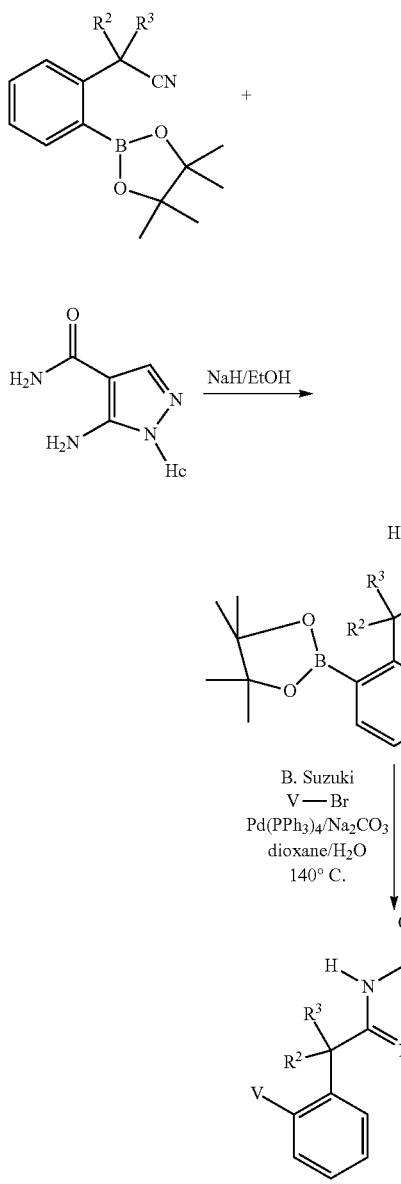

Scheme 7

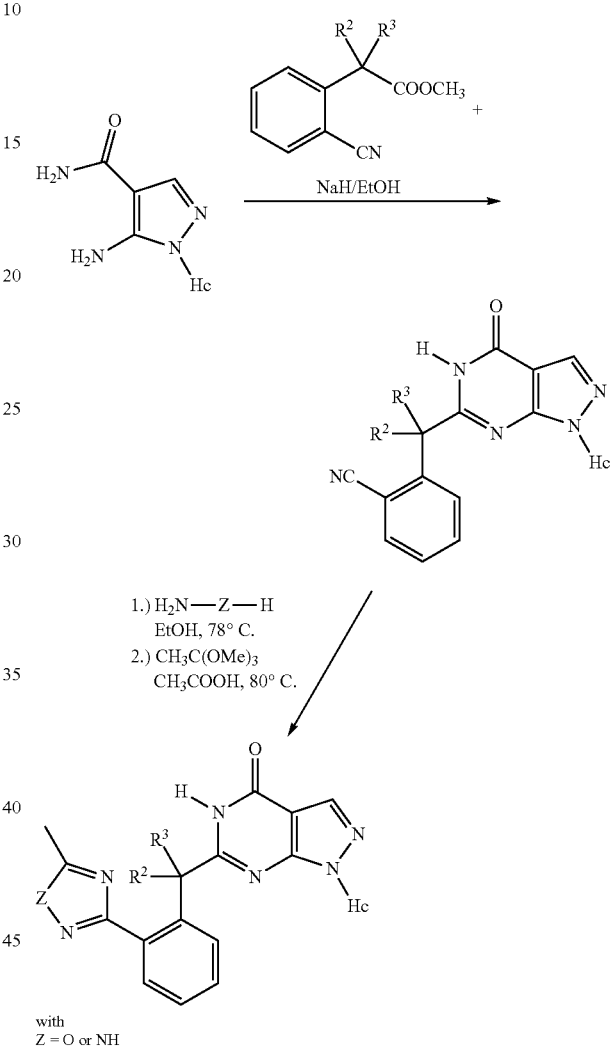

with
Z = O or NH

Further alternative processes for preparing pyrazolo[3,4-d]pyrimidin-4-ones are known in the art and can likewise be employed for synthesizing the compounds of the invention (see, for example: P. Schmidt et al., *Helvetica Chimica Acta* 1962, 189, 1620ff.).

The mono-substituted hydrazine derivatives, that are used in step 1 of scheme 1 can be prepared either by nucleophilic displacement on the corresponding mesylate derivative (scheme 8) or by reduction of the hydrazone intermediate as depicted in scheme 9 [cf., for example, J. W. Timberlake et al., "*Chemistry of Hydrazo-, Azo-, and Azoxy Groups*"; Patai, S., Ed.; 1975, Chapter 4; S. C. Hung et al., *Journal of organic Chemistry* 1981, 46, 5413-5414].

Scheme 8

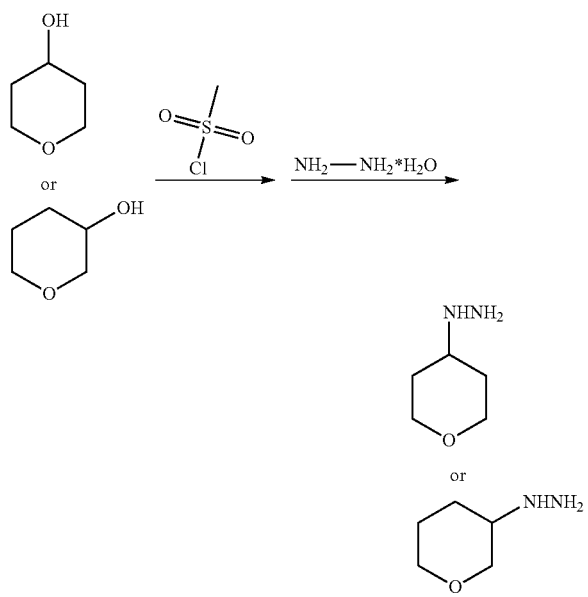

The tetrahydropyranyl-group optionally may be further substituted as defined.

Scheme 9

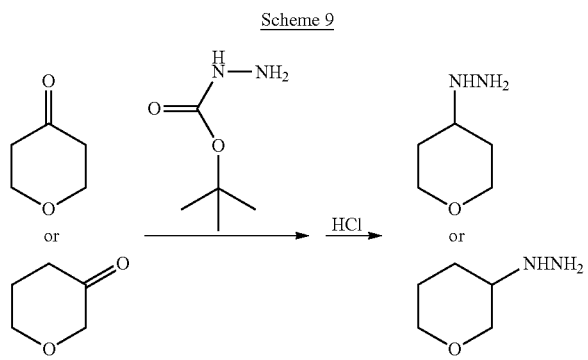

The tetrahydropyranyl-group optionally may be further substituted as defined.

Further information also can be found in WO04099210 (in particular page 9, last paragraph to page 14, line 8, incorporated by reference).

The compounds of the invention show a valuable range of pharmacological effects which could not have been predicted. They are characterised in particular by inhibition of PDE9A.

Preferably the compounds according to the present invention show a high selectivity profile in view of inhibiting or modulating specific members within the PDE9 family or other PDE families, with a clear preference (selectivity) towards PDE9A inhibition.

The compounds of the present invention are supposed to show a favourable safety profile for the purpose of medical treatment.

The compounds of the present invention are supposed to show a favourable profile with respect to metabolic stability over a certain period of time for the purpose of medical treatment.

The compounds of the present invention are supposed to show a favourable profile with respect to bioavailability for the purpose of medical treatment.

Method of Treatment

The present invention refers to compounds, which are considered effective in the treatment of diseases. The compounds according to the invention are effective and selective inhibitors of phosphodiesterase 9A and can be used for the development of medicaments. Such medicaments shall preferably be used for the treatment of diseases in which the inhibition of PDE9A can evolve a therapeutic, prophylactic or disease modifying effect. Preferably the medicaments shall be used to improve perception, concentration, cognition, learning or memory, like those occurring in particular in situations/diseases/syndromes such as: mild cognitive impairment, age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, epilepsy, temporal lobe epilepsy, schizophrenia or Korsakoff's psychosis.

Another aspect of the present invention concerns the treatment of a disease which is accessible by PDE9A modulation, in particular sleep disorders like insomnia or narcolepsy, bipolar disorder, metabolic syndrome, obesity, diabetes mellitus, including type 1 or type 2 diabetes, hyperglycemia, dyslipidemia, impaired glucose tolerance, or a disease of the testes, brain, small intestine, skeletal muscle, heart, lung, thymus or spleen.

Thus, the medical aspect of the present invention can be summarised in that it is considered that a compound according to any of the generic (genius) embodiments of the invention as outlined herein or a compound selected from the group of the specifically disclosed ones ("species") is used as a medicament.

Such a medicament preferably is for the treatment of a CNS disease.

In an alternative use, the medicament is for the treatment of a CNS disease, the treatment of which is accessible by the inhibition of PDE9.

In an alternative use, the medicament is for the treatment of a disease that is accessible by the inhibition of PDE9, specifically PDE9A.

In an alternative use, the medicament is for the treatment, amelioration and/or prevention of cognitive impairment being related to perception, concentration, cognition, learning or memory.

In an alternative use, the medicament is for the treatment, amelioration and/or prevention of cognitive impairment being related to age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, epilepsy, temporal lobe epilepsy, schizophrenia with dementia or Korsakoff's psychosis.

In an alternative use, the medicament is for use in the treatment of Alzheimer's disease.

In an alternative use, the medicament is for the treatment of sleep disorders, bipolar disorder, metabolic syndrome, obesity, diabetis mellitus, hyperglycemia, dyslipidemia, impaired glucose tolerance, or a disease of the testes, brain, small intestine, skeletal muscle, heart, lung, thymus or spleen.

In a further aspect of the invention, the present invention relates to the method of treatment or prevention of a condition or disease selected from the above listed groups of conditions and diseases, whereby the method comprises the administration of a therapeutically effective amount of a compound according to the invention in a human being in need thereof.

Pharmaceutical Compositions

Medicaments for administration, which are also subject to the present invention, comprise a compound according to the present invention in a therapeutically effective amount and a pharmaceutical carrier. By "therapeutically effective amount" it is meant that if the medicament is applied via the appropriate regimen adapted to the patient's condition, the amount of said compound of formula (I) will be sufficient to effectively treat, to prevent or to decelerate the progression of the corresponding disease, or otherwise to ameliorate the estate of a patient suffering from such a disease. It may be the case that the "therapeutically effective amount" in a monotherapy will differ from the "therapeutically effective amount" in a combination therapy with another medicament.

The dose range of the compounds of general formula (I) applicable per day may be from 0.1 to 5000 mg, preferably from 0.1 to 1000 mg, preferably from 2 to 500 mg, more preferably from 5 to 250 mg, most preferably from 10 to 100 mg. A dosage unit (e.g. a tablet) preferably may contain between 2 and 250 mg, particularly preferably between 10 and 100 mg of the compounds according to the invention.

The actual pharmaceutically effective amount or therapeutic dosage will depend on factors known by those skilled in the art such as age, weight, gender or other condition of the patient, route of administration, severity of disease, and the like.

The compounds according to the invention may be administered by oral, parenteral (intravenous, intramuscular etc.), intranasal, sublingual, inhalative, intrathecal, topical or rectal route. Suitable preparations for administering the compounds according to the present invention include for example patches, tablets, capsules, pills, pellets, dragees, powders, troches, suppositories, liquid preparations such as solutions, suspensions, emulsions, drops, syrups, elixirs, or gaseous preparations such as aerosols, sprays and the like. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may contain, in addition to the carriers specified, additives such as sodium citrate, calcium carbonate and dicalcium phosphate together with various additional substances such as starch, preferably potato starch, gelatin and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

The dosage of the compounds according to the invention is naturally highly dependent on the method of administration and the complaint which is being treated.

Combinations with Other Active Substances

In another aspect the present invention relates to a combination therapy in which a compound according to the present invention is administered together with another active compound. Accordingly, the invention also refers to pharmaceutical formulations that provide such a combination of active ingredients, whereby one of which is a compound of the present invention. Such combinations may be fixed dose combinations (the active ingredients that are to be combined are subject of the same pharmaceutical formulation) or free dose combinations (active ingredients are in separate pharmaceutical formulations).

Consequently, a further aspect of the present invention refers to a combination of each of the compounds of the present invention, preferably at least one compound according to the present invention, with another compound selected from the group of for example beta-secretase inhibitors; gamma-secretase inhibitors; gamma-secretase modulators; amyloid aggregation inhibitors such as e.g. alzhemed; directly or indirectly acting neuroprotective and/or disease-modifying substances; anti-oxidants, such as e.g. vitamin E, ginko biloba or ginkolide; anti-inflammatory substances, such as e.g. Cox inhibitors, NSAIDs additionally or exclusively having Aβ (Abeta) lowering properties; HMG-CoA reductase inhibitors, such as statins; acetylcholine esterase inhibitors, such as donepezil, rivastigmine, tacrine, galantamine; NMDA receptor antagonists such as e.g. memantine; AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5 and/or PDE10 inhibitors, GABAA receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; metabotropic glutamate receptor 5 positive modulators; metabotropic glutamate receptor 2 antagonists, and other substances that modulate receptors or enzymes in a manner such that the efficacy and/or safety of the compounds according to the invention is increased and/or unwanted side effects are reduced.

This invention further relates to pharmaceutical compositions containing one or more, preferably one active substance. At least one active substance is selected from the compounds according to the invention and/or the corresponding salts thereof. Preferably the composition comprises only one such active compound. In case of more than one active compound the other one can be selected from the aforementioned group of combination partners such as alzhemed, vitamin E, ginkolide, donepezil, rivastigmine, tacrine, galantamine, memantine, ibutamoren mesylate, capromorelin, minocyclin and/or rifampicin. Optionally the composition comprises further ingredients such as inert carriers and/or diluents.

The compounds according to the invention may also be used in combination with immunotherapies such as e.g. active immunisation with Abeta or parts thereof or passive immunisation with humanised anti-Abeta antibodies or antibody-fragments for the treatment of the above mentioned diseases and conditions.

The compounds according to the invention also may be combined with Dimebon.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e the compounds of the present invention are provided in one dosage form and one or more of the above mentioned combination partners is provided in another dosage form. These two dosage forms may be equal dosage forms, for example a co-administration of two tablets, one containing a therapeutically effective amount of the compound of the present invention and one containing a therapeutically effective amount of the above mentioned combination partner. It is also possible to combine different administration forms, if desired. Any type of suitable administration forms may be provided.

The compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above mentioned combination partners is expediently ⅕ of the normally recommended lowest dose up to 1/1 of the normally recommended dose.

The dosage forms are administered to the patient for example 1, 2, 3, or 4 times daily depending on the nature of the formulation. In case of retarding or extended release formulations or other pharmaceutical formulations, the same may be applied differently (e.g. once weekly or monthly etc.). It is preferred that the compounds of the invention be administered either three or fewer times, more preferably once or twice daily.

EXAMPLES

Pharmaceutical Compositions

Examples for illustration, without being meant to be limiting:

For illustration, pharmaceutical formulations will now be described, wherein the term "active substance" denotes one or more compounds according to the invention including the salts thereof. In the case of one of the aforementioned combinations with one or more other active substances the term "active substance" may also include the additional active substances.

Example A

Tablets Containing 100 Mg of Active Substance

Composition: Tablet

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Example B

Tablets Containing 150 Mg of Active Substance

Composition: Tablet

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Example C

Hard Gelatine Capsules Containing 150 Mg of Active Substance

Composition: Capsule

| | |
|---|---|
| active substance | 150.0 mg |
| corn starch (dried) | approx. 80.0 mg |
| lactose | approx. 87.0 mg |
| magnesium stearate | 3.0 mg |
| | approx. 320.0 mg |

Example D

Composition: Suppository

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Example E

Composition: Ampoules Containing 10 Mg Active Substance

| | |
|---|---|
| active substance | 10.0 mg |
| 0.01N hydrochloric acid q.s. | |
| double-distilled water | ad 2.0 mL |

Example F

Composition: Ampoules Containing 50 Mg of Active Substance

| | |
|---|---|
| active substance | 50.0 mg |
| 0.01N hydrochloric acid q.s. | |
| double-distilled water | ad 10.0 mL |

The preparation of any the above mentioned formulations can be done following standard procedures.

Biological Assay

The in vitro effect of the compounds of the invention can be shown with the following biological assays.

PDE9A2 Assay Protocol:

The PDE9A2 enzymatic activity assay was run as scintillation proximity assay (SPA), in general according to the protocol of the manufacturer (GE Healthcare, former Amersham Biosciences, product number: TRKQ 7100).

As enzyme source, lysate (PBS with 1% Triton X-100 supplemented with protease inhibitors, cell debris removed by centrifugation at 13.000 rpm for 30 min) of SF 9 cell expressing the human PDE9A2 was used. The total protein amount included in the assay varied upon infection and production efficacy of the SF9 cells and lay in the range of 0.1-100 ng.

In general, the assay conditions were as follows:
total assay volume: 40 microliter
protein amount: 0.1-50 ng
substrate concentration (cGMP): 20 nanomolar; ~1 mCi/I
incubation time: 60 min at room temperature
final DMSO concentration: 0.2-1%

The assays were run in 384-well format. The test reagents as well as the enzyme and the substrate were diluted in assay buffer. The assay buffer contained 50 mM Tris, 8.3 mM $MgCl_2$, 1.7 mM EGTA, 0.1% BSA, 0.05% Tween 20; the pH of assay buffer was adjusted to 7.5. The reaction was stopped by applying a PDE9 specific inhibitor (e.g. compounds according to WO04099210 or WO04099211, like one of the enantiomeres of example 37, e.g. 1-(2-Chlorophenyl)-6-[(2R)-3,3,3-trifluoro-2-methyl-propyl]-1,5-dihydro-4H-pyrazolo[3,4-d]pyrimidine-4-one) in excess.

REFERENCES

Wunder F, Tersteegen A, Rebmann A, Erb C, Fahrig T, Hendrix M. Characterization of the first potent and selective PDE9 inhibitor using a cGMP reporter cell line. *Molecular Pharmacology.* 2005 December; 68(6):1775-81.

van der Staay F J, Rutten K, Bärfacker L, Devry J, Erb C, Heckroth H, Karthaus D, Tersteegen A, van Kampen M, Blokland A, Prickaerts J, Reymann K G, Schröder UH, Hendrix M. The novel selective PDE9 inhibitor BAY 73-6691 improves learning and memory in rodents. *Neuropharmacology.* 2008 October; 55(5):908-18.

PDE1C Assay Protocol:

The assay was run in an analogue manner as the PDE9A2 assay, with the following differences: instead of PDE9A2 PDE1C has been used and the assay buffer contained in addition 50 nM Calmodulin, 3 mM $CaCl_2$. The reaction can be stopped by applying the same inhibitor than the one that is outlined above (1-(2-Chlorophenyl)-6-[(2R)-3,3,3-trifluoro-2-methyl-propyl]-1,5-dihydro-4H-pyrazolo[3,4-d]pyrimidine-4-one).

Determination of % Inhibition:

The activity of the positive control (minus the negative control=background) is set to 100% and activity in the presence of test compound is expressed relative to these 100%. Within this setting, an inhibition above 100% might be possible due to the nature of the variation of the positive control within the assay. In the following inhibition of PDE9A2 is presented for a concentration at 10 µM, if not indicated otherwise.

Determination of $IC_{50}$:

$IC_{50}$ can be calculated with GraphPadPrism or other suited software setting the positive control as 100 and the negative control as 0. For calculation of $IC_{50}$ dilutions of the test compounds (substrates) are to be selected and tested following the aforementioned protocol.

Data

In the following, % inhibition (% I) data at 10 micromolar concentration (at 10 microM) and $IC_{50}$ values for PDE9A2 inhibition [nanomolar (nM)] will illustrate that the compounds according to the present invention are suited to inhibit PDE9, specifically PDE9A2. This evidences that the compounds provide useful pharmacological properties (Table 4). The examples are not meant to be limiting.

Within this setting, an inhibition above 100% might be possible due to the nature of the variation of the positive control within the assay.

The table also provides selectivity values (S) that show a preference of the compounds for PDE9A versus PD1C. Selectivity is the ratio ($IC_{50}$ for PDE1C inhibition)/($IC_{50}$ for PDE9A2 inhibition).

The example numbers refer to the final examples as outlined in the section "Exemplary embodiments".

All data are measured according to the procedure described herein.

TABLE 4

| Example No. | I % (at 10 microM) | $IC_{50}$ (nM) | S |
|---|---|---|---|
| 219 | 103 | 12 | 179 |
| 220 | 104 | 5 | 526 |
| 221 | 103 | 6 | 98 |
| 222 | 104 | 15 | 131 |
| 223 | 100 | 5 | 1717 |
| 224 | 100 | 12 | 146 |
| 225 | 102 | 6 | 290 |
| 226 | 101 | 9 | 225 |
| 227 | 101 | 8 | 147 |
| 228 | 101 | 6 | 244 |
| 229 | 99 | 14 | 135 |
| 230 | 101 | 12 | 145 |
| 230-1 | 98 | 5 | 197 |
| 230-2 | 102 | 5 | 286 |
| 230-3 | 99 | 11 | 135 |
| 230-5 | 98 | 6 | 274 |
| 231 | 95 | 18 | 245 |
| 232 | 99 | 7 | 255 |
| 234 | 101 | 3 | >3333 |
| 239 | 92 | 2 | 400 |
| 240 | 100 | 5 | 126 |
| 241 | 100 | 6 | 368 |
| 242 | 96 | 23 | >429 |
| 243 | 96 | 18 | 114 |
| 244 | 99 | 26 | 110 |
| 245 | 95 | 21 | 22 |
| 246 | 94 | 55 | 17 |
| 247 | 98 | 27 | 42 |
| 248 | 97 | 45 | 28 |
| 249 | 101 | 28 | 68 |
| 250 | 99 | 24 | 184 |
| 251 | 101 | 38 | 27 |
| 252 | 96 | 11 | 493 |
| 253 | 99 | 34 | 56 |
| 254 | 97 | 20 | 238 |
| 255 | 101 | 41 | 12 |
| 256 | 103 | 5 | 123 |
| 257 | 103 | 31 | 10 |
| 258 | 100 | 7 | 122 |
| 259 | 102 | 3 | 942 |
| 260 | 103 | 7 | 266 |
| 261 | 102 | 4 | 580 |
| 262 | 101 | 20 | 451 |
| 263 | 102 | 8 | 1116 |

I % (at 10 microM): inhibition at 10 micromolar concentration.
$IC_{50}$ (nM): $IC_{50}$ values for PDE9A2 inhibition [nanomolar (nM)]
S: selectivity values [= ($IC_{50}$ for PDE1C inhibition)/($IC_{50}$ for PDE9A2 inhibition)]

In Vivo Effect:

The in vivo effect of the compounds of this invention can be tested in the Novel Object Recognition test according to the procedure of Prickaerts et al. (*Neuroscience* 2002, 113, 351-361) or T-maze spontaneous alternation test according to the procedures described by van der Staay et al. (*Neuropharmacology* 2008, 55, 908-918). For further information concerning biological testing it is also referred to these two citations.

Beside the inhibition property toward the target PDE9, compounds according to the present invention may provide further pharmacokinetic properties of advantage.

E.g. compounds according to the invention may show one or more advantages in the area of balanced metabolism, low risk of causing drug-drug interaction and/or balanced clearance.

Compounds also might show one or more additional or alternative advantages in the area of bioavailability, high fraction absorbed, blood brain transport properties, a favourable (e.g. high mean) residence time (mrt), favourable exposure in the effect compartment and so on.

Chemical Manufacture

In this section, compounds according to the invention will be disclosed as well as chemically similar compounds that do not show the exact motif as defined for $R^1$. The way of manufacture for both types of compounds will illustrate the manufacturing method for the compounds according to the invention.

| Abbreviations: | |
|---|---|
| APCI | Atmospheric pressure chemical ionization |
| DAD | diode array detector |
| DMSO | dimethyl sulphoxide |
| ESI | electrospray ionization (in MS) |
| Exp. | example |
| Fp. | melting point |
| h | hour(s) |
| HPLC | high performance liquid chromatography |
| HPLC-MS | coupled high performance liquid chromatography with mass spectrometric detection |
| GC-MS | gas chromatography with mass spectrometric detection |
| MPLC | medium pressure liquid chromatography |
| mL | millilitre |
| μL | microlitre |
| min | minutes |
| MS | mass spectrometry |
| racem. | racemic |
| rt | room temperature |
| $R_t$ | retention time (in HPLC) |
| Rf | retardation factor (in TLC) |
| TBTU | 2-(1 H-Benzotriazole-1-yl)-1,1,3,3-Tetramethyluronium tetrafluoroborate |
| TFA | trifluoroacetic acid |
| TLC | thin-layer chromatography |

LC-MS Methods:

Method A

Instrument: HPLC/MS ThermoFinnigan. HPLC Surveyor DAD, LCQduo Ion trap.; column: Sunryse MS-C18, 5 um, 4.6×100 mm; eluent A: water+20 mM ammonium formate; eluent B: acetonitrile+20 mM ammonium formate; gradient: A/B (95:5) for 1 min, then to A/B (5:95) in 7 min for 1.5 min; flow rate: 0.85 mL/min; UV detection: 254 nm; ion source: ESI Method 1

MS apparatus type: Waters Micromass ZQ; HPLC apparatus type: Waters Alliance 2695, Waters 2996 diode array detector; column: Varian Microsorb 100 C18, 30×4.6 mm, 3.0 μm; eluent A: water+0.13% TFA, eluent B: acetonitrile; gradient: 0.0 min 5% B→0.18 min 5% B→2.0 min 98% B→2.2 min 98% B→2.3 min 5% B→2.5 min 5% B; flow rate: 3.5 mL/min; UV detection: 210-380 nm.

Method 2

MS apparatus type: Waters Micromass ZQ; HPLC apparatus type: Waters Alliance 2695, Waters 2996 diode array detector; column: Merck Chromolith Performance RP18e, 100×1 mm; eluent A: water+0.13% TFA, eluent B: acetonitrile; gradient: 0.0 min 5% B→0.2 min 5% B→1.6 min 98% B→1.9 min 98% B→2.0 min 5% B→2.2 min 5% B; flow rate: 3.5 mL/min; UV detection: 210-380 nm.

Method 1D

Instrument: HPLC-MS ThermoFinnigan. HPLC Surveyor DAD, MSQ Quadrupole; column: Sunryse MS-C18, 5 um, 4.6×100 mm; eluent A: 90% water+10% acetonitrile+ammonium formate 10 mM; eluent B: acetonitrile 90%+10% water+ammonium formate 10 mM; gradient: A (100) for 1 min, then to B (100) in 7 min for 1 min; flow rate: 1.2 mL/min; UV detection: 254 nm; ion source: APCI.

Method 1E

Instrument: HPLC-MS ThermoFinnigan. HPLC Surveyor DAD, MSQ Quadrupole; column: Symmetry C8, 5 μm, 3×150 mm; eluent A: 90% water+10% acetonitrile+ammonium formate 10 mM; eluent B: acetonitrile 90%+10% $H_2O$+ammonium formate 10 mM; gradient: A (100) for 1.5 min, then to B (100) in 10 min for 1.5 min; flow rate: 1.2 mL/min; UV detection: 254 nm; ion source: APCI Method 1E Fusion Instrument: HPLC-MS ThermoFinnigan. HPLC Surveyor DAD, MSQ Quadrupole; column: Synergi Fusion-RP80A, 4 μm, 4.60×100 mm; eluent A: 90% water+10% acetonitrile+ammonium formate 10 mM; eluent B: acetonitrile 90%+10% $H_2O$+ammonium formate 10 mM; gradient: A (100%) for 1.5 min, then to B (100%) in 10 min for 1.5 min; flow rate: 1.2 mL/min; UV detection: 254 nm; ion source: APCI Method 1E Hydro Instrument: HPLC-MS ThermoFinnigan. HPLC Surveyor DAD, MSQ Quadrupole; column: Synergi Hydro-RP80A, 4 μm, 4.60×100 mm; eluent A: 90% water+10% acetonitrile+ammonium formate 10 mM; eluent B: acetonitrile 90%+10% $H_2O$+ammonium formate 10 mM; gradient: A (100%) for 1.5 min, then to B (100%) in 10 min for 1.5 min; flow rate: 1.2 mL/min; UV detection: 254 nm; ion source: APCI Method 2F Instrument: HPLC-MS ThermoFinnigan. HPLC Surveyor DAD, Finnigan LCQduo Ion trap; column: Symmetry-C18, 5 um, 3×150 mm; eluent A: 95% water+5% acetonitrile+formic acid 0.1%; eluent B: acetonitrile 95%+5% water+formic acid 0.1%; gradient: A/B (95/5) for 1.5 min, then to A/B (5/95) in 10 min for 1.5 min; flow rate: 1 mL/min; UV detection: 254 nm; ion source: ESI Method 2L Instrument: HPLC-MS ThermoFinnigan. HPLC Surveyor DAD, Finnigan LCQduo Ion trap;

column: Symmetry Shield, 5 um, 4.6×150 mm; eluent A: 90% water+10% acetonitrile+formic acid 0.1%; eluent B: acetonitrile 90%+10% water+formic acid 0.1%; gradient: A/B (70/30) in 1.5 min to A/B (50/50) then to B (100%) in 7 min and for 9.5 min; flow rate: 0.85 mL/min; UV detection: 254 nm; ion source: ESI Method 2M Instrument: HPLC-MS ThermoFinnigan. HPLC Surveyor DAD, Finnigan LCQduo Ion trap;

column: Symmetry Shield, 5 um, 4.6×150 mm; eluent A: 90% water+10% acetonitrile+formic acid 0.1%; eluent B: acetonitrile 90%+10% water+formic acid 0.1%; gradient: A/B (90/10) for 1.5 min, then to A/B (5/95) in 10 min for 2 min; flow rate: 1.2 mL/min; UV detection: 254 nm; ion source: APCI Method Grad_C8_Acidic Instrument: HPLC-MS Waters. HPLC Alliance 2695 DAD, ZQ Quadrupole; column: Xterra MS-C8, 3.5 μm, 4.6×50 mm; eluent A: water+0.1% TFA+10% acetonitrile; eluent B: acetonitrile; gradient: A/B (80:20), then to A/B (10:90) in 3.25 min for 0.75 min; flow rate: 1.3 mL/min; UV detection: 254 nm; ion source: ESI Method Grad_C18_Acidic Instrument: HPLC-MS Waters. HPLC Alliance 2695 DAD, ZQ Quadrupole; column: Sunfire MS-C18, 3.5 μm, 4.6×50 mm; eluent A: water+0.1% TFA+10% acetonitrile; eluent B: acetonitrile; gradient: A/B (80:20), then to A/B (10:90) in 3.25 min for 0.75 min; flow rate: 1.3 mL/min; UV detection: 254 nm; ion source: ESI.

Method Grad__90__10_C8_Acidic

Instrument: HPLC-MS Waters. HPLC Alliance 2695 DAD, ZQ Quadrupole; column: Xterra MS-C8, 3.5 μm, 4.6×50 mm; eluent A: water+0.1% TFA+10% acetonitrile; eluent B: acetonitrile; gradient: A (100%), then to A/B (10:90) in 3.25 min for 0.75 min; flow rate: 1.3 mL/min; UV detection: 254 nm; ion source: ESI.

Method Grad__90__10_C18_Acidic

Instrument: HPLC-MS Waters. HPLC Alliance 2695 DAD, ZQ Quadrupole; column: Xterra MS-C18, 3.5 μm, 4.6×50 mm; eluent A: water+0.1% TFA+10% acetonitrile; eluent B: acetonitrile; gradient: A (100), then to A/B (10:90) in 3.25 min for 0.75 min; flow rate: 1.3 mL/min; UV detection: 254 nm; ion source: ESI.

Method Grad_C8_$NH_4COOH$

Instrument: HPLC-MS Waters. HPLC Alliance 2695 DAD, ZQ Quadrupole. Column: Xterra MS-C8, 3.5 μm, 4.6×50 mm; eluent A: water+ammonium formate 5 mM+10% acetonitrile; eluent B: acetonitrile; gradient: A 100%, then to A/B (10:90) in 3.25 min for 0.75 min; flow rate: 1.3 mL/min; UV detection: 254 nm; ion source: ESI.

Method 5

MS apparatus type: Waters Micromass ZQ; HPLC apparatus type: Waters Alliance 2695, Waters 2996 diode array detector; column: Varian Microsorb 100 C18, 30×4.6 mm, 5.0 μm; eluent A: water+0.15% TFA, eluent B: methanol; gradient: 0.0 min 5% B→0.15 min 5% B→2.55 min 100% B→2.70 min 100% B→2.80 min 5% B 3.05 min 5% B; flow rate: 4.8 mL/min; UV detection: 210-400 nm.

Method 6

MS apparatus type: Waters Micromass ZQ; HPLC apparatus type: Waters Alliance 2695, Waters 2996 diode array detector; column: Waters Sunfire C18, 20×4.6 mm, 5.0 μm; eluent A: water+0.15% TFA, eluent B: methanol; gradient: 0.0 min 5% B→0.25 min 5% B→1.90 min 100% B→2.05 min 100% B→2.15 min 5% B→2.30 min 5% B; flow rate: 5.2 mL/min; UV detection: 210-400 nm.

Method 7

MS apparatus type: Waters Micromass ZQ; HPLC apparatus type: Waters Alliance 2695, Waters 2996 diode array detector; column: Waters Varian Microsorb C18, 20×4.6 mm, 5.0 μm; eluent A: water+0.15% TFA, eluent B: methanol; gradient: 0.0 min 5% B→0.25 min 5% B→1.90 min 100% B→2.05 min 100% B→2.15 min 5% B→2.30 min 5% B; flow rate: 5.2 mL/min; UV detection: 210-400 nm.

Chiral HPLC Methods

Instrument: Agilent 1100. Column: Chiralpak AS-H Daicel, 4.6 μm, 4.6×250 mm;

Method Chiral 1: eluent: hexane/ethanol 97/3 (isocratic); flow rate: 1.0 mL/min; UV detection: 254 nm.

Method Chiral 2: eluent: hexane/ethanol 98/2 (isocratic); flow rate: 1.0 mL/min; UV detection: 254 nm Method Chiral 3: eluent: hexane/ethanol 80/20 (isocratic); flow rate: 1.0 mL/min; UV detection: 254 nm GC/MS Methods Method 3A Instrument: GC/MS Finnigan. Trace GC, MSQ quadrupole. Column: DB-5MS, 25 m×0.25 mm×0.25 µm; carrier gas: helium, 1 mL/min constant flow; oven program: 50° C. (hold 1 minute), to 100° C. in 10° C./min, to 200° C. in 20° C./min, to 300° C. in 30° C./min eluent, detection: trace MSQ, quadrupole ion source: IE scan range: 50-450 u.

Method 3A.1

Instrument: GC/MS Finnigan Thermo Scientific. Trace GC Ultra, DSQ II single quadrupole. Column: DB-5MS UI, 25 m×0.25 mm×0.25 µm; carrier gas: helium, 1 mL/min constant flow; oven program: 50° C. (hold 1 minute), to 100° C. in 10° C./min, to 200° C. in 20° C./min, to 300° C. in 30° C./min eluent, detection: trace DSQ, single quadrupole Microwave Heating:

Microwave Apparatus Types:
  Discover® CEM instruments, equipped with 10 and 35 mL vessels;
  Microwave apparatus type: Biotage Initiator Sixty.

General Comment Concerning the Presentation of the Structures

Some compounds have one or more chiral centres. The depicted structure will not necessarily show all the possible stereochemical realisation of the compound but only one. However, in such cases a term like "cis-racemic mixture" is depicted next to the structure in order to point to the other stereochemical options.

An example is given for Example 7D, below. The presented structural formula is

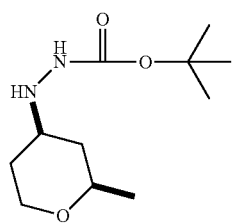 [SMILES: C[C@@H]1C[C@H](NNC(=O)OC(C)(C)C)CCO1]

Cis-Racemic Mixture

The added term "cis-racemic mixture" points to the second stereochemical option:

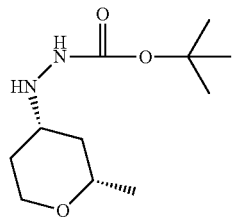

This principle applies to other depicted structures as well.

Synthesis

In the following the manufacture of compounds which exemplify the present invention is described. In case the process of manufacture of a specific compound has not been disclosed literally, the skilled person in the art will find a description of analogue procedures within these descriptions which he can follow in principle. At some places it is said, the examples can be prepared in analogy to another example. If reference should be made to such an "analogue process" the reactions conditions are about the same, even if molar ratios of reagents and educts might to be adjusted. It also will be evident that starting materials within a described process can be varied chemically to achieve the same results, i.e. if a condensation reaction of an ester is described, in that the alcoholic component is a leaving group but not subject of the product, this alcoholic component may vary without significant changes of the procedure as such.

Starting Compounds:

Example 1A

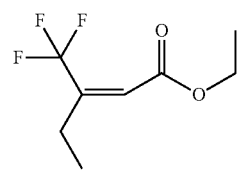

A solution of 70 g (201 mmol) carbethoxymethylene triphenylphosphorane in 300 mL diethyl ether was cooled to 0° C. and 25 g (198 mmol) 1,1,1-trifluorobutanone was added. The solution was warmed to room temperature and stirred over night. The reaction mixture was filtered and the filtrate was concentrated under reduced pressure (700 mbar and 40° C. bath temperature). The residue was purified by vacuum distillation (170 mbar and 130° C. bath temperature, main fraction: 95-96° C.). 29 g (75%) of the product were obtained as colourless oil.

HPLC-MS (Method 1): $R_t$: 1.77 min

MS (ESI pos): m/z=196 (M+H)$^+$

Example 1AA

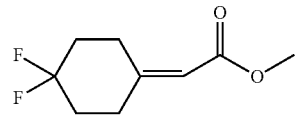

400 mg (10.0 mmol) sodium hydride (60% in mineral oil) was suspended in 10 ml THF and cooled to 4° C. While being stirred, a solution of 1.3 ml (8.99 mmol) trimethylphosphono acetate in 10 ml THF was added. The mixture was stirred for 1 h at the same temperature. After this, a solution of 4,4-difluorocyclohexanone in 10 ml THF was added at 0° C. The mixture was allowed to warm to room temperature and stirred for 14 h. THF and water was added and the THF evaporated. The remainder was diluted with ethyl acetate, washed with water and saturated sodium hydrogen carbonate solution and evaporated to yield 1.49 g (95%) of the product.

MS (EI): m/z=190 (M)$^+$

The following examples 1B, 1C, 1D, 1E, 2A, 2B, 2C and 2D show how the racemic acids 3-trifluoromethyl-pentanoic acid and 3-trifluoromethyl-butyric acid can be transferred into the two enantiomeric forms of the free acid. The resolution can be done via separation of diastereomeric intermediates. The two pure enantiomeric forms of the free acid will be called enantiomer A, enantiomer B respectively. The corresponding diastereomeric intermediates will be called diastereomer A, diastereomer B respectively.

The same principle may be applied for enantiomeric resolution of other racemic mixtures if appropriate.

Example 1B

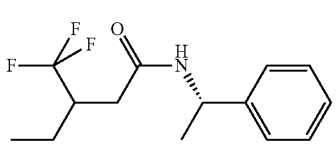

Diastereoisomer A

A solution of racemic 3-trifluoromethyl-pentanoic acid (8 g, 47 mmol), TBTU (16.6 g, 52 mmol) and diisopropylethylamine (24.1 mL, 141 mmol) in dimethylformamide (80 mL) was stirred at 20° C. for 1 h then (S)-(−)-1-phenylethylamine (10 g, 82 mmol) was added and the mixture was stirred for 16 h at 20° C. The solvent was removed and dichloromethane (200 mL) was added. The resulting mixture was washed with citric acid 10% in water (200 mL), $K_2CO_3$ 20% in water (100 mL) and dried over sodium sulphate. Evaporation of the solvent gave a crude solid that was mixed with methanol (10 mL) and filtered through a pad of activated basic alumina. Separation of diastereoisomers was obtained by flash chromatography on $SiO_2$ eluting with a mixture of cyclohexane/ethyl acetate 85/15.

4.5 g (35.8%) of the title compound were obtained as white solid.

Rf: 0.25 (cyclohexane/ethyl acetate 85/15, stained with basic $KMnO_4$)

HPLC-MS (Method 1 E hydro): $R_t$: 9.35 min

MS (APCI pos): m/z=274 (M+H)$^+$.

Chiral HPLC (Method Chiral 1): $R_t$: 5.58 min de: >99%

Example 1C

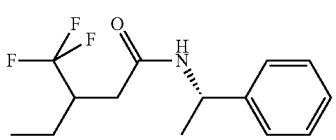

Diastereoisomer B 4.4 g (34.2%) of a white solid were obtained as second product from flash chromatography of Example 1B.

Rf: 0.20 (cyclohexane/ethyl acetate 85/15, stained with basic $KMnO_4$)

HPLC-MS (Method 1 E hydro): $R_t$: 9.33 min

MS (APCI pos): m/z=274 (M+H)$^+$.

Chiral HPLC (Method Chiral 1): $R_t$: 6.18 min de: >99%

Example 1D

3-Trifluoromethyl-pentanoic acid, Enantiomer A

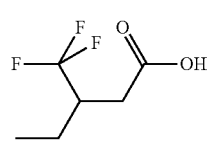

Enantiomer A

A solution of Example 1B (4.6 g, 17 mmol) in dioxane (15 mL) was treated with $H_2SO_4$ 70% in water (25 mL) and refluxed for 16 h. The mixture was cooled, basified to pH 14 with NaOH 32% in water, diluted with water (50 mL) and extracted with dichloromethane (2×200 mL). The resulting solution was acidified to pH 1 with 9N HCl, extracted with dichloromethane (3×500 mL) and the combined organic phases were dried. Evaporation of solvent afforded 2.47 g (86.3%) of a brown oil.

Rf: 0.66 (dichloromethane/methanol 9/1, stained with Bromocresol Green) Chiral HPLC (Method Chiral 1): $R_t$ 5.58 min ee: >99%

Example 1E

3-Trifluoromethyl-pentanoic acid, Enantiomer B

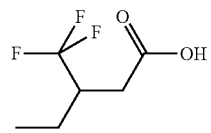

Enantiomer B

In analogy to the preparation of Example 1D, the title compound was obtained using Example 10 as starting material.

Yield: 80.3%

Rf: 0.66 (dichloromethane/methanol 9/1, stained with Bromocresol Green)

Chiral HPLC (Method Chiral 1): $R_t$: 5.08 min ee: >99%

Example 2A 4,4,4-Trifluoro-N—((R)-2-hydroxy-1-phenyl-ethyl)-3-methyl-butyramide, Diastereoisomer A

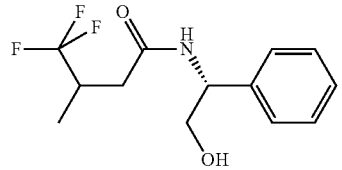 [SMILES: CC(CC(=O)N[C@@H](CO)c1ccccc1)C(F)(F)F]

A solution of 3-(trifluoromethyl)butyric acid (10 g, 64 mmol) in dimethylformamide (100 mL) was treated with N-(3-dimethylaminopropyl)-N'-ethylcarbodiimide hydrochloride (14.7 g, 77 mmol), 4-dimethyl-amino pyridine (11 g, 89.7 mmol) and (R)-(−)-phenylglycinol (9.9 g, 70.5 mmol). The mixture was stirred at 20° C. for 16 h, then concentrated to reduce the volume and treated with 10% citric acid in water (300 mL). The mixture was extracted with ethyl ether (2×200 mL) and the separated organic phase were washed with 10% NaHCO$_3$ (150 mL) and brine (150 mL). The organic phase was dried and evaporated to give 13.1 g of a crude white solid.

Separation of diastereoisomers was achieved by flash chromatography on SiO$_2$ eluting with a mixture of ethyl acetate/hexane 6/4.

5.32 g (30.2%) of the title compound were obtained as white solid.

Rf: 0.23 (ethyl acetate/hexane 6/4)
HPLC-MS (1 E hydro): R$_t$: 6.97 min
MS (APCI pos): m/z=276 (M+H)$^+$.

Example 2B 4,4,4-Trifluoro-N—((R)-2-hydroxy-1-phenyl-ethyl)-3-methyl-butyramide, Diastereoisomer B

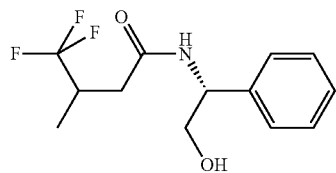 [SMILES: CC(CC(=O)N[C@@H](CO)c1ccccc1)C(F)(F)F]

3.08 g (17.5%) of a white solid were obtained as second product from flash chromatography of Example 2A.

Rf: 0.16 (ethyl acetate/hexane 6/4)
HPLC-MS (1E hydro): R$_t$: 6.92 min
MS (APCI pos): m/z=276 (M+H)$^+$.

Example 2C

Enantiomer A

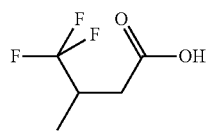

A solution of Example 2A (2 g, 7.26 mmol) in tetrahydrofuran (10 mL) was treated with H$_2$SO$_4$ 70% in water (10 mL) and refluxed for 16 h. The mixture was cooled, basified to pH 14 with NaOH 32% in water, diluted with water (50 mL) and extracted with dichloromethane (2×50 mL). The resulting solution was acidified to pH 1 with 9N HCl, extracted with dichloromethane (3×50 mL) and the combined organic phases were dried. Evaporation of solvent afforded 0.84 g (74.1%) of a brown oil.

HPLC-MS (1E hydro): R$_t$: 1.73 min
MS (APCI neg): m/z=155 (M−H)$^−$.
Chiral HPLC (Method Chiral 2): R$_t$: 6.92 min ee: 99%

Example 2D

Enantiomer B

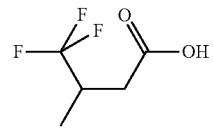

In analogy to the preparation of Example 2C, the title compound was obtained using Example 2B as starting material. Obtained 1.4 g (8.96 mmol)

Yield: 82.3%
HPLC-MS (1E hydro): R$_t$: 1.30 min
MS (APCI neg): m/z=155 (M−H)$^−$.
Chiral HPLC (Method Chiral 2): R$_t$: 6.49 min ee: 98.6%

Example 3A 2-(4-Trifluoromethyl-pyridin-2-yl)-malonic acid diethyl ester

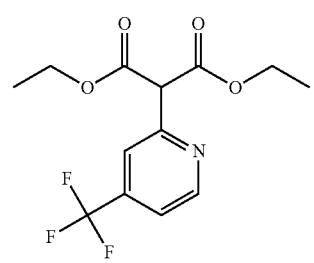 [SMILES: CCOC(=O)C(C(=O)OCC)c1cc(C(F)(F)F)ccn1]

A suspension of sodium hydride 60% in mineral oil (1.65 g, 41 mmol) in anhydrous dioxane (36 mL) was treated with diethylmalonate (6.3 mL, 41 mmol) at 25° C. and heated to 60° C. for 30 min. Cuprous chloride (1.63 g, 17 mmol) was added, the mixture was heated to 80° C. and 2-chloro-4-(trifluoromethyl)-pyridine was added and the was heating increased to 100° C. for 16 h.

After cooling to 20° C. the mixture was acidified with 37% HCl, diluted with water (120 mL) and extracted with dichloromethane (2×60 mL). The organic phase was dried and evaporated to give a crude oil that was purified by flash chromatography eluting with n-hexane/ethyl acetate from 95/5 to 60/40.

1.9 g (38%) were obtained as a colourless oil.
HPLC-MS (2F): R$_t$: 12.24 min
MS (ESI pos): m/z=306 (M+H)$^+$.

Example 4A

The following example was synthesized in analogy to the preparation of Example 5U, using the corresponding acid (Sinova Inc., Bethesda, Md. 20814, USA) as starting material.

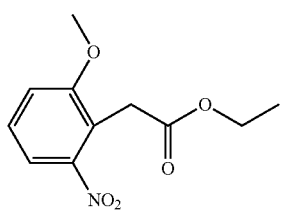 [SMILES: CCOC(=O)Cc1c(OC)cccc1[N+](=O)[O-]]

HPLC-MS (Method 1): $R_t$: 1.47 min
MS (ESI pos): m/z=194 (M+H-EtOH)$^+$

Example 4B

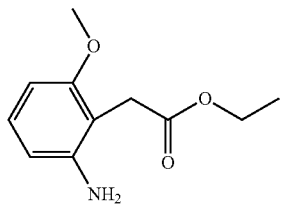

2.0 g (8.6 mmol) of Example 4A was dissolved in 40 mL ethanol, Pd (10% on charcoal) was added, and the mixture was hydrogenated at room temperature (2 h, 50 psi). The reaction mixture was filtered and the residue washed with ethanol. The solvent was evaporated by reduced pressure. 1.80 g (100%) of the product were obtained.

HPLC-MS (Method 1): $R_t$: 0.91 min
MS (ESI pos): m/z=210 (M+H)$^+$

Example 5A

3-Trifluoromethyl-pentanoic acid methyl ester, Enantiomer A

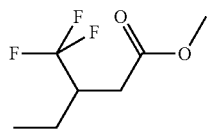

Enantiomer A

To a stirred solution of Example 1D (250 mg, 1.47 mmol) in dichloromethane (10 mL) and methanol (0.25 mL), under nitrogen atmosphere, trimethylsilyldiazomethane (2.0 M solution in diethyl ether) (2.1 mL, 4.19 mmol) was added drop wise at 0° C. The reaction mixture was stirred keeping the temperature below 5° C. for 1 h. The solvent was removed (40° C., 25 bar) yielding 250 mg (75.4%) of a yellow oil that was used in the next step without further purification.

GC (Method 3A): $R_t$: 3.29 min
MS (EI): m/z: 165 (M−19)$^+$, 155 (M−29)$^+$, 153 (M−31)$^+$ The following examples were synthesized in analogy to the preparation of Example 5A, using the corresponding acids as starting materials:

| | structure | starting material: carboxylic acid | $R_t$ [min] | MS m/z |
|---|---|---|---|---|
| Example 5B Enantiomer A | 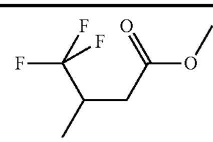 | Example 2C | 8.01 (Method 3A) | 170 [EI] |
| Example 5C Enantiomer B | 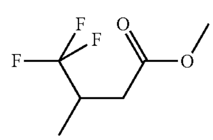 | Example 2D | 8.01 (Method 3A) | 170 [EI] |
| Example 5D Enantiomer B | 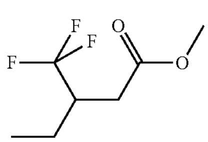 | Example 1E | 3.29 (Method 3A) | 165 (M − 19)$^+$, 155 (M − 29)$^+$, 153 (M − 31)$^+$ [EI] |
| Example 5E | 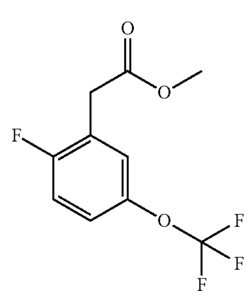 [SMILES: COC(=O)Cc1cc(OC(F)(F)F)ccc1F] | | 7.82 (Method 3A) | 252 [EI] |

-continued

| | structure | starting material: carboxylic acid | $R_t$ [min] | MS m/z |
|---|---|---|---|---|
| Example 5F | 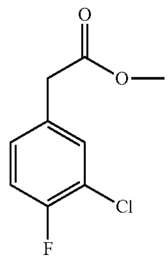 | | 9.53 (Method 3A) | 202 [EI] |
| Example 5G Enantiomer S | 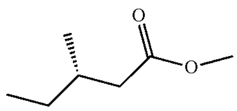 | | 3.92 (Method 3A) | 130 [EI] |
| Example 5H | 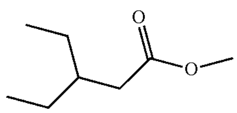 | | 5.09 (Method 3A) | 115 $(M-29)^{\pm}$ [EI] |
| Example 5HA cis, racem. mixture | 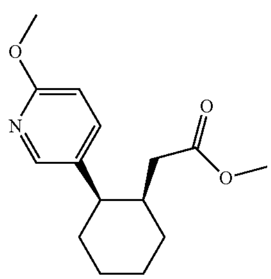 [SMILES: COC(=O)C[C@H]1CCCC[C@H]1c1ccc(OC)nc1] | Example 18A | 1.22 (Method 1) | 264 [ESI, $(M+H)^+$] |

Example 5I

[2-(1-Acetyl-piperidin-4-yloxy)-phenyl]acetic acid methyl ester

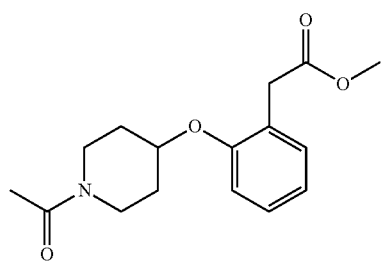 [SMILES: COC(=O)Cc1ccccc1OC1CCN(C(C)=O)CC1]

Di-tert-butylazodicarboxylate (305 mg, 1.32 mmol) was dropped to a solution of 1-(4-hydroxy-piperidin-1-yl)-ethanone (259 mg, 1.8 mmol) in tetrahydrofuran (4 mL) under nitrogen atmosphere. Then (2-hydroxy-phenyl)-acetic acid methyl ester (200 mg, 1.2 mmol) and triphenylphosphine (347 mg, 1.3 mmol) were added. The yellow mixture was stirred at 20° C. for 16 h. The solvent was evaporated and the residue was purified on silica using hexane/ethyl acetate mixture of increasing polarity (from 70% to 100% ethyl acetate) as eluent to give 195 mg (55.6%) of a colourless oil.

HPLC-MS (Method Grad_C8_NH$_4$COOH): $R_t$: 2.67 min MS (ESI pos): m/z=292 (M+H)$^+$.

The following examples were synthesized in analogy to the preparation of Example 5G, using the corresponding alcohols as starting materials:

| | Structure | starting material: Alcohol | Rf | $R_t$ [min] | MS m/z |
|---|---|---|---|---|---|
| Example 5J racem. mixture | 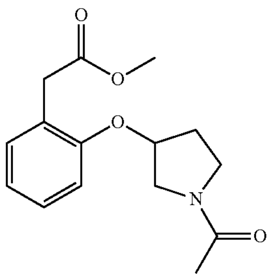 | | | 2.53 (Method Grad_C8_NH₄COOH) | 292 (M + H)⁺ |
| Example 5K | 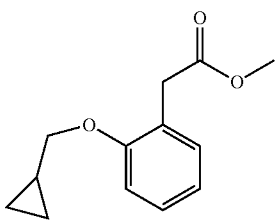 [SMILES: COC(=O)Cc1ccccc1OCC1CC1] | | 0.35 (hexane/ethyl acetate 8/2) | | |
| Example 5L | 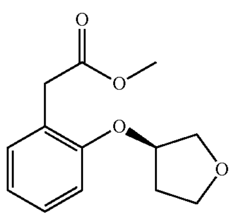 [SMILES: COC(=O)Cc1ccccc1O[C@@H]1CCOC1] | | 0.2 (hexane/ethyl acetate 7/3) | | |
| Example 5M | 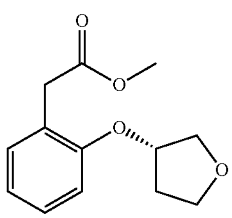 [SMILES: COC(=O)Cc1ccccc1O[C@H]1CCOC1] | | 0.2 (hexane/ethyl acetate 7/3) | | |
| Example 5O | 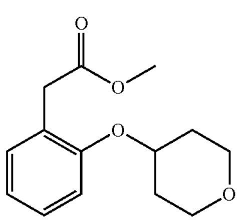 [SMILES: COC(=O)Cc1ccccc1OC1CCOCC1] | | 0.25 (hexane/ethyl acetate 7/3) | | |
| Example 5P | 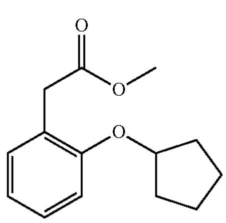 [SMILES: COC(=O)Cc1ccccc1OC1CCCC1] | | 0.35 (hexane/ethyl acetate) | | |

Example 5Q (3-Methoxy-pyridin-2-yl)-acetic acid methyl ester

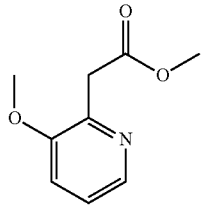

A mixture of (3-methoxy-2-pyridin-2-yl)acetonitrile (400 mg, 2.7 mmol) in 2 mL of methanol and 96% sulphuric acid (1.8 mL, 32 mmol) was heated in a microwave oven at 120° C. for 1 h. The mixture was cooled to 0° C., basified with solid NaHCO$_3$, diluted with water (2 mL) and extracted with dichloromethane. The separated organic phase was dried and evaporated to give 450 mg (92%) of a dark yellow oil that was used in the next step without further purification.

HPLC-MS (Method Grad_C8_NH$_4$COOH): R$_t$: 1.92 min

MS (ESI pos): m/z=182 (M+H)$^+$.

Example 5R (4-Trifluoromethyl-pyridin-2-yl)-acetic acid ethyl ester

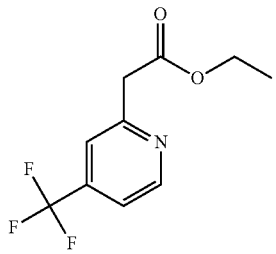 [SMILES: CCOC(=O)Cc1cc(C(F)(F)F)ccn1]

A solution of Example 3A (1.0 g, 3.27 mmol) in anhydrous DMSO (8 mL) was treated with water (60 microL, 3.27 mmol) and lithium chloride (347 mg, 8.2 mmol). The resulting mixture was heated at 120° C. for 16 h. After cooling to 20° C. the mixture was treated with brine (12 mL) and extracted with ethyl acetate (3×20 mL). The organic phase was dried and evaporated to give a crude oil that was purified by flash chromatography eluting with n-hexane/ethyl acetate 8/2.

390 mg (51%) were obtained as a colourless oil.

HPLC-MS (Method 2F): R$_t$: 11.09 min

MS (ESI pos): m/z=234 (M+H)$^+$

Example 5S (6-Trifluoromethyl-pyridin-2-yl)-acetic acid ethyl ester

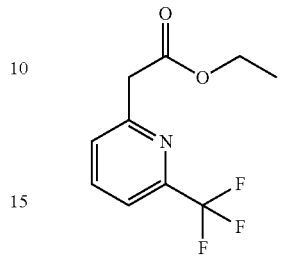

A mixture of caesium carbonate (1.87 g, 5.75 mmol) and tri-t-butylphosphine (107 μL, 0.44 mmol) in dry 1,2 dimethoxyethane (10 mL) was treated with tris-(dibenzylideneacetone)di-palladium (81 mg, 0.09 mmol), 2-Bromo-6-(trifluoromethyl)pyridine (1 g, 4.42 mmol) and diethylmalonate (0.8 mL, 5.3 mmol) under nitrogen atmosphere. The mixture was heated to 150° C. for 30 min in a microwave oven. After cooling to 20° C. the mixture was treated with a saturated solution of ammonium chloride (120 mL) and extracted with ethyl ether (3×80 mL). The organic phase was dried and evaporated to give a crude oil that was purified by flash chromatography eluting with n-hexane/ethyl ether 6/1.

460 mg (81%) were obtained as a colourless oil.

GC (Method 3A): R$_t$: 8.28 min

MS (EI): m/z=233 (M)$^+$

Example 5T

Racemic Mixture

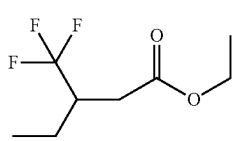

29 g (148 mmol) of Example 1A was combined with 2 g Pd/C (10%) and hydrogenated at room temperature (6 h, 15 psi). The reaction mixture was filtered and washed with diethyl ether. The solvent was evaporated under reduced pressure (500 mbar, 40° C. bath temperature). 27.6 g (94%) of the product were obtained as a colourless liquid.

HPLC-MS (Method 1): R$_t$: 1.65 min

Example 5TA

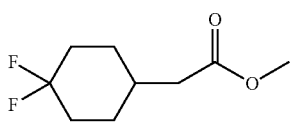

1.49 g (95%, 7.43 mmol) was dissolved in 20 ml ethanol and hydrogenated over 150 mg Pd/C (10%) at atmospheric pressure for 14 h. The mixture was filtered and the solvent removed to yield 1.27 g (89%) of the product.

Example 5U

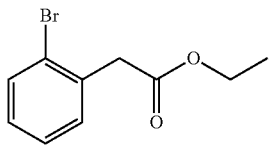

A solution of 15 g (69.8 mmol) of (2-bromo-phenyl)-acetic acid in 50 mL ethanol was cooled to 0° C. and 8 mL (110 mmol) thionylchloride was added drop wise. The reaction mixture was heated to 50° C. over night. After cooling to room temperature the solvent was removed under reduced pressure. The residue was mixed with ethyl acetate and filtered over 30 g basic aluminium oxide. The filtrate was evaporated under reduced pressure. 18 g (92%) of the product were obtained.

HPLC-MS (Method 1): $R_t$: 1.62 min

MS (ESI pos): m/z=243/45 (Br) (M+H)$^+$

The following examples were synthesized in analogy to the preparation of Example 5U, using the corresponding acids as starting materials.

| | structure | starting material | $R_t$ [min] | MS (ESI m/z) |
|---|---|---|---|---|
| Exp. 5V | 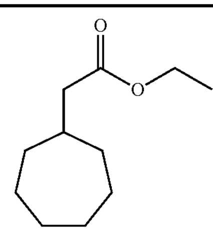 | | | 185 (M + H)$^+$ |
| Exp. 5Y | 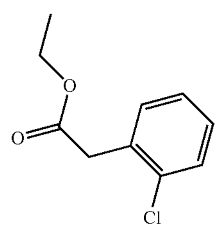 | | 1.56 (Method 1) | 199/201 (Cl) (M + H)$^+$ |
| Exp. 5W | 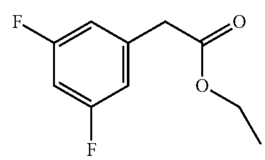 | | 1.53 (Method 1) | 201 (M + H)$^+$ |
| Exp. 5X | 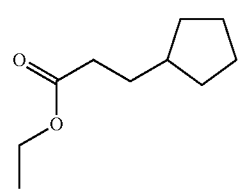 | | | 171 (M + H)$^+$ |
| Exp. 5Z | 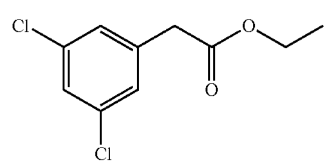 | | 1.74 (Method 1) | 233/235/237 (2Cl) (M + H)$^+$ |
| Exp. 5AA racem. mixture | 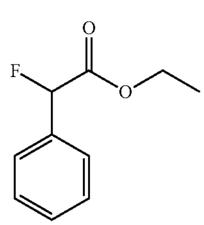 | | | 133 (M + H)$^+$ |

| | structure | starting material | R$_t$ [min] | MS (ESI m/z) |
|---|---|---|---|---|
| Exp. 5AB | ethyl 2,2-difluoro-2-phenylacetate | 2,2-difluoro-2-phenylacetic acid | | 201 (M + H)$^+$ |
| Exp. 5AC | ethyl 2-cyclopentylacetate | 2-cyclopentylacetic acid | 1.65 (Method 1) | 157/58 (M + H)$^+$ |
| Exp. 5AD | ethyl 2-(2-methoxyphenyl)acetate | 2-(2-methoxyphenyl)acetic acid | 1.36 (Method 1) | 195 (M + H)$^+$ |
| Exp. 5AE | ethyl 2-(2-(trifluoromethoxy)phenyl)acetate | 2-(2-(trifluoromethoxy)phenyl)acetic acid | 1.69 (Method 1) | 249/50 (M + H)$^+$ |
| Exp. 5AF racem. mixture | methyl 2-phenylpropanoate | 2-phenylpropanoic acid | | commercially available |
| Exp. 5AG | ethyl 2-(2-fluorophenyl)acetate | 2-(2-fluorophenyl)acetic acid | 1.46 (Method 1) | |
| Exp. 5AH | ethyl 2-(3-(trifluoromethyl)phenyl)acetate | 2-(3-(trifluoromethyl)phenyl)acetic acid | 1.63 (Method 1) | |

| | structure | starting material | R$_t$ [min] | MS (ESI m/z) |
|---|---|---|---|---|
| Exp. 5AI | 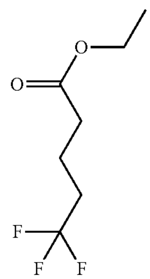 | | | 185 (M + H)$^+$ |
| Exp. 5AJ | 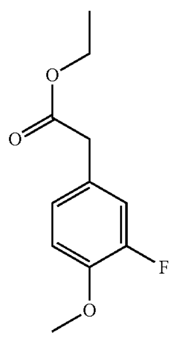 | | 1.43 (Method 1) | 213 (M + H)$^+$ |
| Exp. 5AK | 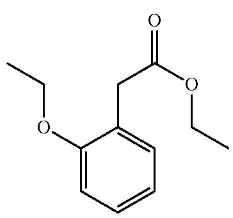 | | | |
| Exp. 5AL | 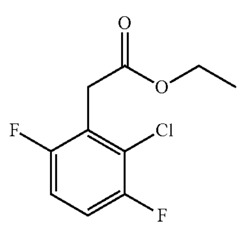 | | 1.58 (Method 1) | 235/237 (Cl) (M + H)$^+$ |
| Exp. 5ALA | 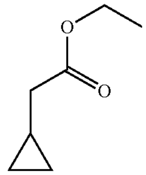 | | 1.29 (Method 1) | 129 (M + H)$^+$ |
| Exp. 5ALB | 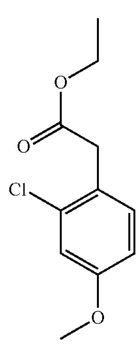 | | 1.55 (Method 1) | 229/231 (Cl) (M + H)$^+$ |

| | structure | starting material | $R_t$ [min] | MS (ESI m/z) |
|---|---|---|---|---|
| Exp. 5ALC | ethyl 3-cyclobutylpropanoate | 3-cyclobutylpropanoic acid | 1.62 (Method 1) | 157 (M + H)⁺ |
| Exp. 5ALD | ethyl 3-(2-methoxyphenyl)propanoate | 3-(2-methoxyphenyl)propanoic acid | 1.56 (Method 1) | 209 (M + H)⁺ |
| Exp. 5ALE | ethyl 2-(o-tolyl)acetate | 2-(o-tolyl)acetic acid | 1.59 (Method 1) | 291 (M + H)⁺ |
| Exp. 5ALF | ethyl 2-(2-bromo-5-chlorophenyl)acetate | 2-(2-bromo-5-chlorophenyl)acetic acid | 1.86 (Method 5) | 277/279/281 (M + H)⁺ (Cl/Br) |
| Exp. 5ALG | ethyl 2-(2-bromo-5-fluorophenyl)acetate | 2-(2-bromo-5-fluorophenyl)acetic acid | 1.60 (Method 1) | 261/263 (Br) (M + H)⁺ |

Example 5AM

The following example was synthesized in analogy to the preparation of Example 5U, using the corresponding acid as starting material and methanol as solvent.

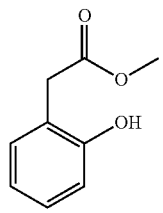

HPLC-MS (Method 1): $R_t$: 1.04 min

MS (ESI pos): m/z=167 (M+H)⁺

The following examples were synthesized in analogy to the preparation of Example 5AM, using the corresponding acids as starting materials.

| structure | starting material | R$_t$ [min] | MS (ESI, m/z) |
|---|---|---|---|
| 5AMA 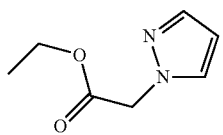 | | 152 (Method 1) | 236 (M + NH$_4$)$^+$ |

Example 5AN 6.0 g (88.5 mmol) pyrazole was dissolved in 60 mL DMSO and 10.4 g (93 mmol) potassium-tert-butylate was added in portions, keeping the temperature between 20-25° C. The reaction mixture stirred 10 min at room temperature. 10.8 mL (98 mmol) ethyl bromacetate was added drop wise, keeping the temperature between 25-35° C. The reaction mixture was stirred for 2 h at room temperature. The reaction mixture was added to a saturated aqueous solution of NaCl and extracted with ethyl acetate. The organic layer was dried, filtered, and the filtrate was evaporated under reduced pressure. The residue was purified by preparative MPLC (SiO$_2$, eluent dichloromethane/methanol 95/5). 10.4 g (38%) of the product were obtained.

Example 5AO

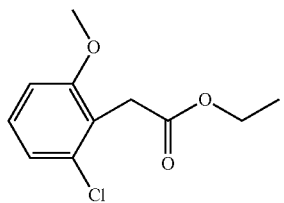

1.83 g (7.7 mmol) of Example 4B was mixed with in 60 mL 4N HCl and cooled with an ice bath. A solution of 1.15 g (16.4 mmol) sodium nitrite in 13.5 mL water was added drop wise. After 10 min a solution of 3.9 g (39.5 mmol) copper(I)chloride in 20 mL conc. HCl was added drop wise. The reaction mixture was allowed to turn to room temperature and stirred for 30 min. The mixture was extracted with ethyl acetate. The organic layer was neutralized with potassium carbonate, filtered over celite and the filtrate extracted with water. The organic layer was dried, filtered and the filtrate was evaporated under reduced pressure. 1.24 g (62%) of the product were obtained.

HPLC-MS (Method 1): R$_t$: 1.60 min
MS (ESI pos): m/z=229/231 (Cl) (M+H)$^+$

Example 5AP

Under argon 1.00 g (4.11 mmol) of example 5U, 540 mg (4.95 mmol) 3-methylpyridone and 80 mg (0.42 mmol) copper-(I) iodide were mixed with 5 ml DMSO and 1.14 g (8.25 mmol) potassium carbonate and 120 mg (0.82 mmol) 8-hydroxyquinoline were added. The mixture was stirred for 48 h at 120° C. After cooling to room temperature the mixture was dissolved in ethyl acetate and washed with 1 M HCl and saturated sodium chloride solution. The organic phase was separated, dried and evaporated. The residue was purified by HPLC (eluent A: water+0.13% TFA, eluent B: acetonitrile). The acetonitrile was evaporated and the remainder extracted with ethyl acetate. The organic phase was dried and evaporated to yield 633 mg (57%) of the desired product.

HPLC-MS (Method 1): R$_t$: 1.56 min
MS (ESI pos): m/z=272 (M+H)$^+$

Example 6A

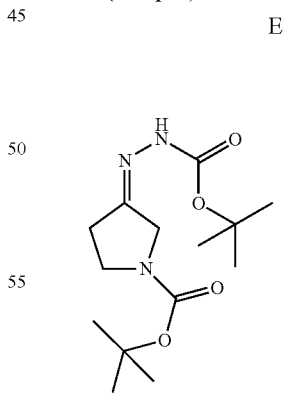

10 g (54 mmol) 1-N-Boc-3-pyrrolidinone was dissolved in 50 mL ethanol and 7.3 g (55.2 mmol) tert-butyl carbazate was added. The reaction mixture was stirred at room temperature for 2 h. The solvent was evaporated by reduced pressure. The residue was purified by preparative MPLC (SiO$_2$, eluent dichloromethane/methanol 95/5). 18 g (89%) of the product were obtained as oil.

HPLC-MS (Method 1): R$_t$: 1.35 min
MS (ESI neg.): m/z=298 (M−H)$^-$

Example 6B

The following example was synthesized in analogy to the preparation of Example 6A, using 1-N-Boc-3-piperidone as starting material.

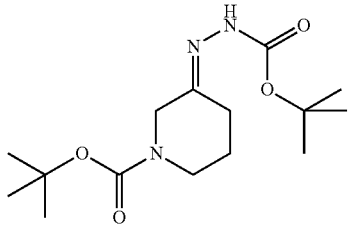 [SMILES: CC(C)(C)OC(=O)N/N=C1\CCCN(C(=O)OC(C)(C)C)C1]

HPLC-MS (Method 1): R$_t$: 1.45 min

Example 7A

Racemic Mixture

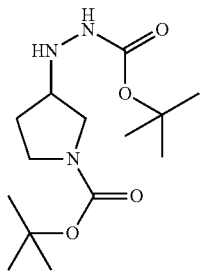 [SMILES: CC(C)(C)OC(=O)NNC1CCN(C(=O)OC(C)(C)C)C1]

18 g (48 mmol) of Example 6A was dissolved in 300 mL methanol, 2.5 g Pd/C (10%) was added, and the mixture was hydrogenated at room temperature (8 h, 50 psi). The reaction mixture was filtered and the residue washed with methanol. The solvent was evaporated by reduced pressure. 16 g of product were obtained as a colourless oil and used without further purification.

HPLC-MS (Method 1): R$_t$: 1.36 min

Example 7B

Racemic Mixture

The following example was synthesized in analogy to the preparation of Example 7A, using Example 6B as starting material.

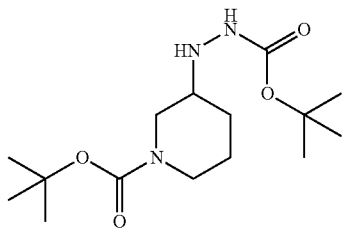 [SMILES: CC(C)(C)OC(=O)NNC1CCCN(C(=O)OC(C)(C)C)C1]

HPLC-MS (Method 1): R$_t$: 1.42 min
MS (ESI pos): m/z=316 (M+H)$^+$

Example 7C

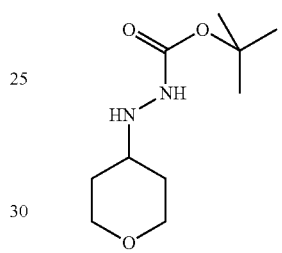

10 g (100 mmol) of tetrahydropyran-4-one was dissolved in 100 mL methanol and 14.5 g (110 mmol) tert-butylcarbazate was added. The reaction mixture was stirred at room temperature for 2 h. The solvent was evaporated by reduced pressure. The residue was mixed with 140 mL acetic acid (50%), 6.9 g (110 mmol) sodium cyanoborohydride was added and the mixture was stirred at room temperature over night. The reaction mixture was neutralized with 4M NaOH and extracted with dichloromethane. The organic layer was washed with a saturated aqueous solution of sodium hydrogen carbonate and a saturated aqueous solution of sodium chloride.

The organic layer was dried over sodium sulphate, filtered, and the filtrate was concentrated under reduced pressure. 19 g (88%) of the product were obtained as a white solid.

MS (ESI pos): m/z=217 (M+H)$^+$

The following example was synthesized in analogy to the preparation of Example 7C using the corresponding keton as starting material.

| | Structure | starting material: keton | R$_t$ [min] | MS m/z |
|---|---|---|---|---|
| Example 7CA cis, racem. mixture | 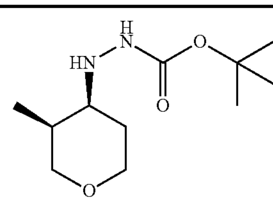 | | 11.12 (Method 3A) | 174 [EI, (M − 56)$^+$] |

-continued

| Structure | starting material: keton | $R_t$ [min] | MS m/z |
|---|---|---|---|
| Example 7CB trans, racem. mixture | | 11.22- (Method 3A) | 174 [EI, (M − 56)⁺] |
| Example 7CC | | 0.99 (Method 1) | 177 [ESI, (M − 56 + H)⁺] |

Example 7D

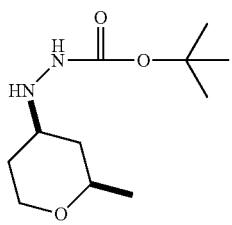 [SMILES: C[C@@H]1C[C@H](NNC(=O)OC(C)(C)C)CCO1]

Cis-Racemic Mixture

A solution of 2-methyl-tetrahydro-pyran-4-one (2.2 g, 19.7 mmol) in methanol (30 mL) was treated with tert-butyl carbazate (2.6 g, 19.7 mmol) and stirred for 3 h at 20° C. Evaporation of solvent affords a white solid that was mixed with 30 mL acetic acid (50% in water), and treated with sodium cyanoborohydride (1.2 g, 19.7 mmol) portion wise. The mixture was stirred at 20° C. for 16 h then neutralized with 5N NaOH and extracted with dichloromethane. The organic phase was washed with a saturated solution of NaHCO$_3$ and brine, dried, filtered and evaporated to give a crude solid. Separation of diastereoisomers was obtained by flash chromatography on SiO$_2$ eluting with a mixture of cyclohexane/ethyl acetate mixture of increasing polarity (from 7/3 to 1/1) to give 1.85 g (41%) of a white solid.

Rf: 0.29 (hexane/ethyl acetate 1:1)

HPLC-MS (Method Grad_90_10_C8_acidic): R$_t$: 1.79 min

MS (ESI pos): m/z=131 (M−100+H)⁺

The cis configuration between methyl and carbazyl group was implied by the ROESY correlation for H-2/H-4.

Example 7E

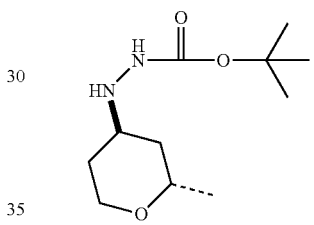

Trans-Racemic mixture 0.7 g (16%) of a colourless oil were obtained as the second product from flash chromatography of Example 7D Rf: 0.29 (hexane/ethyl acetate 1:1 stained with Pancaldi's reagent)

HPLC-MS (Method Grad_90_10_C8_acidic): R$_t$: 1.96 min

MS (ESI pos): m/z=131 (M−100+H)⁺

Example 8A

Racemic Mixture

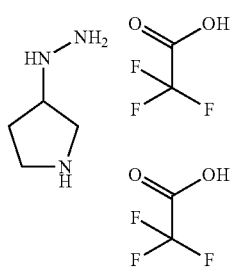

14 g (46.5 mmol) of Example 7A were dissolved in 50 mL dichloromethane, cooled with an ice bath and 25 mL (325 mmol) trifluoroacetic acid was added. The reaction mixture was stirred 3 h at room temperature. The solvent was evaporated under reduced pressure. The residue was purified by preparative MPLC (SiO$_2$, eluent dichloromethane/methanol 8/2). 12 g (78%) of the product were obtained.

Example 8B

The following example was synthesized in analogy to the preparation of Example 8A, using Example 7C as starting material.

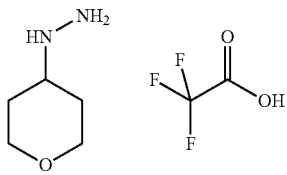 [SMILES: NNC1CCOCC1 ; O=C(O)C(F)(F)F]

MS (ESI pos): m/z=117 (M+H)$^+$

Example 8C

Racemic Mixture

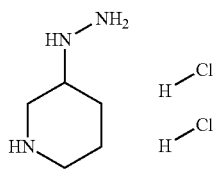

13.0 g (37.1 mmol) of Example 7B were dissolved in 5 mL dioxane and 93 mL (371 mmol) of hydrochloride acid in dioxane (4 M) were added. The reaction mixture was stirred over night at room temperature. 40 mL diethyl ether were added and the mixture stirred 15 min at room temperature. The reaction mixture was filtered. 7.0 g (100%) of the product were obtained as white solid.

The following examples were synthesized in analogy to the preparation of example 8C using the corresponding Boc-hydrazine as starting material.

| Structure | | starting material: Boc-hydrazine | MS m/z |
|---|---|---|---|
| Example 8CA cis, racem. mixture | 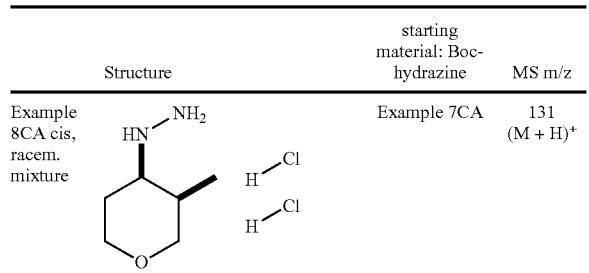 | Example 7CA | 131 (M + H)$^+$ |
| Example 8CB trans, racem. mixture | 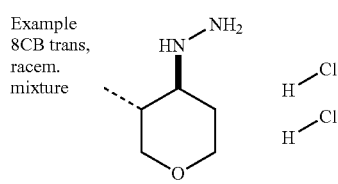 | Example 7CB | 131 (M + H)$^+$ |

-continued

| Structure | | starting material: Boc-hydrazine | MS m/z |
|---|---|---|---|
| Example 8CC | 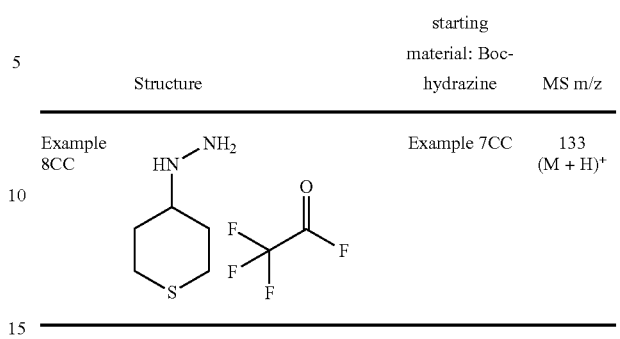 | Example 7CC | 133 (M + H)$^+$ |

Example 8D

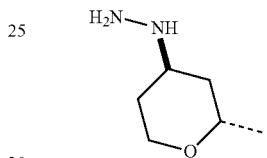

Trans-Racemic Mixture

A solution of Example 7E (700 mg, 3 mmol) in dioxane (5 mL) was treated with 4N HCl in dioxane (15 mL, 60 mmol) and the mixture stirred at 20° C. for 18 h. The solvent was evaporated to give 560 mg (91%) of a sticky solid that was used in the next step without further purification.

HPLC-MS (Grad_C8_NH$_4$COOH_Lowmass): R$_t$: 0.67 min

MS (ESI pos): m/z=131 (M+H)$^+$

Example 8E

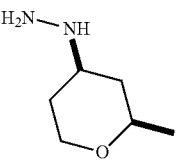

Cis-Racemic Mixture

In analogy to the preparation of Example 8D, the title compound was obtained using Example 7D as starting material.

Yield: 68.3%

HPLC-MS (Method Grad_C8_NH$_4$COOH_Lowmass): R$_t$: 0.70 min

MS (ESI pos): m/z=131 (M+H)$^+$

Example 9A

Racemic Mixture

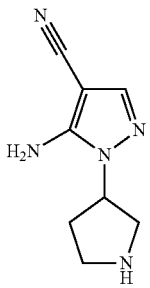

32.0 g (77.8 mmol) of Example 8A was mixed with 12.0 g (98.3 mmol) of ethoxymethylene-malonodinitrile in 250 mL ethanol, and 40 mL (288 mmol) of triethylamine were added. The reaction mixture was heated to 50° C. for 2 h. After cooling to room temperature the solvent was removed under reduced pressure. The residue was purified by preparative MPLC (SiO$_2$, eluent dichloromethane/methanol 8/2).

HPLC-MS (Method 1): R$_t$: 0.29 min

The following examples were synthesized in analogy to the preparation of Example 9A, using the corresponding hydrazines as starting materials.

| | structure | starting material | R$_t$ [min] | MS (ESI, m/z) |
|---|---|---|---|---|
| Exp. 9B racem. mixture | 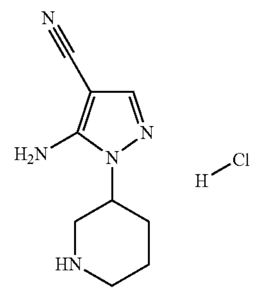 [SMILES: N#Cc1cnn(C2CCCNC2)c1N ; Cl] | Example 8C | 0.59 (Method 1) | 192 (M + H)$^+$ |
| Exp. 9C | 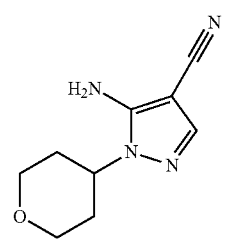 [SMILES: N#Cc1cnn(C2CCOCC2)c1N] | Example 8b | 0.76 (Method 1) | 193 (M + H)$^+$ |
| Exp. 9D | 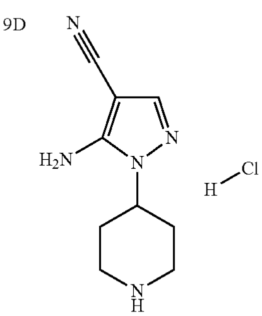 | | 0.32 (Method 1) | 192 (M + H)$^+$ |
| Exp. 9E | 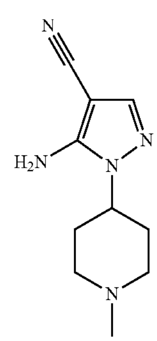 | | 0.40 (Method 1) | 206 (M + H)$^+$ |

| structure | starting material | R$_t$ [min] | MS (ESI, m/z) |
|---|---|---|---|
| Example 9EA cis, racem. mixture | Example 8CA | 1.90 Grad C8—NH$_4$CCOH | 207 (M + H)$^+$ |
| Example 9EB trans, racem. mixture | Example 8CB | 1.87 Grad C8—NH$_4$CCOH | 207 (M + H)$^+$ |
| Example 9EC | Example 8CC | 1.01 (Method 1) | 209 (M + H)$^+$ |

Example 9F

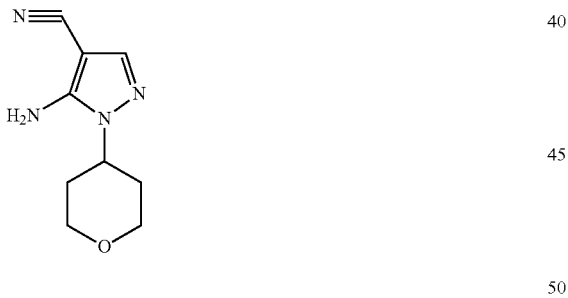

A mixture of 4.4 g (38 mmol) of (tetrahydro-pyran-4-yl)-hydrazine and 4.7 g (38 mmol) of ethoxymethylene-malono-nitrile in 90 mL of ethanol and 10.5 mL (103 mmol) of triethylamine was stirred at 50° C. for 30 min. After cooling to 20° C. the solvent was removed under reduced pressure and the residue was treated with a mixture of water/dichloromethane=1/1. The resulting suspension was stirred for 15 min and then filtered to give a yellow solid that was washed subsequently with dichloromethane, water and dichloromethane. The solid was dried at 45° C. under reduced pressure. 2.7 g (37%) of the title compound were obtained as yellow solid and used in the next step without further purification.

The following examples were synthesized in analogy to the preparation of Example 9F, using the corresponding hydrazines as starting materials:

| Structure | starting material: hydrazine | R_t [min] | MS m/z |
|---|---|---|---|
| Example 9G racem. mixture 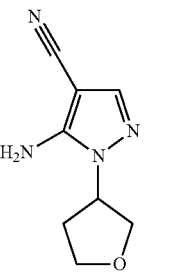 [SMILES: N#Cc1cnn(C2CCOC2)c1N] | 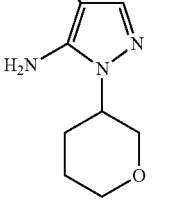 | 1.31 (Method Grad_90_10_C8_ acidic) | 179 (M + H)+ |
| Example 9H racem. mixture 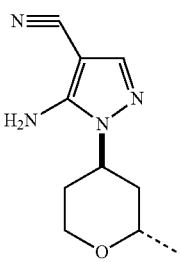 | 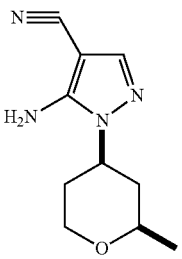 | 4.97 (Method 1E hydro) | 193 (M + H)+ |
| Example 9I trans; racem. mixture | Example 8D | 2.14 (Method Grad_10_90_C8_ acidic) | 207 (M + H)+ |
| Example 9J cis; racem. mixture | Example 8E | 1.91 (Method Grad_10_90_C8_ acidic) | 207 (M + H)+ |

Example 9GA

Enantiomer A

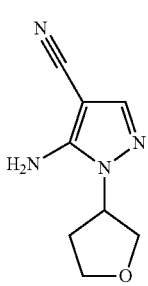

Enantiomer A

Example 9G was submitted for chiral separation to isolate its enantiomers. The enantiomer labeled A, of unknown but single stereochemistry was isolated using the following conditions.

| | |
|---|---|
| Amount supplied | 5 g |
| Chiral Column | Daicel Chiralpak AD 50 × 300 mm |
| Mobile phase | n-Hexane (60%)/methyl-tert-butyl ether (40%)/Ethanol (5%) v/v |
| Flow rate | 20 mL/min |
| Detection | UV at 254 nm |
| Injection mode | continuous |

Obtained 1 g of enantiomer A.

Enantiomeric excess 99.3%; retention time 27.83 min; (analytical method: Chiral 3)

Example 9GB

Enantiomer B

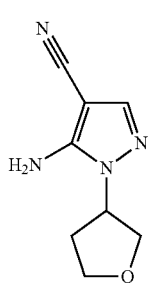

Isolated using the same conditions as enantiomer A, obtaining 0.5 g; enantiomeric excess 96.7%; $R_t$: 30.94 min; (analytical method: Chiral 3).

Example 10A

Racemic Mixture

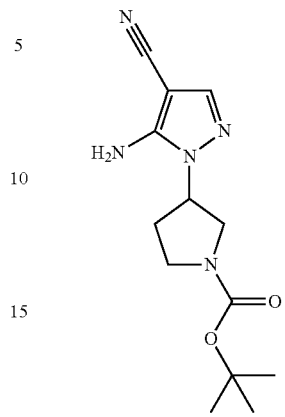

Enantiomer B 4.0 g (22.6 mmol) of Example 9A were mixed with in 60 mL tetrahydrofuran, and 5.7 g (30 mmol) di-tert-butyl-dicarbamate was added. The reaction mixture was heated to 60° C. for 5 h. After cooling to room temperature the solvent was removed under reduced pressure. The residue was purified by preparative MPLC ($SiO_2$, eluent dichloromethane/methanol 9/1).

HPLC-MS (Method 1): $R_t$: 1.28 min

MS (ESI pos): m/z=278 (M+H)$^+$

The following examples were synthesized in analogy to the preparation of Example 10A, using the corresponding pyrazoles as starting materials.

|  | structure | starting material | $R_t$ [min] | MS (ESI, m/z) |
|---|---|---|---|---|
| Exp. 10B | (structure shown) | Example 9D | 1.30 (Method 1) | 292 (M + H)$^+$ |

-continued

| | structure | starting material | R$_t$ [min] | MS (ESI, m/z) |
|---|---|---|---|---|
| Exp. 10C racem. mixture | 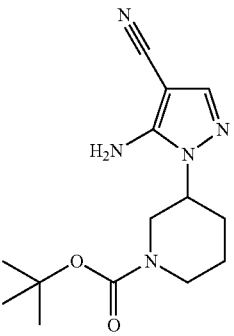 [SMILES: CC(C)(C)OC(=O)N1CCCC(n2ncc(C#N)c2N)C1] | Example 9B | 1.33 (Method 1) | 292 (M + H)$^+$ |

Example 11A

Racemic Mixture

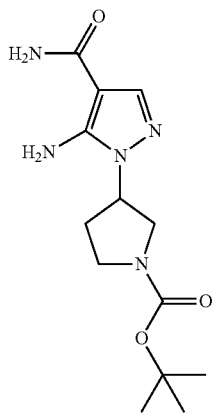

2.4 g (8.96 mmol) of Example 10A were dissolved in 30 mL ethanol. At room temperature a solution of 10 mL (120 mmol) hydrogen peroxide (35% in water) and 50 mL ammonia (25% in water) was added slowly over a period of 10 min. The reaction mixture was stirred at room temperature for 2 h. The solution was carefully concentrated to a volume of 50 mL under reduced pressure. A precipitate formed and was collected by filtration. 1.3 g (50%) of the product were obtained as a solid.

HPLC-MS (Method 1): R$_t$: 1.08 min
MS (ESI pos): m/z=296 (M+H)$^+$

The following examples were synthesized in analogy to the preparation of Example 11A, using the corresponding pyrazoles as starting materials.

| | structure | starting material | R$_t$ [min] | MS (ESI pos/neg, m/z) |
|---|---|---|---|---|
| Exp. 11B | 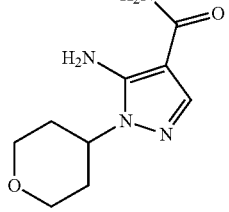 | Example 9C | 0.44 (Method 1) | 211 (M + H)$^+$ |

-continued

| | structure | starting material | R$_t$ [min] | MS (ESI pos/neg, m/z) |
|---|---|---|---|---|
| Exp. 11C | H$_2$N-C(O)-[pyrazole(NH$_2$)]-N-piperidine-N-C(O)O-tBu | Example 10B | 1.12 (Method 1) | 308 (M − H)$^-$ |
| Exp. 11D racem. mixture | H$_2$N-C(O)-[pyrazole(NH$_2$)]-N-piperidin-3-yl-N-C(O)O-tBu | Example 10C | 1.13 (Method 1) | 310/311 (M + H)$^+$ HPLC-MS |
| Exp. 11E racem. mixture | H$_2$N-C(O)-[pyrazole(NH$_2$)]-N-tetrahydrofuran-3-yl | Example 9G | 2.39 (Method 2F) | 197 (M + H)$^+$ |
| Exp. 11F racem. mixture | H$_2$N-C(O)-[pyrazole(NH$_2$)]-N-tetrahydropyran-3-yl | Example 9H | 0.95 (Method Grad_C8_NH$_4$COOH) | 211 (M + H)$^+$ |

-continued

| | structure | starting material | $R_t$ [min] | MS (ESI pos/neg, m/z) |
|---|---|---|---|---|
| Exp. 11G racem. mixture | [structure: 5-amino-1-(2,2-dimethyltetrahydro-2H-pyran-4-yl)-1H-pyrazole-4-carboxamide] | [structure: 5-amino-1-(2,2-dimethyltetrahydro-2H-pyran-4-yl)-1H-pyrazole-4-carbonitrile] | 1.57 (Method Grad_C8_NH4COOH) | 339 (M + H)+ |
| Exp. 11H cis, racem. mixture | [structure: cis 5-amino-1-(2-methyltetrahydro-2H-pyran-4-yl)-1H-pyrazole-4-carboxamide] | Example 9I | 1.27 (Method Grad_90_10_C8_ acidic) | 225 (M + H)+ |
| Exp. 11I trans, racem. mixture | [structure: trans 5-amino-1-(2-methyltetrahydro-2H-pyran-4-yl)-1H-pyrazole-4-carboxamide] | Example 9J | 1.27 (Method Grad_90_10_C8_ acidic) | 225 (M + H)+ |
| Example 11IA cis, racem. mixture | [structure: cis 5-amino-1-(3-methyltetrahydro-2H-pyran-4-yl)-1H-pyrazole-4-carboxamide] | Example 9EA | 1.11 (Method Grad_C8_NH4COOH) | 225 (M + H)+ |

-continued

| structure | starting material | $R_t$ [min] | MS (ESI pos/neg, m/z) |
|---|---|---|---|
| Example 11IB trans, racem. mixture 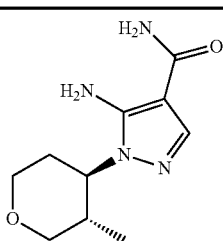 | Example 9EB | 1.14 (Method Grad_C8_NH4COOH) | 225 (M + H)+ |
| Example 11IC 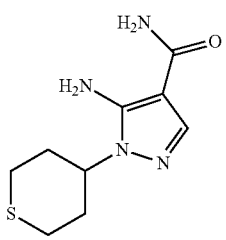 [SMILES: NC(=O)c1cnn(C2CCSCC2)c1N] | Example 9EC | | 227 (M + H)+ |

Example 11J

Racemic Mixture

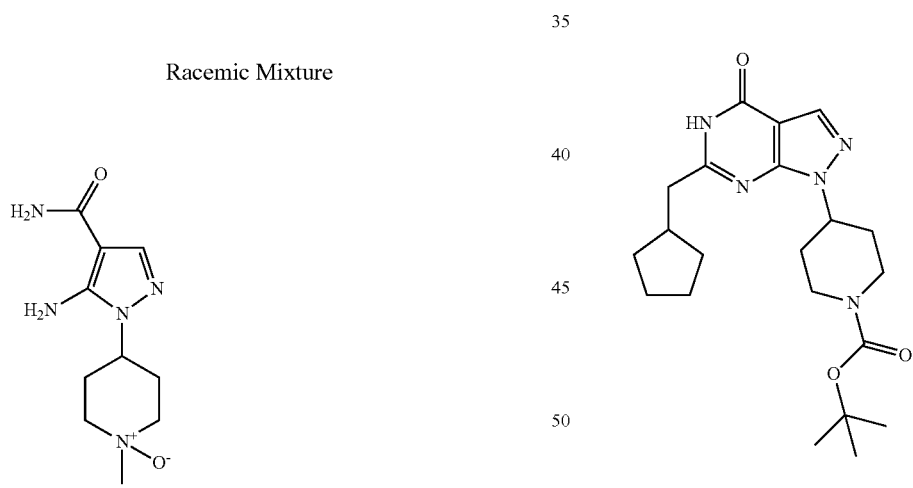

2.30 g (11.2 mmol) of Example 9E were dissolved in 6 mL dimethylsulfoxide. Under ice cooling 8 mL (77.6 mmol) hydrogen peroxide and 1.7 g (12.3 mmol) potassium carbonate were added. Then the reaction mixture was stirred 15 min at room temperature. The reaction mixture was cooled with an ice bath, 100 mL of water were added and extracted with dichloromethane. The water phase was evaporated under reduced pressure. The residue was mixed with in dichloromethane and filtered. 2.8 g (52%) of the product were obtained as a white solid.

HPLC-MS (Method 1): $R_t$: 0.24 min

Example 12A 660 mg (2.13 mmol) of Example 11O were dissolved in 15 mL of absolute ethanol. 1.85 g (10.7 mmol) of Example 5AC and 430 mg (10.7 mmol) of sodium hydride (60% suspension in mineral oil) were added. The reaction mixture was heated to 150° C. for 30 min in a microwave oven. Cooling to room temperature was followed by evaporation of the solvent under reduced pressure. The residue was purified by preparative HPLC (eluent A: water+0.13% TFA, eluent B: acetonitrile). 320 mg (38%) of the product were obtained as a white solid.

HPLC-MS (Method 1): $R_t$: 1.61 min

MS (ESI pos): m/z=402 (M+H)+

The following examples were synthesized in analogy to the preparation of Example 12A, using the corresponding pyrazoles and esters as starting materials.

| Structure | starting material: pyrazole | starting material: ester | $R_t$ [min] | MS (ESI pos/neg, m/z) |
|---|---|---|---|---|
| Exp. 12B 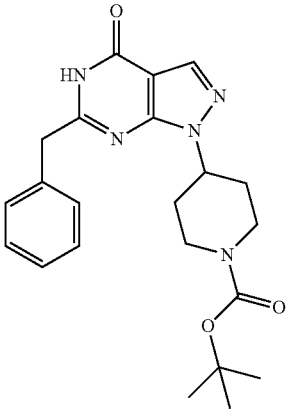 [SMILES: CC(C)(C)OC(=O)N1CCC(n2ncc3c(=O)[nH]c(Cc4ccccc4)nc32)CC1] | Exp. 11C | 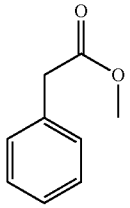 | 1.52 (Method 1) | 410 (M + H)+ |
| Exp. 12C 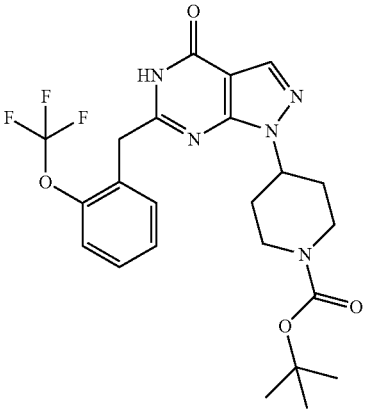 [SMILES: CC(C)(C)OC(=O)N1CCC(n2ncc3c(=O)[nH]c(Cc4ccccc4OC(F)(F)F)nc32)CC1] | Exp. 11C | Example 5AE | 1.66 (Method 1) | 492 (M − H)− |
| Exp. 12D mixture of stereoisomers 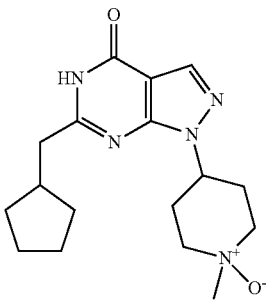 [SMILES: C[N+]1([O-])CCC(n2ncc3c(=O)[nH]c(CC4CCCC4)nc32)CC1] | Exp. 11J | Example 5AC | 1.02 (Method 1) | 332 (M + H)+ |
| Exp. 12E mixture of stereoisomers 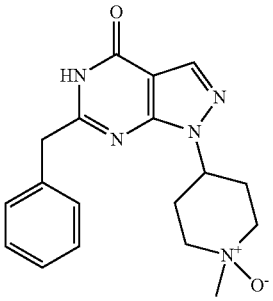 [SMILES: C[N+]1([O-])CCC(n2ncc3c(=O)[nH]c(Cc4ccccc4)nc32)CC1] | Exp. 11J | 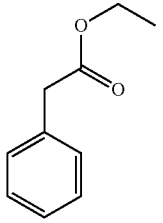 | 0.96 (Method 1) | 340 (M + H)+ |

| | Structure | starting material: pyrazole | starting material: ester | R$_t$ [min] | MS (ESI pos/neg, m/z) |
|---|---|---|---|---|---|
| Exp. 12F mixture of stereoisomers | 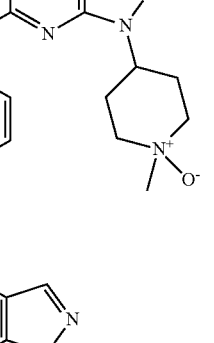 | Exp. 11J | Example 5AE | 1.12 (Method 1) | 424 (M + H)$^+$ |
| Exp. 12G racem. mixture | 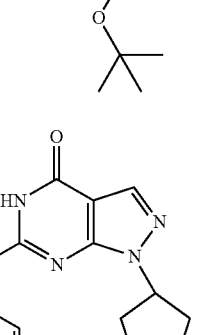 | Exp. 11A | 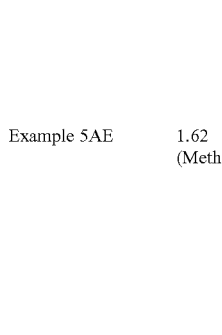 | 1.49 (Method 1) | 396 (M + H)$^+$ |
| Exp. 12H racem. mixture | 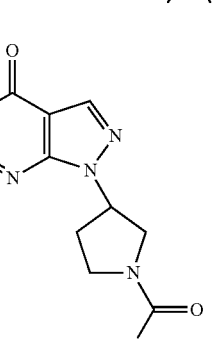 | Exp. 11A | Example 5AE | 1.62 (Method 1) | 480 (M + H)$^+$ |
| Exp. 12I racem. mixture | 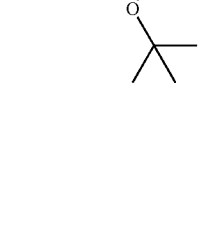 | Exp. 11A | Example 5AD | 1.52 (Method 1) | 426 (M + H)$^+$ |

-continued
| | Structure | starting material: pyrazole | starting material: ester | R$_t$ [min] | MS (ESI pos/neg, m/z) |
|---|---|---|---|---|---|
| Exp. 12J racem. mixture | 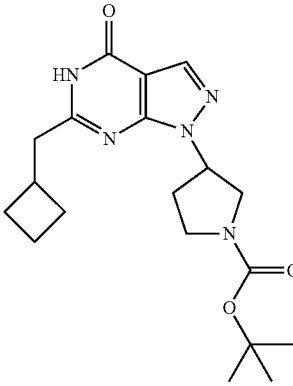 | Exp. 11A | 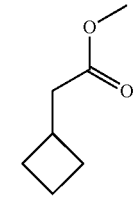 | 1.49 (Method 1) | 374 (M + H)$^+$ |
| Exp. 12K mixture of stereoisomers | 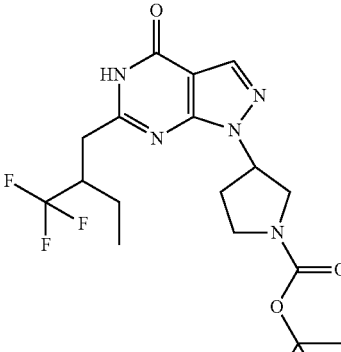 | Exp. 11A | Example 5T | 1.58 (Method 1) | 428 (M − H)$^-$ |
| Exp. 12L racem. mixture | 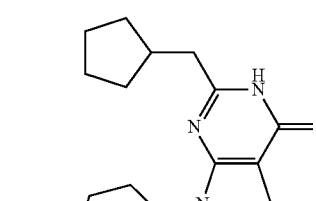 | Exp. 11D | Example 5AC | 1.65 (Method 1) | 402 (M + H)$^+$ |

-continued
| Structure | starting material: pyrazole | starting material: ester | R_t [min] | MS (ESI pos/neg, m/z) |
|---|---|---|---|---|
| Exp. 12M racem. mixture 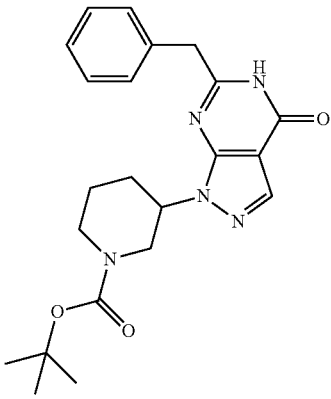 [SMILES: CC(C)(C)OC(=O)N1CCCC(n2ncc3c(=O)[nH]c(Cc4ccccc4)nc32)C1] | Exp. 11D | 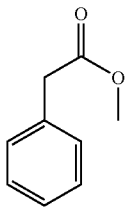 | 1.55 (Method 1) | 408 (M + H)+ |
| Exp. 12N racem. mixture 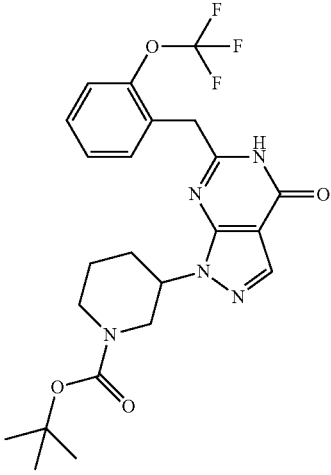 [SMILES: CC(C)(C)OC(=O)N1CCCC(n2ncc3c(=O)[nH]c(Cc4ccccc4OC(F)(F)F)nc32)C1] | Exp. 11D | Example 5AE | 1.67 (Method 1) | 494 (M + H)+ |
| Example 12O racem. mixture 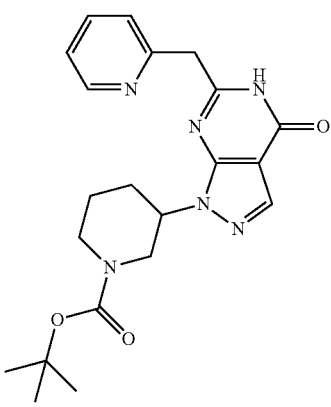 [SMILES: CC(C)(C)OC(=O)N1CCCC(n2ncc3c(=O)[nH]c(Cc4ccccn4)nc32)C1] | Exp. 11D | 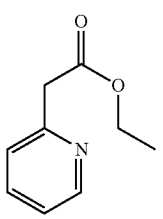 | 1.13 (Method 1) | 411 (M + H)+ |

-continued

| Structure | starting material: pyrazole | starting material: ester | R$_t$ [min] | MS (ESI pos/neg, m/z) |
|---|---|---|---|---|
| Exp. 12P mixture of stereoisomers | Exp. 11D | Example 5T | 1.63 (Method 1) | 444 (M + H)$^+$ |
| Exp. 12Q racem. mixture | Exp. 11D | Example 5AG | 1.53 (Method 1) | 428 (M + H)$^+$ |
| Exp. 12R racem. mixture | Exp. 11D | Example 5AH | 1.66 (Method 1) | 478 (M + H)$^+$ |

| Structure | starting material: pyrazole | starting material: ester | $R_t$ [min] | MS (ESI pos/neg, m/z) |
|---|---|---|---|---|
| Exp. 12S racem. mixture | Exp. 11D | (ethyl 3-methylbutanoate) | 1.51 (Method 1) | 376 (M + H)+ |
| Exp. 12T racem. mixture | Exp. 11D | Example 5AK | 1.63 (Method 1) | 454 (M + H)+ |
| Exp. 12U racem. mixture | Exp. 11D | (methyl cyclobutylacetate) | 1.56 (Method 1) | 388 (M + H)+ |

-continued

| Structure | starting material: pyrazole | starting material: ester | R_t [min] | MS (ESI pos/neg, m/z) |
|---|---|---|---|---|
| Exp. 12V | (3-amino-1H-pyrazole-4-carboxamide; and its sulfate) | ethyl 2-(pyridin-2-yl)acetate | 1.77 (Method 2F) | 228 (M + H)+ |
| Exp. 12W | (3-amino-1H-pyrazole-4-carboxamide; and its sulfate) | ethyl 3-methylbutanoate | 6.96 (Method 2F) | 193 (M + H)+ |
| Exp. 12X | (3-amino-1H-pyrazole-4-carboxamide; and its sulfate) | Example 5AC | 8.28 (Method 2F) | 219 (M + H)+ |
| Exp. 12Y | (3-amino-1H-pyrazole-4-carboxamide; and its sulfate) | Example 5AMA | 9.15 (Method 2F) | 295 (M + H)+ |

| Structure | starting material: pyrazole | starting material: ester | $R_t$ [min] | MS (ESI pos/neg, m/z) |
|---|---|---|---|---|
| Example 12Z | (pyrazole-4-carboxamide with NH₂; also sulfuric acid salt form) | Example 5AH | 9.54 (Method 2F) | 295 (M + H)⁺ |
| Example 12AA | (pyrazole-4-carboxamide with NH₂; two forms including sulfuric acid salt) | Example 5ALA | 6.48 (Method 2F) | 191 (M + H)⁺ |

Example 13A

Racemic Mixture

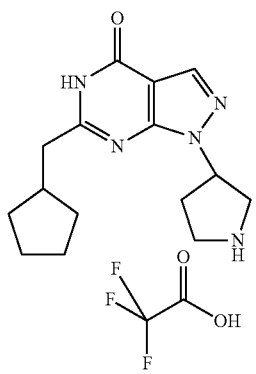

Example 13B

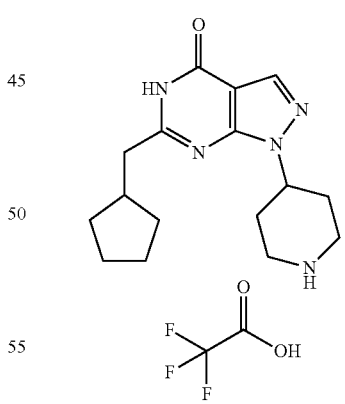

HPLC-MS (Method 1): $R_t$: 0.93 min
MS (ESI pos): m/z=288 (M+H)⁺

400 mg (1.35 mmol) of Example 11A were dissolved in 8 mL of absolute ethanol, 840 mg (5.4 mmol) of Example 5AC and 220 mg (5.5 mmol) of sodium hydride (60% suspension in mineral oil) were added. The reaction mixture was heated to 150° C. for 30 min in a microwave oven. After cooling to room temperature the reaction mixture was acidified with 4N hydrochloride acid. The solvent was removed under reduced pressure. The residue was purified by preparative HPLC (eluent A: water+0.13% TFA, eluent B: acetonitrile). 250 mg (46%) of the product were obtained as a white solid.

330 mg (0.82 mmol) of Example 12A was dissolved in 3 mL dichloromethane and 1 mL trifluoroacetic acid was added. The reaction mixture was stirred at room temperature over night. The solvent was evaporated under reduced pressure. The remaining product was purified by preparative HPLC (eluent A: water+0.13% TFA, eluent B: acetonitrile). 240 mg (70%) of the product were obtained.
HPLC-MS (Method 1): $R_t$: 0.96 min
MS (ESI pos): m/z=302 (M+H)⁺

The following examples were synthesized in analogy to the preparation of Example 13B, using the corresponding Boc-protected amines as starting materials

| | Structure | starting material | $R_t$ [min] | MS (ESI, m/z) |
|---|---|---|---|---|
| Exp. 13C racem. mixture | 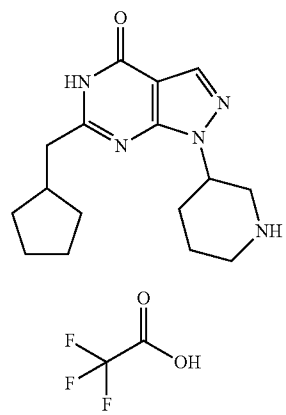 [SMILES: O=c1[nH]c(CC2CCCC2)nc2c1cnn2C1CCCNC1 ; O=C(O)C(F)(F)F] | Exp. 12L | 1.01 (Method 1) | 302 $(M + H)^+$ |
| Exp. 13D racem. mixture | 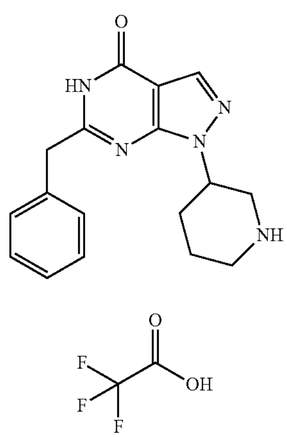 [SMILES: O=c1[nH]c(Cc2ccccc2)nc2c1cnn2C1CCCNC1 ; O=C(O)C(F)(F)F] | Exp. 12M | 0.93 (Method 1) | 310 $(M + H)^+$ |
| Exp. 13E racem. mixture | 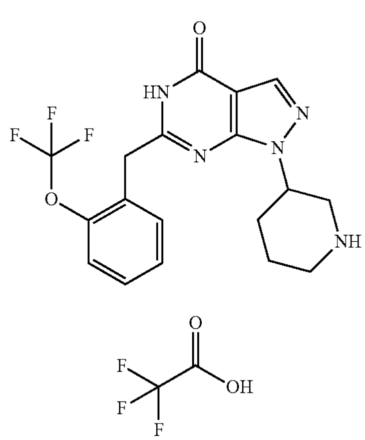 [SMILES: O=c1[nH]c(Cc2ccccc2OC(F)(F)F)nc2c1cnn2C1CCCNC1 ; O=C(O)C(F)(F)F] | Exp. 12N | 1.09 (Method 1) | 394 $(M + H)^+$ |

-continued
| | Structure | starting material | R$_t$ [min] | MS (ESI, m/z) |
|---|---|---|---|---|
| Exp. 13F racem. mixture | 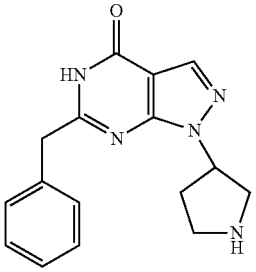 | Exp. 12G | 0.92 (Method 1) | 296 (M + H)$^+$ |
| Exp. 13G racem. mixture | 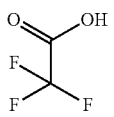 | Exp. 12H | 1.08 (Method 1) | 380 (M + H)$^+$ |
| Exp. 13H racem. mixture | 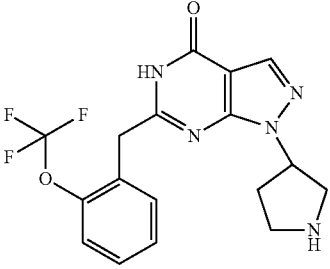 | Exp. 12I | 0.96 (Method 1) | 326 (M + H)$^+$ |

-continued
| | Structure | starting material | $R_t$ [min] | MS (ESI, m/z) |
|---|---|---|---|---|
| Exp. 13I racem. mixture | 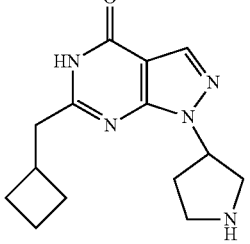 | Exp. 12J | 0.89 (Method 1) | 274 (M + H)$^+$ |
| Exp. 13J racem. mixture | 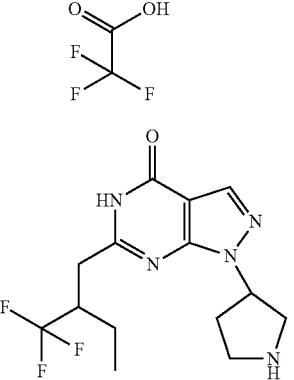 | Exp. 12K | 1.0 (Method 1) | 330 (M + H)$^+$ |
| Exp. 13K | 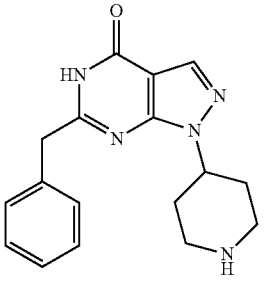 | Exp. 12B | 0.92 (Method 1) | 310 (M + H)$^+$ |
| Exp. 13L | 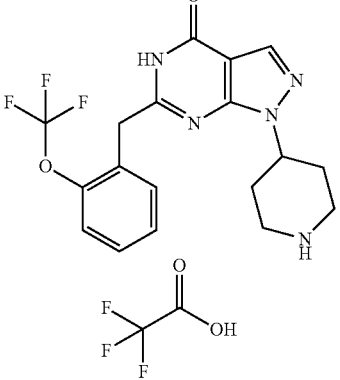 | Exp. 12C | 1.07 (Method 1) | 394 (M + H)$^+$ |

| Structure | starting material | R$_t$ [min] | MS (ESI, m/z) |
|---|---|---|---|
Exp. 13M
mixture of
stereoisomers
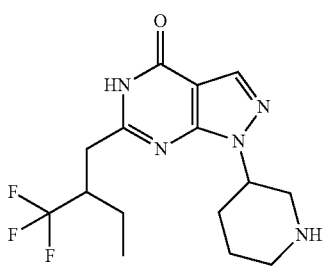
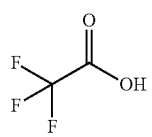
Exp. 12P  1.04 (Method 1)  344 (M + H)$^+$
Exp. 13N
racem.
mixture
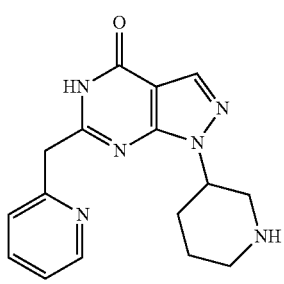
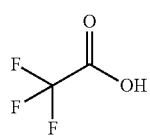
Exp. 12O  0.37 (Method 1)  319 (M + H)$^+$
Exp. 13O
racem.
mixture
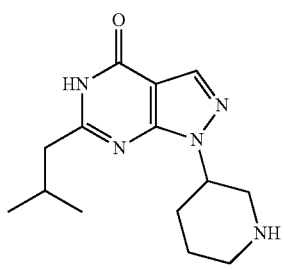
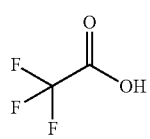
Exp. 12S  0.89 (Method 1)  276 (M + H)$^+$ -continued

| Structure | starting material | $R_t$ [min] | MS (ESI, m/z) |
|---|---|---|---|
| Exp. 13P racem. mixture 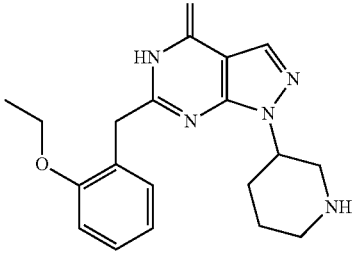 | Exp. 12T | 1.04 (Method 1) | 354 (M + H)+ |
| Exp. 13Q racem. mixture 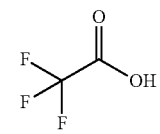 | Exp. 12U | 0.94 (Method 1) | 288 (M + H)+ |

Example 15A

Enantiomer A

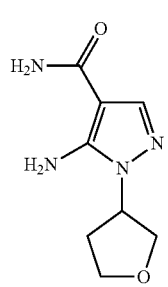

200 mg (1.12 mmol) of Example 9GA was mixed with 4.5 mL ammonia solution (30% in water). The reaction mixture was heated to 130° C. for 30 min in a microwave oven. Cooling to room temperature was followed by evaporation of the solvent under reduced pressure. 180 mg (82%) of the product were obtained.

GC-MS (Method 3A. 1): $R_t$: 12.62 min

[M]+=196

Example 16A

Enantiomer B

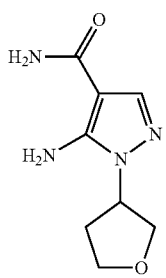

150 mg (0.84 mmol) of Example 9 GB were mixed with 2.10 mL ammonia solution (30% in water). The reaction mixture was heated to 130° C. for 30 min in a microwave oven. Cooling to room temperature was followed by evaporation of the solvent under reduced pressure. 100 mg (60%) of the product were obtained.

GC-MS (Method 3A. 2): $R_t$: 12.59 min

[M]+=196

Example 17A

Mixture of Stereoisomers

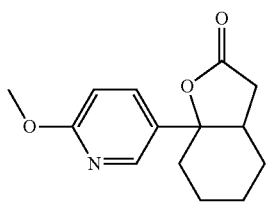 [SMILES: COc1ccc(C23CCCCC2CC(=O)O3)cn1]

A solution of 1.00 g (5.32 mmol) 2-methoxy-5-bromopyridine in 10 mL anhydrous THF was cooled to −78° C. and n-BuLi (3.66 mL, 5.85 mmol, 1.6 M in hexane) was added. After 10 min at −78° C. 1.18 g (6.38 mmol) 2-oxo-cyclohexyl-acetic acid ethyl ester was added and the mixture was warmed to 25° C. Water was added (1 mL) and the mixture was concentrated under reduced pressure. The residue was purified by preparative HPLC (eluent A: water+0.13% TFA, eluent B: acetonitrile). 370 mg (28%) of the product were obtained as an oil.

HPLC-MS (Method 1): $R_t$: 1.23 min
MS (ESI pos): m/z=248 (M+H)$^+$

Example 18A

Cis, Racemic Mixture

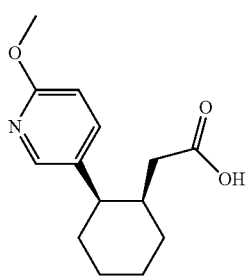 [SMILES: COc1ccc([C@@H]2CCCC[C@@H]2CC(=O)O)cn1]

380 mg (1.54 mmol) of Example 17A was mixed with 5 mL methanol, 50 mg Pd/C (10%) was added, and the mixture was hydrogenated at room temperature (8 h, 50 psi). The reaction mixture was filtered and the residue was washed with methanol. The solvent was evaporated under reduced pressure. 340 mg (89%) of product were obtained as colourless oil and used without further purification.

HPLC-MS (Method 1): $R_t$: 1.01 min
MS (ESI pos): m/z=250 (M+H)$^+$

Example 19A

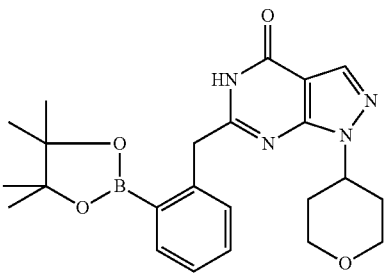 [SMILES: CC1(C)OB(c2ccccc2Cc2nc3c(cnn3C3CCOCC3)c(=O)[nH]2)OC1(C)C]

100 mg (0.48 mmol) of Example 11B were dissolved in 2 mL of absolute ethanol, 346 mg (1.43 mmol) of [2-(4,4,5,5-Tetramethyl-[1,3,2]dioxaborolan-2-yl)-phenyl]-acetonitrile and 25.3 mg (0.63 mmol) of sodium hydride (60% suspension in mineral oil) were added. The reaction mixture was heated to 130° C. for 40 min in a microwave oven; cooling to room temperature was followed by addition of 25.3 mg (0.63 mmol) of sodium hydride (60% suspension in mineral oil) and a second microwave irradiation (130° C.; 40 min). Cooling to room temperature was followed by addition of ammonium chloride and dichloromethane; the two phases were separated and the residue was purified by flash chromatography on SiO2. 55 mg (26%) of the product were obtained as a solid.

HPLC-MS (Method 1 E hydro): $R_t$: 9.98 min
MS (APCI pos): m/z=331 (M+H)$^+$

Example 20A

[2-(3-Methyl-pyrazol-1-yl)-phenyl]acetonitrile

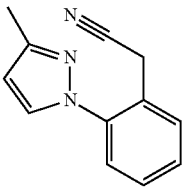

A round bottom flask was charged under inert atmosphere with copper iodide (760 mg, 4 mmol), cesium carbonate (3.91 g, 12 mmol) then dimethylformamide (20 mL), previously degassed, was added followed by 2-Bromophenylacetonitrile (519 μL, 4 mmol), 3-Methylpyrazole (3.32 mL, 40 mmol) and N—N'-dimethylethylenediamine (425.86 μL, 4 mmol). The reaction mixture was heated to 120° C. for 2.5 hours. After cooling the reaction mixture was filtered through a Celite pad that was rinsed with dimethylformamide. The volume was reduced under reduced pressure, saturated ammonium chloride aqueous solution was added and extracted with ethyl acetate. The organic phase was washed with saturated aqueous NH$_4$Cl solution, brine then dried over Na$_2$SO$_4$ and the solvent was removed under reduced pressure. The crude product was purified by flash chromatography on SiO$_2$ using cyclohexane/ethyl acetate mixture of increasing polarity (from 100% cyclohexane to 100% ethyl acetate) as eluent. The oil obtained was further purified by SPE Stratosphere "PL-THIOL MP" to completely remove copper salts. The title compound was obtained as a thick dark oil (300 mg, 38%).
GC-MS (Method 3A.1): R$_t$: 10.47 min
MS: 197 [M]$^+$.

Example 21A (2-Pyrrol-1-yl-phenyl)-acetonitrile

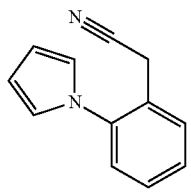 [SMILES: N#CCc1ccccc1-n1cccc1]

Under inert atmosphere a solution of 500 mg (3.783 mmol) of 2-Aminophenylacetonitrile and 1 mL (7.566 mmol) of 2,5-Dimethoxytetrahydrofuran in 5 mL of acetic acid was heated to 60° C. for 2 hours. After cooling the reaction mixture was concentrated under reduced pressure. The residue was purified by flash chromatography on SiO$_2$ using cyclohexane/ethyl acetate mixture of increasing polarity (from 100% cyclohexane to 100% ethyl acetate) as eluent. The title compound was obtained as a light yellow oil (470 mg, 68.2%).
GC-MS (Method 3A): R$_t$: 9.75 min
MS: 182 [M]$^+$.

Exemplary Embodiments

The following section presents for illustration compounds that have PDE 9 inhibiting properties, be it for to illustrate the compounds according to the invention or to provide insight in their manufacturing process. Among these examples are the compounds that are subject to the present invention. Further details about the scope of the present invention are given in the description.

Example 1

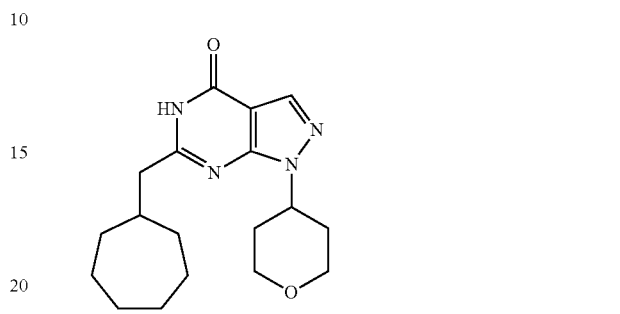

100 mg (0.48 mmol) of Example 11B were dissolved in 5 mL of absolute ethanol, 400 mg (2.17 mmol) of Example 5V and 100 mg (2.5 mmol) of sodium hydride (60% suspension in mineral oil) were added. The reaction mixture was heated to 150° C. for 30 min in a microwave oven. Cooling to room temperature was followed by evaporation of the solvent under reduced pressure. The residue was purified by preparative HPLC (eluent A: water+0.13% TFA, eluent B: acetonitrile). 29 mg (18%) of the product were obtained as a white solid.
HPLC-MS (Method 1): R$_t$: 1.08 min
MS (ESI pos): m/z=331 (M+H)$^+$ The following examples were synthesized in analogy to the preparation of Example 1, using the corresponding pyrazoles and esters or nitriles as starting materials

| structure | starting material: pyrazole | starting material: ester or nitrile | R$_t$ [min] | MS (ESI-APCI pos/neg, m/z) |
|---|---|---|---|---|
| Exp. 2 | Example 11B | | 1.27 (Method 1) | 325 (M + H)$^+$ |
| Exp. 3 | Example 11B | | 1.22 (Method 1) | 291 (M + H)$^+$ |

-continued
| | structure | starting material: pyrazole | starting material: ester or nitrile | R$_t$ [min] | MS (ESI-APCI pos/neg, m/z) |
|---|---|---|---|---|---|
| Exp. 4 | 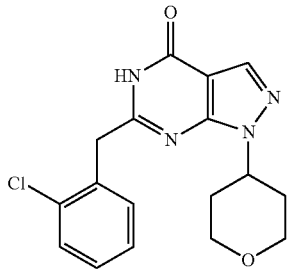 [SMILES: O=c1[nH]c(Cc2ccccc2Cl)nc2c1cnn2C1CCOCC1] | Example 11B | Example 5Y | 1.23 (Method 1) | 345/347 (Cl) (M + H)$^+$ |
| Exp. 5 | 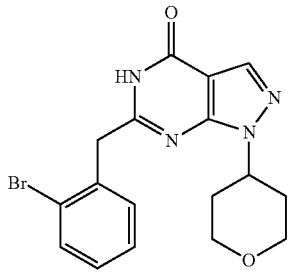 [SMILES: O=c1[nH]c(Cc2ccccc2Br)nc2c1cnn2C1CCOCC1] | Example 11B | Example 5U | 1.29 (Method 1) | 389/91 (Br) (M + H)$^+$ |
| Exp. 6 | 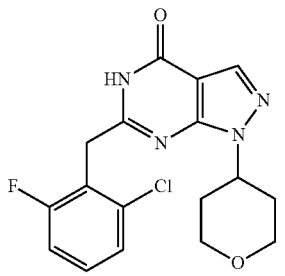 [SMILES: O=c1[nH]c(Cc2c(F)cccc2Cl)nc2c1cnn2C1CCOCC1] | Example 11B | 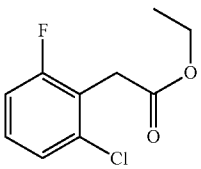 | 1.28 (Method 1) | 363/65 (Cl) (M + H)$^+$ |
| Exp. 7 | 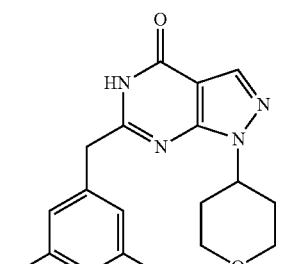 | Example 11B | Example 5W | 1.22 (Method 1) | 345 (M − H)$^−$ |
| Exp. 8 | 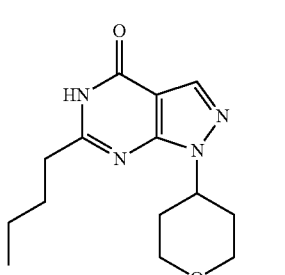 | Exp. 11B | 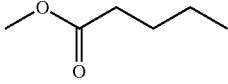 | 1.14 (Method 1) | 277 (M + H)$^+$ |

-continued

| structure | starting material: pyrazole | starting material: ester or nitrile | R$_t$ [min] | MS (ESI-APCI pos/neg, m/z) |
|---|---|---|---|---|
| Exp. 9 | Exp. 11B | Example 5X | 1.37 (Method 1) | 317 (M + H)$^+$ |
| Exp. 10 | Exp. 11B | (structure: methyl 2-(2-chloro-4-fluorophenyl)acetate) | 1.30 (Method 1) | 361/63 (Cl) (M + H)$^+$ |
| Exp. 11 | Exp. 11B | (structure: ethyl 2-(4-methoxyphenyl)acetate) | 1.18 (Method 1) | 341 (M + H)$^+$ |
| Exp. 12 racem. mixture | Exp. 11B | Example 5AA | 1.44 (Method 1) | 329 (M + H)$^+$ |
| Exp. 13 | Exp. 11B | Example 5AB | 1.26 (Method 1) | 347 (M + H)$^+$ |

-continued

| | structure | starting material: pyrazole | starting material: ester or nitrile | R$_t$ [min] | MS (ESI-APCI pos/neg, m/z) |
|---|---|---|---|---|---|
| Exp. 14 racem. mixture | 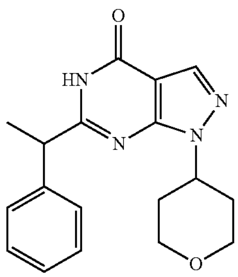 [SMILES: CC(c1ccccc1)c1nc2c(cnn2C2CCOCC2)c(=O)[nH]1] | Exp. 11B | Example 5AF | 1.28 (Method 1) | 325 (M + H)$^+$ |
| Exp. 15 racem. mixture | 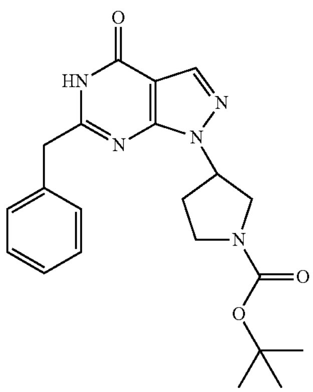 [SMILES: CC(C)(C)OC(=O)N1CCC(n2ncc3c(=O)[nH]c(Cc4ccccc4)nc32)C1] | Exp. 11A | | 1.49 (Method 1) | 396 (M + H)$^+$ |
| Exp. 16 racem. mixture | 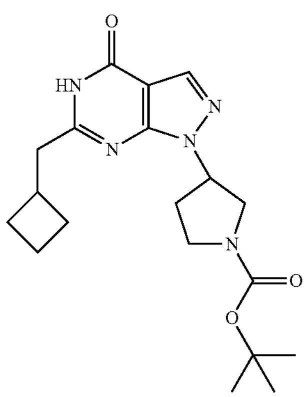 [SMILES: CC(C)(C)OC(=O)N1CCC(n2ncc3c(=O)[nH]c(CC4CCC4)nc32)C1] | Exp. 11A | | 1.49 (Method 1) | 374 (M + H)$^+$ |
| Exp. 17 racem. mixture | 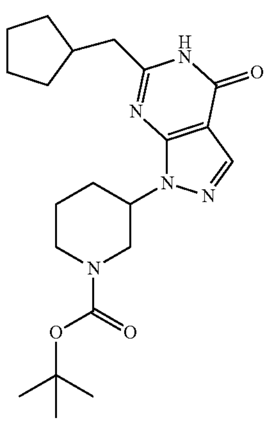 [SMILES: CC(C)(C)OC(=O)N1CCCC(n2ncc3c(=O)[nH]c(CC4CCCC4)nc32)C1] | Exp. 11D | Example 5AC | 1.65 (Method 1) | 402 (M + H)$^+$ |

-continued

| | structure | starting material: pyrazole | starting material: ester or nitrile | R$_t$ [min] | MS (ESI-APCI pos/neg, m/z) |
|---|---|---|---|---|---|
| Exp. 18 racem. mixture | 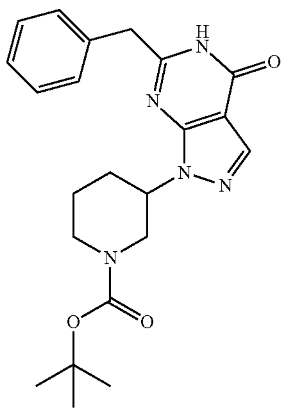 [SMILES: CC(C)(C)OC(=O)N1CCCC(n2ncc3c(=O)[nH]c(Cc4ccccc4)nc32)C1] | Exp. 11D | | 1.55 (Method 1) | 408 (M + H)$^+$ |
| Exp. 19 racem. mixture | 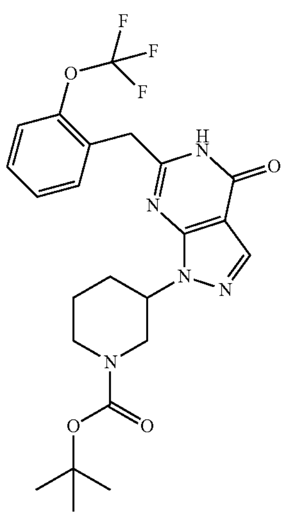 [SMILES: CC(C)(C)OC(=O)N1CCCC(n2ncc3c(=O)[nH]c(Cc4ccccc4OC(F)(F)F)nc32)C1] | Exp. 11D | Example 5AE | 1.67 (Method 1) | 494 (M + H)$^+$ |
| Exp. 20 racem. mixture | 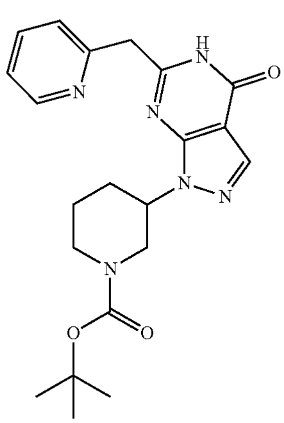 [SMILES: CC(C)(C)OC(=O)N1CCCC(n2ncc3c(=O)[nH]c(Cc4ccccn4)nc32)C1] | Exp. 11D | | 1.13 (Method 1) | 411 (M + H)$^+$ |

|  | structure | starting material: pyrazole | starting material: ester or nitrile | R$_t$ [min] | MS (ESI-APCI pos/neg, m/z) |
|---|---|---|---|---|---|
| Exp. 21 racem. mixture | 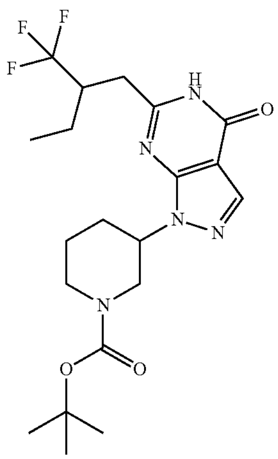 [SMILES: CCC(Cc1nc2c(cnn2C2CCCN(C(=O)OC(C)(C)C)C2)c(=O)[nH]1)C(F)(F)F] | Exp. 11D | Example 5T | 1.63 (Method 1) | 444 (M + H)$^+$ |
| Exp. 22 racem. mixture | 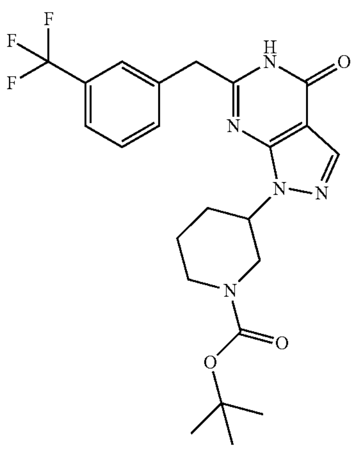 [SMILES: CC(C)(C)OC(=O)N1CCCC(n2ncc3c(=O)[nH]c(Cc4cccc(C(F)(F)F)c4)nc32)C1] | Exp. 11D | Example 5AH | 1.66 (Method 1) | 478 (M + H)$^+$ |
| Exp. 23 racem. mixture | 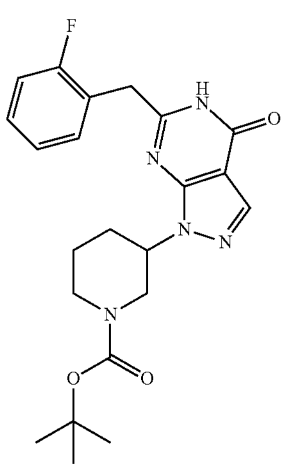 [SMILES: CC(C)(C)OC(=O)N1CCCC(n2ncc3c(=O)[nH]c(Cc4ccccc4F)nc32)C1] | Exp. 11D | | 1.53 (Method 1) | 428 (M + H)$^+$ |

-continued

| | structure | starting material: pyrazole | starting material: ester or nitrile | R$_t$ [min] | MS (ESI-APCI pos/neg, m/z) |
|---|---|---|---|---|---|
| Exp. 24 | 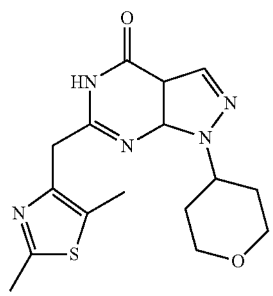 [SMILES: Cc1nc(CC2=NC3C(C=NN3C3CCOCC3)C(=O)N2)c(C)s1] | Exp. 11B | | 0.91 (Method 1) | 346 (M + H)$^+$ |
| Exp. 25 | 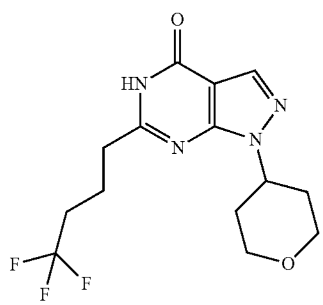 [SMILES: O=c1[nH]c(CCCC(F)(F)F)nc2c1cnn2C1CCOCC1] | Exp. 11B | Example 5AI | 1.17 (Method 1) | 331 (M + H)$^+$ |
| Exp. 26 | 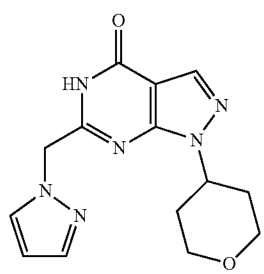 [SMILES: O=c1[nH]c(Cn2cccn2)nc2c1cnn2C1CCOCC1] | Exp. 11B | Example 5AN | 0.87 (Method 1) | 301 (M + H)$^+$ |
| Exp. 27 | 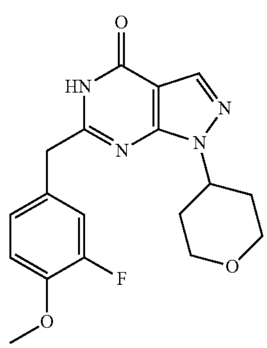 [SMILES: COc1ccc(Cc2nc3c(cnn3C3CCOCC3)c(=O)[nH]2)cc1F] | Exp. 11B | Example 5AJ | 1.17 (Method 1) | 359 (M + H)$^+$ |
| Exp. 28 | 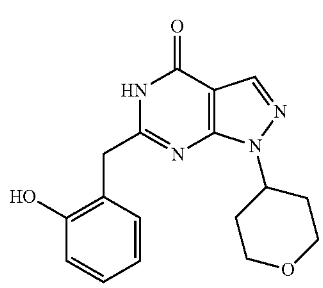 [SMILES: O=c1[nH]c(Cc2ccccc2O)nc2c1cnn2C1CCOCC1] | Exp. 11B | Example 5AM | 1.08 (Method 1) | 327 (M + H)$^+$ |

-continued
| | structure | starting material: pyrazole | starting material: ester or nitrile | R$_t$ [min] | MS (ESI-APCI pos/neg, m/z) |
|---|---|---|---|---|---|
| Exp. 29 | 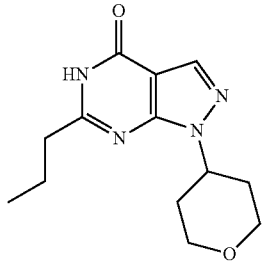 [SMILES: CCCc1nc2c(cnn2C2CCOCC2)c(=O)[nH]1] | Exp. 11B | 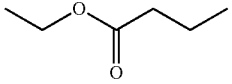 | 1.02 (Method 1) | 263 (M + H)$^+$ |
| Exp. 30 racem. mixture | 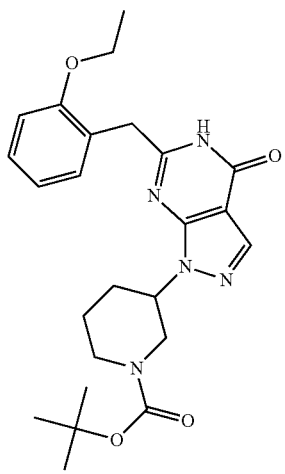 [SMILES: CCOc1ccccc1Cc1nc2c(cnn2C2CCCN(C(=O)OC(C)(C)C)C2)c(=O)[nH]1] | Exp. 11D | Example 5AK | 1.63 (Method 1) | 454 (M + H)$^+$ |
| Exp. 31 racem. mixture | 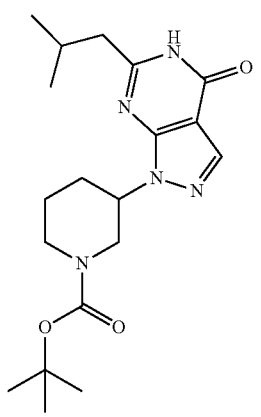 [SMILES: CC(C)Cc1nc2c(cnn2C2CCCN(C(=O)OC(C)(C)C)C2)c(=O)[nH]1] | Exp. 11D | 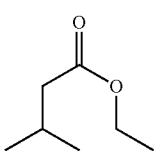 | 1.51 (Method 1) | 376 (M + H)$^+$ |
| Exp. 32 racem. mixture | 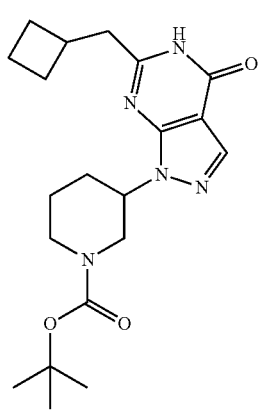 [SMILES: CC(C)(C)OC(=O)N1CCCC(n2ncc3c(=O)[nH]c(CC4CCC4)nc32)C1] | Exp. 11D | 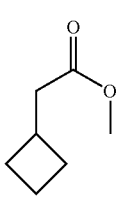 | 1.56 (Method 1) | 388 (M + H)$^+$ |

-continued

| structure | starting material: pyrazole | starting material: ester or nitrile | R$_t$ [min] | MS (ESI-APCI pos/neg, m/z) |
|---|---|---|---|---|
| Exp. 33 | Exp. 11B | Example 5AO | 1.29 (Method 1) | 375/377 (Cl) (M + H)$^+$ |
| Exp. 34 | Exp. 11B | | 1.11 (Method 1) | 317 (M + H)$^+$ |
| Exp. 35 | Exp. 11B | | 1.17 (Method 1) | 366 (M + H)$^+$ |
| Exp. 36 | Exp. 11B | | 1.36 (Method 1) | 339 (M + H)$^+$ |
| Exp. 37 | Exp. 11B | Example 5AL | 1.3 (Method 1) | 381/383 (Cl) (M + H)$^+$ |

-continued
| | structure | starting material: pyrazole | starting material: ester or nitrile | R$_t$ [min] | MS (ESI-APCI pos/neg, m/z) |
|---|---|---|---|---|---|
| Exp. 38 | 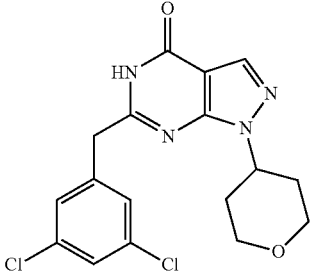 [SMILES: O=c1[nH]c(Cc2cc(Cl)cc(Cl)c2)nc2c1cnn2C1CCOCC1] | Exp. 11B | Example 5Z | 1.44 (Method 1) | 379/381/383 (Cl$_2$) (M + H)$^+$ |
| Exp. 39 | 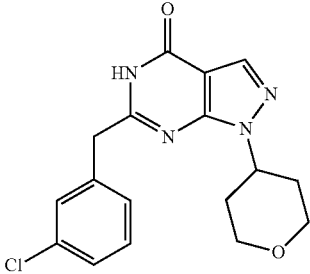 [SMILES: O=c1[nH]c(Cc2cccc(Cl)c2)nc2c1cnn2C1CCOCC1] | Exp. 11B | 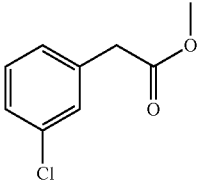 | 1.28 (Method 1) | 345/347 (Cl) (M + H)$^+$ |
| Exp. 40 | 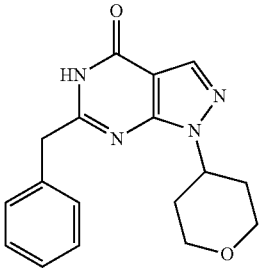 [SMILES: O=c1[nH]c(Cc2ccccc2)nc2c1cnn2C1CCOCC1] | Exp. 11B | 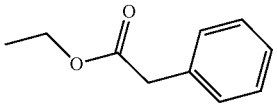 | 1.16 (Method 1) | 311 (M + H)$^+$ |
| Exp. 40-1 | 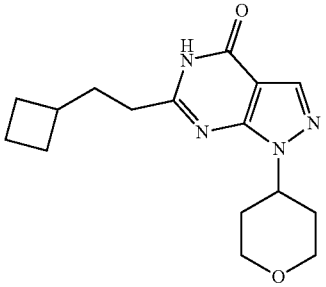 [SMILES: O=c1[nH]c(CCC2CCC2)nc2c1cnn2C1CCOCC1] | Exp. 11B | Exp. 5ALC | 1.30 (Method 1) | 303 (M + H)$^+$ |
| Exp. 40-2 | 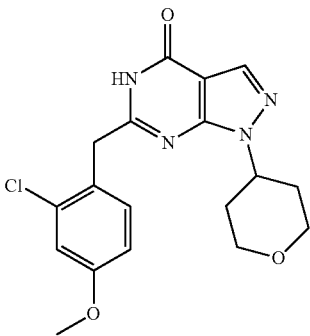 [SMILES: COc1ccc(Cc2nc3c(cnn3C3CCOCC3)c(=O)[nH]2)c(Cl)c1] | Exp. 11B | Example 5ALB | 1.31 (Method 1) | 3.75 (M + H)$^+$ |

-continued

| structure | starting material: pyrazole | starting material: ester or nitrile | R$_t$ [min] | MS (ESI-APCI pos/neg, m/z) |
|---|---|---|---|---|
| Exp. 40-3 | Exp. 11B | Example 5ALD | 1.25 (Method 1) | 355 (M + H)$^+$ |
| Exp. 40-4 cis, racem. mixture | Exp. 11B | Exp. 5HA | 1.18 (Method 1) | 424 (M + H)$^+$ |
| Exp. 40-5 | Exp. 11IC | Exp. 5ALA | 1.24 (Method 1) | 291 (M + H)$^+$ |
| Exp. 40-6 | Exp. 11B | Example 5TA | 1.22 (Method 1) | 353 (M + H)$^+$ |

| structure | starting material: pyrazole | starting material: ester or nitrile | R$_t$ [min] | MS (ESI-APCI pos/neg, m/z) |
|---|---|---|---|---|
| Exp. 40-7 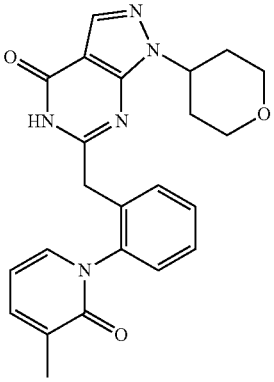 [SMILES: Cc1cccn(-c2ccccc2Cc2nc3c(cnn3C3CCOCC3)c(=O)[nH]2)c1=O] | Exp. 11B | Example 5AP | 1.35 (Method 1) | 418 (M + H)$^+$ |
| Exp. 40-8 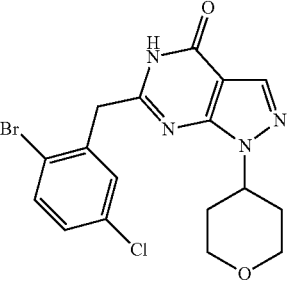 [SMILES: O=c1[nH]c(Cc2cc(Cl)ccc2Br)nc2c1cnn2C1CCOCC1] | Exp. 11B | Example 5ALF | 1.78 (Method 5) | 423/425/427 (M + H)$^+$ (Cl/Br) |
| Exp. 40-9 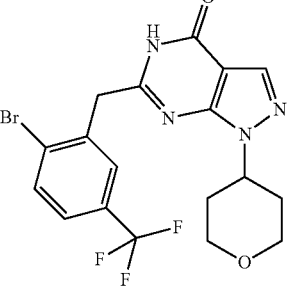 | Exp. 11B | 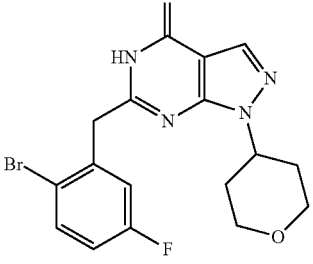 | 1.81 (Method 5) | 458/460 (M + H)$^+$ (Br) |
| Exp. 40-10 | Exp. 11B | Example 5ALG | 1.33 (Method 1) | 407/409 (M + H)$^+$ (Br) |

Example 41

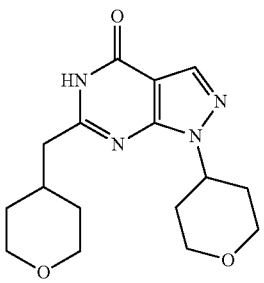 [SMILES: O=c1[nH]c(CC2CCOCC2)nc2c1cnn2C1CCOCC1]

80 mg (0.38 mmol) of Example 11B were dissolved in 1 mL of absolute ethanol, 262 mg (1.52 mmol) of ethyl tetrahydropyran-4-yl-acetate, and 45.1 mg (1.10 mmol) of sodium hydride (60% suspension in mineral oil) were added. The reaction mixture was heated to 150° C. for 40 min in a microwave oven. Cooling to 20° C. was followed by evaporation of the solvent under reduced pressure. The residue was treated with water (10 mL), acidified with HCl (10% in water) and extracted two times with dichloromethane (2 mL). The organic layer was dried over sodium sulphate, filtered and the filtrate was concentrated under reduced pressure. The residue was triturated with ether to give 65 mg (53.7%) of the product as a white solid.

HPLC-MS (Method Grad_C8_NH$_4$COOH): R$_t$: 1.89 min

MS (ESI pos): m/z=319 (M+H)$^+$.

The following examples were synthesized in analogy to the preparation of Example 41, using the corresponding pyrazolyl-carboxamides and esters as starting materials.

| | Structure | pyrazolyl-carbox-amide | Ester | R$_t$ [min] | MS (ESI APCI, m/z) |
|---|---|---|---|---|---|
| Exp. 42 racem. mixture | 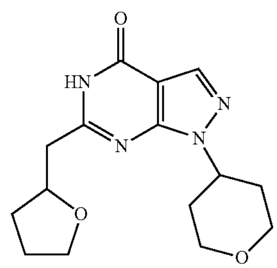 [SMILES: O=c1[nH]c(CC2CCCO2)nc2c1cnn2C1CCOCC1] | Exp. 11B | | 2.02 (Method Grad_C8_NH$_4$COOH) | 305 (M + H)$^+$ |
| Exp. 43 | 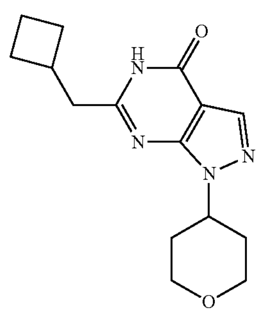 [SMILES: O=c1[nH]c(CC2CCC2)nc2c1cnn2C1CCOCC1] | Exp. 11B | | 2.40 (Method Grad_C8_NH$_4$COOH) | 289 (M + H)$^+$ |
| Exp. 44 | 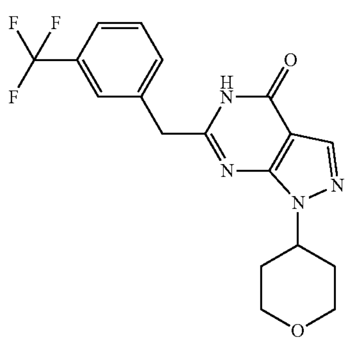 [SMILES: O=c1[nH]c(Cc2cccc(C(F)(F)F)c2)nc2c1cnn2C1CCOCC1] | Exp. 11B | | 3.06 (Method Grad_C8_NH$_4$COOH) | 379 (M + H)$^+$ |

-continued

| | Structure | pyrazolyl-carbox-amide | Ester | R$_t$ [min] | MS (ESI APCI, m/z) |
|---|---|---|---|---|---|
| Exp. 45 | 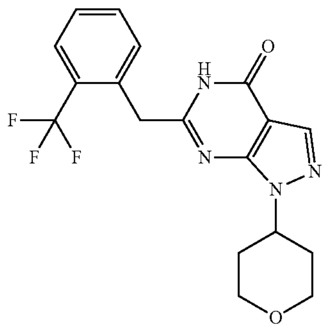 [SMILES: O=c1[nH]c(Cc2ccccc2C(F)(F)F)nc2c1cnn2C1CCOCC1] | Exp. 11B | | 3.04 (Method Grad_C8_ NH$_4$COOH) | 379 (M + H)$^+$ |
| Exp. 46 racem. mixture | 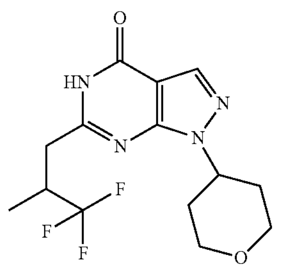 [SMILES: CC(Cc1nc2c(cnn2C2CCOCC2)c(=O)[nH]1)C(F)(F)F] | Exp. 11B | | 2.77 (Method Grad_C8_ NH$_4$COOH) | 331 (M + H)$^+$ |
| Exp. 47 | 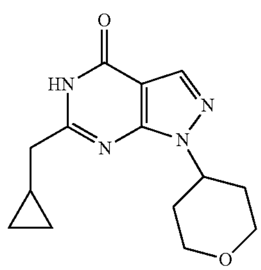 [SMILES: O=c1[nH]c(CC2CC2)nc2c1cnn2C1CCOCC1] | Exp. 11B | | 2.21 (Method Grad_C8_ NH$_4$COOH) | 275 (M + H)$^+$ |
| Exp. 48 racem. mixture | 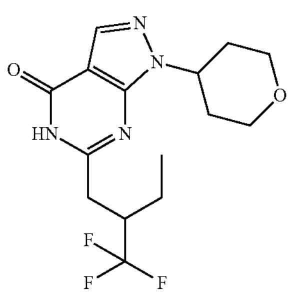 [SMILES: CCC(Cc1nc2c(cnn2C2CCOCC2)c(=O)[nH]1)C(F)(F)F] | Exp. 11B | Exp. 5T | 2.84 (Method Grad_C8_ NH$_4$COOH) | 345 (M + H)$^+$ |
| Exp. 49 | 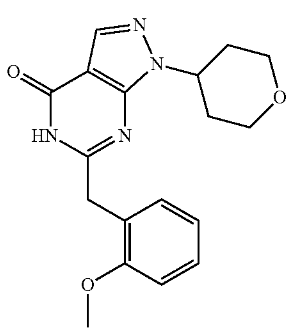 [SMILES: COc1ccccc1Cc1nc2c(cnn2C2CCOCC2)c(=O)[nH]1] | Exp. 11B | | 2.57 (Method Grad_C8_ NH$_4$COOH) | 341 (M + H)$^+$ |

-continued

| | Structure | pyrazolyl-carbox-amide | Ester | R$_t$ [min] | MS (ESI APCI, m/z) |
|---|---|---|---|---|---|
| Exp. 50 | 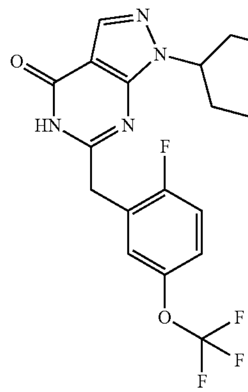 | Exp. 11B | Exp. 5E | 3.02 (Method Grad_C8_NH$_4$COOH) | 413 (M + H)$^+$ |
| Exp. 51 | 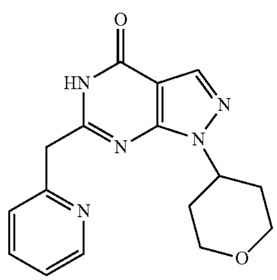 [SMILES: O=c1[nH]c(Cc2ccccn2)nc2c1cnn2C1CCOCC1] | Exp. 11B | | 5.97 (Method 1E hydro) | 312 (M + H)$^+$ |
| Exp. 52 | 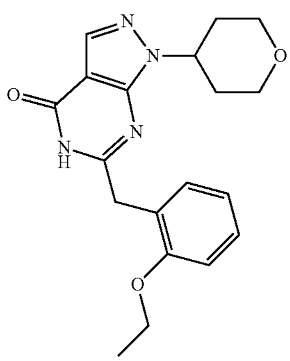 [SMILES: CCOc1ccccc1Cc1nc2c(cnn2C2CCOCC2)c(=O)[nH]1] | Exp. 11B | Exp. 5AK | 2.75 (Method Grad_C8_NH$_4$COOH) | 355 (M + H)$^+$ |
| Exp. 53 | 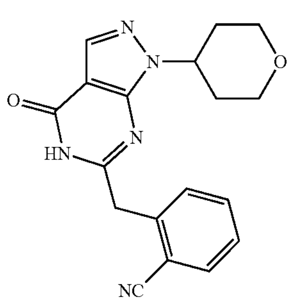 [SMILES: N#Cc1ccccc1Cc1nc2c(cnn2C2CCOCC2)c(=O)[nH]1] | Exp. 11B | | 2.75 (Method Grad_C8_NH$_4$COOH) | 336 (M + H)$^+$ |

-continued
| | Structure | pyrazolyl-carbox-amide | Ester | $R_t$ [min] | MS (ESI APCI, m/z) |
|---|---|---|---|---|---|
| Exp. 54 | 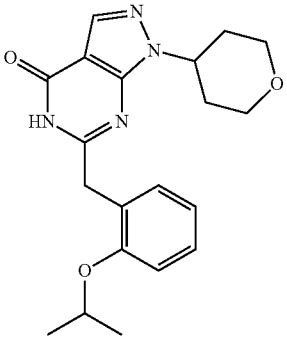 [SMILES: CC(C)Oc1ccccc1Cc1nc2c(cnn2C2CCOCC2)c(=O)[nH]1] | Exp. 11B | 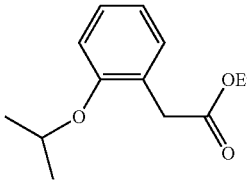 | 3.15 (Method Grad_C8_ NH$_4$COOH) | 369 (M + H)$^+$ |
| Exp. 55 | 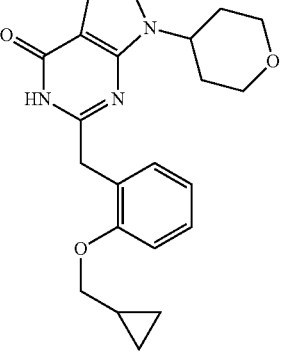 | Exp. 11B | Exp. 5K | 3.21 (Method Grad_C8_ NH$_4$COOH) | 381 (M + H)$^+$ |
| Exp. 56 | 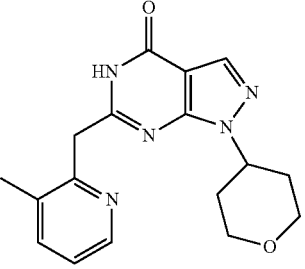 [SMILES: Cc1cccnc1Cc1nc2c(cnn2C2CCOCC2)c(=O)[nH]1] | Exp. 11B | 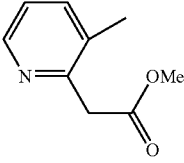 | 6.52 (Method 1E hydro) | 326 (M + H)$^+$ |
| Exp. 57 Enantio- mer R | 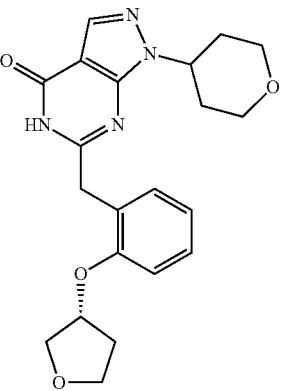 [SMILES: O=c1[nH]c(Cc2ccccc2O[C@@H]2CCOC2)nc2c1cnn2C1CCOCC1] | Exp. 11B | Exp. 5M | 2.64 (Method Grad_C8_ NH$_4$COOH) | 397 (M + H)$^+$ |

| | Structure | pyrazolyl-carbox-amide | Ester | R$_t$ [min] | MS (ESI APCI, m/z) |
|---|---|---|---|---|---|
| Exp. 58 Enantiomer S | | Exp. 11B | Exp. 5L | 2.64 (Method Grad_C8_NH$_4$COOH) | 397 (M + H)$^+$ |
| Exp. 60 | | Exp. 11B | Exp. 5O | 2.78 (Method Grad_C8_NH$_4$COOH) | 411 (M + H)$^+$ |
| Exp. 61 Enantiomer A | | Exp. 11B | Exp. 5A | 2.68 (Method Grad_C8_NH$_4$COOH) 15.32 (Chiral 1) | 345 (M + H)$^+$ |
| Exp. 62 Enantiomer B | | Exp. 11B | Exp. 5D | 2.68 (Method Grad_C8_NH$_4$COOH) 18.74 (Chiral 1) | 345 (M + H)$^+$ |

-continued

| | Structure | pyrazolyl-carbox-amide | Ester | R$_t$ [min] | MS (ESI APCI, m/z) |
|---|---|---|---|---|---|
| Exp. 63 | 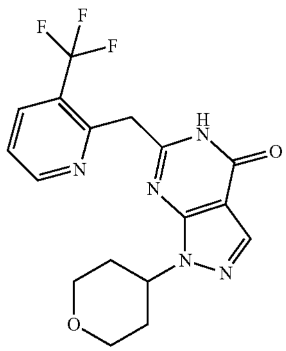 [SMILES: O=c1[nH]c(Cc2ncccc2C(F)(F)F)nc2c1cnn2C1CCOCC1] | Exp. 11B | | 9.37 (Method 2F) | 380 (M + H)$^+$ |
| Exp. 64 | 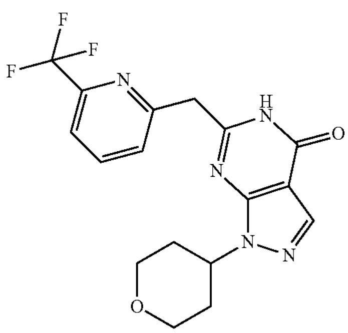 [SMILES: O=c1[nH]c(Cc2cccc(C(F)(F)F)n2)nc2c1cnn2C1CCOCC1] | Exp. 11B | Exp. 5S | 6.75 (Method 1E hydro) | 380 (M + H)$^+$ |
| Exp. 65 | 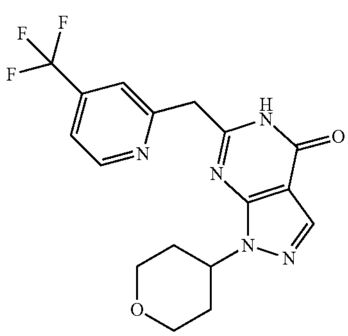 [SMILES: O=c1[nH]c(Cc2cc(C(F)(F)F)ccn2)nc2c1cnn2C1CCOCC1] | Exp. 11B | Exp. 5R | 9.45 (Method 2F) | 380 (M + H)$^+$ |
| Exp. 66 | 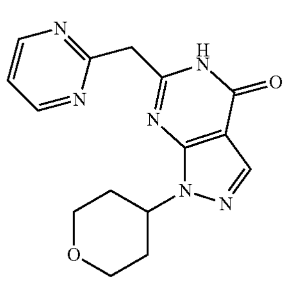 [SMILES: O=c1[nH]c(Cc2ncccn2)nc2c1cnn2C1CCOCC1] | Exp. 11B | | 6.70 (Method 2F) | 313 (M + H)$^+$ |

-continued

| | Structure | pyrazolyl-carbox-amide | Ester | R_t [min] | MS (ESI APCI, m/z) |
|---|---|---|---|---|---|
| Exp. 67 | 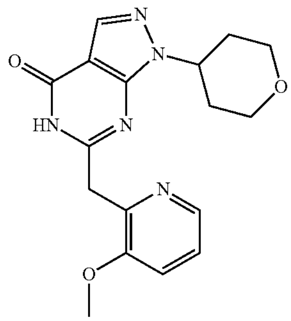 [SMILES: COc1cccnc1Cc1nc2c(cnn2C2CCOCC2)c(=O)[nH]1] | Exp. 11B | Exp. 5Q | 2.38 (Method Grad_C8_NH4COOH) | 342 (M + H)+ |
| Exp. 68 | 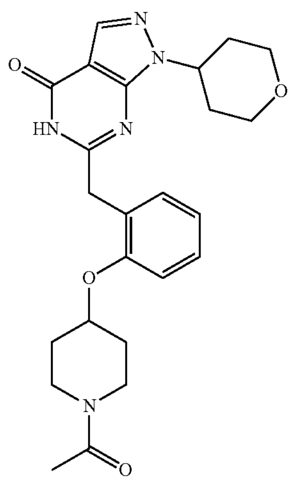 [SMILES: CC(=O)N1CCC(Oc2ccccc2Cc2nc3c(cnn3C3CCOCC3)c(=O)[nH]2)CC1] | Exp. 11B | Exp. 5I | 1.95 (Method Grad_C8_NH4COOH) | 452 (M + H)+ |
| Exp. 69 racem. mixture | 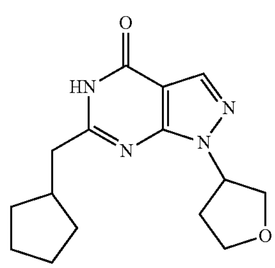 [SMILES: O=c1[nH]c(CC2CCCC2)nc2c1cnn2C1CCOC1] | Exp. 11E | Exp. 5AC | 7.30 (Method 1E) | 289 (M + H)+ |
| Exp. 70 racem. mixture | 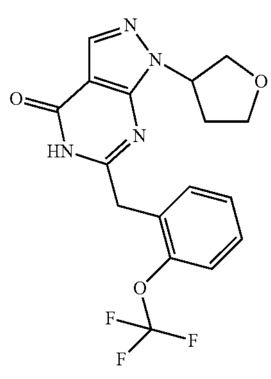 [SMILES: O=c1[nH]c(Cc2ccccc2OC(F)(F)F)nc2c1cnn2C1CCOC1] | Exp. 11E | Exp. 5AE | 7.70 (Method 1E fusion) | 381 (M + H)+ |

| | Structure | pyrazolyl-carbox-amide | Ester | R_t [min] | MS (ESI APCI, m/z) |
|---|---|---|---|---|---|
| Exp. 71 racem. mixture | 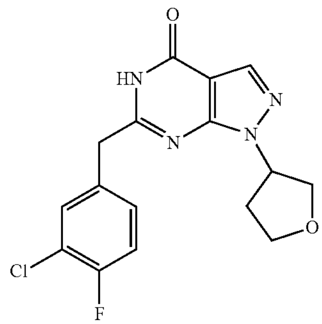 [SMILES: O=c1[nH]c(Cc2ccc(F)c(Cl)c2)nc2c1cnn2C1CCOC1] | Exp. 11E | Exp. 5F | 7.68 (Method 1E fusion) | 349 (M + H)+ |
| Exp. 72 mixture of stereo-isomers | 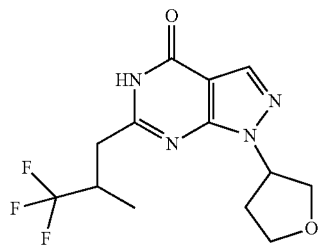 [SMILES: CC(Cc1nc2c(cnn2C2CCOC2)c(=O)[nH]1)C(F)(F)F] | Exp. 11E | | 9.82 (Method 2F) | 317 (M + H)+ |
| Exp. 73 racem. mixture | 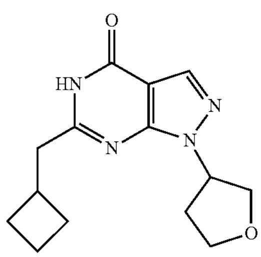 [SMILES: O=c1[nH]c(CC2CCC2)nc2c1cnn2C1CCOC1] | Exp. 11E | | 9.44 (Method 2F) | 275 (M + H)+ |
| Exp. 74 racem. mixture | 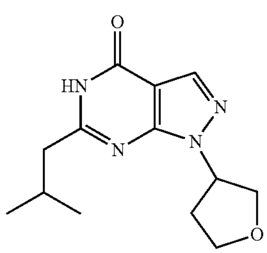 [SMILES: CC(C)Cc1nc2c(cnn2C2CCOC2)c(=O)[nH]1] | Exp. 11E | | 8.89 (Method 2F) | 263 (M + H)+ |
| Exp. 75 racem. mixture | 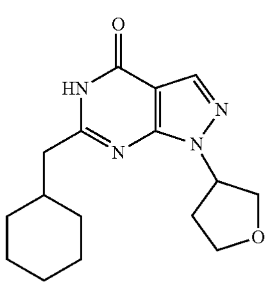 [SMILES: O=c1[nH]c(CC2CCCCC2)nc2c1cnn2C1CCOC1] | Exp. 11E | | 10.69 (Method 2F) | 303 (M + H)+ |

-continued
| | Structure | pyrazolyl-carbox-amide | Ester | R$_t$ [min] | MS (ESI APCI, m/z) |
|---|---|---|---|---|---|
| Exp. 76 racem. mixture | 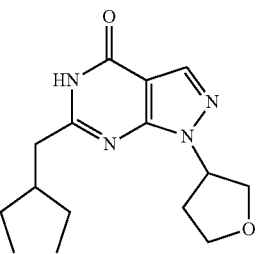 [SMILES: CCC(CC)Cc1nc2c(cnn2C2CCOC2)c(=O)[nH]1] | Exp. 11E | Exp. 5H | 10.57 (Method 2F) | 291 (M + H)+ |
| Exp. 77 mixture of stereo-isomers | 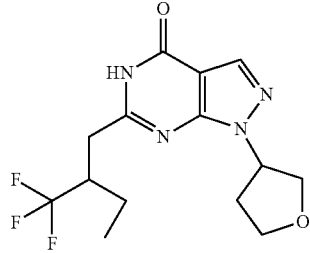 [SMILES: CCC(Cc1nc2c(cnn2C2CCOC2)c(=O)[nH]1)C(F)(F)F] | Exp. 11E | Exp. 5T | 10.55 (Method 2F) | 331 (M + H)+ |
| Exp. 78 racem. mixture | 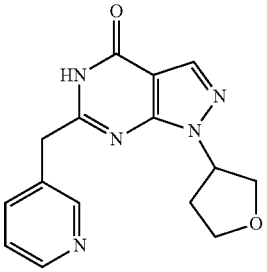 [SMILES: O=c1[nH]c(Cc2cccnc2)nc2c1cnn2C1CCOC1] | Exp. 11E | 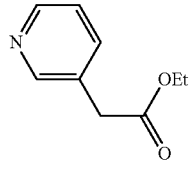 | 4.83 (Method 1E Hydro) | 298 (M + H)+ |
| Exp. 79 racem. mixture | 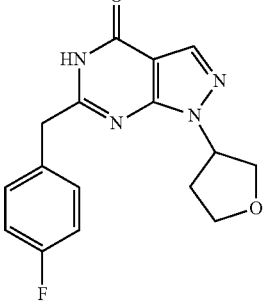 | Exp. 11E | 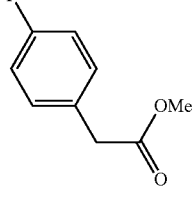 | 7.10 (Method 1E fusion) | 315 (M + H)+ |
| Exp. 80 racem. mixture | 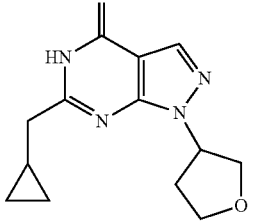 | Exp. 11E | 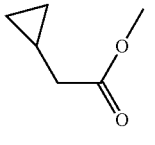 | 5.97 (Method 1E fusion) | 261 (M + H)+ |

-continued
| | Structure | pyrazolyl-carbox-amide | Ester | $R_t$ [min] | MS (ESI APCI, m/z) |
|---|---|---|---|---|---|
| Exp. 81 mixture of stereo-isomers | 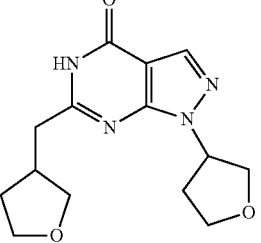 | Exp. 11E | 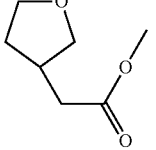 | 4.73 (Method 1E hydro) | 291 (M + H)+ |
| Exp. 82 racem. mixture | 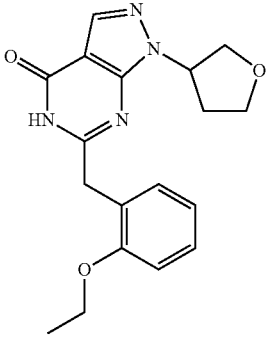 [SMILES: CCOc1ccccc1Cc1nc2c(cnn2C2CCOC2)c(=O)[nH]1] | Exp. 11E | Exp. 5AK | 7.37 (Method 1E hydro) | 341 (M + H)+ |
| Exp. 83 racem. mixture | 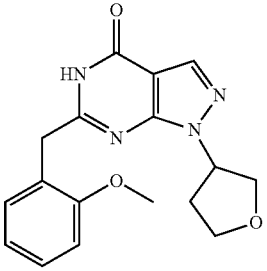 [SMILES: COc1ccccc1Cc1nc2c(cnn2C2CCOC2)c(=O)[nH]1] | Exp. 11E | Exp. 5AD | 6.85 (Method 1E hydro) | 327 (M + H)+ |
| Exp. 84 mixture of stereo-isomers | 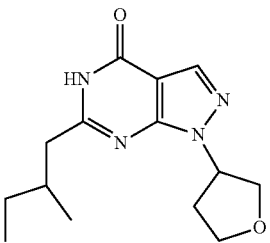 [SMILES: CCC(C)Cc1nc2c(cnn2C2CCOC2)c(=O)[nH]1] | Exp. 11E | 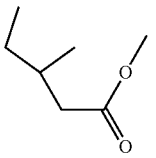 | 6.88 (Method 1E hydro) | 277 (M + H)+ |
| Exp. 85 racem. mixture | 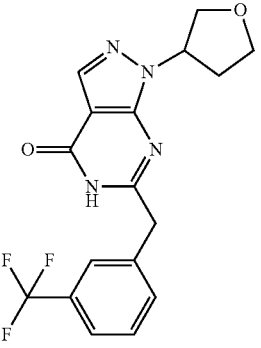 [SMILES: O=c1[nH]c(Cc2cccc(C(F)(F)F)c2)nc2c1cnn2C1CCOC1] | Exp. 11E | Exp. 5AH | 7.93 (Method 1E hydro) | 365 (M + H)+ |

| | Structure | pyrazolyl-carbox-amide | Ester | R$_r$ [min] | MS (ESI APCI, m/z) |
|---|---|---|---|---|---|
| Exp. 86 racem. mixture | 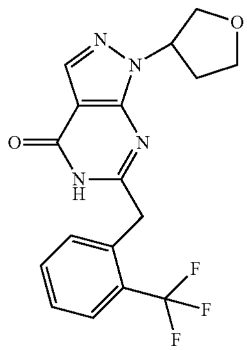 [SMILES: O=c1[nH]c(Cc2ccccc2C(F)(F)F)nc2c1cnn2C1CCOC1] | Exp. 11E | 2-(trifluoromethyl)phenyl acetic acid methyl ester | 10.93 (Method 2F) | 365 (M + H)$^+$ |
| Exp. 87 racem. mixture | 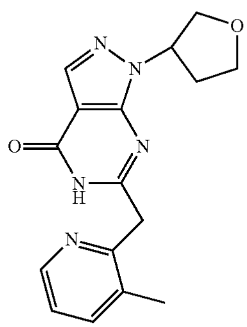 [SMILES: Cc1cccnc1Cc1nc2c(cnn2C2CCOC2)c(=O)[nH]1] | Exp. 11E | methyl 2-(3-methylpyridin-2-yl)acetate | 5.43 (Method 1E hydro) | 312 (M + H)$^+$ |
| Exp. 88 racem. mixture | 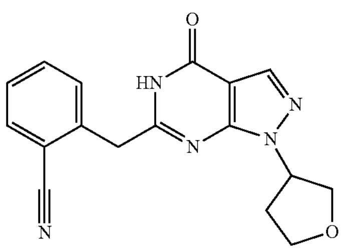 [SMILES: N#Cc1ccccc1Cc1nc2c(cnn2C2CCOC2)c(=O)[nH]1] | Exp. 11E | methyl 2-(2-cyanophenyl)acetate | 5.43 (Method 1E hydro) | 312 (M + H)$^+$ |
| Exp. 89 racem. mixture | 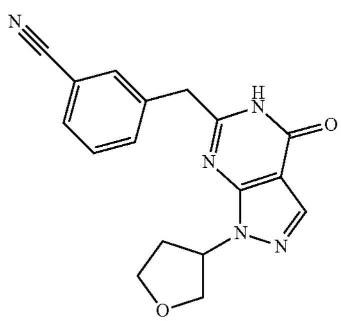 [SMILES: N#Cc1cccc(Cc2nc3c(cnn3C3CCOC3)c(=O)[nH]2)c1] | Example 11E | methyl 2-(3-cyanophenyl)acetate | 5.28 (Method 1E hydro) | 322 (M + H)$^+$ |
| Exp. 90 racem. mixture | 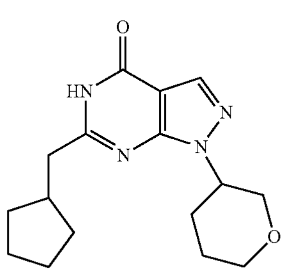 [SMILES: O=c1[nH]c(CC2CCCC2)nc2c1cnn2C1CCCOC1] | Exp. 11F | Exp. 5AC | 8 (Method 1E hydro) | 303 (M + H)$^+$ |

-continued

| | Structure | pyrazolyl-carbox-amide | Ester | R_t [min] | MS (ESI APCI, m/z) |
|---|---|---|---|---|---|
| Exp. 91 racem. mixture | 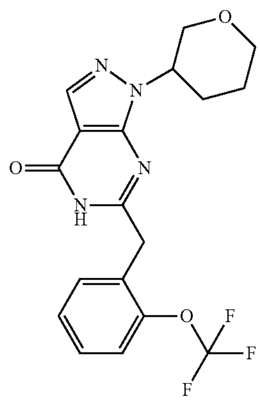 [SMILES: O=c1[nH]c(Cc2ccccc2OC(F)(F)F)nc2c1cnn2C1CCCOC1] | Exp. 11F | Exp. 5AE | 8.45 (Method 1E hydro) | 395 (M + H)+ |
| Exp. 92 racem. mixture | 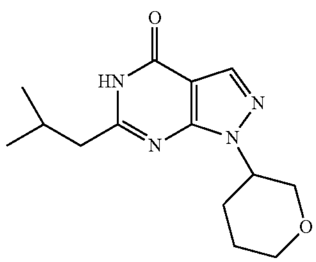 [SMILES: CC(C)Cc1nc2c(cnn2C2CCCOC2)c(=O)[nH]1] | Exp. 11F | | 6.93 (Method 1E hydro) | 277 (M + H)+ |
| Exp. 93 racem. mixture | 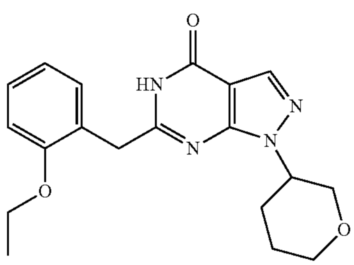 [SMILES: CCOc1ccccc1Cc1nc2c(cnn2C2CCCOC2)c(=O)[nH]1] | Exp. 11F | Exp. 5AK | 8.20 (Method 1E hydro) | 355 (M + H)+ |
| Exp. 94 racem. mixture | 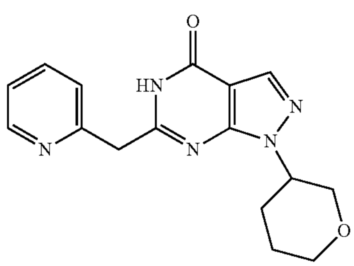 [SMILES: O=c1[nH]c(Cc2ccccn2)nc2c1cnn2C1CCCOC1] | Exp. 11F | | 6.28 (Method 1E hydro) | 312 (M + H)+ |
| Exp. 95 mixture of stereo-isomers | 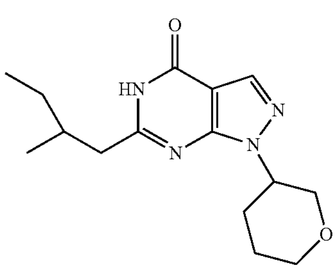 [SMILES: CCC(C)Cc1nc2c(cnn2C2CCCOC2)c(=O)[nH]1] | Exp. 11F | | 7.70 (Method 1E hydro) | 291 (M + H)+ |

-continued

| | Structure | pyrazolyl-carbox-amide | Ester | R, [min] | MS (ESI APCI, m/z) |
|---|---|---|---|---|---|
| Exp. 96 racem. mixture | 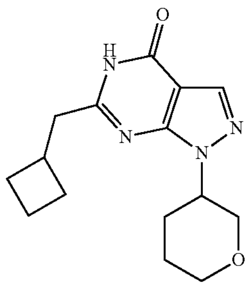 [SMILES: O=c1[nH]c(CC2CCC2)nc2c1cnn2C1CCCOC1] | Exp. 11F | cyclobutyl-CH2-C(O)OMe | 7.33 (Method 1E hydro) | 289 (M + H)+ |
| Exp. 97 racem. mixture | 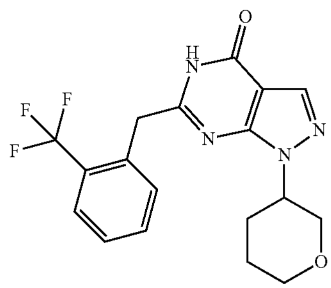 [SMILES: O=c1[nH]c(Cc2ccccc2C(F)(F)F)nc2c1cnn2C1CCCOC1] | Exp. 11F | 2-(trifluoromethyl)phenyl-CH2-C(O)OMe | 8.17 (Method 1E hydro) | 379 (M + H)+ |
| Exp. 98 racem. mixture | 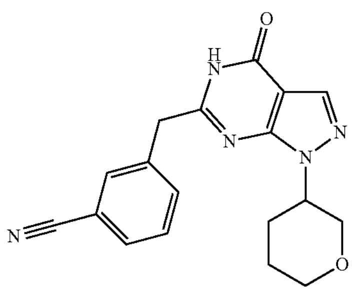 [SMILES: N#Cc1cccc(Cc2nc3c(cnn3C3CCCOC3)c(=O)[nH]2)c1] | Exp. 11F | 3-cyanophenyl-CH2-C(O)OMe | 6.80 (Method 1E hydro) | 336 (M + H)+ |
| Exp. 99 racem. mixture | 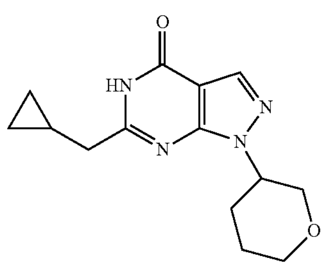 [SMILES: O=c1[nH]c(CC2CC2)nc2c1cnn2C1CCCOC1] | Exp. 11F | cyclopropyl-CH2-C(O)OMe | 6.43 (Method 1E hydro) | 275 (M + H)+ |
| Exp. 100 racem. mixture | 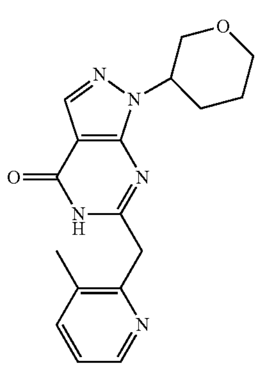 [SMILES: Cc1cccnc1Cc1nc2c(cnn2C2CCCOC2)c(=O)[nH]1] | Exp. 11F | 3-methylpyridin-2-yl-CH2-C(O)OMe | 2.38 (Method 2F) | 326 (M + H)+ |

-continued

| | Structure | pyrazolyl-carbox-amide | Ester | R$_t$ [min] | MS (ESI APCI, m/z) |
|---|---|---|---|---|---|
| Exp. 101 racem. mixture | 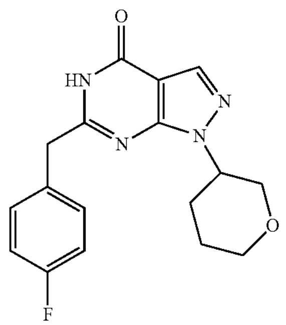 [SMILES: O=c1[nH]c(Cc2ccc(F)cc2)nc2c1cnn2C1CCCOC1] | Exp. 11F | | 7.52 (Method 1E hydro) | 329 (M + H)$^+$ |
| Exp. 102 racem. mixture | 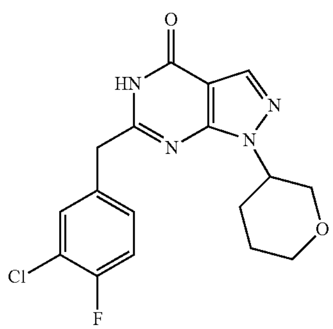 [SMILES: O=c1[nH]c(Cc2ccc(F)c(Cl)c2)nc2c1cnn2C1CCCOC1] | Exp. 11F | Exp. 5F | 8.28 (1E hydro) | 363 (M + H)$^+$ |
| Exp. 103 racem. mixture | 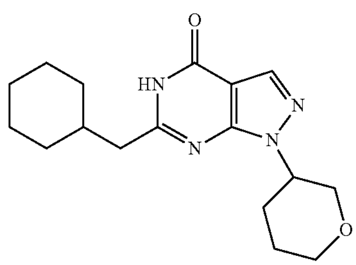 [SMILES: O=c1[nH]c(CC2CCCCC2)nc2c1cnn2C1CCCOC1] | Exp. 11F | | 8.70 (Method 1E hydro) | 317 (M + H)$^+$ |
| Exp. 104 racem. mixture | 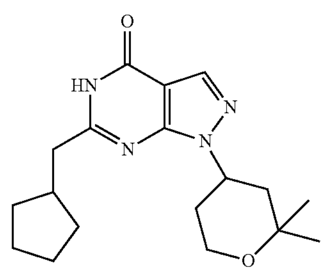 [SMILES: CC1(C)CC(n2ncc3c(=O)[nH]c(CC4CCCC4)nc32)CCO1] | Exp. 11G | Exp. 5AC | 8.57 (Method 1E hydro) | 331 (M + H)$^+$ |
| Exp. 105 racem. mixture | 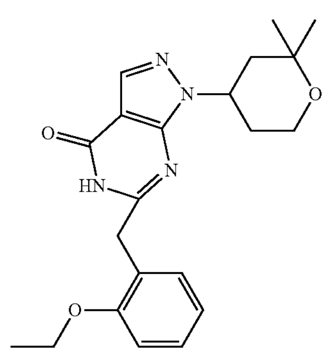 [SMILES: CCOc1ccccc1Cc1nc2c(cnn2C2CCOC(C)(C)C2)c(=O)[nH]1] | Exp. 11G | Exp. 5AK | 8.62 (Method 1E hydro) | 383 (M + H)$^+$ |

-continued

| | Structure | pyrazolyl-carbox-amide | Ester | R_t [min] | MS (ESI APCI, m/z) |
|---|---|---|---|---|---|
| Exp. 106 racem. mixture | 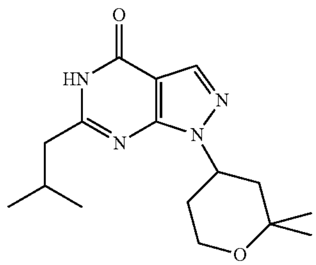 [SMILES: CC(C)Cc1nc2c(cnn2C2CCOC(C)(C)C2)c(=O)[nH]1] | Exp. 11G | Methyliso-valerate | 7.58 (Method 1E hydro) | 305 (M + H)+ |
| Exp. 108 racem. mixture | 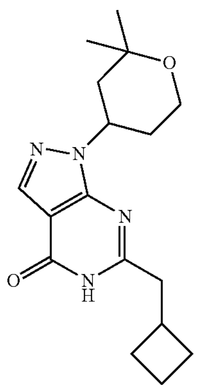 [SMILES: CC1(C)CC(n2ncc3c(=O)[nH]c(CC4CCC4)nc32)CCO1] | Exp. 11G | Cyclobutyl-acetic acid methyl ester | 7.93 (Method 1E) | 317 (M + H)+ |
| Exp. 111 trans; racem. mixture | 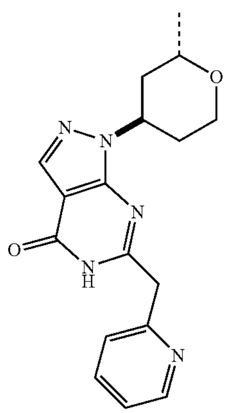 | Exp. 11H | | 2.05 (Method 2F) | 326 (M + H)+ |
| Exp. 112 trans; racem. mixture | 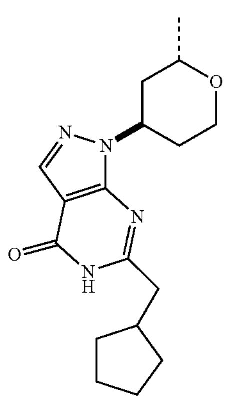 | Exp. 11H | Exp. 5AC | 8.25 (Method 2F) | 317 (M + H)+ |

-continued

| | Structure | pyrazolyl-carbox-amide | Ester | R, [min] | MS (ESI APCI, m/z) |
|---|---|---|---|---|---|
| Exp. 113 trans; racem. mixture | 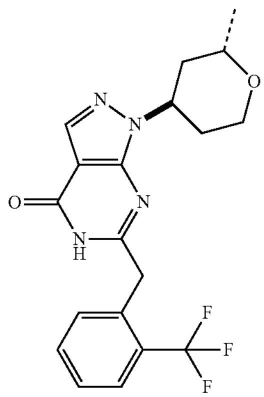 | Exp. 11H | | 8.42 (Method 1E hydro) | 393 (M + H)+ |
| Exp. 114 trans; racem. mixture | 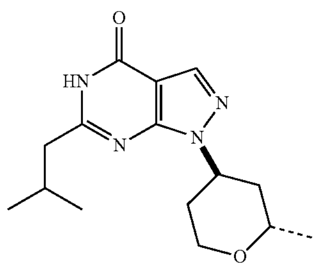 | Exp. 11H | | 7.15 (Method 1E hydro) | 291 (M + H)+ |
| Exp. 115 cis; racem. mixture | 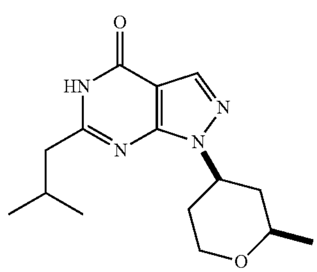 | Exp. 11I | | 9.90 (Method 2F) | 291 (M + H)+ |
| Exp. 116 cis; racem. mixture | 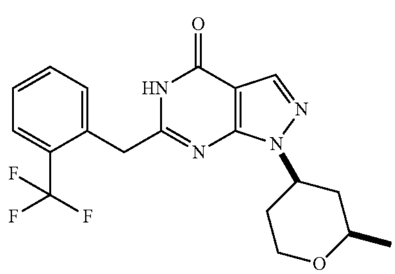 | Exp. 11I | | 8.18 (Method 1E hydro) | 393 (M + H)+ |
| Exp. 117 cis; racem. mixture | 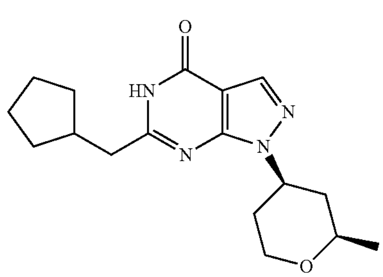 [SMILES: C[C@@H]1C[C@H](n2ncc3c(=O)[nH]c(CC4CCCC4)nc32)CCO1] | Exp. 11I | Exp. 5AC | 7.98 (Method 1E hydro) | 317 (M + H)+ |

-continued

| | Structure | pyrazolyl-carbox-amide | Ester | R_t [min] | MS (ESI APCI, m/z) |
|---|---|---|---|---|---|
| Exp. 118 cis; racem. mixture | 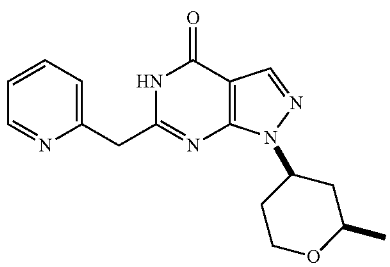 | Exp. 11I | (pyridin-2-yl methyl acetate) | 5.80 (Method 1E hydro) | 326 (M + H)+ |
| Exp. 119 cis; racem. mixture | 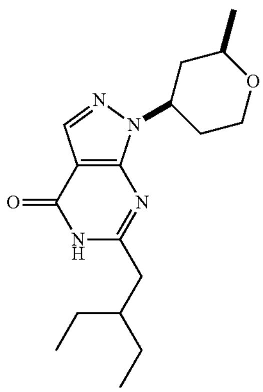 | Exp. 11I | Exp. 5H | 8.42 (Method 1E hydro) | 319 (M + H)+ |
| Exp. 120 cis; racem. mixture | 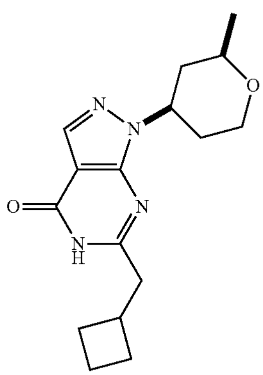 | Exp. 11I | (methyl cyclobutylacetate) | 7.33 (Method 1E hydro) | 303 (M + H)+ |
| Exp. 121 cis; racem. mixture | 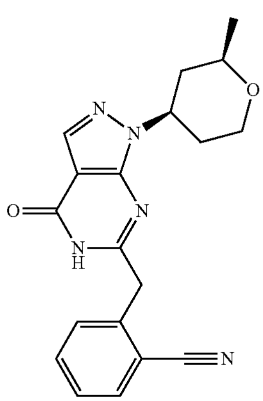 [SMILES: C[C@@H]1C[C@H](n2ncc3c(=O)[nH]c(Cc4ccccc4C#N)nc32)CCO1] | Exp. 11I | (methyl 2-cyanophenylacetate) | 9.91 (Method 2F) | 350 (M + H)+ |

-continued

| | Structure | pyrazolyl-carbox-amide | Ester | R_t [min] | MS (ESI APCI, m/z) |
|---|---|---|---|---|---|
| Exp. 122 racem. mixture | 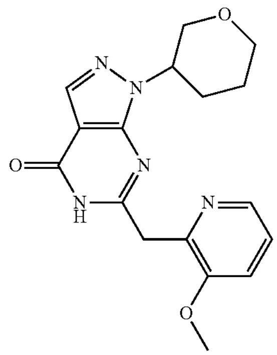 [SMILES: COc1cccnc1Cc1nc2c(cnn2C2CCCOC2)c(=O)[nH]1] | Exp. 11F | | 6.95 (Method 2F) | 342 (M + H)+ |
| Exp. 123 | 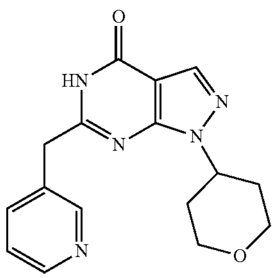 [SMILES: O=c1[nH]c(Cc2cccnc2)nc2c1cnn2C1CCOCC1] | Exp. 11B | | 2.12 (Method Grad_C8_NH4COOH) | 312 (M + H)+ |
| Exp. 124 racem. mixture | 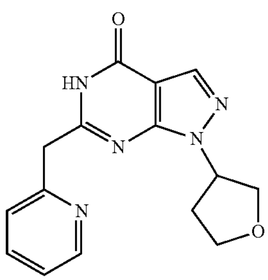 [SMILES: O=c1[nH]c(Cc2ccccn2)nc2c1cnn2C1CCOC1] | Exp. 11E | | 4.98 (Method 1E hydro) | 298 (M + H)+ |
| Exp. 125 | 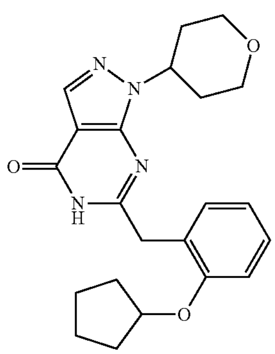 [SMILES: O=c1[nH]c(Cc2ccccc2OC2CCCC2)nc2c1cnn2C1CCOCC1] | Exp. 11B | Exp. 5P | 8.72 (Method 1E hydro) | 395 (M + H)+ |
| Exp. 126 racem. mixture | 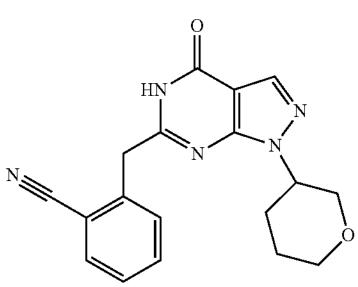 [SMILES: N#Cc1ccccc1Cc1nc2c(cnn2C2CCCOC2)c(=O)[nH]1] | Exp. 11F | | 9.72 (Method 2F) | 336 (M + H)+ |

-continued

| | Structure | pyrazolyl-carbox-amide | Ester | R$_t$ [min] | MS (ESI APCI, m/z) |
|---|---|---|---|---|---|
| Exp. 127 racem. mixture | 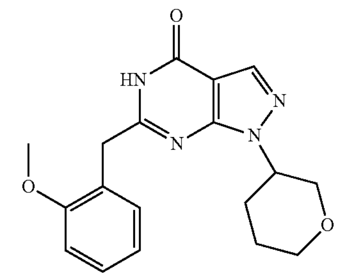 [SMILES: COc1ccccc1Cc1nc2c(cnn2C2CCCOC2)c(=O)[nH]1] | Exp. 11F | Exp. 5AB | 7.62 (Method 1E hydro) | 341 (M + H)$^+$ |
| Exp. 128 Enantiomer S | | Exp. 11B | Exp. 5G | 9.83 (Method 2F) | 291 (M + H)$^+$ |
| Exp. 129 racem. mixture | 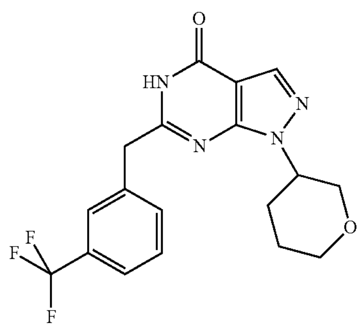 [SMILES: O=c1[nH]c(Cc2cccc(C(F)(F)F)c2)nc2c1cnn2C1CCCOC1] | Exp. 11F | Exp. 5AF | 11.56 (Method 2F) | 379 (M + H)$^+$ |
| Exp. 130 racem. mixture | 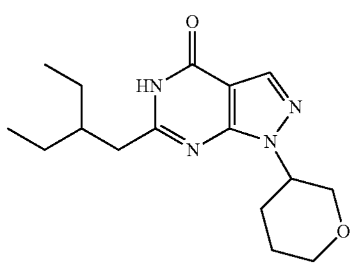 [SMILES: CCC(CC)Cc1nc2c(cnn2C2CCCOC2)c(=O)[nH]1] | Exp. 11F | Exp. 5H | 8.38 (Method 1E hydro) | 305 (M + H)$^+$ |
| Exp. 131 Enantiomer A | | Exp. 11B | Exp. 5B | 9.93 (Method 2F) | 331 (M + H)$^+$ |

-continued

| | Structure | pyrazolyl-carbox-amide | Ester | R$_t$ [min] | MS (ESI APCI, m/z) |
|---|---|---|---|---|---|
| Exp. 132 Enantiomer B | | Exp. 11B | Exp. 5C | 9.93 (Method 2F) | 331 (M + H)$^+$ |
| Exp. 132-1 cis; racem. mixture | | Exp. 11IA | | 9.83 (Method 2F) | 291 (M + H)$^+$ |
| Exp. 132-2 cis; racem. mixture | | Exp. 11IA | Exp. 5AC | 10.96 (Method 2F) | 317 (M + H)$^+$ |
| Exp. 132-3 Enantiomer A | | Exp. 15A | | 8.84 (Method 2F) | 263 (M + H)$^+$ |
| Exp. 132-4 Enantiomer B | | Exp. 16A | | 8.96 (Method 2F) | 263 (M + H)$^+$ |

-continued

| | Structure | pyrazolyl-carboxamide | Ester | R_t [min] | MS (ESI APCI, m/z) |
|---|---|---|---|---|---|
| Exp. 132-5 trans, racem. mixture | | Exp. 11IB | Exp. 5AC | 10.21 (Method 2F) | 317 (M + H)+ |
| Exp. 132-6 Enantiomer B | | Exp. 16A | | 7.15 (Method 1E Hydro) | 275 (M + H)+ |
| Exp. 132-7 Enantiomer B | | Exp. 16A | | 5.68 (Method 1E Hydro) | 298 (M + H)+ |
| Exp. 132-8 trans, racem. mixture | | Exp. 11IB | | 9.23 (Method 2F) | 291 (M + H)+ |
| Exp. 132-9 Enantiomer A | | Exp. 15A | | 8.83 (Method 2L) | 275 (M + H)+ |

Example 133

6-(2-Ethyl-butyl)-1-(tetrahydro-pyran-4-yl)-1,5-dihydro-pyrazolo[3,4-d]pyrimidin-4-one

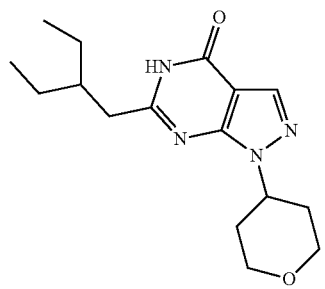 [SMILES: CCC(CC)Cc1nc2c(cnn2C2CCOCC2)c(=O)[nH]1]

Example 11B (0.1 g, 0.48 mmol) was mixed with polyphosphoric acid (1.0 g) and 2-(trifluoromethoxy)phenylacetic acid (248 mg, 1.9 mmol) was added. The mixture was heated to 120° C. during 16 hours. Temperature was lowered to 20° C. and the pH value was adjusted to 7 by addition of ammonia (30% solution in water). The aqueous phase was extracted with dichloromethane (2×20 mL) and the organic phase was dried over sodium sulphate. The crude mixture was purified by flash chromatography. Eluent: hexane/ethyl acetate 40/60.

Obtained 23.5 mg (16%) as a white solid

HPLC-MS (1E) $R_t$: 6.77 min

MS (APCI pos): m/z=305 $(M+H)^+$

The following examples were synthesized in analogy to the preparation of Example 133, using the corresponding carboxylic acids as starting materials:

| | structure | starting material | $R_t$ [min] | MS ESI-APCI, m/z) |
|---|---|---|---|---|
| Example 134 | 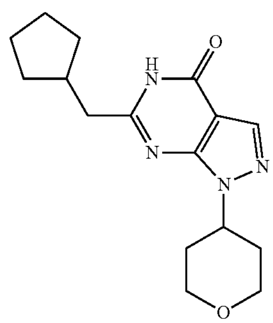 [SMILES: O=c1[nH]c(CC2CCCC2)nc2c1cnn2C1CCOCC1] | | 6.37 (Method 1E) | 303 $(M + H)^+$ |
| Example 135 racem. mixture | 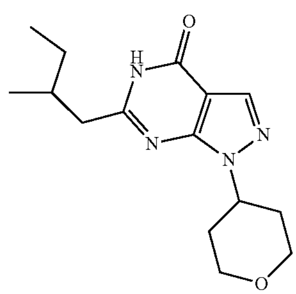 [SMILES: CCC(C)Cc1nc2c(cnn2C2CCOCC2)c(=O)[nH]1] | | 5.95 (Method 1E) | 291 $(M + H)^+$ |
| Example 136 | 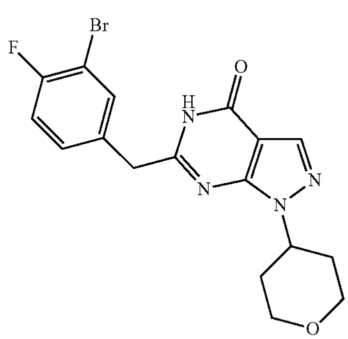 [SMILES: O=c1[nH]c(Cc2ccc(F)c(Br)c2)nc2c1cnn2C1CCOCC1] | | 6.57 (Method 1E) | 407 $(M + H)^+$ |

-continued
| structure | starting material | R$_t$ [min] | MS ESI-APCl, m/z |
|---|---|---|---|
| Example 137 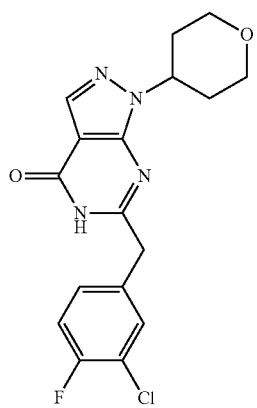 [SMILES: O=c1[nH]c(Cc2ccc(F)c(Cl)c2)nc2c1cnn2C1CCOCC1] | 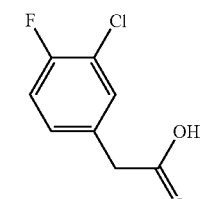 | 6.48 (Method 1E) | 363 (M + H)$^+$ |
| Example 138 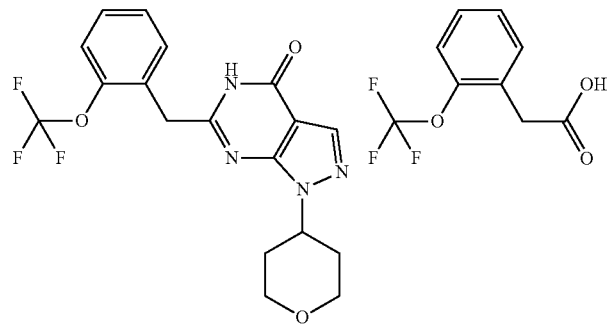 | 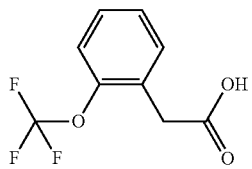 [SMILES: O=C(O)Cc1ccccc1OC(F)(F)F] | 6.72 (Method 1E) | 395 (M + H)$^+$ |
| Example 139 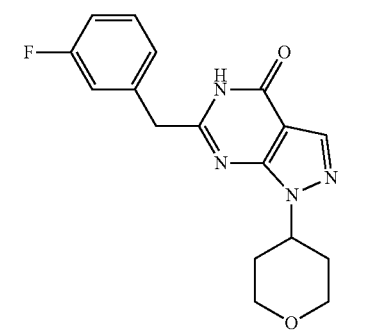 [SMILES: O=c1[nH]c(Cc2cccc(F)c2)nc2c1cnn2C1CCOCC1] | 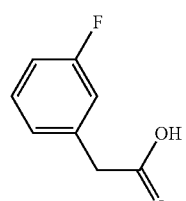 | 2.71 (Method Grad_C8_NH$_4$COOH) | 329 (M + H)$^+$ |
| Example 140 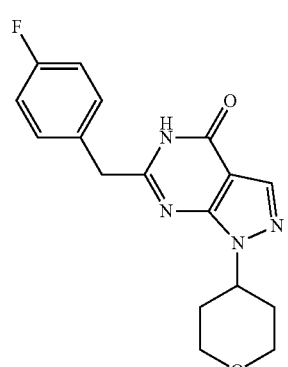 | 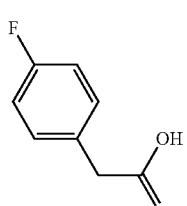 | 2.77 (Method Grad_C8_NH$_4$COOH) | 329 (M + H)$^+$ |

-continued
| | structure | starting material | R$_t$ [min] | MS ESI-APCl, m/z |
|---|---|---|---|---|
| Example 141 | 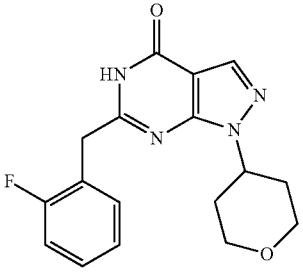 [SMILES: O=c1[nH]c(Cc2ccccc2F)nc2c1cnn2C1CCOCC1] | 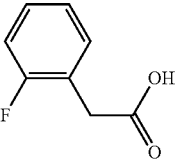 | 2.90 (Method Grad_C8_NH$_4$COOH) | 329 (M + H)$^+$ |
| Example 142 | 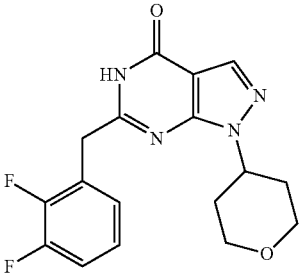 [SMILES: O=c1[nH]c(Cc2cccc(F)c2F)nc2c1cnn2C1CCOCC1] | 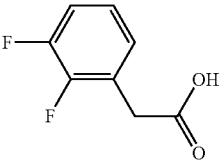 [SMILES: O=C(O)Cc1cccc(F)c1F] | 3.07 (Method Grad_C8_NH$_4$COOH) | 347 (M + H)$^+$ |
| Example 143 | 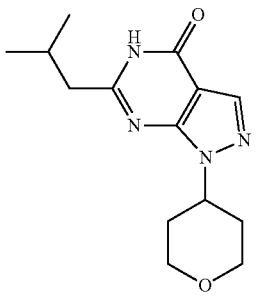 [SMILES: CC(C)Cc1nc2c(cnn2C2CCOCC2)c(=O)[nH]1] | 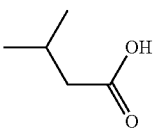 | 2.71 (Method Grad_C8_NH$_4$COOH) | 277 (M + H)$^+$ |
| Example 144 | 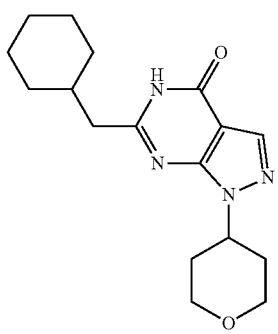 [SMILES: O=c1[nH]c(CC2CCCCC2)nc2c1cnn2C1CCOCC1] | 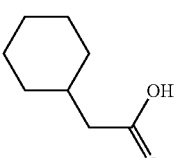 | 3.28 (Method Grad_C8_NH$_4$COOH) | 317 (M + H)$^+$ |

Example 145

Racemic Mixture

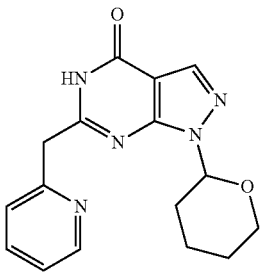 [SMILES: O=c1[nH]c(Cc2ccccn2)nc2c1cnn2C1CCCCO1]

106 mg (0.47 mmol) Example 12V was mixed with 4 mL ethyl acetate and 0.5 mL dimethylformamide, 51 mg (0.61 mmol) 3,4-dihydro-2H-pyran and 88.4 mg (0.51 mmol) p-toluenesulfonic acid were added. The reaction mixture was heated to 60° C. and stirred for 2 h. After cooling to room temperature ethyl acetate was added and the mixture was washed with saturated sodium hydrogen carbonate and with saturated sodium chloride. The organic layer was evaporated under reduced pressure. The residue was purified by preparative HPLC-MS. 31.5 mg (21.7%) were obtained.

MS (APCI pos): m/z=312 (M+H)$^+$

HPLC-MS (Method 2F) $R_t$: 8.26 min

The following examples were synthesized in analogy to the preparation of Example 145, using the corresponding pyrazolopyrimidinones as starting materials.

| | structure | starting material | $R_t$ [min] | MS (ESI-APCI, m/z) |
|---|---|---|---|---|
| Exp. 146 racem. mixture | 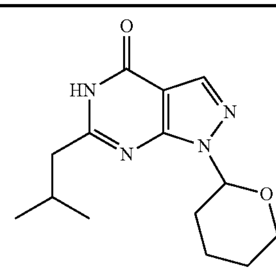 | Example 12W | 9.99 (Method 2F) | 277 (M + H)$^+$ |
| Exp. 147 racem. mixture | 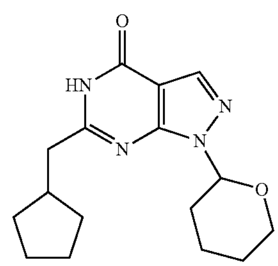 [SMILES: O=c1[nH]c(CC2CCCC2)nc2c1cnn2C1CCCCO1] | Example 12X | 10.98 (Method 2F) | 303 (M + H)$^+$ |
| Exp. 147-1 racem. mixture | 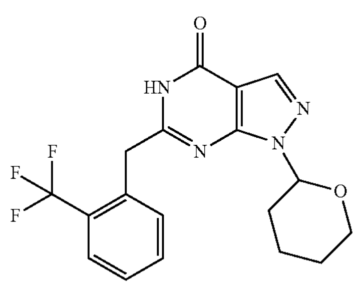 [SMILES: O=c1[nH]c(Cc2ccccc2C(F)(F)F)nc2c1cnn2C1CCCCO1] | Example 12Y | 10.98 (Method 2F) | 303 (M + H)$^+$ |
| Example 147-2 racem. mixture | 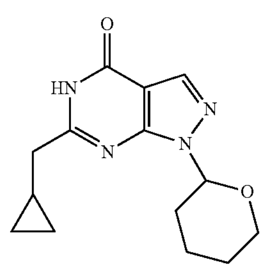 [SMILES: O=c1[nH]c(CC2CC2)nc2c1cnn2C1CCCCO1] | Example 12AA | 9.56 (Method 2F) | 275 (M + H)$^+$ |

| | structure | starting material | $R_t$ [min] | MS (ESI-APCI, m/z) |
|---|---|---|---|---|
| Example 147-3 racem. mixture | 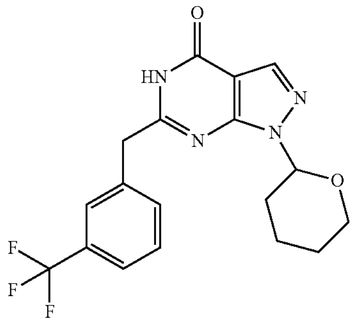 [SMILES: O=c1[nH]c(Cc2cccc(C(F)(F)F)c2)nc2c1cnn2C1CCCCO1] | Example 12Z | 11.62 (Method 2F) | 379 (M + H)⁺ |

Example 148

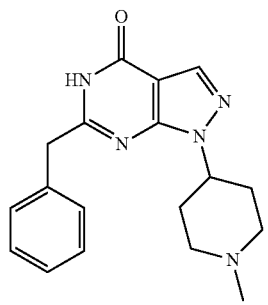 [SMILES: CN1CCC(n2ncc3c(=O)[nH]c(Cc4ccccc4)nc32)CC1]

160 mg (470 mmol) of Example 12E was dissolved in 10 mL methanol and 350 mg Raney nickel was added. The reaction mixture was hydrogenated at room temperature for 6 h, filtered and the solvent evaporated under reduced pressure. 100 mg (65%) of the product were obtained.

HPLC-MS (Method 1): $R_t$: 0.95 min

MS (ESI pos): m/z=324 (M+H)

The following examples were synthesized in analogy to the preparation of Example 148, using the corresponding N-oxides as starting materials.

| | structure | starting material | Rt [min] | MS (ESI, m/z) |
|---|---|---|---|---|
| Exp. 149 | 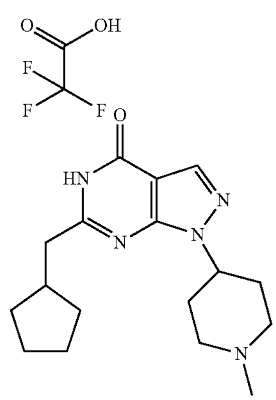 | Example 12D | 0.95 (Method 1) | 316 (M + H)⁺ |

| | structure | starting material | Rt [min] | MS (ESI, m/z) |
|---|---|---|---|---|
| Exp. 150 | 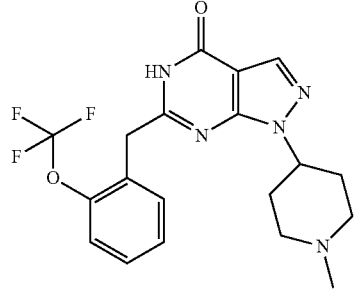 [SMILES: CN1CCC(n2ncc3c(=O)[nH]c(Cc4ccccc4OC(F)(F)F)nc32)CC1] | Example 12F | 1.11 (Method 1) | 408 (M + H)+ |

Example 151

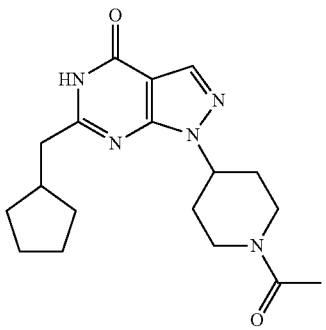 [SMILES: CC(=O)N1CCC(n2ncc3c(=O)[nH]c(CC4CCCC4)nc32)CC1]

62 mg (150 mmol) of Example 13B were dissolved in 4 mL dichloromethane, 22.5 µL (300 mmol) acetyl chloride and 42 µL (300 mmol) triethylamine were added. The reaction mixture was stirred at room temperature over night. The solvent was removed under reduced pressure. The residue was purified by preparative HPLC (eluent A: water+0.13% TFA, eluent B: acetonitrile). 28 mg (55%) of the product were obtained.

HPLC-MS (Method 1): $R_t$: 1.18 min
MS (ESI pos): m/z=344 (M+H)+

The following examples were synthesized in analogy to the preparation of Example 151, using the corresponding starting materials. It will be evident that as acylating agent not for all compounds acetylchloride has been introduced but other acylating agents like commercially available methoxychloroformate, substituted or unsubstituted aminocarbonylchloride, unsubstituted or substituted phenoxycarbonylchloride, unsubstituted or substituted benzoylchloride were used.

| | structure | starting material | $R_t$ [min] | MS (ESI, m/z) |
|---|---|---|---|---|
| Exp. 152 | 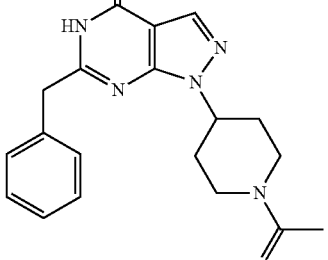 | Example 13K | 1.09 (Method 1) | 352 (M + H)+ |
| Exp. 153 | 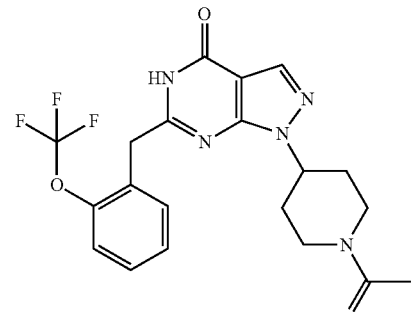 | Example 13L | 1.25 (Method 1) | 436 (M + H)+ |

-continued
| | structure | starting material | R$_t$ [min] | MS (ESI, m/z) |
|---|---|---|---|---|
| Exp. 154 racem. mixture | 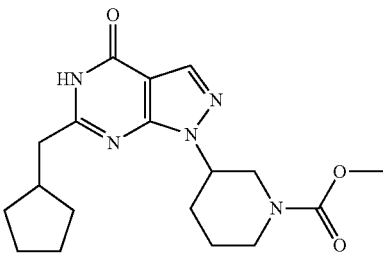 [SMILES: COC(=O)N1CCCC(n2ncc3c(=O)[nH]c(CC4CCCC4)nc32)C1] | Example 13C | 1.38 (Method 1) | 360 (M + H)$^+$ |
| Exp. 155 racem. mixture | 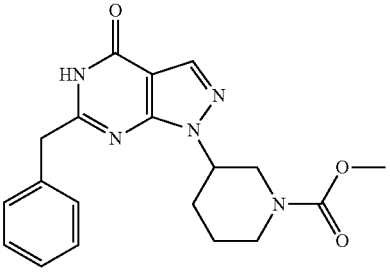 [SMILES: COC(=O)N1CCCC(n2ncc3c(=O)[nH]c(Cc4ccccc4)nc32)C1] | Example 13D | 1.30 (Method 1) | 368 (M + H)$^+$ |
| Exp. 156 racem. mixture | 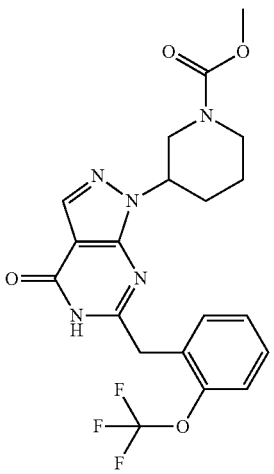 [SMILES: COC(=O)N1CCCC(n2ncc3c(=O)[nH]c(Cc4ccccc4OC(F)(F)F)nc32)C1] | Example 13E | 1.44 (Method 1) | 452 (M + H)$^+$ |
| Exp. 157 racem. mixture | 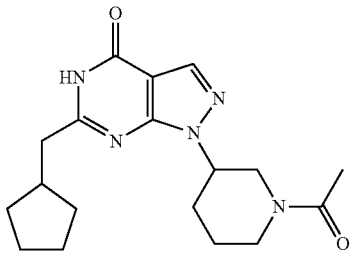 [SMILES: CC(=O)N1CCCC(n2ncc3c(=O)[nH]c(CC4CCCC4)nc32)C1] | Example 13C | 1.20 (Method 1) | 344 (M + H)$^+$ |
| Exp. 158 racem. mixture | 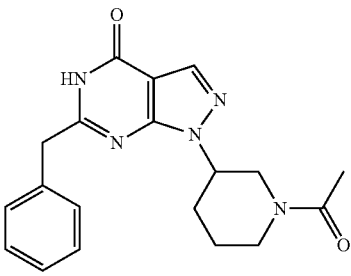 [SMILES: CC(=O)N1CCCC(n2ncc3c(=O)[nH]c(Cc4ccccc4)nc32)C1] | Example 13D | 1.16 (Method 1) | 352 (M + H)$^+$ |

-continued

| | structure | starting material | R_t [min] | MS (ESI, m/z) |
|---|---|---|---|---|
| Exp. 159 racem. mixture | 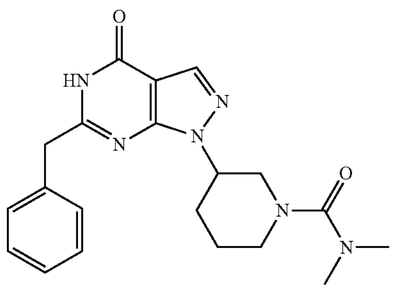 [SMILES: CN(C)C(=O)N1CCCC(n2ncc3c(=O)[nH]c(Cc4ccccc4)nc32)C1] | Example 13D | 1.25 (Method 1) | 381 (M + H)+ |
| Exp. 160 racem. mixture | 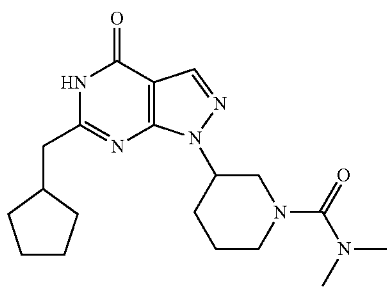 [SMILES: CN(C)C(=O)N1CCCC(n2ncc3c(=O)[nH]c(CC4CCCC4)nc32)C1] | Example 13C | 1.30 (Method 1) | 373 (M + H)+ |
| Exp. 161 racem. mixture | 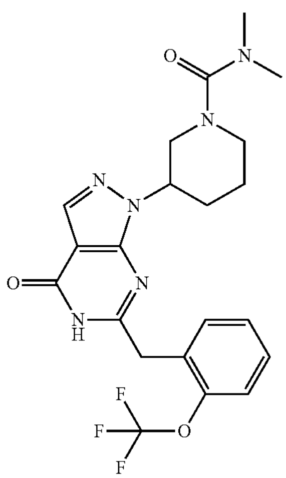 [SMILES: CN(C)C(=O)N1CCCC(n2ncc3c(=O)[nH]c(Cc4ccccc4OC(F)(F)F)nc32)C1] | Example 13E | 1.38 (Method 1) | 465 (M + H)+ |
| Exp. 162 racem. mixture | 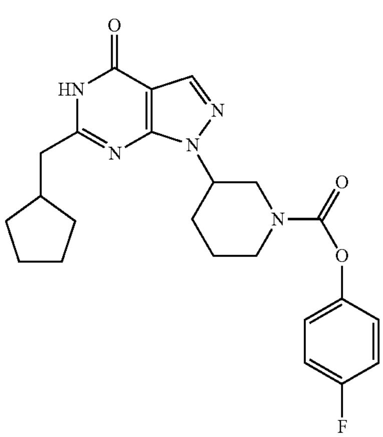 [SMILES: O=C(Oc1ccc(F)cc1)N1CCCC(n2ncc3c(=O)[nH]c(CC4CCCC4)nc32)C1] | Example 13C | 1.62 (Method 1) | 440 (M + H)+ |

| | structure | starting material | R$_t$ [min] | MS (ESI, m/z) |
|---|---|---|---|---|
| Exp. 163 racem. mixture | 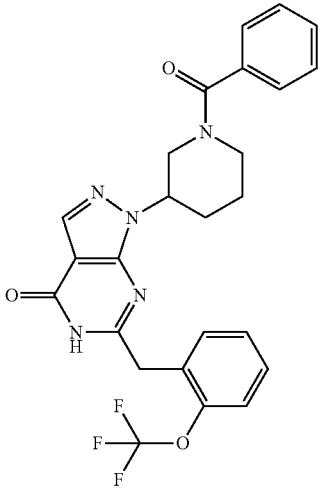 [SMILES: O=C(c1ccccc1)N1CCCC(n2ncc3c(=O)[nH]c(Cc4ccccc4OC(F)(F)F)nc32)C1] | Example 13E | 1.48 (Method 1) | 498 (M + H)$^+$ |
| Exp. 164 racem. mixture | 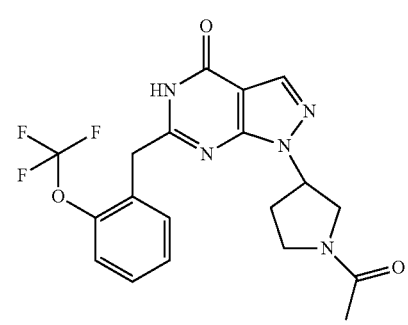 [SMILES: CC(=O)N1CCC(n2ncc3c(=O)[nH]c(Cc4ccccc4OC(F)(F)F)nc32)C1] | Example 13G | 1.23 (Method 1) | 422 (M + H)$^+$ |
| Exp. 165 racem. mixture | 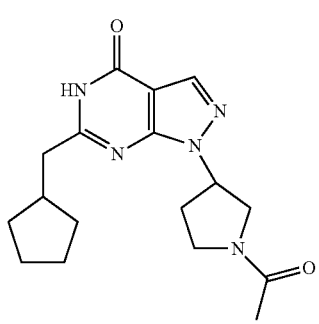 [SMILES: CC(=O)N1CCC(n2ncc3c(=O)[nH]c(CC4CCCC4)nc32)C1] | Example 13A | 1.14 (Method 1) | 330 (M + H)$^+$ |
| Exp. 166 racem. mixture | 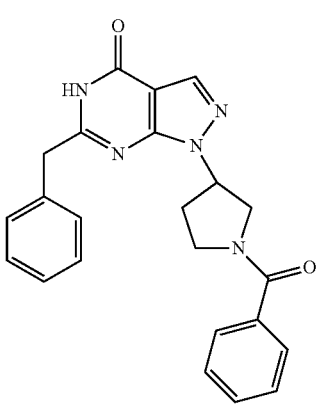 [SMILES: O=C(c1ccccc1)N1CCC(n2ncc3c(=O)[nH]c(Cc4ccccc4)nc32)C1] | Example 13F | 1.28 (Method 1) | 400 (M + H)$^+$ |

-continued
| | structure | starting material | $R_t$ [min] | MS (ESI, m/z) |
|---|---|---|---|---|
| Exp. 167 racem. mixture | 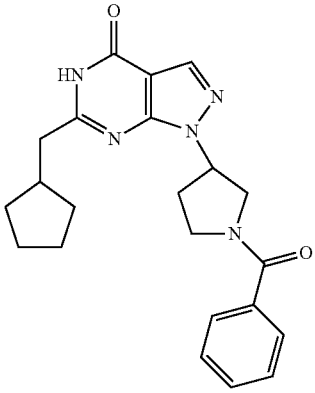 [SMILES: O=C(c1ccccc1)N1CCC(n2ncc3c(=O)[nH]c(CC4CCCC4)nc32)C1] | Example 13A | 1.36 (Method 1) | 392 $(M + H)^+$ |
| Exp. 168 racem. mixture | 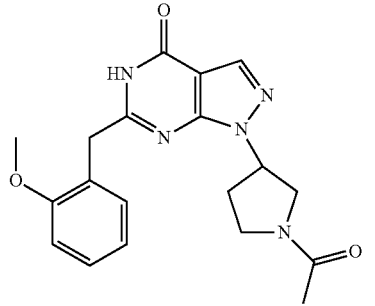 [SMILES: COc1ccccc1Cc1nc2c(cnn2C2CCN(C(C)=O)C2)c(=O)[nH]1] | Example 13H | 1.1 (Method 1) | 368 $(M + H)^+$ |
| Exp. 169 racem. mixture | 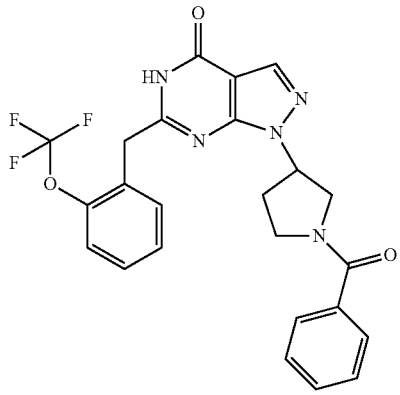 [SMILES: O=C(c1ccccc1)N1CCC(n2ncc3c(=O)[nH]c(Cc4ccccc4OC(F)(F)F)nc32)C1] | Example 13G | 1.44 (Method 1) | 484 $(M + H)^+$ |
| Exp. 170 racem. mixture | 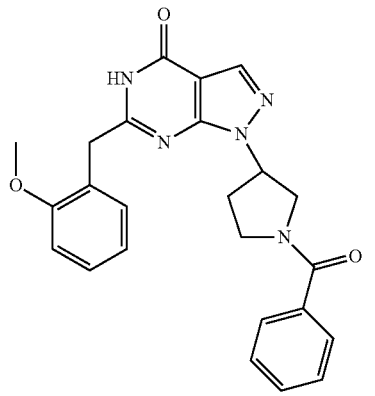 [SMILES: COc1ccccc1Cc1nc2c(cnn2C2CCN(C(=O)c3ccccc3)C2)c(=O)[nH]1] | Example 13H | 1.32 (Method 1) | 430 $(M + H)^+$ |

-continued

| | structure | starting material | R$_t$ [min] | MS (ESI, m/z) |
|---|---|---|---|---|
| Exp. 171 racem. mixture | 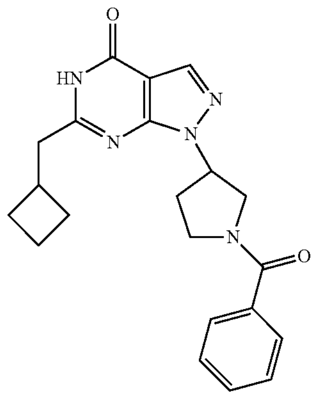 [SMILES: O=C(c1ccccc1)N1CCC(n2ncc3c(=O)[nH]c(CC4CCC4)nc32)C1] | Example 13I | 1.29 (Method 1) | 378 (M + H)$^+$ |
| Exp. 172 racem. mixture | 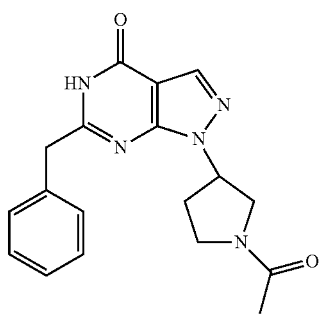 [SMILES: CC(=O)N1CCC(n2ncc3c(=O)[nH]c(Cc4ccccc4)nc32)C1] | Example 13F | 1.07 (Method 1) | 338 (M + H)$^+$ |
| Exp. 173 mixture of stereo-isomers | 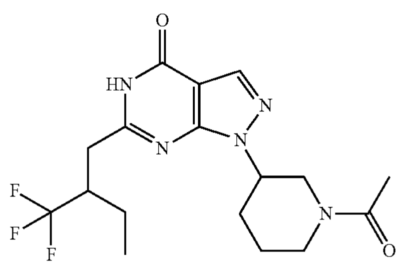 [SMILES: CCC(Cc1nc2c(cnn2C2CCCN(C(C)=O)C2)c(=O)[nH]1)C(F)(F)F] | Example 13M | 1.25 (Method 1) | 386 (M + H)$^+$ |
| Exp. 174 mixture of stereo-isomers | 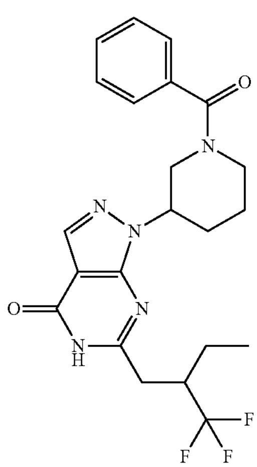 [SMILES: CCC(Cc1nc2c(cnn2C2CCCN(C(=O)c3ccccc3)C2)c(=O)[nH]1)C(F)(F)F] | Example 13M | 1.44 (Method 1) | 448 (M + H)$^+$ |

-continued

| | structure | starting material | R$_t$ [min] | MS (ESI, m/z) |
|---|---|---|---|---|
| Exp. 175 racem. mixture | 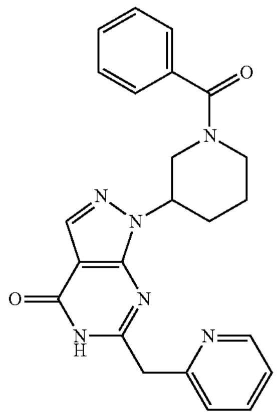 [SMILES: O=C(c1ccccc1)N1CCCC(n2ncc3c(=O)[nH]c(Cc4ccccn4)nc32)C1] | Example 13N | 1.04 (Method 1) | 415 (M + H)$^+$ |
| Exp. 176 racem. mixture | 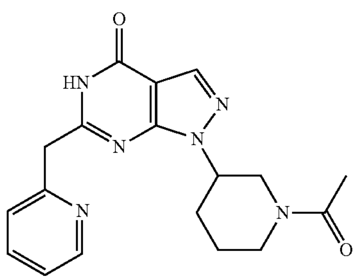 [SMILES: CC(=O)N1CCCC(n2ncc3c(=O)[nH]c(Cc4ccccn4)nc32)C1] | Example 13N | 0.84 (Method 1) | 353 (M + H)$^+$ |
| Exp. 177 racem. mixture | 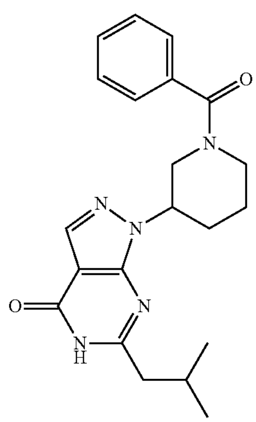 [SMILES: CC(C)Cc1nc2c(cnn2C2CCCN(C(=O)c3ccccc3)C2)c(=O)[nH]1] | Example 13O | 1.31 (Method 1) | 380 (M + H)$^+$ |
| Exp. 178 racem. mixture | 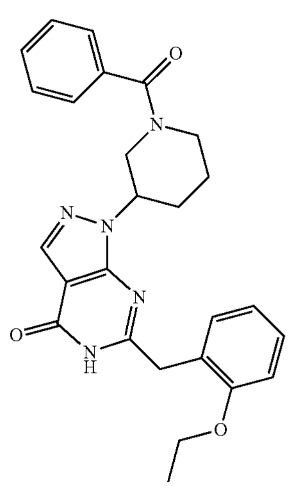 [SMILES: CCOc1ccccc1Cc1nc2c(cnn2C2CCCN(C(=O)c3ccccc3)C2)c(=O)[nH]1] | Example 13P | 1.43 (Method 1) | 458 (M + H)$^+$ |

-continued
| | structure | starting material | R$_t$ [min] | MS (ESI, m/z) |
|---|---|---|---|---|
| Exp. 179 racem. mixture | 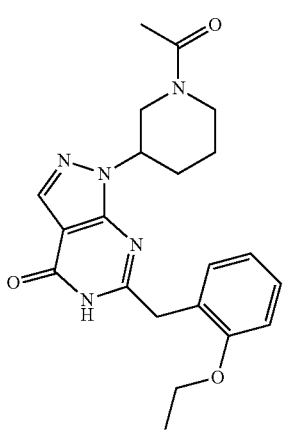 [SMILES: CCOc1ccccc1Cc1nc2c(cnn2C2CCCN(C(C)=O)C2)c(=O)[nH]1] | Example 13P | 1.24 (Method 1) | 396 (M + H)$^+$ |
| Exp. 180 racem. mixture | 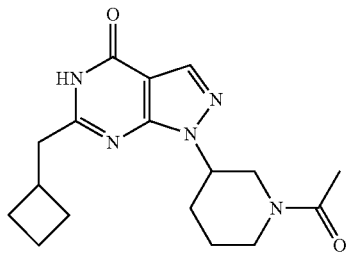 [SMILES: CC(=O)N1CCCC(n2ncc3c(=O)[nH]c(CC4CCC4)nc32)C1] | Example 13Q | 1.14 (Method 1) | 330 (M + H)$^+$ |
| Exp. 181 racem. mixture | 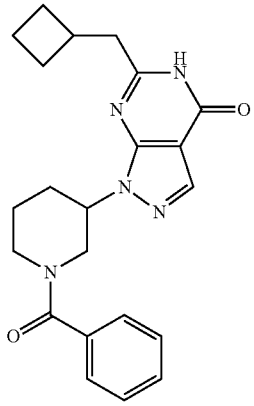 [SMILES: O=C(c1ccccc1)N1CCCC(n2ncc3c(=O)[nH]c(CC4CCC4)nc32)C1] | Example 13Q | 1.34 (Method 1) | 392 (M + H)$^+$ |
| Exp. 182 racem. mixture | 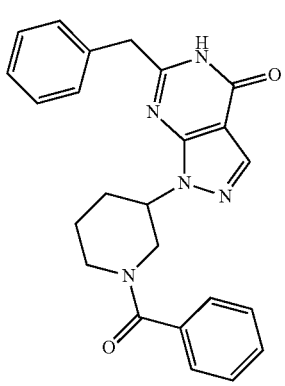 [SMILES: O=C(c1ccccc1)N1CCCC(n2ncc3c(=O)[nH]c(Cc4ccccc4)nc32)C1] | Example 13D | 1.35 (Method 1) | 414 (M + H)$^+$ |

|  | structure | starting material | R$_t$ [min] | MS (ESI, m/z) |
|---|---|---|---|---|
| Exp. 183 racem. mixture | 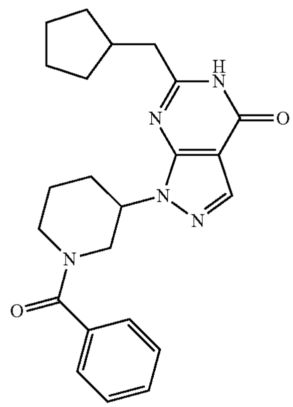 [SMILES: O=C(c1ccccc1)N1CCCC(n2ncc3c(=O)[nH]c(CC4CCCC4)nc32)C1] | Example 13C | 1.41 (Method 1) | 406 (M + H)$^+$ |
| Exp. 184 racem. mixture | 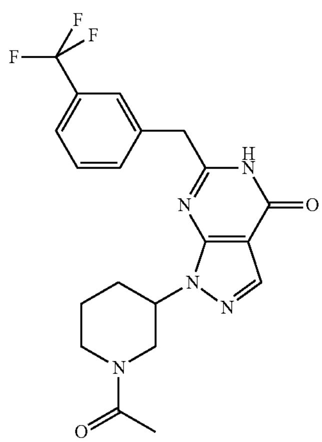 [SMILES: CC(=O)N1CCCC(n2ncc3c(=O)[nH]c(Cc4cccc(C(F)(F)F)c4)nc32)C1] | Example 205 | 1.30 (Method 1) | 420 (M + H)$^+$ |
| Exp. 185 racem. mixture | 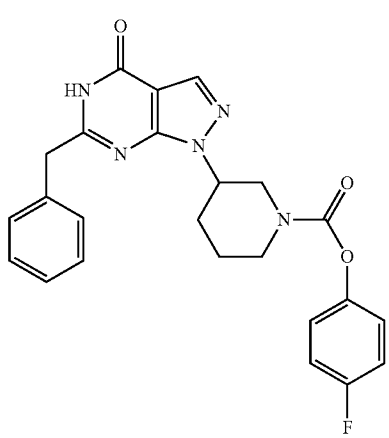 [SMILES: O=C(Oc1ccc(F)cc1)N1CCCC(n2ncc3c(=O)[nH]c(Cc4ccccc4)nc32)C1] | Example 13D | 1.53 (Method 1) | 448 (M + H)$^+$ |

| | structure | starting material | $R_t$ [min] | MS (ESI, m/z) |
|---|---|---|---|---|
| Exp. 186 racem. mixture | 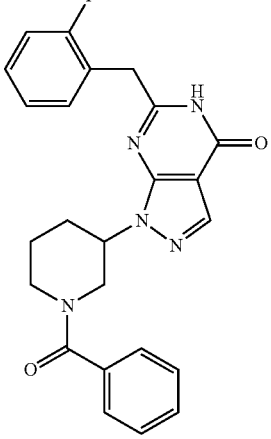 | Example 204 | 1.35 (Method 1) | 432 (M + H)⁺ |
| Exp. 187 racem. mixture | 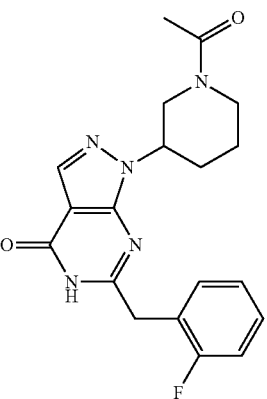 [SMILES: CC(=O)N1CCCC(n2ncc3c(=O)[nH]c(Cc4ccccc4F)nc32)C1] | Example 204 | 1.15 (Method 1) | 370 (M + H)⁺ |
| Exp. 188 racem. mixture | 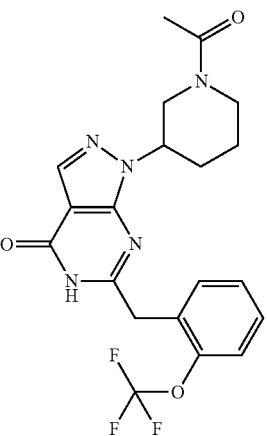 [SMILES: CC(=O)N1CCCC(n2ncc3c(=O)[nH]c(Cc4ccccc4OC(F)(F)F)nc32)C1] | Example 13E | 1.29 (Method 1) | 436 (M + H)⁺ |

| | structure | starting material | R$_t$ [min] | MS (ESI, m/z) |
|---|---|---|---|---|
| Exp. 189 racem. mixture | 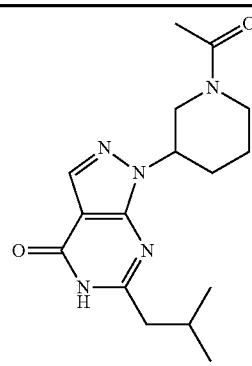 | Example 13O | 1.08 (Method 1) | 318 (M + H)$^+$ |
| Exp. 190 racem. mixture | 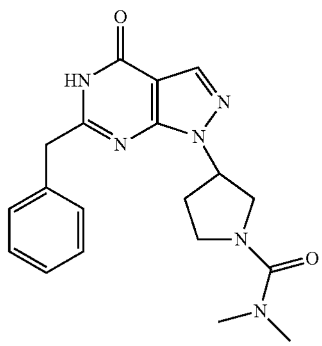 [SMILES: CN(C)C(=O)N1CCC(n2ncc3c(=O)[nH]c(Cc4ccccc4)nc32)C1] | Example 13F | 1.18 (Method 1) | 367 (M + H)$^+$ |

Example 191
Racemic Mixture

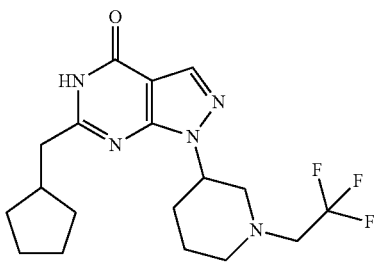 [SMILES: O=c1[nH]c(CC2CCCC2)nc2c1cnn2C1CCCN(CC(F)(F)F)C1]

60 mg (0.2 mmol) of Example 13C were dissolved in 5 mL xylene and 57 mg (0.2 mmol) 2,2,2-trifluoroethyl-trichloromethansulfonate were added drop wise. The reaction mixture was heated to 140° C. and stirred for 5 h. The solvent was removed under reduced pressure. The residue was purified by preparative HPLC (eluent A: water+0.13% TFA, eluent B: acetonitrile). 24.8 mg (32%) of the product were obtained.

HPLC-MS (Method 1): R$_t$: 1.45 min

MS (ESI pos): m/z=384 (M+H)$^+$

The following examples were synthesized in analogy to the preparation of Example 191, using the corresponding starting materials.

| | structure | starting material | R$_t$ [min] | MS (ESI, m/z) |
|---|---|---|---|---|
| Exp. 192 racem. mixture | 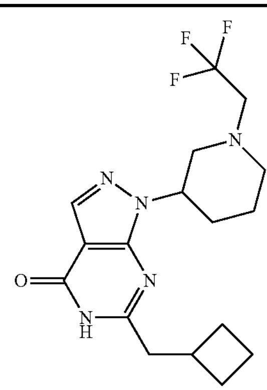 | Example 13Q | 1.35 (Method 1) | 370 (M + H)$^+$ |

-continued

| | structure | starting material | $R_t$ [min] | MS (ESI, m/z) |
|---|---|---|---|---|
| Exp. 193 racem. mixture | 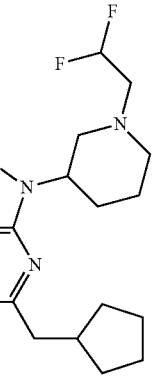 | Example 13C | 1.07 (Method 1) | 366 (M + H)$^+$ |

Example 194

Racemic Mixture

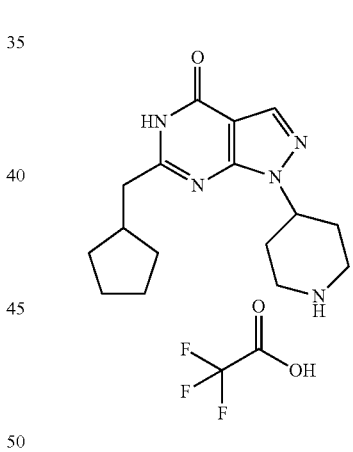

HPLC-MS (Method 1): $R_t$: 0.93 min
MS (ESI pos): m/z=288 (M+H)$^+$ 400 mg (1.35 mmol) of Example 11A were dissolved in 8 mL of absolute ethanol, 840 mg (5.4 mmol) of Example 5AC, and 220 mg (5.5 mmol) of sodium hydride (60% suspension in mineral oil) were added. The reaction mixture was heated to 150° C. for 30 min in a microwave oven. After cooling to room temperature, the reaction mixture was acidified with 4N hydrochloride acid. The solvent was removed under reduced pressure. The residue was purified by preparative HPLC (eluent A: water+0.13% TFA, eluent B: acetonitrile). 250 mg (46%) of the product were obtained as a white solid.

Example 195

330 mg (0.82 mmol) of Example 12A were dissolved in 3 mL dichloromethane and 1 mL trifluoroacetic acid was added. The reaction mixture was stirred at room temperature over night. The solvent was evaporated under reduced pressure. The residue was purified by preparative HPLC (eluent A: water+0.13% TFA, eluent B: acetonitrile). 240 mg (70%) of the product were obtained.

HPLC-MS (Method 1): $R_t$: 0.96 min
MS (ESI pos): m/z=302 (M+H)$^+$

The following examples were synthesized in analogy to the preparation of Example 195, using the corresponding Boc-protected amines as starting materials.

| | structure | starting material | R$_t$ [min] | MS (ESI, m/z) |
|---|---|---|---|---|
| Exp. 196 racem. mixture | 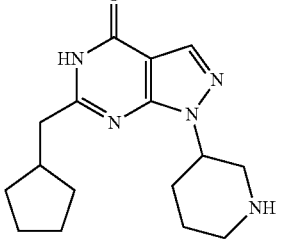 | Example 12L | 1.01 (Method 1) | 302 (M + H)$^+$ |
| Exp. 197 racem. mixture | 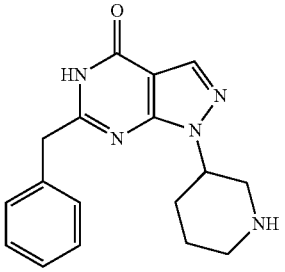 [SMILES: O=c1[nH]c(Cc2ccccc2)nc2c1cnn2C1CCCNC1] | Example 12M | 0.93 (Method 1) | 310 (M + H)$^+$ |
| Exp. 198 racem. mixture | 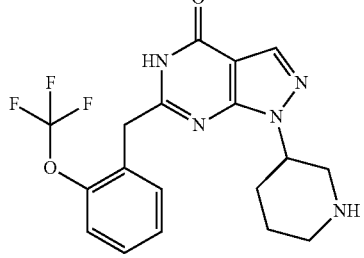 | Example 12N | 1.09 (Method 1) | 394 (M + H)$^+$ |
| Exp. 199 racem. mixture | 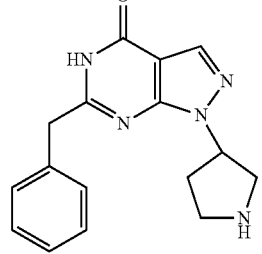 | Example 12G | 0.92 (Method 1) | 296 (M + H)$^+$ |

-continued
| | structure | starting material | R$_t$ [min] | MS (ESI, m/z) |
|---|---|---|---|---|
| Exp. 200 racem. mixture | 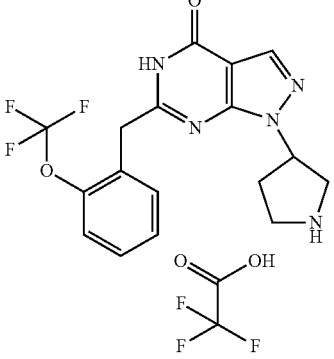 | Example 12H | 1.08 (Method 1) | 380 (M + H)$^+$ |
| Exp. 201 racem. mixture | 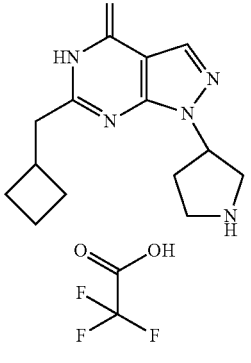 | Example 12J | 0.89 (Method 1) | 274 (M + H)$^+$ |
| Exp. 202 | 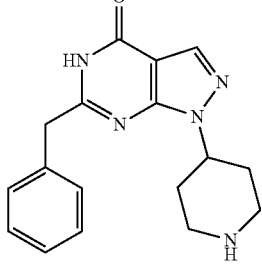 | Example 12B | 0.92 (Method 1) | 310 (M + H)$^+$ |
| Exp. 203 | 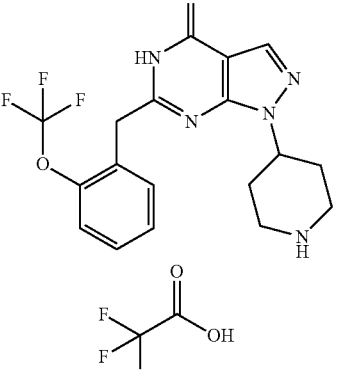 | Example 12C | 1.07 (Method 1) | 394 (M + H)$^+$ |

-continued
| | structure | starting material | R$_t$ [min] | MS (ESI, m/z) |
|---|---|---|---|---|
| Exp. 204 racem. mixture | 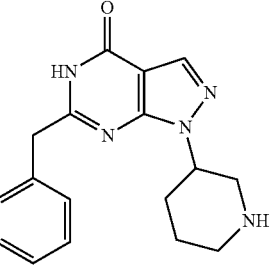 | Example 12Q | 0.95 (Method 1) | 328 (M + H)$^+$ |
| Exp. 205 racem. mixture | 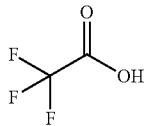 | Example 12R | 1.13 (Method 1) | 378 (M + H)$^+$ |
| Exp. 206 racem. mixture | 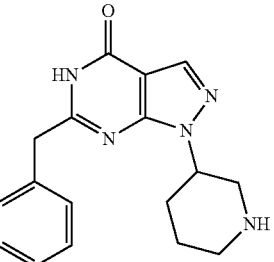 | Example 12U | 0.94 (Method 1) | 288 (M + H)$^+$ |

Example 207

Racemic Mixture

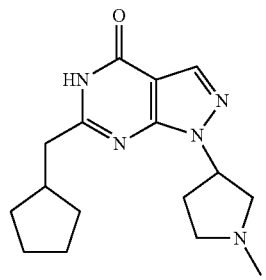

50 mg (120 mmol) of Example 13A were dissolved in 5 mL dichloromethane and 15 mg (500 mmol) of formaldehyde were added. The reaction mixture was stirred at room temperature for 1 h. 15 µL (260 mmol) acetic acid and 35 mg (160 mmol) sodiumtriacetoxyborohydride were added. The reaction mixture was stirred 2 h at room temperature. The solvent was removed under reduced pressure. The residue was purified by preparative HPLC (eluent A: water+0.13% TFA, eluent B: acetonitrile). 34 mg (65%) of the product were obtained.

HPLC-MS (Method 1): $R_t$: 0.99 min

MS (ESI pos): m/z=302 (M+H)$^+$

The following examples were synthesized in analogy to the preparation of Example 207 using the corresponding amines as starting materials

| | structure | starting material | $R_t$ [min] | MS (ESI, m/z) |
|---|---|---|---|---|
| Exp. 208 racem. mixture | 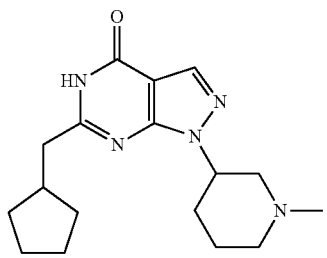 [SMILES: CN1CCCC(n2ncc3c(=O)[nH]c(CC4CCCC4)nc32)C1]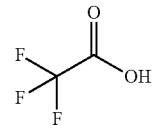 | Example 13C | 1.02 (Method 1) | 316 (M + H)$^+$ |
| Exp. 209 racem. mixture | 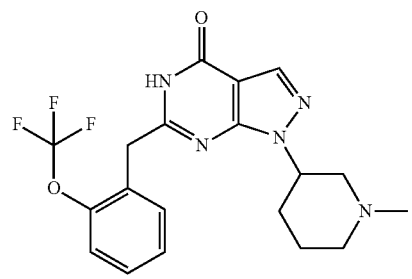 [SMILES: CN1CCCC(n2ncc3c(=O)[nH]c(Cc4ccccc4OC(F)(F)F)nc32)C1]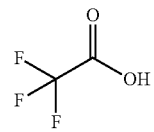 | Example 13E | 1.13 (Method 1) | 408 (M + H)$^+$ |

-continued
| | structure | starting material | R$_t$ [min] | MS (ESI, m/z) |
|---|---|---|---|---|
| Exp. 210 racem. mixture | 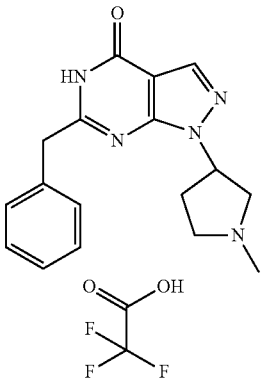 | Example 13F | 0.93 (Method 1) | 310 (M + H)$^+$ |
| Exp. 211 racem. mixture | 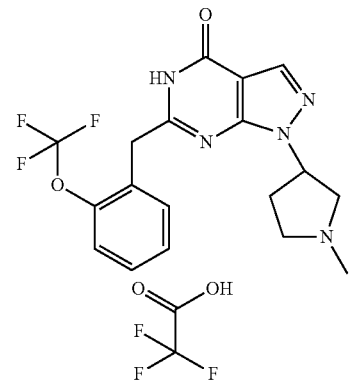 | Example 13G | 1.11 (Method 1) | 394 (M + H)$^+$ |
| Exp. 212 racem. mixture | 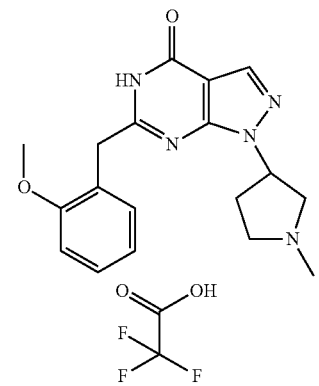 | Example 13H | 0.98 (Method 1) | 340 (M + H)$^+$ |
| Exp. 213 mixture of stereoisomers | 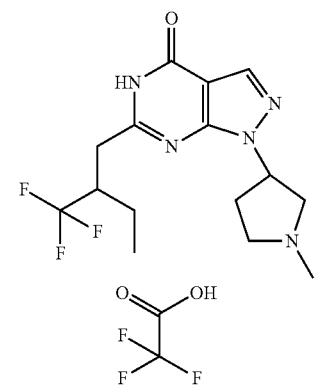 | Example 13J | 1.02 (Method 1) | 344 (M + H)$^+$ |

-continued
| | structure | starting material | R$_t$ [min] | MS (ESI, m/z) |
|---|---|---|---|---|
| Exp. 214 racem. mixture | 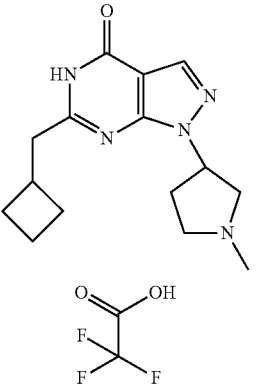 | Example 13I | 0.91 (Method 1) | 288 (M + H)$^+$ |
| Exp. 215 racem. mixture | 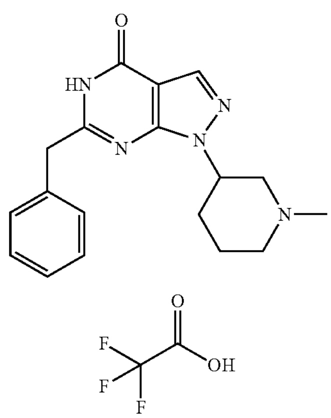 | Example 13D | 0.97 (Method 1) | 324 (M + H)$^+$ |
| Exp. 216 racem. mixture | 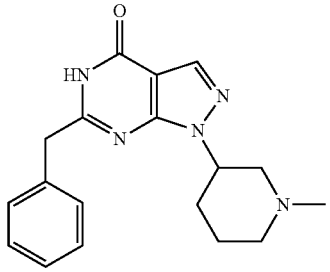 | Example 205 | 1.16 (Method 1) | 392 (M + H)$^+$ |

| | structure | starting material | R$_t$ [min] | MS (ESI, m/z) |
|---|---|---|---|---|
| Exp. 217 racem. mixture | 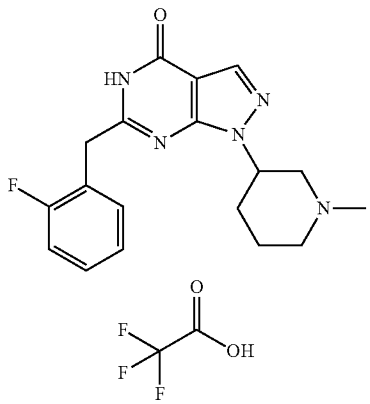 | Example 204 | 0.98 (Method 1) | 342 (M + H)$^+$ |
| Exp. 218 racem. mixture | 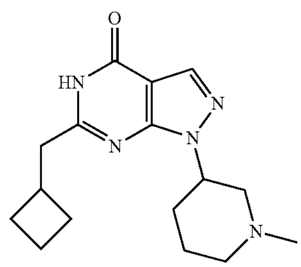 [SMILES: CN1CCCC(n2ncc3c(=O)[nH]c(CC4CCC4)nc32)C1] | Example 13Q | 0.95 (Method 1) | 302 (M + H)$^+$ |

Example 219

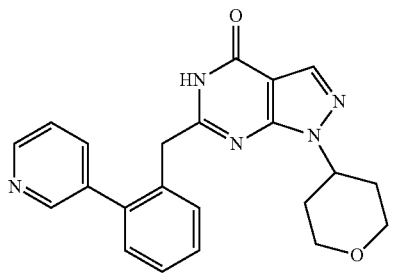 [SMILES: O=c1[nH]c(Cc2ccccc2-c2cccnc2)nc2c1cnn2C1CCOCC1]

Under a argon atmosphere 100 mg (0.26 mmol) of example 5, 95 mg (0.77 mmol) pyridine-3-boronic acid, 310 µL (2.41 mmol) aqueous sodium carbonate solution (2 M), 5 mL dioxane and 20 mg (0.02 mmol) tetrakis-(triphenylphosphine)palladium(0) were combined. The reaction mixture was heated to 140° C. for 35 min in a microwave oven. After cooling to room temperature the reaction mixture was filtered over celite. The filtrate was evaporated under reduced pressure. The residue was purified by preparative HPLC. 82 mg (83%) of the product were obtained.

HPLC-MS (Method 1): R$_t$: 1.00 min

MS (ESI pos): m/z=388 (M+H)$^+$

The following examples were synthesized in analogy to the preparation of example 219 using the corresponding boronic acids as starting materials.

| | structure | starting material | R$_t$ [min] | MS (ESI, m/z) |
|---|---|---|---|---|
| Example 220 | 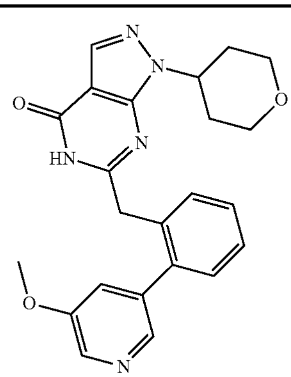 | | 1.01 (Method 1) | 418 (M + H)$^+$ |

-continued
| | structure | starting material | R$_t$ [min] | MS (ESI, m/z) |
|---|---|---|---|---|
| Example 221 | 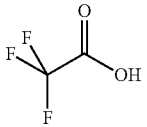 | 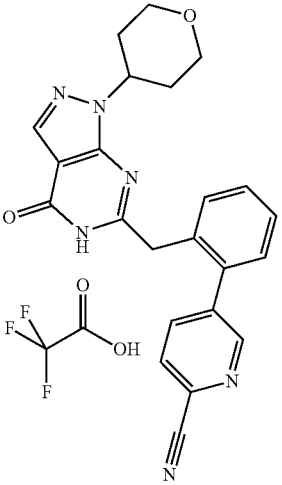 | 1.24 (Method 1) | 413 (M + H)$^+$ |
| Example 222 | 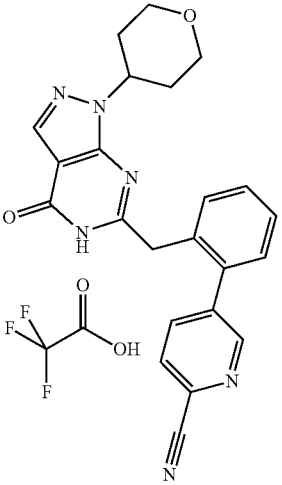 | 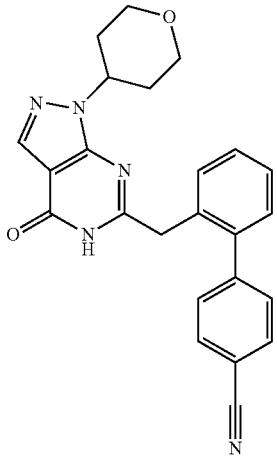 [SMILES: N#Cc1ccc(-c2ccccc2Cc2nc3c(cnn3C3CCOCC3)c(=O)[nH]2)cc1] | 1.34 (Method 1) | 412 (M + H)$^+$ |
| Example 223 | 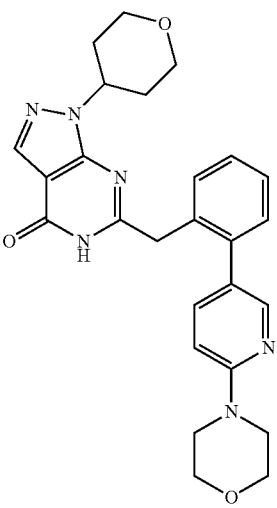 [SMILES: O=c1[nH]c(Cc2ccccc2-c2ccc(N3CCOCC3)nc2)nc2c1cnn2C1CCOCC1] | | 1.03 (Method 1) | 473 (M + H)$^+$ |

-continued
| | structure | starting material | $R_t$ [min] | MS (ESI, m/z) |
|---|---|---|---|---|
| Example 224 | 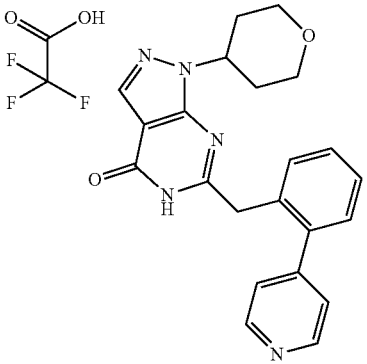 | 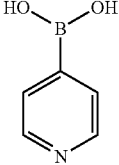 | 0.96 (Method 1) | 388 (M + H)⁺ |
| Example 225 | 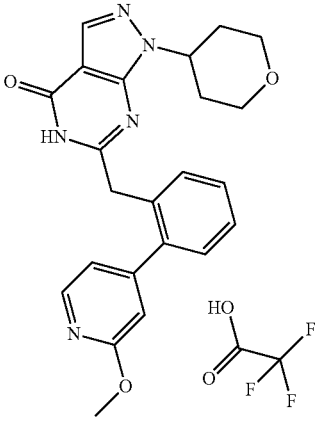 | 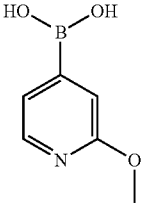 | 1.18 (Method 1) | 418 (M + H)⁺ |
| Example 226 | 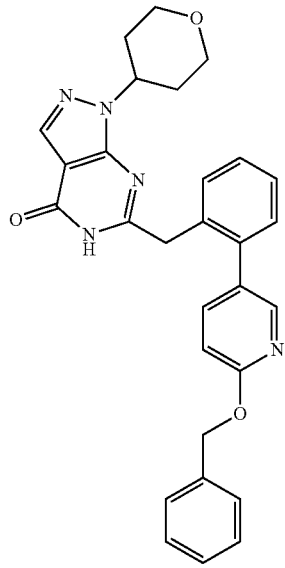 [SMILES: O=c1[nH]c(Cc2ccccc2-c2ccc(OCc3ccccc3)nc2)nc2c1cnn2C1CCOCC1] | 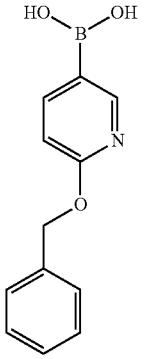 | 1.57 (Method 1) | 494 (M + H)⁺ |

-continued
| | structure | starting material | R$_t$ [min] | MS (ESI, m/z) |
|---|---|---|---|---|
| Example 227 | 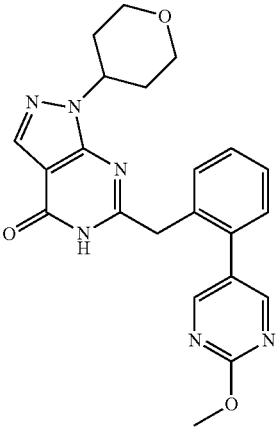 [SMILES: COc1ncc(-c2ccccc2Cc2nc3c(cnn3C3CCOCC3)c(=O)[nH]2)cn1] | 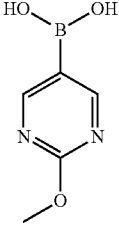 | 1.19 (Method 1) | 419 (M + H)$^+$ |
| Example 228 | 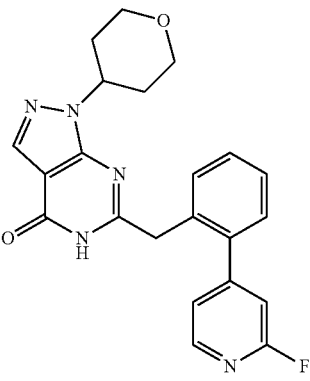 [SMILES: O=c1[nH]c(Cc2ccccc2-c2ccnc(F)c2)nc2c1cnn2C1CCOCC1] | 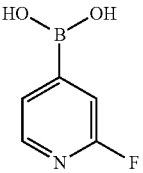 | 1.26 (Method 1) | 406 (M + H)$^+$ |
| Example 229 | 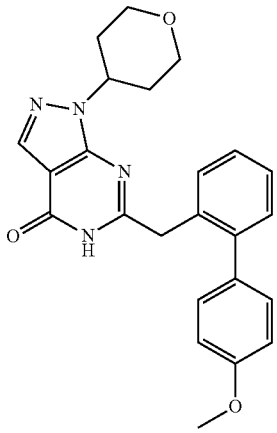 [SMILES: COc1ccc(-c2ccccc2Cc2nc3c(cnn3C3CCOCC3)c(=O)[nH]2)cc1] | 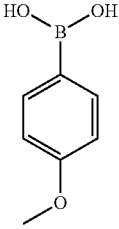 | 1.40 (Method 1) | 417 (M + H)$^+$ |

-continued
| | structure | starting material | R$_t$ [min] | MS (ESI, m/z) |
|---|---|---|---|---|
| Example 230 | 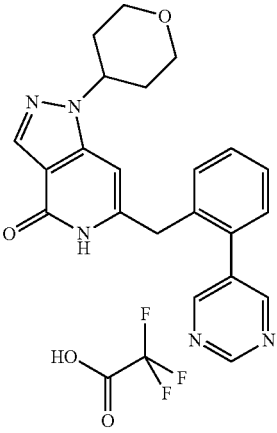 | 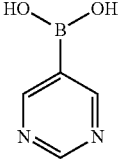 | 1.06 (Method 1) | 389 (M + H)$^+$ |
| Example 230-1 | 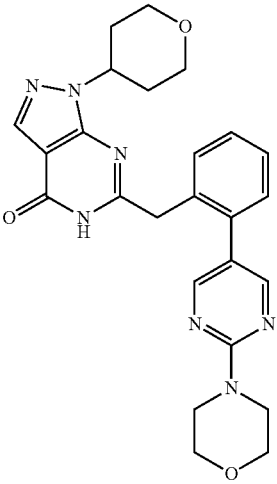 [SMILES: O=c1[nH]c(Cc2ccccc2-c2cnc(N3CCOCC3)nc2)nc2c1cnn2C1CCOCC1] | 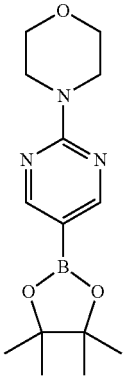 | 1.24 (Method 1) | 474 (M + H)$^+$ |
| Example 230-2 | 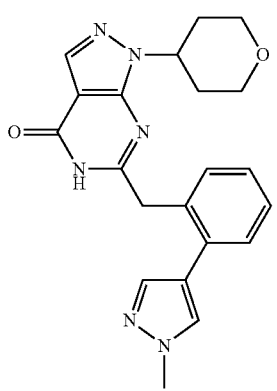 [SMILES: Cn1cc(-c2ccccc2Cc2nc3c(cnn3C3CCOCC3)c(=O)[nH]2)cn1] | 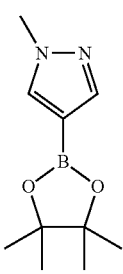 | 1.16 (Method 1) | 391 (M + H)$^+$ |

| | structure | starting material | R$_t$ [min] | MS (ESI, m/z) |
|---|---|---|---|---|
| Example 230-3 | 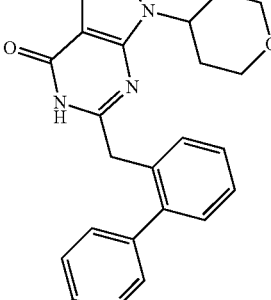 | 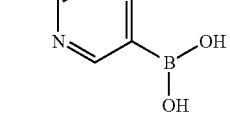 | 1.25 (Method 1) | 404 (M + H)$^+$ |
| Example 230-4 | 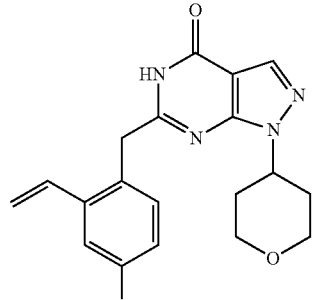 | 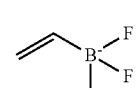 | 1.28 (Method 1) | 367 (M + H)$^+$ |
| Example 230-5 | 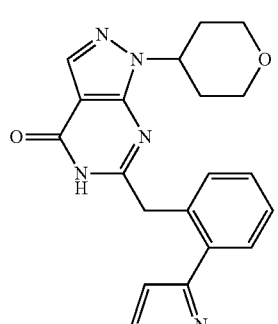 | 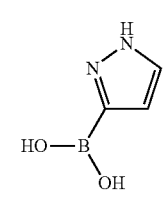 | 1.27 (Method 1) | 377 (M + H)$^+$ |

Example 231

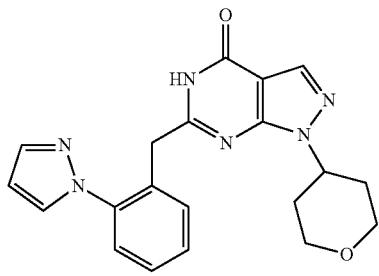 [SMILES: O=c1[nH]c(Cc2ccccc2-n2cccn2)nc2c1cnn2C1CCOCC1]

A vial was charged under inert atmosphere with Example 5 (175 mg, 0.45 mmol), pyrazole (306 mg, 4.49 mmol), copper iodide (85 mg, 0.45 mmol) and cesium carbonate (439 mg, 1.35 mmol). Dimethylformamide (5 ml), previously degassed, was then added, followed by N—N'-dimethylethylenediamine (47.87 µl; 0.45 mmol). The reaction mixture was heated to 120° C. for three hours. The suspension was then filtered over a Celite pad; Celite was washed with DMF. The volume of the organic phase was reduced under reduced pressure and, afterwards, ammonium chloride saturated solution was added, followed by ethyl acetate. The phases were separated and the organic phase was washed with brine and then dried. The crude product was purified by SPE cartridge and the product obtained was further purified by SPE Stratosphere "PL-THIOL MP" to completely remove copper salts. The solid obtained was triturated with diethyl ether. 15.5 mg of the desired compound were obtained (yield=9.2%).

HPLC-MS (Method 1 E hydro): R$_t$: 7.80 min
MS (APCI pos): m/z=377 (M+H)$^+$

Example 232

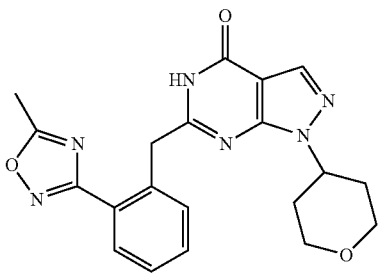 [SMILES: Cc1nc(-c2ccccc2Cc2nc3c(cnn3C3CCOCC3)c(=O)[nH]2)no1]

Example 53 (100 m, 0.298 mmol) and hydroxylamine (0.073 ml, 1.19 mmol) were mixed together in absolute ethanol (4 ml) in a 50 ml flask. The reaction mixture was refluxed for 3 hours before being worked up. The solvent was then removed under reduced pressure to obtain 120 mg (content 70%, 0.228 mmol) of N-Hydroxy-2-[4-oxo-1-(tetrahydro-pyran-4-yl)-4,5-dihydro-1H-pyrazolo[3,4-d]pyrimidin-6-yl-methyl]-benzamidine as solid that was used as such in the next step.

N-Hydroxy-2-[4-oxo-1-(tetrahydro-pyran-4-yl)-4,5-dihydro-1H-pyrazolo[3,4-d]pyrimidin-6-ylmethyl]-benzamidine (120 mg, content 70%; 0.228 mmol) was suspended in trimethylorthoacetate (5 ml) and acetic acid was added afterwards (1 ml); the mixture was heated to 100° C. for one hour. The mixture was cooled at room temperature and the precipitation of a solid was observed. The filtrate was evaporated under reduced pressure; the crude product was purified by flash chromatography. The product was then triturated with diethyl ether. 24 mg of the desired compound were obtained (yield 26.6%).

HPLC/MS (Method 1 E hydro)
MS (APCI pos): m/z=393 (M+H)$^+$

Example 233

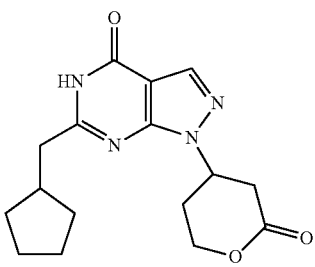 [SMILES: O=C1CC(n2ncc3c(=O)[nH]c(CC4CCCC4)nc32)CCO1]

Example 12X (250 mg, 1.14 mmol) was dissolved in 20 ml of hot methanol. Alumina (neutral) was added and the solvent was then removed to give a white powder which was transferred into a 2 ml Wheaton vial; 5,6-Dihydro-2H-pyran-2-oxo was added followed by DMFe (1 ml) and the vial was closed tightly. The suspension was heated to 80° C. with orbital shaking during 4 days. The reaction was then filtered and the alumina was washed with methanol, ethyl acetate and dicholoromethane; the organic solutions were combined and solvents removed under reduced pressure. The crude product was purified by flash chromatography.

Eluent: (gradient starting with n-hexane/ethyl acetate 9/1 to ethyl acetate (100%) followed by ethyl acetate/methanol 99/1 to 94/6). 70 mg of the desired compound were obtained as solid (19.3%).

HPLC-MS (Method 2F): R$_t$: 9.06 min
MS (ESI pos): m/z=317 (M+H)$^+$

Example 234

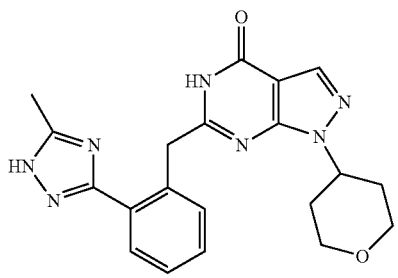 [SMILES: Cc1nc(-c2ccccc2Cc2nc3c(cnn3C3CCOCC3)c(=O)[nH]2)n[nH]1]

Example 53 (160 mg, content 80%, 0.38 mmol) and hydrazine hydrate (0.186 ml, 3.81 mmol) were mixed together in absolute ethanol (4 ml) in a 25 ml flask. The reaction mixture was refluxed for 6 hours before being worked up. The solvent was removed under reduced pressure to obtain 200 mg (content 70%, 0.38 mmol) of the desired material used as such in the next step. The material (200 mg, 70% content, 0.38 mmol) was suspended in trimethylorthoacetate (6 ml). Acetic acid is added (0.6 ml) and the solution was heated to 80° C. for 30 minutes. Trimethylortoacetate and acetic acid were removed under reduced pressure and the crude product was partitioned between water and dichloromethane. The organic phase is dried and the crude product purified by flash chromatography. (gradient: starting with dichloromethane/methanol 98/2 and finishing with dichloromethane/methanol 90/10). The product was further purified by trituration with diethyl ether. 8 mg of the desired compound were obtained (4%).

HPLC-MS (Method 1 E hydro): R$_t$: 6.82 min
MS (APCI pos): m/z=392 (M+H)$^+$

Example 235

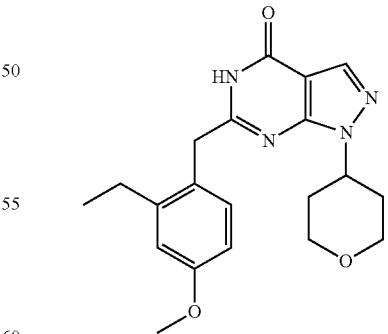

22 mg (0.06 mmol) of example 230-4 in 3 ml methanol were hydrogenated over Pd/C (10%) under atmospheric pressure. The catalyst was removed. The solvent was evaporated and the residue chromatographed by HPLC (eluent A: water+0.13% TFA, eluent B: acetonitrile) to yield 15.7 mg (71%) of the product.

HPLC-MS (Method 1): R$_t$: 1.35 min

MS (ESI pos): m/z=369 (M+H)$^+$

Example 236

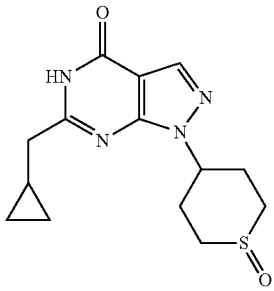 [SMILES: O=c1[nH]c(CC2CC2)nc2c1cnn2C1CCS(=O)CC1]

100 mg (73%, 0.251 mmol) of example 40-5 were dissolved in 2 ml acetic acid and 30 µL (0.35 mmol) hydrogen peroxide solution in water (35%) were added. The mixture was stirred for 3 h and acetonitrile/water was added. The mixture was chromatographed by HPLC (eluent A: water+ 0.13% TFA, eluent B: acetonitrile) to yield 50.3 mg (65%) of the product.

HPLC-MS (Method 1): R$_t$: 0.88 min

MS (ESI pos): m/z=307 (M+H)$^+$

Example 237

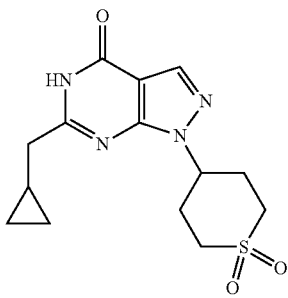 [SMILES: O=c1[nH]c(CC2CC2)nc2c1cnn2C1CCS(=O)(=O)CC1]

100 mg (73%, 0.251 mmol) of example 40-5 were dissolved in 2 ml acetic acid and 200 µL (2.33 mmol) hydrogen peroxide solution in water (35%) were added. The mixture was stirred for 3 days and acetonitrile/water was added. The mixture was chromatographed by HPLC (eluent A: water+ 0.13% TFA, eluent B: acetonitrile) to yield 21.5 mg (27%) of the product.

HPLC-MS (Method 1): R$_t$: 0.93 min

MS (ESI pos): m/z=323 (M+H)$^+$

Example 239

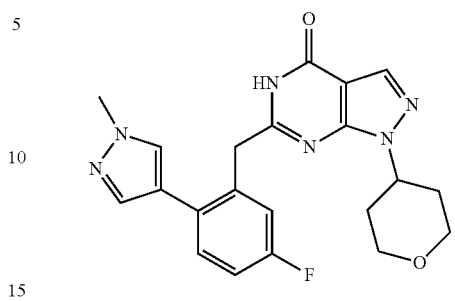

Under a nitrogen atmosphere 50.0 mg (0.12 mmol) of example 40-10 and 51 mg (0.25 mmol) 1-methyl-4-(4,4,5,5-tetramethyl-1,3,2-dioxaborolan-2-yl)-1H-pyrazole were dissolved in 2 mL DMF. 156 mg (0.74 mmol) potassium phosphate, 0.78 mg (2.45 µmol) tris(dibenzylideneacetone) dipalladium and 2.85 mg tri(tert-butylphosphonium) tetrafluoroborate were added. The reaction mixture was heated to 150° C. for 30 min in a microwave oven. The mixture was evaporated under reduced pressure. The residue was purified by preparative HPLC. 29 mg (58%) of the product were obtained.

HPLC-MS (Method 1): R$_t$: 1.23 min

MS (ESI pos): m/z=409 (M+H)$^+$

Example 240

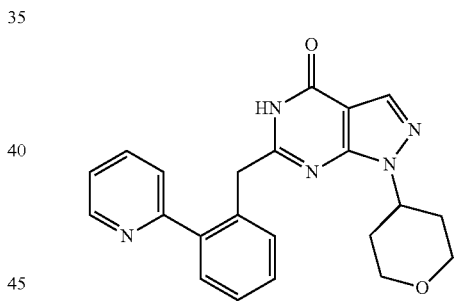

Step A:

1.00 g (6.33 mmol) 2-bromo-pyridine and 1.53 mL (6.46 mmol) triisopropyl borate were dissolved in 10 mL THF under nitrogen. The mixture was cooled to −30° C. 6.76 mL (10.8 mmol) n-buthyllithium were added dropwise. After stirring for 1.5 h the mixture was allowed to warm to room temperature within 1 h. The precipitate was filtered off and dried to yield 0.84 g of solid material.

Step B:

To 100 mg (0.26 mmol) of example 5 and 213 mg of the product obtained in step A, 3 mL DMF, 436 mg (2.05 mmol) of potassium phosphate and 26.7 mg (0.02 mmol) tetrakis-(triphenylphosphine)-palladium(0) were added. The reaction mixture was heated to 145° C. for 90 min in a microwave oven. The mixture was evaporated under reduced pressure. The residue was taken up in dichloromethane and washed with water and brine. The organic layer was separated, dried and evaporated under reduced pressure. The residue was purified by preparative HPLC (eluent A: water+0.1% conc.

ammonia, eluent B: methanol). The resulting material was further purified by a three step procedure: (1) conversion into the corresponding hydrochloride salt by addition of dichloromethane followed by hydrochloric acid (6 M in isopropanol) and subsequent evaporation of the volatiles under reduced pressure; (2) trituration with acetonitrile and subsequent removal of the solvent by filtration; and (3) liberation of the free base by addition of dichloromethane and extraction with an aqueous solution of potassium carbonate followed by phase separation and removal of the solvent from the organic layer under reduced pressure. 9.1 mg (9.1%) of the product were obtained.

HPLC-MS (Method 4): $R_t$=2.57 min

MS (ESI pos): m/z=388 (M+H)$^+$

The following example was synthesized in analogy to the preparation of example 240, using the corresponding starting materials.

| | structure | starting material: bromopyridine | $R_t$ | MS (ESI pos, m/z) |
|---|---|---|---|---|
| Example 241 | 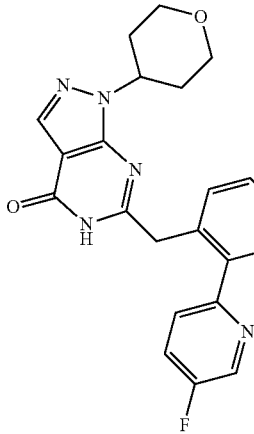 | 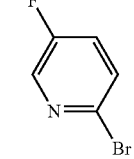 | 3.04 min (Method 4) | 406 (M + H)$^+$ |
| Example 242 | 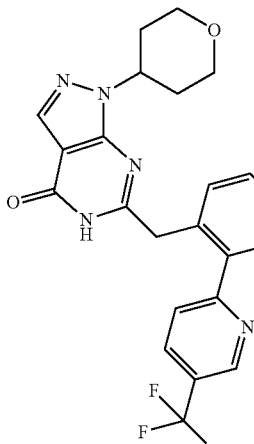 | 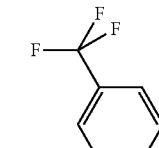 | 3.29 min (Method 4) | 456 (M + H)$^+$ |
| Example 243 | 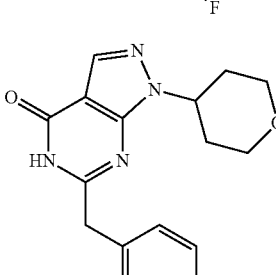 | 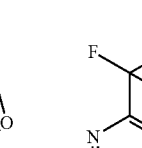 | 3.10 min (Method 4) | 456 (M + H)$^+$ |

| | structure | starting material: bromo-pyridine | $R_t$ | MS (ESI pos, m/z) |
|---|---|---|---|---|
| Example 244 | 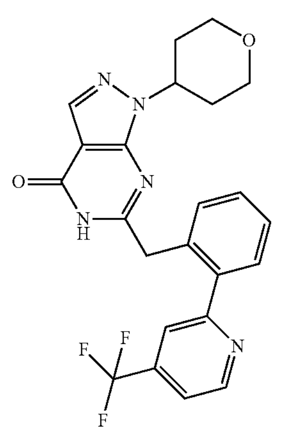 [SMILES: O=c1[nH]c(Cc2ccccc2-c2cc(C(F)(F)F)ccn2)nc2c1cnn2C1CCOCC1] | | 3.37 min (Method 4) | 456 (M + H)+ |

Example 245

Example 246

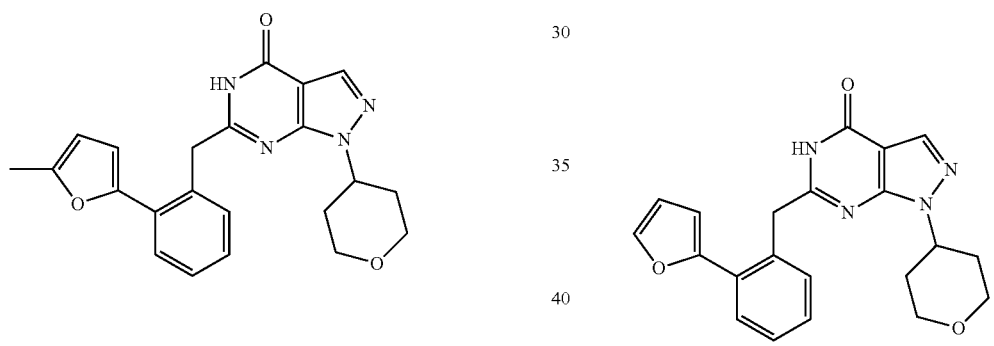

A microwave vial was charged with Example 5 (100 mg, 0.257 mmol), 5-Methylfuran-2-boronic acid (161.75 mg, 1.285 mmol), Tetrakis(triphenylphosphine)palladium(0) (118.84 mg, 0.104 mmol) in Dioxane (1 mL); afterwards 1.02 mL (2.056 mmol) of a 2M aqueous solution of $Na_2CO_3$ were added. The reaction mixture was heated to 130° C. for 4 hours in a microwave oven. Cooling to 20° C. was followed by acidification with HCl 37% until acidic pH and then extraction with dichloromethane (2×2 mL). The organic layer was dried over $Na_2SO_4$, filtered and the filtrate was concentrated under reduced pressure. The remaining residue was purified by flash chromatography on $SiO_2$ using cyclohexane/ethyl acetate mixture of increasing polarity (from 100% cyclohexane to 100% ethyl acetate) as eluent. The product obtained was further purified by preparative TLC (ethyl acetate/cyclohexane 80/20 as eluent). The solid was freeze-dried with a water/acetonitrile 1:1 mixture yielding the title compound as a white solid (23 mg, 22.9%).

HPLC-MS (Method 1 E hydro): $R_t$: 8.93 min

MS (APCI pos): m/z=391 (M+H)+

A microwave vial was charged with Example 5 (90 mg, 0.231 mmol), 2-Furanboronic acid (77.74 mg, 0.694 mmol), Tetrakis(triphenylphosphine)palladium(0) (40.74 mg, 0.035 mmol) in Dioxane (1 mL); afterwards 0.46 mL (0.925 mmol) of a 2M aqueous solution of $Na_2CO_3$ were added. The reaction mixture was heated to 130° C. for 80 min in a microwave oven. Cooling to 20° C. was followed by dilution with water and acidification with HCl 10% aqueous solution then extraction with dichloromethane (2×2 mL). The organic layer was dried over $Na_2SO_4$, filtered and the filtrate was concentrated under reduced pressure. The remaining residue was purified preparative HPLC (eluent A: water+$NH_4COOH$ 5 mM, eluent B: acetonitrile). After freeze-drying the title compound was obtained as a white solid (28 mg, 32.2%).

HPLC-MS (Method 1 E hydro): $R_t$: 8.42 min

MS (APCI pos): m/z=377 (M+H)+

Example 247

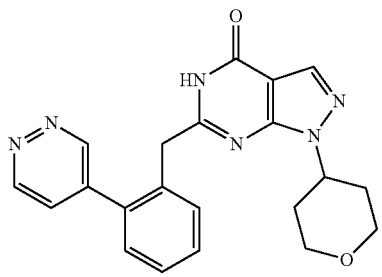 [SMILES: O=c1[nH]c(Cc2ccccc2-c2ccnnc2)nc2c1cnn2C1CCOCC1]

A vial was charged under inert atmosphere with Example 5 (100 mg, 0.514 mmol) and 4-(tributylstannyl)pyridazine (227.6 mg, 0.617 mmol) in previously degassed toluene (7 mL), afterwards Tetrakis(triphenylphosphine)palladium(0) (59.37 mg, 0.051 mmol) and copper iodide (9.79 mg, 0.051 mmol) were added. The reaction mixture was heated to 120° C. for 2 hours in a microwave oven. The reaction mixture was diluted with saturated $NH_4Cl$ water solution and extracted with dichloromethane. The organic layer was dried over $Na_2SO_4$, filtered and the filtrate was concentrated under reduced pressure. The residue was purified by flash chromatography on $SiO_2$ using dichloromethane/methanol 98/2 as eluent. The solid obtained was further purified by preparative HPLC (eluent A: water+$NH_4COOH$ 5 mM, eluent B: acetonitrile). The title compound was obtained as a white solid (22 mg, 11%).

HPLC-MS (Method 1 E hydro): $R_t$: 6.33 min

MS (APCI pos): m/z=389 $(M+H)^+$

Example 248

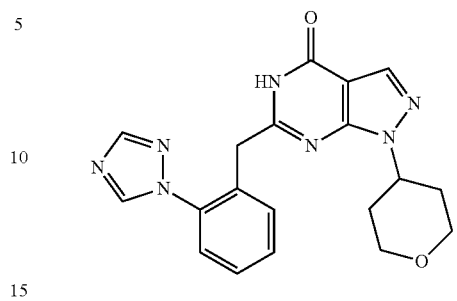

A round bottom flask was charged under inert atmosphere with copper iodide (97.86 mg, 0.514 mmol), cesium carbonate (502.23 mg, 1.541 mmol), Example 5 (200 mg, 0.514 mmol), 1,2,4-triazole (384.56 mg, 5.138 mmol) and then dimethylformamide (12 mL), previously degassed, followed by N—N'-dimethylethylenediamine (109.4 µL, 1.028 mmol). The reaction mixture was heated to 120° C. for 3 hours. After cooling the reaction mixture was filtered through a Celite pad that was rinsed with dimethylformamide then saturated $NH_4Cl$ aqueous solution was added and extracted with ethyl acetate. The organic phase was washed with saturated $NH_4Cl$ aqueous solution, brine then dried over $Na_2SO_4$ and the solvent was removed under reduced pressure. The crude product was purified by preparative HPLC (eluent A: water+$NH_4COOH$ 5 mM, eluent B: acetonitrile). The title compound was obtained as a solid (7.2 mg, 3.7%).

HPLC-MS (Method 1 E Hydro): $R_t$: 6.37 min

MS (APCI pos): m/z=378 $(M+H)^+$

The following examples were synthesized in analogy to the preparation of Example 248, using the corresponding bromides and heterocycles as starting materials:

| | Structure | starting material: heterocycle | $R_t$ [min] | MS (APCI pos, m/z) |
|---|---|---|---|---|
| Example 249 | 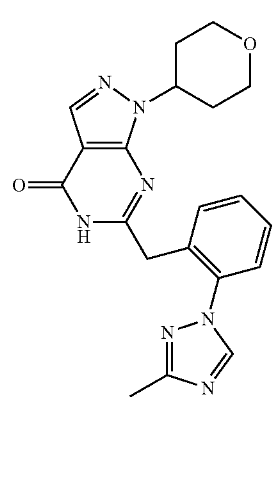 [SMILES: Cc1ncn(-c2ccccc2Cc2nc3c(cnn3C3CCOCC3)c(=O)[nH]2)n1] | | 6.52 (Method 1E hydro) | 392 $(M + H)^+$ |

| | Structure | starting material: heterocycle | $R_t$ [min] | MS (APCI pos, m/z) |
|---|---|---|---|---|
| Example 250 | 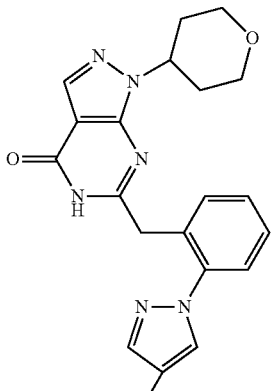 | 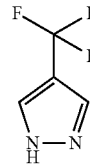 | 8.75 Method 1E hydro | 445 $(M + H)^+$ |
| Example 251 | 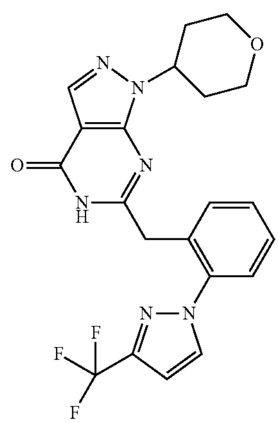 [SMILES: O=c1[nH]c(Cc2ccccc2-n2ccc(C(F)(F)F)n2)nc2c1cnn2C1CCOCC1] | | 8.63 Method 1E hydro | 445 $(M + H)^+$ |

Example 252

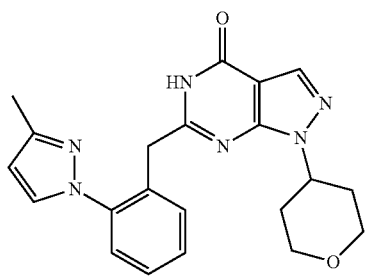

79.89 mg (0.380 mmol) of Example 11B were dissolved in absolute ethanol (2 mL) and 76 mg (1.9 mmol) of sodium hydride (60% suspension in mineral oil) were added. The mixture was stirred for 10 minutes before the addition of 300 mg (1.521 mmol) of [2-(3-Methyl-pyrazol-1-yl)-phenyl]acetonitrile (Example 20A). Then the reaction mixture was heated to 140° C. for 40 minutes in a microwave oven. Cooling to 20° C. was followed by evaporation of the solvent under reduced pressure. The residue was dissolved in 10% citric acid aqueous solution (2 mL) then extracted with dichloromethane (2×2 mL). The organic phase was dried over $Na_2SO_4$, filtered and the solvent was removed under reduced pressure. The residue was purified by preparative HPLC (eluent A: water+0.05% TFA, eluent B: acetonitrile). The solid obtained was triturated with diisopropyl ether to give the title compound as a solid (50.8 mg, 34.2%).

HPLC-MS (Method 2M): $R_t$=8.41 min

MS (APCI pos): m/z=391 (M+H)+

The following examples were synthesized in analogy to the preparation of Example 252, using the corresponding ester or nitrile as starting materials:

| | Structure | pyrazolyl-carboxamide | nitrile | $R_t$ [min] | MS (ESI pos, m/z) |
|---|---|---|---|---|---|
| Example 253 | 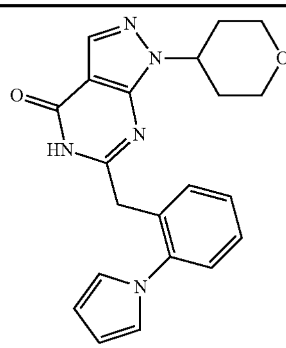 | Example 11B | Example 21A | 10.09 Method 2F | 376 (M + H)+ |

Example 254

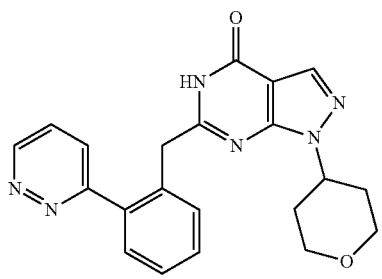 [SMILES: O=c1[nH]c(Cc2ccccc2-c2cccnn2)nc2c1cnn2C1CCOCC1]

A microwave vial was charged with Example 19A (50 mg, 0.115 mmol), 3-bromopyridazine (15 mg, 0.094 mmol) and 1,2-Dimethoxyethane (2.5 mL). The mixture was degassed and then Tetrakis(triphenylphosphine)palladium(0) (16.35 mg, 0.014 mmol) and 165.11 µL (0.33 mmol) of a 2M aqueous solution of $Na_2CO_3$ were added. The reaction mixture was heated to 120° C. for 1 hour in a microwave oven. After cooling to 20° C. the reaction mixture was diluted with saturated $NH_4Cl$ aqueous solution and extracted with dichloromethane, dried over $Na_2SO_4$ and the solvent was removed under reduced pressure. The crude product was purified by flash chromatography on $SiO_2$ using Dichloromethane/Methanol 98/2 as eluent. The title compound was obtained as a solid (12 mg, 32.8%).

HPLC-MS (Method 1E Hydro): $R_t$: 7.12 min
MS (APCI pos): m/z=389 (M+H)+

Example 255

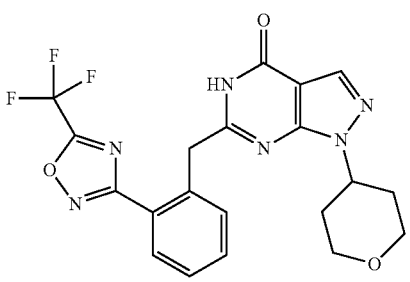 [SMILES: O=c1[nH]c(Cc2ccccc2-c2noc(C(F)(F)F)n2)nc2c1cnn2C1CCOCC1]

Example 53 (200 mg, 0.596 mmol) and hydroxylamine 50% in water (146.18 µL, 2.385 mmol) were mixed together in absolute ethanol (6 mL). The reaction mixture was refluxed for 5 hours. The solvent was then removed under reduced pressure to obtain 229 mg (0.621 mmol) of N-Hydroxy-2-[4-oxo-1-8tetrahydro-pyran-4-yl)-4,5-dihydro-1H-pyrazolo[3,4-d]pyrimidin-6-ylmethyl]-benzamidine as a yellow solid that was used as such in the next step.

N-Hydroxy-2-[4-oxo-1-8tetrahydro-pyran-4-yl)-4,5-dihydro-1H-pyrazolo[3,4-d]pyrimidin-6-ylmethyl]benzamidine (225 mg, 0.611 mmol) was suspended in dry dichloromethane (4.5 mL), N,N-Diisopropylethylamine (0.79 mL, 4.616 mmol) was added and the reaction mixture was cooled to 0° C. before the addition of Trifluoroacetic anhydride (0.402 mL, 2.89 mmol). The mixture was stirred at 0° C. for 5 hours before being diluted with dichloromethane and washed with water and brine. The organic phase was dried over $Na_2SO_4$, filtered and the solvent was removed under reduced pressure. The remaining residue was purified by flash chromatography on $SiO_2$ using dichloromethane/methanol mixture of increasing polarity (from 100% Dichloromethane to 99/1 Dichloromethane/Methanol) as eluant. The product was obtained as a light yellow solid (55 mg, 20.2%).

HPLC-MS (Method 1 E Hydro): $R_t$: 9.22 min
MS (APCI pos): m/z=447 (M+H)+

Example 256

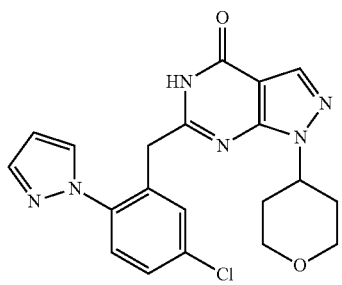 [SMILES: O=c1[nH]c(Cc2cc(Cl)ccc2-n2cccn2)nc2c1cnn2C1CCOCC1]

A microwave reactor vial was charged under inert atmosphere with copper(I)oxide (5.1 mg, 0.04 mmol), cesium carbonate (154 mg, 0.47 mmol), 2-hydroxy-benzaldehyde oxime (9.7 mg, 0.07 mmol), Example 40-8 (100 mg, 0.24 mmol) and pyrazole (32.1 mg, 0.47 mmol). Acetonitrile (5 mL), previously degassed, was added. The reaction mixture was heated to 80° C. for 2 hours using a microwave oven. After cooling the reaction mixture was diluted with dichloromethane and filtered through a Celite pad. The solvent was removed under reduced pressure. The crude product was purified by preparative HPLC (A: water+0.05% TFA, eluent B: methanol). The resulting material was further purified by a three step procedure: (1) conversion into the corresponding hydrochloride salt by addition of ethyl acetate followed by hydrochloric acid (6 M in isopropanol) and subsequent evaporation of the volatiles under reduced pressure; (2) trituration with ethyl acetate and subsequent removal of the solvent by filtration; and (3) liberation of the free base by addition of ethyl acetate and extraction with an aqueous solution of potassium carbonate followed by phase separation and removal of the solvent from the organic layer under reduced pressure. 30 mg (31%) of the product were obtained.

HPLC-MS (Method 6): $R_t$=1.45 min

MS (ESI pos): m/z=411/413 (M+H)$^+$ (Cl)

The following example was synthesized in analogy to the preparation of Example 256, using the corresponding bromide and heterocycle as starting materials:

| | Structure | starting material: bromide | starting material: heterocycle | $R_t$ [min] | MS (ESI pos, m/z) |
|---|---|---|---|---|---|
| Example 257 | 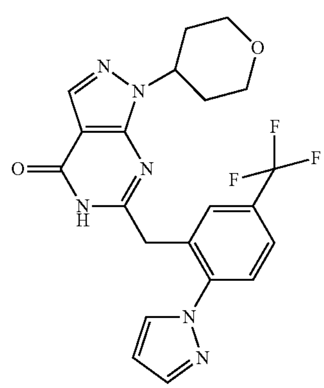 [SMILES: O=c1[nH]c(Cc2cc(C(F)(F)F)ccc2-n2cccn2)nc2c1cnn2C1CCOCC1] | Example 40-9 | | 1.50 (Method 6) | 445 (M + H)$^+$ |
| Example 258 | 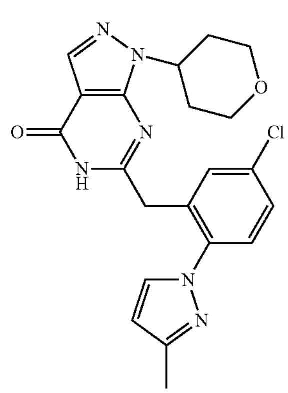 [SMILES: Cc1ccn(-c2ccc(Cl)cc2Cc2nc3c(cnn3C3CCOCC3)c(=O)[nH]2)n1] | Example 40-8 | | 1.46 (Method 7) | 425/427 (M + H)$^+$ (Cl) |

| | Structure | starting material: bromide | starting material: heterocycle | $R_t$ [min] | MS (ESI pos, m/z) |
|---|---|---|---|---|---|
| Example 257 | (structure shown) | Example 40-9 | (pyrazole) | 1.50 (Method 6) | 445 (M + H)+ |

Example 259

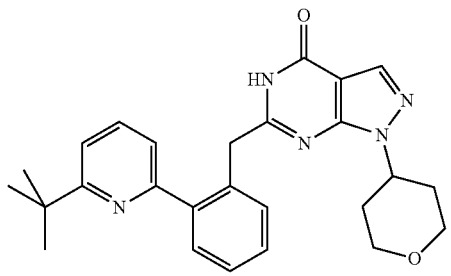 [SMILES: CC(C)(C)c1cccc(-c2ccccc2Cc2nc3c(cnn3C3CCOCC3)c(=O)[nH]2)n1]

A microwave vial was charged with Example 19A (70 mg, 0.16 mmol), 2-bromo-6-tert-butyl-pyridine (69 mg, 0.32 mmol) and DMF (2.0 mL). The mixture was degassed then Tetrakis(triphenylphosphine)palladium(0) (9.2 mg, 0.01 mmol) and potassium acetate (55.1 mg, 0.56 mmol) were added. The reaction mixture was heated to 145° C. for 45 min in a microwave oven. After cooling to 20° C. the solvent was removed under reduced pressure. The crude product was purified by preparative HPLC (A: water+0.05% TFA, eluent B: methanol). The resulting material was further purified by a two step procedure: (1) conversion into the corresponding hydrochloride salt by addition of dichloromethane followed by hydrochloric acid (6 M in isopropanol) and subsequent evaporation of the volatiles under reduced pressure; and (2) trituration with ethyl acetate and subsequent removal of the solvent by filtration. 47 mg (61%) of the product were obtained as the hydrochloride salt.

HPLC-MS (Method 7): $R_t$=1.42 min
MS (ESI pos): m/z=444 (M+H)+

The following example was synthesized in analogy to the preparation of example 259, using the corresponding bromopyridines as starting materials:

| | structure | starting material: bromo-pyridine | $R_t$ | MS (ESI pos, m/z) |
|---|---|---|---|---|
| Example 260 | (structure shown) | (structure shown) | 1.62 min (Method 7) | 458 (M + H)+ |

-continued
| | structure | starting material: bromo-pyridine | R$_t$ | MS (ESI pos, m/z) |
|---|---|---|---|---|
| Example 261 | 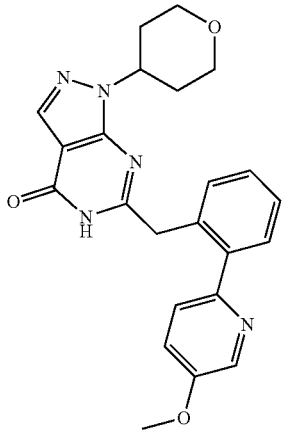 [SMILES: COc1ccc(-c2ccccc2Cc2nc3c(cnn3C3CCOCC3)c(=O)[nH]2)nc1] | 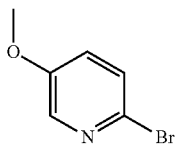 | 1.38 min (Method 7) | 418 (M + H)$^+$ |
| Example 262 | 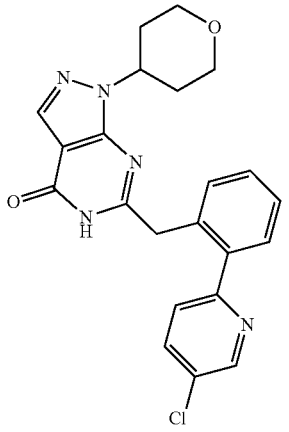 [SMILES: O=c1[nH]c(Cc2ccccc2-c2ccc(Cl)cn2)nc2c1cnn2C1CCOCC1] | 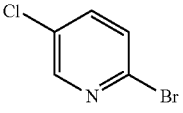 | 1.53 min (Method 7) | 422 (M + H)$^+$ |
| Example 263 | 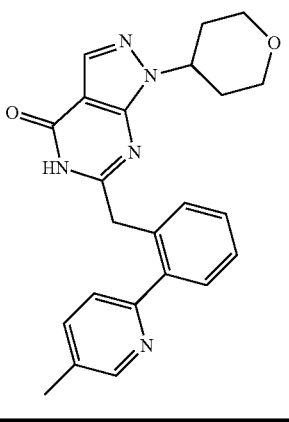 | 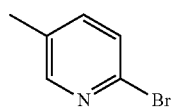 | 1.22 min (Method 7) | 402 (M + H)$^+$ |

The invention claimed is:
1. A compound according to general formula (I)

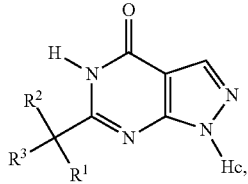

wherein
is tetrahydropyranyl,
wherein one or more carbon ring atom(s) thereof optionally may be substituted by one or by two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo;
$R^1$ is the group

V-W-* wherein
W is phenyl;
V is selected from the group of phenyl or heteroaryl, said heteroaryl being selected from the group of oxadiazolyl, triazolyl, pyrazolyl, pyrrolyl, furanyl, pyridyl, pyrimidyl and pyridazinyl;
-* is the binding point by which W is attached to the $CR^2R^3$ group in formula (I);
wherein W and V independently of each other optionally may be substituted by one or more substituents selected from the group of fluorine, chlorine, bromine, $C_{1-6}$-alkyl-, $F_3C$—, $HF_2C$—, $FH_2C$—, $F_3C$—$CH_2$—, $F_3C$—O—, $HF_2C$—O—, $C_{3-7}$-heterocycloalkyl-, H—O—$C_{1-6}$-alkyl-, $C_{1-6}$-alkyl-O—$C_{1-6}$-alkyl-, $C_{3-7}$-cycloalkyl-O—$C_{1-6}$-alkyl-, $C_{3-7}$-cycloalkyl-$C_{1-3}$alkyl-O—$C_{1-6}$-alkyl-, phenyl-O—$C_{1-6}$-alkyl-, benzyl-O—$C_{1-6}$-alkyl-, H—O—, $C_{1-6}$-alkyl-O—, $C_{3-7}$-cycloalkyl-O—, $C_{3-7}$-cycloalkyl-$C_{1-3}$-alkyl-O—, phenyl-O—, benzyl-O—, N-morpholinyl, and NC—;
$R^2$ is selected from the group of H—, fluorine, $F_3C$—, $HF_2C$—, $FH_2C$—, and $C_{1-3}$-alkyl;
$R^3$ is selected from the group of H—, fluorine, $F_3C$—, $HF_2C$—, $FH_2C$—, and $C_{1-3}$-alkyl.
2. A compound according to claim 1, wherein
Hc is tetrahydropyranyl-,
wherein one or more carbon ring atom(s) thereof optionally may be substituted by one or two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo;
$R^1$ is the group

V-W-* wherein
W is phenyl,
V is selected from the group of phenyl or heteroaryl, said heteroaryl being selected from the group of oxadiazolyl, triazolyl, pyrazolyl, furanyl, pyridyl, pyrimidyl and pyridazinyl,
wherein W and V independently of each other optionally may be substituted by one or more substituents selected from the group of fluorine, chlorine, bromine, $C_{1-6}$-alkyl-, $F_3C$—, $HF_2C$—, $FH_2C$—, $F_3C$—$CH_2$—, $F_3C$—O—, $HF_2C$—O—, $C_{3-7}$-heterocycloalkyl-, H—O—$C_{1-6}$-alkyl-, $C_{1-6}$-alkyl-O—$C_{1-6}$-alkyl-, $C_{3-7}$-cycloalkyl-O—$C_{1-6}$-alkyl-, $C_{3-7}$-cycloalkyl-$C_{1-3}$alkyl-O—$C_{1-6}$-alkyl-, phenyl-O—$C_{1-6}$-alkyl-, benzyl-O—$C_{1-6}$-alkyl-, H—O—, $C_{1-6}$-alkyl-O—, $C_{3-7}$-cycloalkyl-O—, $C_{3-7}$-cycloalkyl-$C_{1-3}$-alkyl-O—, phenyl-O—, benzyl-O—, N-morpholinyl, and NC—,
$R^2$ is selected from the group of H—, fluorine, $F_3C$—, $HF_2C$—, $FH_2C$—, and $C_{1-3}$-alkyl;
$R^3$ is selected from the group of H—, fluorine, $F_3C$—, $HF_2C$—, $FH_2C$—, and $C_{1-3}$-alkyl.
3. A compound according to claim 1, wherein
Hc is tetrahydropyranyl-,
wherein one or more carbon ring atom(s) thereof optionally may be substituted by one or two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo;
$R^1$ is the group

V-W-* wherein
W is phenyl,
V is selected from the group of phenyl or heteroaryl, said heteroaryl being selected from the group of oxadiazolyl, triazolyl, pyrazolyl, pyrrolyl, furanyl, pyridyl, pyrimidyl and pyridazinyl,
wherein W optionally may be substituted by one or more substituents selected from the group of fluorine, chlorine, bromine, $H_3C$—, $F_3C$—, $CH_3O$— and NC—;
and wherein V optionally may be substituted by one or more substituents selected from the group of fluorine, chlorine, $H_3C$—, tert-butyl-, $F_3C$—, $CH_3O$—, cyclobutyloxy-, N-morpholinyl, benzyl-O— and NC—;
$R^2$ is selected from the group of H—, fluorine, $F_3C$—, $HF_2C$—, $FH_2C$—, and $C_{1-3}$-alkyl;
$R^3$ is selected from the group of H—, fluorine, $F_3C$—, $HF_2C$—, $FH_2C$—, and $C_{1-3}$-alkyl.
4. A compound according to claim 1, wherein
Hc is tetrahydropyranyl-,
wherein one or more carbon ring atom(s) thereof optionally may be substituted by one or two substituents independently selected from the group of fluorine, NC—, $F_3C$—, $HF_2C$—, $FH_2C$—, $F_3C$—$CH_2$—, $C_{1-6}$-alkyl-, $C_{1-6}$-alkyl-O— and up to one carbon ring atom may be substituted with oxo;
$R^1$ is the group

V-W-* wherein
W is phenyl wherein W optionally is substituted by a fluorine, chlorine or $F_3C$—;
V is heteroaryl being selected from the group of oxadiazolyl, triazolyl, pyrazolyl, pyrrolyl, furanyl, pyridyl, pyrimidyl and pyridazinyl, wherein
V optionally is substituted by 1 to 4 substituents independently of each other selected from the group of fluorine, chlorine, $H_3C$—, tert-butyl-, $F_3C$—, $CH_3O$—, cyclobutyloxy-, N-morpholinyl, benzyl-O— and NC—,
V is attached at the 2 position of W, wherein the 1 position of W is the attachment point of W to the $CR^2R^3$ group in formula (I);
$R^2$ is selected from the group of H—, fluorine, $F_3C$—, $HF_2C$—, $FH_2C$—, and $C_{1-3}$-alkyl;

R[3] is selected from the group of H—, fluorine, F$_3$C—, HF$_2$C—, FH$_2$C—, and C$_{1-3}$-alkyl.

5. A compound according to claim 1, wherein

Hc is 4-tetrahydropyranyl-, wherein each carbon ring atom thereof optionally may be substituted by one or two substituents independently selected from the group of fluorine, NC—, F$_3$C—, HF$_2$C—, FH$_2$C—, F$_3$C—CH$_2$—, C$_{1-6}$-alkyl-, C$_{1-6}$-alkyl-O— and up to one carbon ring atom may be substituted with oxo;

R[1] is the group

V-W-* wherein

W is phenyl,

V is selected from the group of phenyl or heteroaryl, said heteroaryl being selected from the group of oxadiazolyl, triazolyl, pyrazolyl, furanyl, pyridyl, pyrimidyl and pyridazinyl, wherein W and V independently of each other optionally may be substituted by one or more substituents selected from the group of fluorine, chlorine, bromine, C$_{1-6}$-alkyl-, F$_3$C—, HF$_2$C—, FH$_2$C—, F$_3$C—CH$_2$—, F$_3$C—O—, HF$_2$C—O— and C$_{3-7}$-heterocycloalkyl-;

R[2] is selected from the group of H—, fluorine, F$_3$C—, HF$_2$C—, FH$_2$C—, and C$_{1-3}$-alkyl;

R[3] is selected from the group of H—, fluorine, F$_3$C—, HF$_2$C—, FH$_2$C—, and C$_{1-3}$-alkyl.

6. A compound according to claim 1, whereby the compound is selected from the group consisting of:

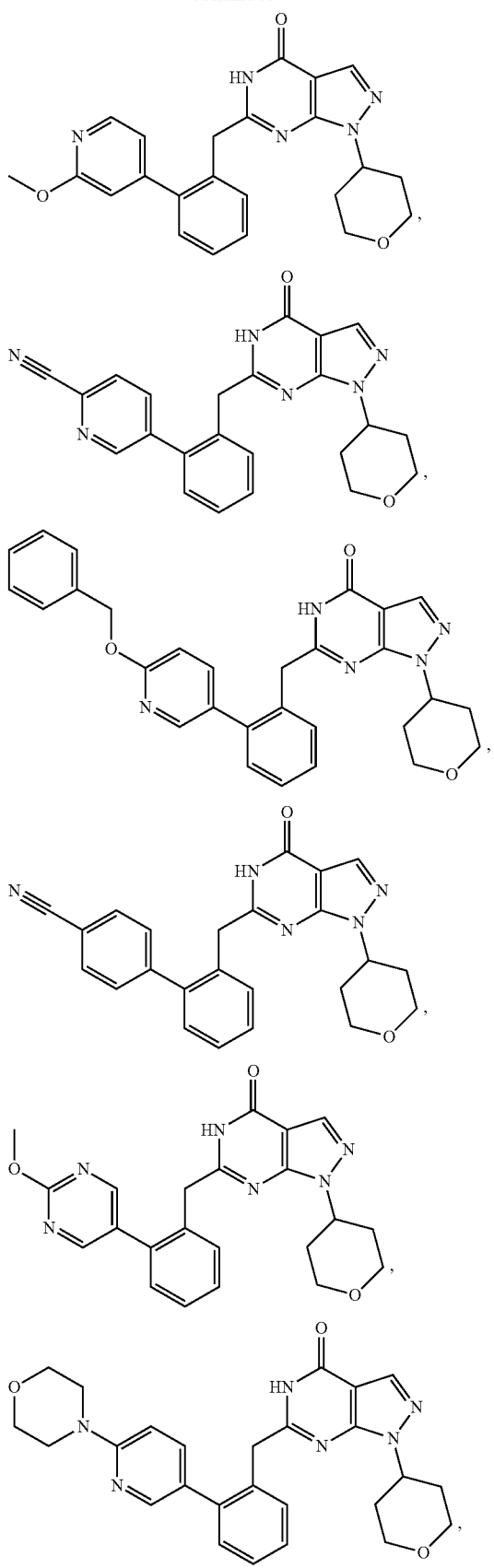

273
-continued
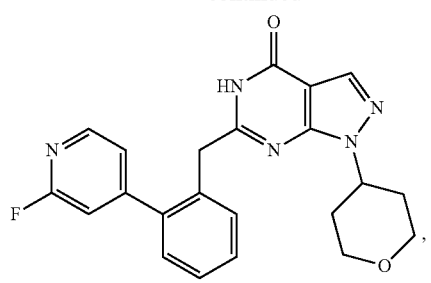
,
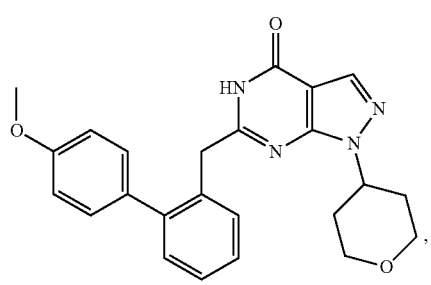
,
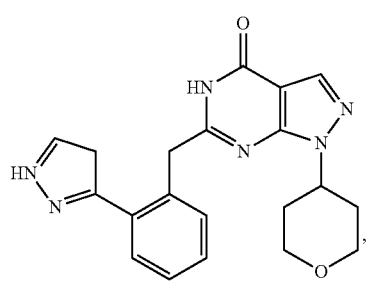
,
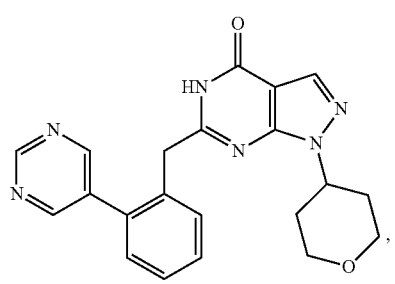
,
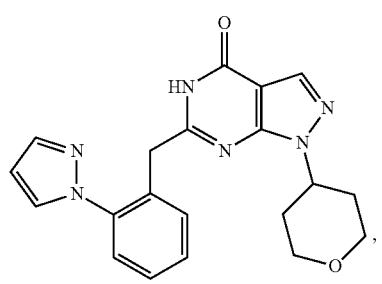
,
274
-continued
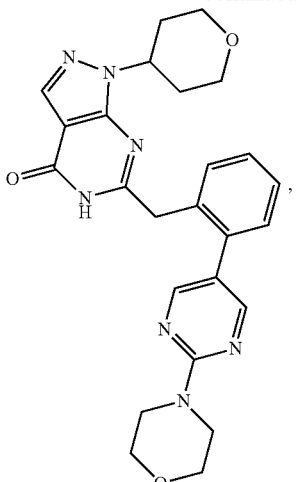
,
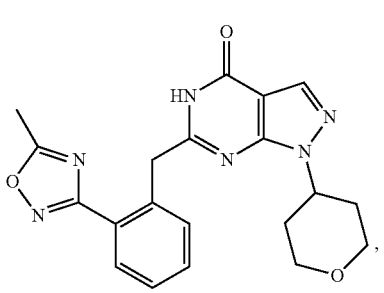
,
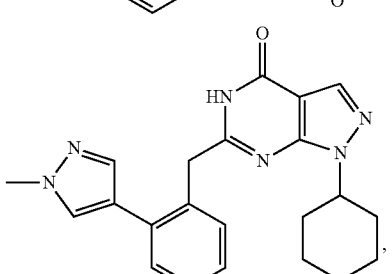
,
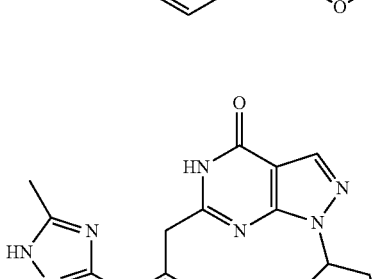
,
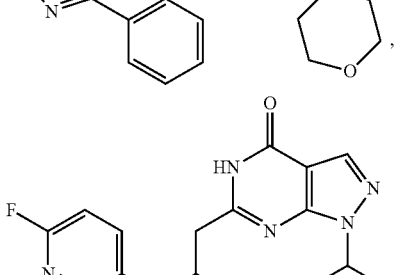
, 275
-continued
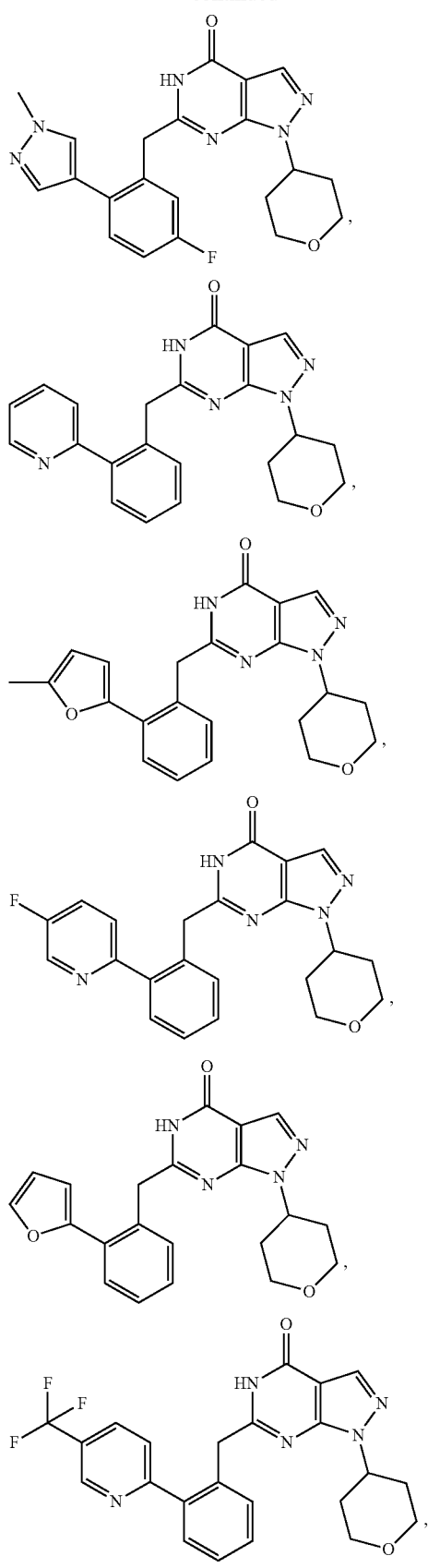
276
-continued
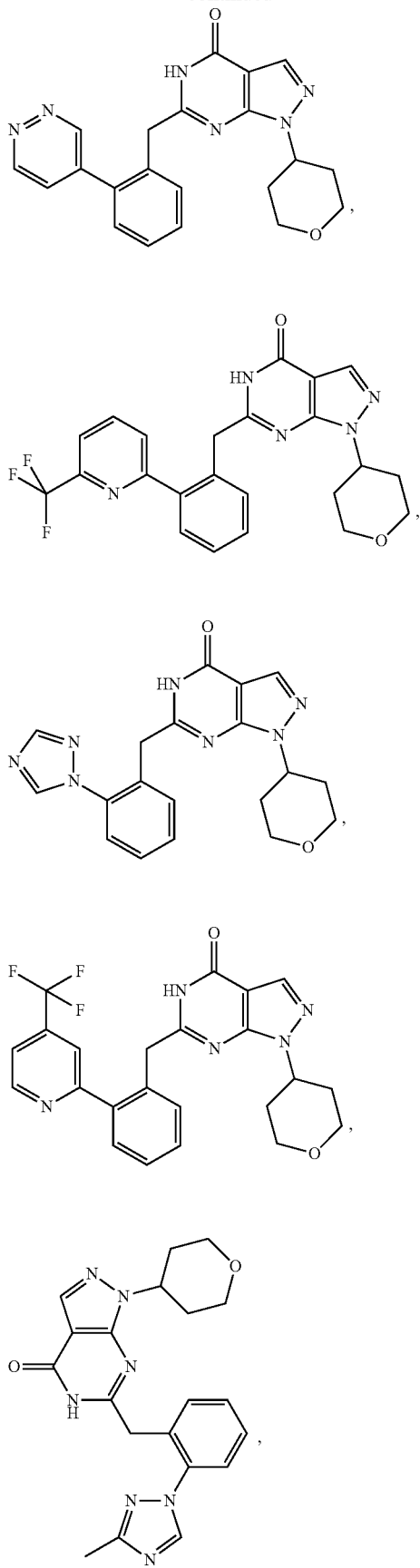

277
-continued
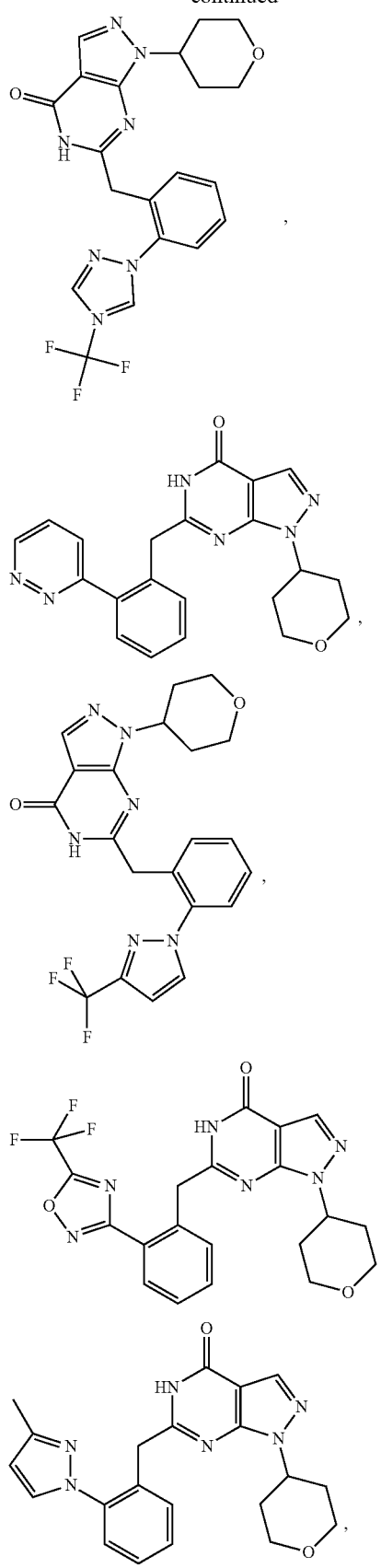
278
-continued
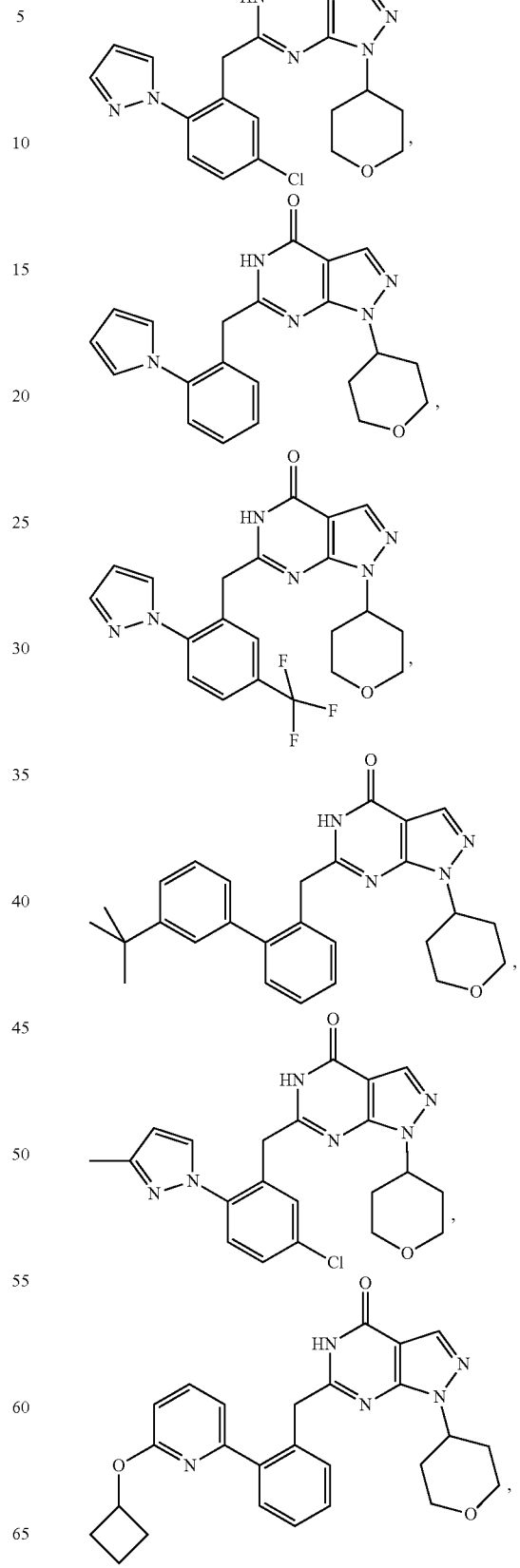

-continued

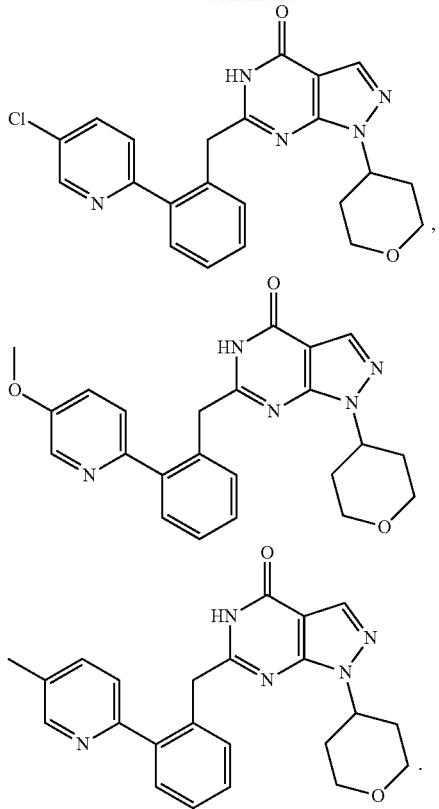

7. A compound according to claim 1 in form of a salt thereof.

8. A pharmaceutical composition comprising a compound according to claim 1 and a pharmaceutical carrier, optionally in combination with another active ingredient selected from the group consisting of beta-secretase inhibitors; gamma-secretase inhibitors; gamma-secretase modulators; amyloid aggregation inhibitors, anti-oxidants, anti-inflammatory substances, HMG-CoA reductase inhibitors, NMDA receptor antagonists, AMPA receptor agonists, AMPA receptor positive modulators, AMPkines, glycine transporter 1 inhibitors; monoamine receptor reuptake inhibitors, CB-1 receptor antagonists or inverse agonists, antibiotics, PDE1, PDE2, PDE4, PDE5 and/or PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists, histamine receptor H3 antagonists, 5-HT4 receptor agonists or partial agonists, 5-HT6 receptor antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate receptor 5 positive modulators and metabotropic glutamate receptor 2 antagonists.

9. A compound according to claim 1 wherein V is attached at the 2 position of W, and wherein the 1 position of W is the attachment point of W to the $CR^2R^3$ group in formula (I).

10. A compound according to claim 1 wherein $R^2$ and $R^3$ are H.

11. The compound according to claim 1, wherein the compound is

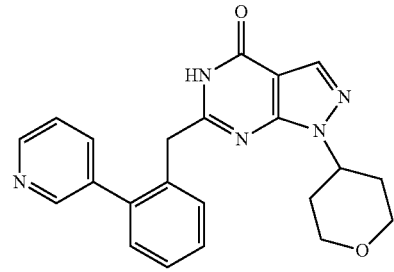

or a pharmaceutically acceptable salt thereof.

12. The compound according to claim 1, wherein the compound is

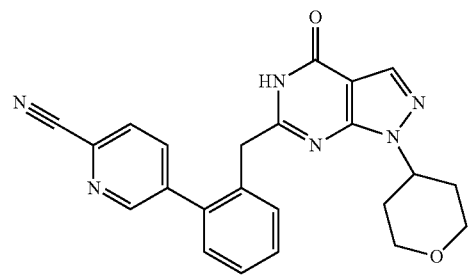

or a pharmaceutically acceptable salt thereof.

13. The compound according to claim 1, wherein the compound is

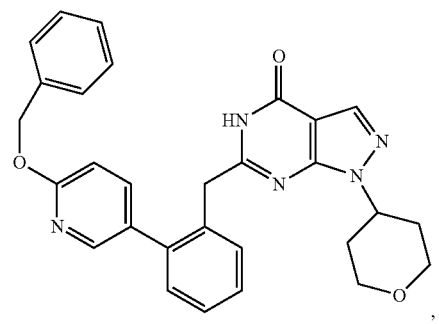 [SMILES: O=c1[nH]c(Cc2ccccc2-c2ccc(OCc3ccccc3)nc2)nc2c1cnn2C1CCOCC1]

or a pharmaceutically acceptable salt thereof.

14. The compound according to claim 1, wherein the compound is

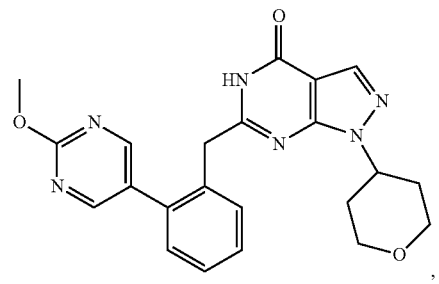 [SMILES: COc1ncc(-c2ccccc2Cc2nc3c(cnn3C3CCOCC3)c(=O)[nH]2)cn1]

or a pharmaceutically acceptable salt thereof.

15. The compound according to claim 1, wherein the compound is

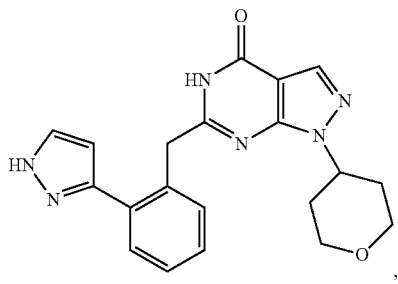 [SMILES: O=c1[nH]c(Cc2ccccc2-c2cc[nH]n2)nc2c1cnn2C1CCOCC1]

or a pharmaceutically acceptable salt thereof.

16. The compound according to claim 1, wherein the compound is

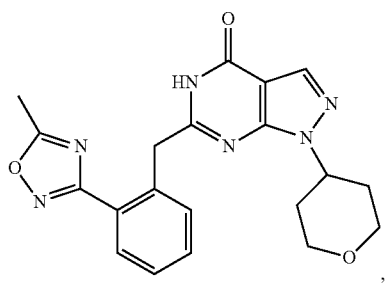 [SMILES: Cc1nc(-c2ccccc2Cc2nc3c(cnn3C3CCOCC3)c(=O)[nH]2)no1]

or a pharmaceutically acceptable salt thereof.

17. The compound according to claim 1, wherein the compound is

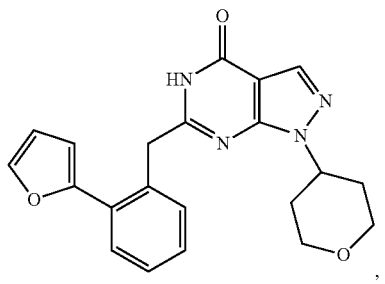 [SMILES: O=c1[nH]c(Cc2ccccc2-c2ccco2)nc2c1cnn2C1CCOCC1]

or a pharmaceutically acceptable salt thereof.

18. The compound according to claim 1, wherein the compound is

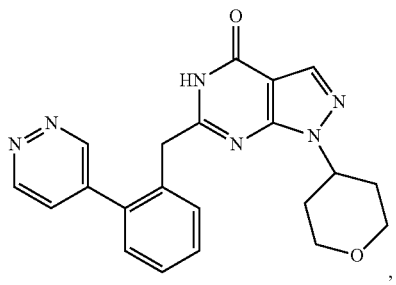 [SMILES: O=c1[nH]c(Cc2ccccc2-c2ccnnc2)nc2c1cnn2C1CCOCC1]

or a pharmaceutically acceptable salt thereof.

19. The compound according to claim 1, wherein the compound is

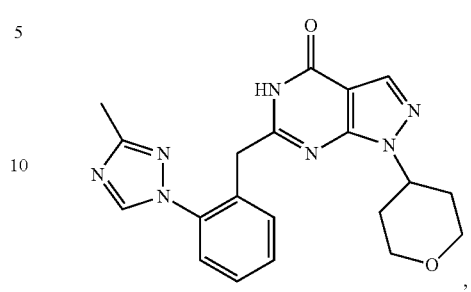

or a pharmaceutically acceptable salt thereof.

20. The compound according to claim 1, wherein the compound is

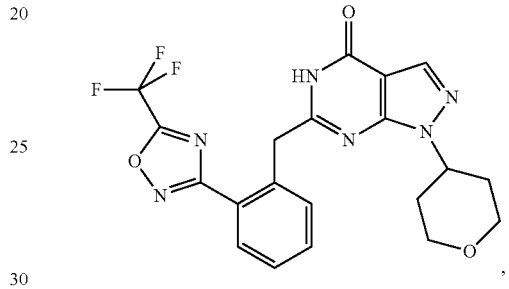

or a pharmaceutically acceptable salt thereof.

21. The compound according to claim 1, wherein the compound is

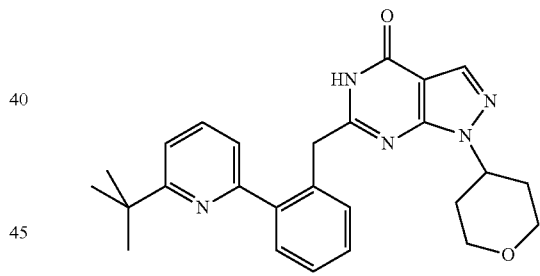

or a pharmaceutically acceptable salt thereof.

22. The compound according to claim 1, wherein the compound is

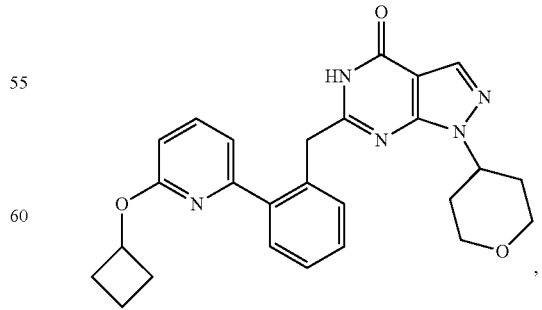

or a pharmaceutically acceptable salt thereof.

* * * * *